(12) United States Patent
Bader et al.

(10) Patent No.: US 12,016,923 B2
(45) Date of Patent: Jun. 25, 2024

(54) CLAUDIN 18.2 T CELL-ANTIGEN COUPLERS AND USES THEREOF

(71) Applicant: Triumvira Immunologics USA, Inc., Austin, TX (US)

(72) Inventors: Andreas Bader, Austin, TX (US); Christopher W. Helsen, Oakville (CA); Philbert Ip, Hamilton (CA); Tania Benatar, Thornhill (CA); Ling Wang, Mississauga (CA)

(73) Assignee: Triumvira Immunologics USA, Inc., Austin, TX (US)

( * ) Notice: Subject to any disclaimer, the term of this patent is extended or adjusted under 35 U.S.C. 154(b) by 0 days.

(21) Appl. No.: 18/246,318

(22) PCT Filed: Jun. 1, 2022

(86) PCT No.: PCT/US2022/031836
§ 371 (c)(1),
(2) Date: Mar. 22, 2023

(87) PCT Pub. No.: WO2022/256449
PCT Pub. Date: Dec. 8, 2022

(65) Prior Publication Data
US 2023/0364237 A1 Nov. 16, 2023

Related U.S. Application Data

(60) Provisional application No. 63/362,594, filed on Apr. 6, 2022, provisional application No. 63/263,809, filed on Nov. 9, 2021, provisional application No. 63/202,211, filed on Jun. 1, 2021.

(51) Int. Cl.
| | | |
|---|---|---|
| *C07K 16/28* | (2006.01) | |
| *A61K 35/17* | (2015.01) | |
| *A61K 39/00* | (2006.01) | |
| *A61P 35/00* | (2006.01) | |
| *C07K 14/725* | (2006.01) | |
| *A61K 38/00* | (2006.01) | |

(52) U.S. Cl.
CPC ...... *A61K 39/4632* (2023.05); *A61K 39/4611* (2023.05); *A61K 39/464402* (2023.05); *A61P 35/00* (2018.01); *C07K 14/7051* (2013.01); *C07K 16/28* (2013.01); *A61K 38/00* (2013.01); *A61K 2039/505* (2013.01); *C07K 2317/569* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 7,083,785 B2 | 8/2006 | Browning et al. | |
| 7,947,805 B2 | 5/2011 | Belloir et al. | |
| 8,084,030 B2 | 12/2011 | Kalled et al. | |
| 9,718,893 B2 | 8/2017 | Jung et al. | |
| 10,435,453 B2 | 10/2019 | Bramson et al. | |
| 10,640,562 B2 | 5/2020 | Bramson et al. | |
| 10,822,408 B2 | 11/2020 | Hamburger et al. | |
| 11,001,621 B1 | 5/2021 | Bramson et al. | |
| 11,008,376 B2 | 5/2021 | Bramson et al. | |
| 11,110,123 B2 | 9/2021 | Bramson et al. | |
| 11,111,298 B2 | 9/2021 | Bramson et al. | |
| 11,198,737 B2 | 12/2021 | Helsen et al. | |
| 11,406,667 B2 | 8/2022 | Bramson et al. | |
| 11,421,014 B2 | 8/2022 | Bader et al. | |
| 11,453,723 B1* | 9/2022 | Bramson | C07K 16/2878 |
| 2002/0081296 A1 | 6/2002 | Theill et al. | |
| 2002/0107869 A1 | 8/2002 | Leroy | |
| 2003/0012783 A1 | 1/2003 | Kindsvogel | |
| 2003/0095967 A1 | 5/2003 | MacKay et al. | |
| 2004/0162411 A1 | 8/2004 | Lanzavecchia | |
| 2006/0233791 A1 | 10/2006 | Tedder et al. | |
| 2007/0048221 A1 | 3/2007 | Kindsvogel | |
| 2007/0048319 A1 | 3/2007 | Kindsvogel | |
| 2007/0049735 A1 | 3/2007 | Kindsvogel | |
| 2008/0044413 A1 | 2/2008 | Hammond et al. | |
| 2008/0095766 A1 | 4/2008 | Koenig et al. | |
| 2008/0260737 A1 | 10/2008 | Ponce et al. | |
| 2008/0267965 A1 | 10/2008 | Kalled et al. | |
| 2009/0004186 A1 | 1/2009 | Shitara et al. | |
| 2012/0009190 A1 | 1/2012 | Gaffen et al. | |
| 2012/0082661 A1 | 4/2012 | Kalled et al. | |
| 2012/0213768 A1 | 8/2012 | Oh et al. | |
| 2013/0101599 A1 | 4/2013 | Borges et al. | |

(Continued)

FOREIGN PATENT DOCUMENTS

| | | |
|---|---|---|
| CN | 1229436 | 9/1999 |
| CN | 101679966 A | 3/2010 |

(Continued)

OTHER PUBLICATIONS

Ataca et al, 2015 Chimeric Antigen Receptor T Cell Therapy in Hematology Turk J Hematol 2015;32:285-294.*
Dotti et al 2014 Design and Development of Therapies using Chimeric Antigen Receptor-Expressing T cells Immunol Rev. Jan. 2014 ; 257(1): pp. 1-35.*
U.S. Appl. No. 15/117,173, filed Aug. 5, 2016, U.S. Pat. No. 10,435,453, Oct. 8, 2019, Issued.
U.S. Appl. No. 16/547,421, filed Aug. 21, 2019, U.S. Pat. No. 11,421,014, Aug. 23, 2022, Issued.
U.S. Appl. No. 15/929,510, filed May 6, 2020, U.S. Pat. No. 11,008,376, May 18, 2021, Issued.

(Continued)

*Primary Examiner* — Maria G Leavitt
(74) *Attorney, Agent, or Firm* — Goodwin Procter LLP

(57) ABSTRACT

Claudin 18.2 T cell antigen couplers (TACs) polypeptides having (i) an antigen-binding domain that binds Claudin 18.2, (ii) an antigen-binding domain that binds a protein associated with a TCR complex, and (iii) a T cell receptor signaling domain polypeptide are provided. Nucleic acids encoding the claudin 18/2 TACs are also provided.

18 Claims, 32 Drawing Sheets
Specification includes a Sequence Listing.

(56) References Cited

U.S. PATENT DOCUMENTS

| | | |
|---|---|---|
| 2013/0156770 A1 | 6/2013 | Kufer et al. |
| 2013/0171152 A1 | 7/2013 | Spriggs et al. |
| 2013/0273055 A1 | 10/2013 | Borges et al. |
| 2013/0280280 A1 | 10/2013 | Algate et al. |
| 2013/0330323 A1 | 12/2013 | Dunn et al. |
| 2015/0119555 A1 | 4/2015 | Jung et al. |
| 2015/0322169 A1 | 11/2015 | June et al. |
| 2016/0228546 A1 | 8/2016 | Stagliano et al. |
| 2016/0362472 A1 | 12/2016 | Bitter et al. |
| 2016/0368964 A1 | 12/2016 | Bramson et al. |
| 2019/0153115 A1 | 5/2019 | Schellenberger et al. |
| 2020/0024345 A1 | 1/2020 | Bramson et al. |
| 2020/0071377 A1 | 3/2020 | Bramson et al. |
| 2020/0239571 A1 | 7/2020 | Bramson et al. |
| 2020/0261500 A1 | 8/2020 | Bramson et al. |
| 2020/0270330 A1 | 8/2020 | Bramson et al. |
| 2020/0308278 A1 | 10/2020 | Bramson et al. |
| 2020/0392247 A1 | 12/2020 | Helsen et al. |
| 2021/0369780 A1 | 12/2021 | Bramson et al. |
| 2022/0127372 A1 | 4/2022 | Li et al. |
| 2022/0331364 A1 | 10/2022 | Bramson et al. |
| 2022/0332790 A1 | 10/2022 | Bramson et al. |
| 2023/0212258 A1 | 7/2023 | Bramson et al. |
| 2023/0265207 A1 | 8/2023 | Helsen et al. |

FOREIGN PATENT DOCUMENTS

| | | |
|---|---|---|
| CN | 103562221 | 2/2014 |
| JP | 2003111595 A | 4/2003 |
| WO | WO-199744461 A2 | 11/1997 |
| WO | WO-9957268 A1 | 11/1999 |
| WO | WO-2004106380 A2 | 12/2004 |
| WO | WO-2005040220 A1 | 5/2005 |
| WO | WO-2010037835 A2 | 4/2010 |
| WO | WO-2012066058 A1 | 5/2012 |
| WO | WO-2012106587 A1 | 8/2012 |
| WO | WO-2012135345 A1 | 10/2012 |
| WO | WO-2012163805 A1 | 12/2012 |
| WO | WO-2013059885 A2 | 5/2013 |
| WO | WO-2013092001 A1 | 6/2013 |
| WO | WO-2013/123061 A1 | 8/2013 |
| WO | WO-2013132268 A1 | 9/2013 |
| WO | WO-2014011988 A2 | 1/2014 |
| WO | WO-2014122144 A1 | 8/2014 |
| WO | WO-2015006749 A2 | 1/2015 |
| WO | WO-2015061694 A2 | 4/2015 |
| WO | WO-2015117229 A1 | 8/2015 |
| WO | WO-2015142675 A2 | 9/2015 |
| WO | WO-2016166139 A1 | 10/2016 |
| WO | WO-2017040344 A2 | 3/2017 |
| WO | WO-2017087723 A1 | 5/2017 |
| WO | WO-2018027155 A1 | 2/2018 |
| WO | WO-2018121605 A1 | 7/2018 |
| WO | WO-2019071358 A1 | 4/2019 |
| WO | WO-2020018727 A1 | 1/2020 |
| WO | WO-2020156554 A1 | 8/2020 |
| WO | WO-2022256449 A1 | 12/2022 |
| WO | WO-2022266778 A1 | 12/2022 |

OTHER PUBLICATIONS

U.S. Appl. No. 17/248,174, filed Jan. 12, 2021, U.S. Pat. No. 11,001,621, May 11, 2021, Issued.
U.S. Appl. No. 17/808,361, filed Jun. 23, 2022, Pending.
U.S. Appl. No. 18/188,312, filed Mar. 22, 2023, Pending.
U.S. Appl. No. 16/753,577, filed Apr. 3, 2020, Allowed.
U.S. Appl. No. 17/301,884, filed Apr. 16, 2021, U.S. Pat. No. 11,198,737, Dec. 14, 2021, Issued.
U.S. Appl. No. 18/188,318, filed Mar. 22, 2023, Pending.
U.S. Appl. No. 16/442,274, filed Jun. 14, 2019, U.S. Pat. No. 10,640,562, May 5, 2020, Issued.
U.S. Appl. No. 16/826,053, filed Mar. 20, 2020, Pending.
U.S. Appl. No. 15/929,513, filed May 6, 2020, U.S. Pat. No. 11,110,123, Sep. 7, 2021, Issued.
U.S. Appl. No. 16/904,451, filed Jun. 17, 2020, U.S. Pat. No. 11,111,298, Sep. 7, 2021, Issued.
U.S. Appl. No. 17/394,280, filed Aug. 4, 2021, U.S. Pat. No. 11,406,667, Aug. 9, 2022, Issued.
U.S. Appl. No. 17/810,238, filed Jun. 30, 2022, Pending.
U.S. Appl. No. 18/188,326, filed Mar. 22, 2023, Pending.
U.S. Appl. No. 17/304,924, filed Jun. 28, 2021, U.S. Pat. No. 11,453,723, Sep. 27, 2022, Issued.
Acuto et al. T cell activation and the cytoskeleton. Annu. Rev. Immunol. 18:165-184 (2000).
Alabanza et al. Function of Novel Anti-CD19 Chimeric Antigen Receptors with Human Variable Regions Is Affected by Hinge and Transmembrane Domains. Mol Ther 25(11):2452-2465 (2017).
Anderson et al. Comodulation of CD3 and CD4. Evidence for a specific association between CD4 and approximately 5% of the CD3:T cell receptor complexes on helper T lymphocytes. J Immunol 140:1732-1737 (1988).
Apuri, S., et al., "Outcomes in Patients with Acute Myeloid Leukemia Preceded by Breast Cancer", Blood, 120(21): 4316 (2012).
Arcaro et al. Essential role of CD8 palmitoylation in CD8 coreceptor function. J. Immunol. 165:2068-2076 (2000).
Bezverbnaya, K., et al., Development of a B-cell maturation antigen-specific T-cell antigen coupler receptor for multiple myeloma, Cytotherapy, 23(9): 820-832 (2021).
Bezverbnaya, K., et al., Preclinical evaluation of BCMA-specific TAC receptor-engineered T cells for multiple myeloma, 32nd annual meeting and pre-conference programs of the society for immunotherapy of cancer (SITC 2017): Part one, J Immunother Cancer, 5(Suppl 2): 86 (2017).
Carpenter, R.O., et al., B-cell maturation antigen is a promising target for adoptive T-cell therapy of multiple myeloma, Clin Cancer Res, 19(8): 2048-2060 (2013).
Chames et al. Bispecific antibodies for cancer therapy: the light at the end of the tunnel? MAbs 1:539-547 (2009).
Chervin et al. The impact of TCR-binding properties and antigen presentation format on T cell responsiveness. J. Immunol. 183:1166-1178 (2009).
Chiu, A., et al., Hodgkin lymphoma cells express TACI and BCMA receptors and generate survival and proliferation signals in response to BAFF and APRIL, Blood, 109(2): 729-739 (2007).
Compte et al. Inhibition of tumor growth in vivo by in situ secretion of bispecific anti-CEA x anti-CD3 diabodies from lentivirally transduced human lymphocytes. Cancer Gene Therapy 14:380-388 (2007).
De Novo, New Products from R&D Systems, Antibody catalog including BCMA mAB, pp. 1-10 (Mar. 2004).
Deans et al. Interaction of CD4:lck with the T cell receptor/CD3 complex induces early signaling events in the absence of CD45 tyrosine phosphatase. Eur J Immunol 22:661-668 (1992).
Deng, S., et al., B-lymphocyte-induced maturation protein1 up-regulates the expression of B-cell maturation antigen in mouse plasma cells, Mol Biol Rep, 37(8): 3747-3755 (2010).
Deshayes, S., et al., Cell-penetrating peptides: tools for intracellular delivery of therapeutics, Cell Mol Life Sci, 62(16): 1839-1849 (2005).
Dotti et al. Fifteen years of gene therapy based on chimeric antigen receptors: "are we nearly there yet?" Hum. Gene Ther. 20:1229-1239 (2009).
EP15746948.7 Communication pursuant to Rule 114(2) EPC dated Jan. 21, 2019.
Finney et al. Activation of resting human primary T cells with chimeric receptors: costimulation from CD28, inducible costimulator, CD134, and CD137 in series with signals from the TCR zeta chain. J. Immunol. 172:104-113 (2004).
Fournier et al. Bispecific antibodies and trispecific immunocytokines for targeting the immune system against cancer: preparing for the future. BioDrugs 27:35-53 (2013).
Fragoso et al. Lipid raft distribution of CD4 depends on its palmitoylation and association with Lek, and evidence for CD4-induced lipid raft aggregation as an additional mechanism to enhance CD3 signaling. J. Immunol. 170:913-921 (2003).

(56) References Cited

OTHER PUBLICATIONS

Frankel et al. Targeting T cells to tumor cells using bispecific antibodies. Curr Opin Chem Biol 17(3):385-392 (2013).
Fry et al. T-cell adoptive immunotherapy for acute lymphoblastic leukemia. Hematology Am. Soc. Hematol. Educ. Program 2013:348-353 (2013).
Geiger et al. Integrated src kinase and costimulatory activity enhances signal transduction through single-chain chimeric receptors in T lymphocytes. Blood 98(8):2364-2371 (2001).
Geyer et al. Review: Current clinical applications of chimeric antigen receptor (CAR) modified T cells. Cytotherapy 18(11):1393-1409 (2016).
Guadagnoli, M., et al., Development and characterization of APRIL antagonistic monoclonal antibodies for treatment of B-cell lymphomas, Blood, 117(25): 6856-6865 (2011).
Hammill, J.A., Pre-clinical development of synthetic receptor-engineered T lymphocytes for the treatment of cancer-novel receptors and understanding toxicity, Thesis submitted to McMaster Univeristy, pp. 1-220 (2017).
Hammond et al. Selective targeting and potent control of tumor growth using an EphA2/CD3-Bispecific single-chain antibody construct. 67(8):3927-3935 (2007).
Han et al. Chimeric antigen receptor-engineered T cells for cancer immunotherapy: progress and challenges. J. Hematol. Oncol. 6:4 7 (2013).
He et al. T-cell antigen receptor triggering and lipid rafts: a matter of space and time scales. Talking Point on the involvement of lipid rafts in T-cell activation. EMBO Rep. 9:525-530 (2008).
Helsen et al. The chimeric TAC receptor co-opts the T cell receptor yielding robust anti-tumor activity without toxicity. Nature Communications 9:3049 (2018).
Helsen et al. Tri-functional T cell receptor antigen coupler (Tri-TAC): a novel methodto direct T cells against tumors. J Immunother Cancer 2(Supp 3):P17 (2014).
Hexham et al. Optimization of the anti-(human CD3) immunotoxin DT389-scFv(UCHT1) N-terminal sequence to yield a homogeneous protein. Biotechnol Appl Biochem 34(Pt 3):183-187 (2010).
Humphries. Adoptive cell therapy: Honing that killer instinct. Nature 504:S13-15 (2013).
Itano et al. The cytoplasmic domain of CD4 promotes the development of CD4 lineage T cells. J Exp Med. 183(3):731-741 (1996).
Jamal, S., et al., "Immunophenotypic Analysis of Peripheral T-Cell Neoplasms", Am. J. Clin. Pathol., vol. 116, pp. 512-526, (2001).
Kiewe, P., et al., "Phase I Trial of the Trifunctional Anti-HER2 x Anti-CD3 Antibody Ertumaxomab in Matastatic Breast Cancer", Clin. Cancer Res., 12(10), pp. 3085-3091, (2006).
Kim et al. A zinc clasp structure tethers Lek to T cell coreceptors CD4 and CD8. Science 301:1725-1728 (2003).
Kimchi-Sarfaty, C., et al., "A 'silent' polymorphiosm in the MDR1 gene changes substrate specificity", Science, 315:525-528, (2007).
Klinger et al. Harnessing T cells to fight cancer with BiTE® antibody constructs—past developments and future directions. Immunol Rev. 270(1):193-208 (2016).
Kochenderfer et al. Treating B-cell cancer with T cells expressing anti-CD19 chimeric antigen receptors. Nat. Rev. Clin. Oncol. 10:267-276 (2013).
Kuhns et al. TCR Signaling Emerges from the Sum of Many Parts. Front. Immunol. 3:159 (2012).
Löffler et al. A recombinant bispecific single-chain antibody, CD19 X CD3, induces rapid and high lymphoma-directed cytotoxicity by unstimulated T lymphocytes. Blood 95(6):2098-2103 (2000).
Marsden, H.R., et al., Model systems for membrane fusion, Chem Soc Rev, 40(3): 1572-1585 (2011).
Methi et al. Short-interfering RNA-mediated Lek knockdown results in augmented downstream T cell responses. J. Immunol. 175(11):7398-7406 (2005).
Milone et al. Chimeric receptors containing CD137 signal transduction domains mediate enhanced survival of T cells and increased antileukemic efficacy in vivo. Mol. Ther. 17: 1453-1464 (2009).

Molhoj, et al. CD19-/CD3-bispecific antibody of the BiTE class is far superior to tandem diabody with respect to redirected tumor cell lysis. Mol Immunol. Mar. 2007;44(8):1935-43. Epub Nov. 2, 2006.
Nagorsen et al. Immunomodulatory therapy of cancer with T cell-engaging BiTE antibody blinatumomab. Exp Cell Res 317(9): 1255-1260 (2011).
Nagorsen et al. Immunotherapy of lymphoma and leukemia with T-cell engaging BiTE antibody blinatumomab. Leuk Lymph 50(6): 886-891 (2009).
Novak, A.J., et al., Expression of BLyS and its receptors in B-cell non-Hodgkin lymphoma: correlation with disease activity and patient outcome, Blood, 104(8): 2247-2253 (2004).
Panka et al. Variable region framework differences result in decreased or increased affinity of variant anti-digoxin antibodies. PNAS USA 85:3080-3084 (1988).
PCT/CA2015/000068 International Preliminary Report on Patentability dated Aug. 9, 2016.
PCT/CA2015/000068 International Search Report and Written Opinion dated May 4, 2015.
PCT/CA2018/051290 International Search Report and Written Opinion dated Jan. 17, 2019.
PCT/CA2022/051024 International Search Report and Written Opinion dated Aug. 22, 2022.
PCT/US2019/042297 International Search Report and Written Opinion dated Oct. 30, 2019.
PCT/US2022/031836 International Search Report and Written Opinion dated Nov. 3, 2022.
Pilozzi et al. Co-expression of CD79a (JCB117) and CD3 by lymphoblastic lymphoma. J Pathol 186(2):140-143. (1998).
Popik, et al. CD4 receptor localized to non-raft membrane microdomains supports HIV-1 entry. Identification of a novel raft localization marker in CD4. J Biol Chem 279(1):704-712 (2004).
Portell et al. Clinical and pharmacologic aspects of blinatumomab in the treatment of B-cell acute lymphoblastic leukemia. Clin. Pharmacol. 5(Suppl 1):5-11 (2013).
Rosenberg, et al. Use of tumor-infiltrating lymphocytes and interleukin-2 in the immunotherapy of patients with matastatic melanoma. A preliminary report. NEJM 319: 1676 (1988).
Rudikoff et al. Single amino acid substitution altering antigen-binding specificity. PNAS USA 79:1979-1983 (1982).
Ryan, M.C., et al., Antibody targeting of B-cell maturation antigen on malignant plasma cells, Mol Cancer Ther, 6(11): 3009-3018 (2007).
Tai, Y-T., et al., Novel Fc-Engineered Anti-B Cell Maturation Antigen-Monomethyl Auristatin F Antibody-Drug Conjugate (GSK2857916) Induces Potent and Selective Anti-Multiple Myeloma Activity via Enhanced Effector Function and Direct Tumor Cell Killing, Blood, 122(21): 877 (2013).
Thompson et al. CLUSTAL W: improving the sensitivity of progressive multiple sequence alignment through sequence weighting, position-specific gap penalties and weight matrix choice. Nucleic Acid Res. 22:4673-4680 (1994).
Till et al. CD20-specific adoptive immunotherapy for lymphoma using a chimeric antigen receptor with both CD28 and 4-1 BB domains: pilot clinical trial results. Blood 119(17):3940-3950 (2012).
U.S. Appl. No. 15/117,173 Office Action dated Jan. 24, 2018.
U.S. Appl. No. 15/117,173 Office Action dated Jun. 21, 2019.
U.S. Appl. No. 15/117,173 Office Action dated Oct. 24, 2018.
U.S. Appl. No. 15/929,510 Office Action dated Nov. 9, 2020.
U.S. Appl. No. 15/929,513 Office Action dated May 11, 2021.
U.S. Appl. No. 15/929,513 Office Action dated Nov. 30, 2020.
U.S. Appl. No. 16/442,274 Office Action dated Nov. 6, 2019.
U.S. Appl. No. 16/547,421 Office Action dated Nov. 24, 2021.
U.S. Appl. No. 16/904,451 Office Action dated Dec. 1, 2020.
U.S. Appl. No. 16/904,451 Office Action dated May 10, 2021.
U.S. Appl. No. 17/248,174 Office Action dated Mar. 11, 2021.
U.S. Appl. No. 17/304,924 Application filed Jun. 28, 2021.
U.S. Appl. No. 17/394,280 Application filed Aug. 4, 2021.
U.S. Appl. No. 17/394,280 Office Action dated Dec. 10, 2021.
Velasquez. T cells expressing CD19-specific Engager Molecules for the Immunotherapy of CD19-positive Malignancies. Sci Rep 6:27130 (2016).

(56) References Cited

OTHER PUBLICATIONS

Voet, D., et al., Biochemistry, John Wiley and Sons, New York, pp. 126-128, (1990).
Wang, M., et al., Efficient delivery of genome-editing proteins using bioreducible lipid nanoparticles, PNAS, 113(11): 2868-2873 (2016).
Wels et al. Construction, Bacterial Expression and Characterization of a Bifunctional Single-Chain Antibody-Phosphatase Fusion Protein Targeted to the human ERBB-2 receptor. Nature Biotech 10: 1128-1132 (1992).
Wittlich et al. Structural characterization of the transmembrane and cytoplasmic domains of human CD4. Biochimica et Biophysica Acta 1768:2949-2960 (2007).
Wykosky, J., et al. The EphA2 repector and ephrinA1 ligand in solid tumors: function and therapeutic targeting, Mol Cancer Res, 6(12):1795-1806 (2008).
Yin et al. Crystal structure of a complete ternary complex of T-cell receptor, peptide-MHC, and CD4. PNAS USA 109:5405-5410 (2012).
Yong, K. L., et al., Evaluation of Bcma as a Therapeutic Target in Multiple Myeloma Using an Antibody-Drug Conjugate, Blood, 122(21): 4447 (2013).
Zahnd et al. Efficient Tumor Targeting with High-Affinity Designed Ankyrin Repeat Proteins: Effects of Affinity and Molecular Size. Cancer Res 70: 1595-1605 (2010).
Zahnd et al. Selection and Characterization of Her2 Binding-designed Ankyrin Repeat Proteins. The Journal of Biological Chemistry 281 (46):35167-35175 (2006).
Zhang et al. Sequestration of CD4-associated Lek from the TCR complex may elicit T cell hyporesponsiveness in nonobese diabetic mice. J Immunol 160:1148-1157 (1998).
Zhukovsky et al. Bispecific antibodies and CARs: generalized immunotherapeutics harnessing T cell redirection. Curr Opin Immunol 40:24-35 (2016).
U.S. Appl. No. 16/753,577, filed Apr. 3, 2020, U.S. Pat. No. 11,643,472, May 9, 2023, Issued.
U.S. Appl. No. 18/188,318, filed Mar. 22, 2023, Allowed.
U.S. Appl. No. 16/826,053, filed Mar. 20, 2020, Allowed.
U.S. Appl. No. 18/188,326, filed Mar. 22, 2023, U.S. Pat. No. 11,878,035, Jan. 23, 2024, Issued.
Borst, J., et al., Distinct molecular forms of human T cell receptor γ/δ detected on viable T cells by a monoclonal antibody, J Exp Med, 167(5): 1625-1644 (1988).
U.S. Appl. No. 16/826,053 Office Action dated Aug. 14, 2023.
U.S. Appl. No. 18/188,312 Office Action dated Sep. 12, 2023.
U.S. Appl. No. 18/188,318 Office Action dated Sep. 7, 2023.
U.S. Appl. No. 18/188,326 Office Action dated May 18, 2023.

* cited by examiner

| CD3+TAC+ | | | | |
|---|---|---|---|---|
| | Nano1/Y177T MOI = 30 | Nano2/Y177T MOI = 30 | Nano1 MOI = 60 | Nano2 MOI = 60 |
| Day 9 | 54.9 % | 58.7 % | 53.5 % | 59.1 % |

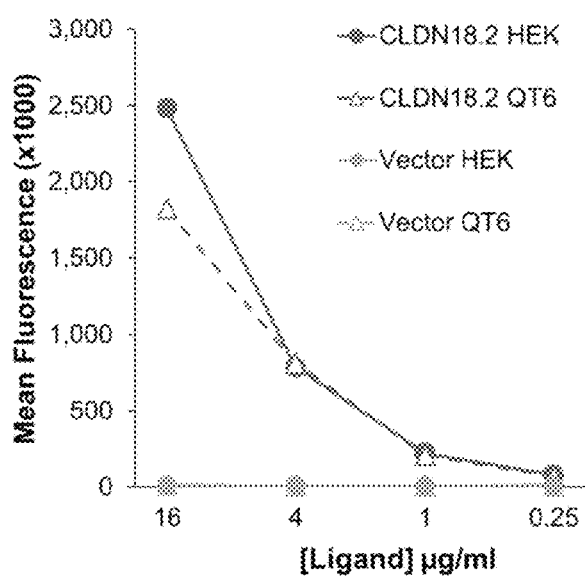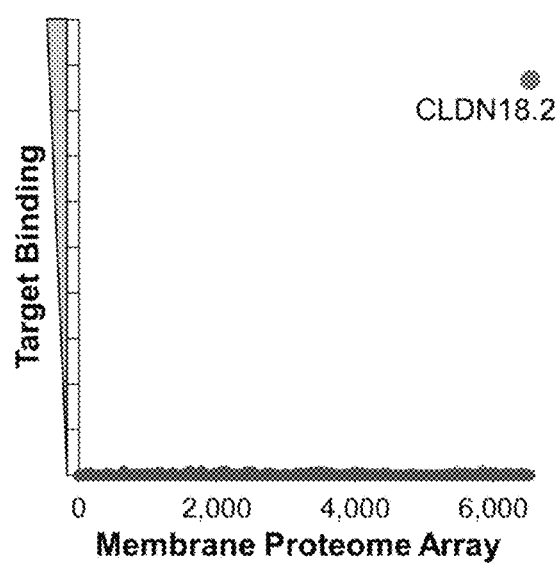

Figure 6A
CLDN18.2
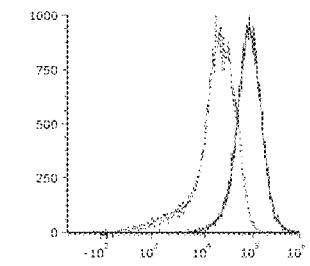
CLDN18.1
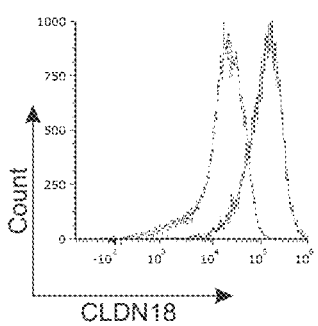
Figure 6B
CLDN18.2
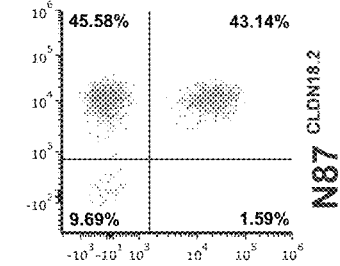
CLDN18.1
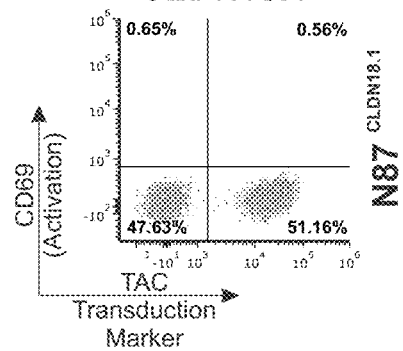
Figure 6C
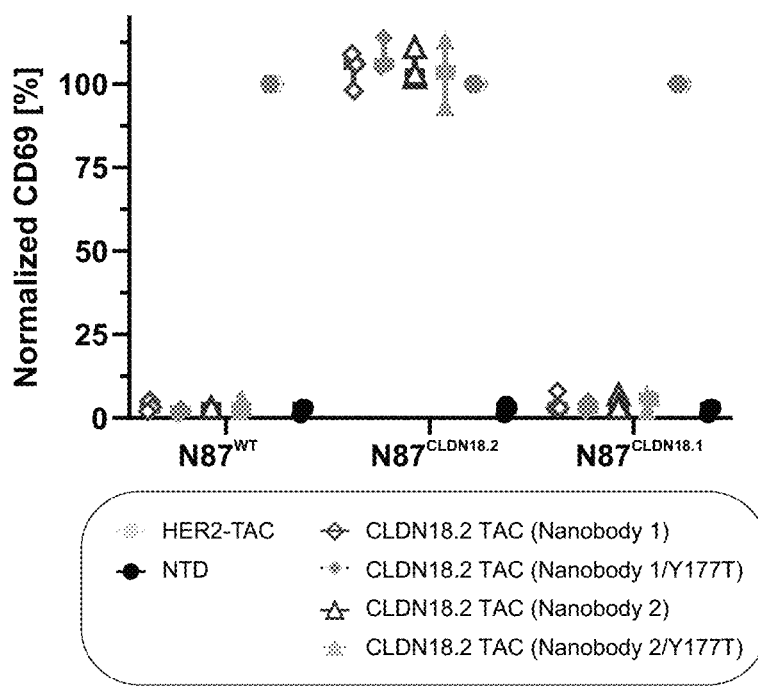

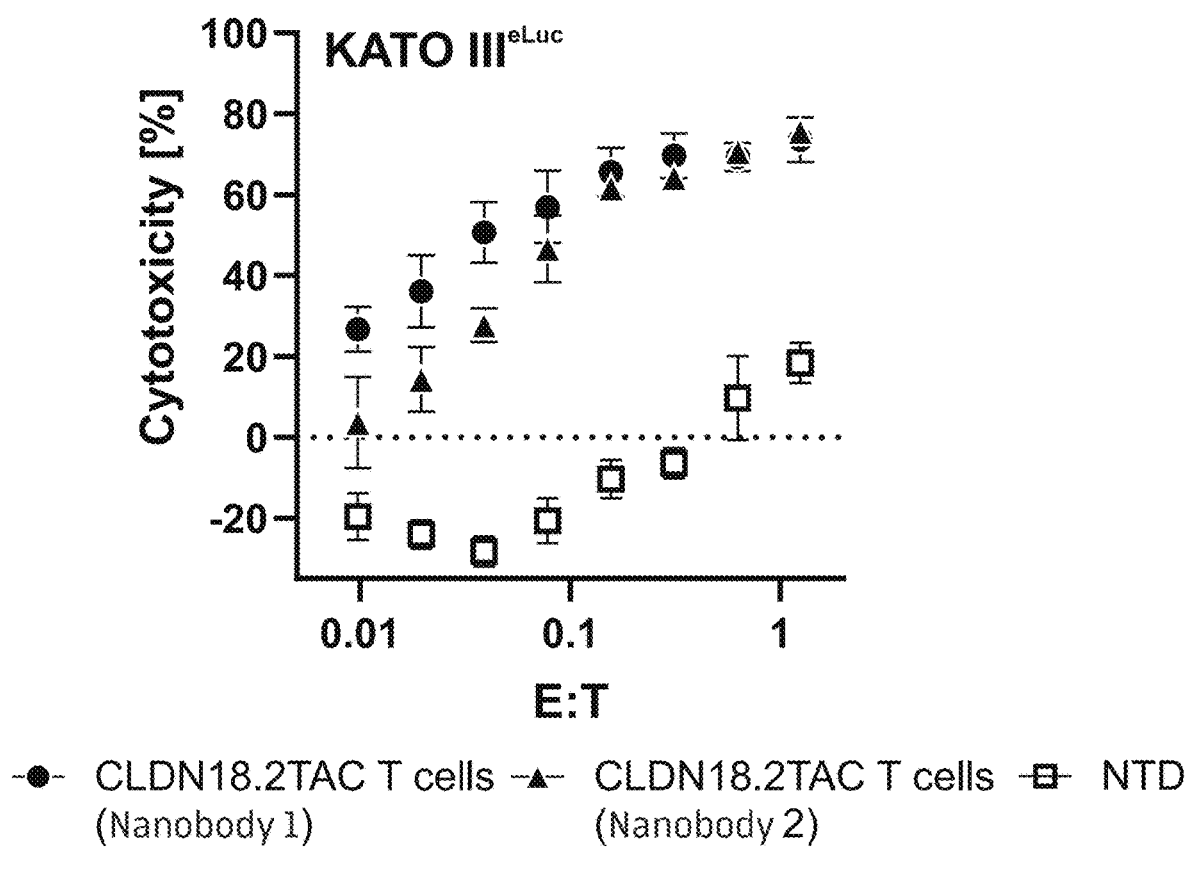

Figure 13

| | Marker | Fluorophore |
|---|---|---|
| Exhaustion/ Activation + Memory | | |
| | TCRab | APC |
| | CD4 | BV605 |
| | CD8 | PECy7 |
| | PD-1 | SB645 |
| | TIM3 | BV421 |
| | CD69 | Pacific Blue |
| | LAG3 | PEeFluor610 |
| | CD27 | BV570 |
| | CD44 | AF700 |
| | TIGIT | PerCP-eFluor710 |
| | CD25 | BV711 |
| | CCR7 | FITC or AF488 |
| | CD45RA | PEFire 640 |
| | CD45RO | BV510 |
| | CD62L | BV785 |
| | CD162 | PE |
| | Viability | NearIR |

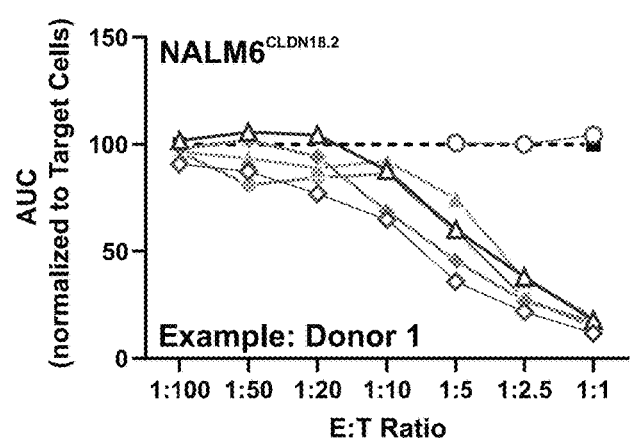
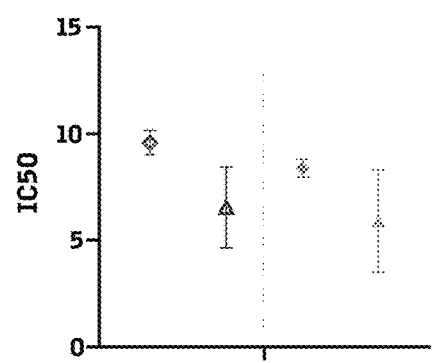
Figure 16A
Figure 16B
◇ CLDN18.2-TAC (Nanobody 1)   CLDN18.2-TAC (Nanobody 1/Y177T)
△ CLDN18.2-TAC (Nanobody 2)   CLDN18.2-TAC (Nanobody 2/Y177T)
CD19-TAC
○ NTD
■ Target Example Donor 1

- HER2-TAC
- CD19-TAC
- ◇ CLDN18.2 TAC (Nanobody 1)
- ◆ CLDN18.2 TAC (Nanobody 1/Y177T)
- △ CLDN18.2 TAC (Nanobody 2)
- ▲ CLDN18.2 TAC (Nanobody 2/Y177T)

◆ NT　　★ CLDN18.2-TAC T cells (Nanobody 2)

■ NTD　● CLDN18.2-TAC T cells (Nanobody 1)

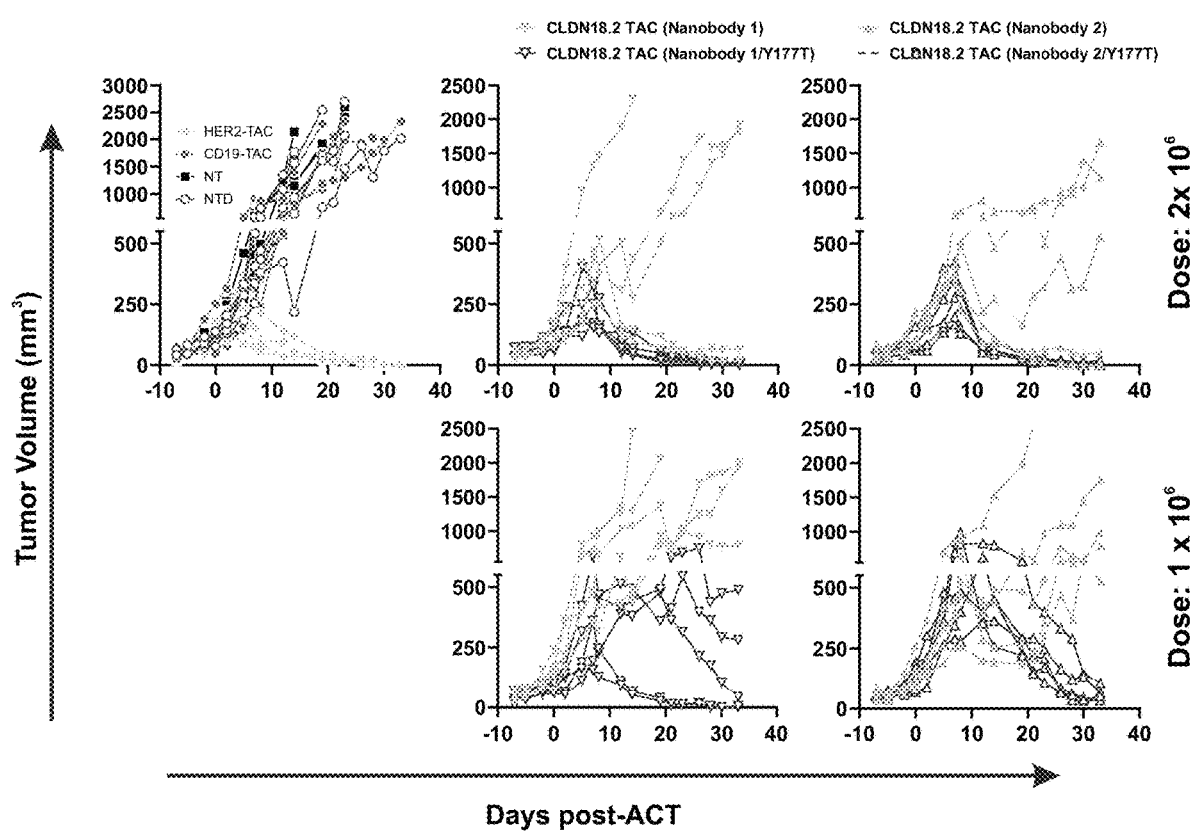

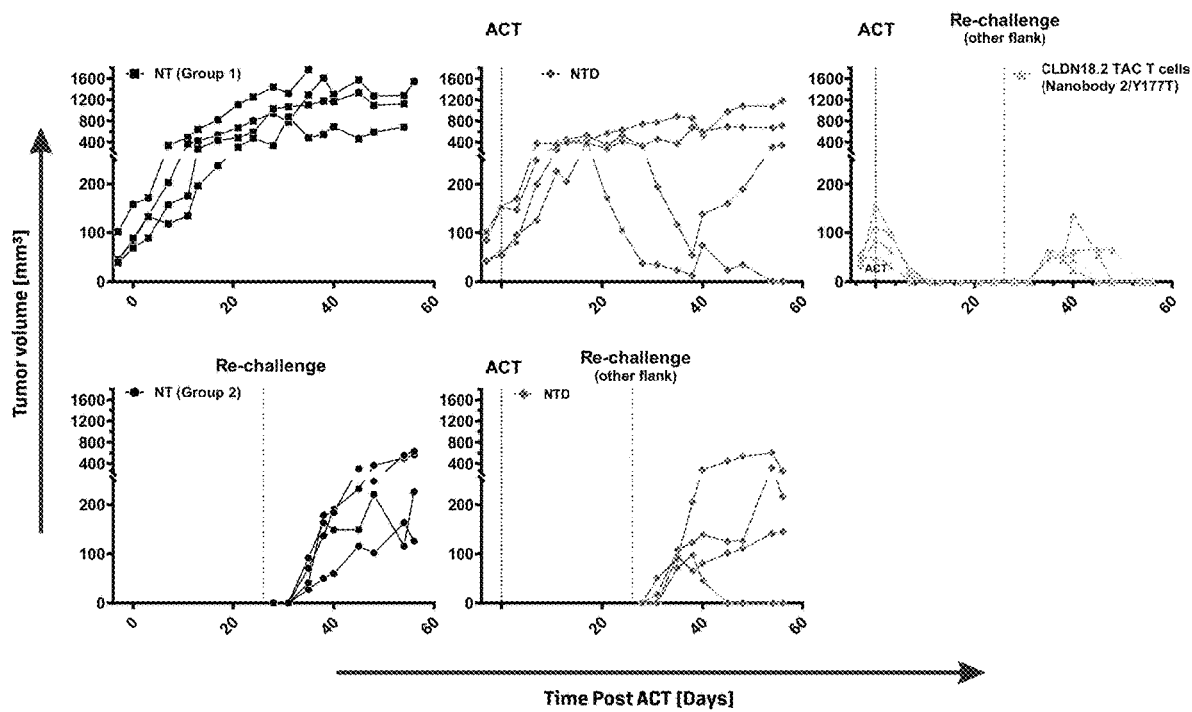

CLAUDIN 18.2 T CELL-ANTIGEN COUPLERS AND USES THEREOF

CROSS-REFERENCE TO RELATED APPLICATIONS

This application claims the benefit of and priority to U.S. Provisional Patent Application No. 63/202,211, filed Jun. 1, 2021; U.S. Provisional Patent Application No. 63/263,809, filed Nov. 9, 2021; and U.S. Provisional Patent Application No. 63/362,594, filed Apr. 6, 2022, the disclosures of each of which are hereby incorporated by reference in their entireties for all purposes.

SEQUENCE LISTING

The instant application contains a Sequence Listing which has been submitted electronically in ASCII format and is hereby incorporated by reference in its entirety. Said ASCII copy, created on May 31, 2022, is named TMV-006WO_SL.txt and is 87,860 bytes in size.

SUMMARY

Disclosed herein, in certain embodiments, are nucleic acids encoding a Claudin 18.2 T cell-antigen coupler (TAC). In some embodiments, the nucleic acid comprises: (a) a first polynucleotide encoding an antigen-binding domain that binds Claudin 18.2; (b) a second polynucleotide encoding an antigen-binding domain that binds a protein associated with a TCR complex; and (c) a third polynucleotide encoding a TCR co-receptor cytosolic domain and transmembrane domain. In some embodiments, the nucleic acid comprises, in order (e.g., from 5' to 3'): (a) a first polynucleotide encoding an antigen-binding domain that binds Claudin 18.2; (b) a second polynucleotide encoding an antigen-binding domain that binds a protein associated with a TCR complex; and (c) a third polynucleotide encoding a TCR co-receptor cytosolic domain and transmembrane domain. In some embodiments, the antigen-binding domain that binds Claudin 18.2 is a designed ankyrin repeat (DARPin) polypeptide, single chain variable fragment (scFv), single domain antibody, diabody, affibody, adnectin, affilin, phylomer, fynomer, affimer, peptide aptamer, knottin, centyrin, anticalin, or nanobody. In some embodiments, the antigen-binding domain that binds Claudin 18.2 comprises an antigen-binding domain derived from an antibody selected from IMAB362 (claudiximab, zolbetuximab), 43-14A, EPR 19202, and aGC182. In some embodiments, the antigen-binding domain that binds Claudin 18.2 comprises an amino acid sequence having at least 80% sequence identity with the amino acid sequence of the antigen-binding domain(s) of IMAB362 (claudiximab, zolbetuximab), 43-14A, EPR 19202, or aGC182. In some embodiments, the antigen-binding domain that binds Claudin 18.2 comprises an amino acid sequence having at least 85% sequence identity with the amino acid sequence of the antigen-binding domain(s) of IMAB362 (claudiximab, zolbetuximab), 43-14A, EPR 19202, or aGC182. In some embodiments, the antigen-binding domain that binds Claudin 18.2 comprises an amino acid sequence having at least 90% sequence identity with the amino acid sequence of the antigen-binding domain(s) of IMAB362 (claudiximab, zolbetuximab), 43-14A, EPR 19202, or GC182. In some embodiments, the antigen-binding domain that binds Claudin 18.2 comprises an amino acid sequence having at least 95% sequence identity with the amino acid sequence of the antigen-binding domain(s) of IMAB362 (claudiximab, zolbetuximab), 43-14A, EPR 19202, or aGC182. In some embodiments, the antigen-binding domain that binds Claudin 18.2 comprises an amino acid sequence having at least 96% sequence identity with the amino acid sequence of the antigen-binding domain(s) of IMAB362 (claudiximab, zolbetuximab), 43-14A, EPR 19202, or aGC182. In some embodiments, the antigen-binding domain that binds Claudin 18.2 comprises an amino acid sequence having at least 97% sequence identity with the amino acid sequence of the antigen-binding domain(s) of IMAB362 (claudiximab, zolbetuximab), 43-14A, EPR 19202, or aGC182. In some embodiments, the antigen-binding domain that binds Claudin 18.2 comprises an amino acid sequence having at least 98% sequence identity with the amino acid sequence of the antigen-binding domain(s) of IMAB362 (claudiximab, zolbetuximab), 43-14A, EPR 19202, or aGC182. In some embodiments, the antigen-binding domain that binds Claudin 18.2 comprises an amino acid sequence having at least 99% sequence identity with the amino acid sequence of the antigen-binding domain(s) of IMAB362 (claudiximab, zolbetuximab), 43-14A, EPR 19202, or aGC182. In some embodiments, the antigen-binding domain that binds Claudin 18.2 comprises the amino acid sequence of the antigen-binding domain(s) of IMAB362 (claudiximab, zolbetuximab), 43-14A, EPR 19202, or aGC182. In some embodiments, the CDR sequences of the antigen-binding domain that binds Claudin 18.2 have 100% identity with the CDR sequences of IMAB362 (claudiximab, zolbetuximab), 43-14A, EPR 19202, or aGC182 (i.e., the antigen-binding domain that binds Claudin 18.2 comprises an amino acid sequence comprising a CDRH1, CDRH2, CDRH3, CDRL1, CDRL2, and CDRL3, each having 100% identity to the corresponding CDR in IMAB362 (claudiximab, zolbetuximab), 43-14A, EPR 19202, or aGC182). In some embodiments, the CDR sequences of the antigen-binding domain that binds Claudin 18.2 have 100% identity with the CDR sequences of IMAB362 (claudiximab, zolbetuximab), 43-14A, EPR 19202, or aGC182, and the non-CDR (e.g., framework) sequences of the antigen-binding domain that binds Claudin 18.2 have at least 80% sequence identity with the non-CDR (e.g., framework) sequences of IMAB362 (claudiximab, zolbetuximab), 43-14A, EPR 19202, or aGC182. In some embodiments, the CDR sequences of the antigen-binding domain that binds Claudin 18.2 have 100% identity with the CDR sequences of IMAB362 (claudiximab, zolbetuximab), 43-14A, EPR 19202, or aGC182, and the non-CDR (e.g., framework) sequences of the antigen-binding domain that binds Claudin 18.2 have at least 85% sequence identity with the non-CDR (e.g., framework) sequences of IMAB362 (claudiximab, zolbetuximab), 43-14A, EPR 19202, or aGC182. In some embodiments, the CDR sequences of the antigen-binding domain that binds Claudin 18.2 have 100% identity with the CDR sequences of IMAB362 (claudiximab, zolbetuximab), 43-14A, EPR 19202, or aGC182, and the non-CDR (e.g., framework) sequences of the antigen-binding domain that binds Claudin 18.2 have at least 90% sequence identity with the non-CDR (e.g., framework) sequences of IMAB362 (claudiximab, zolbetuximab), 43-14A, EPR 19202, or aGC182. In some embodiments, the CDR sequences of the antigen-binding domain that binds Claudin 18.2 have 100% identity with the CDR sequences of IMAB362 (claudiximab, zolbetuximab), 43-14A, EPR 19202, or aGC182, and the non-CDR (e.g., framework) sequences of the antigen-binding domain that binds Claudin 18.2 have at least 95% sequence identity with the non-CDR (e.g., framework) sequences of IMAB362 (claudiximab, zolbetuximab), 43-14A, EPR 19202, or aGC182. In some embodiments, the CDR sequences of the antigen-binding domain that binds Claudin 18.2 have 100% identity with the CDR sequences of IMAB362 (claudiximab, zolbetuximab), 43-14A, EPR 19202, or aGC182, and the non-CDR (e.g., framework) sequences of the antigen-binding domain that binds Claudin 18.2 have at least 96% sequence identity with the non-CDR (e.g., framework) sequences of IMAB362 (claudiximab, zolbetuximab), 43-14A, EPR 19202, or aGC182. In some embodiments, the CDR sequences of the antigen-binding domain that binds Claudin 18.2 have 100% identity with the CDR sequences of IMAB362 (claudiximab, zolbetuximab), 43-14A, EPR 19202, or aGC182, and the non-CDR (e.g., framework) sequences of the antigen-binding domain that binds Claudin 18.2 have at least 97% sequence identity with the non-CDR (e.g., framework) sequences of IMAB362 (claudiximab, zolbetuximab), 43-14A, EPR 19202, or aGC182. In some embodiments, the CDR sequences of the antigen-binding domain that binds Claudin 18.2 have 100% identity with the CDR sequences of IMAB362 (claudiximab, zolbetuximab), 43-14A, EPR 19202, or aGC182, and the non-CDR (e.g., framework) sequences of the antigen-binding domain that binds Claudin 18.2 have at least 98% sequence identity with the non-CDR (e.g., framework) sequences of IMAB362 (claudiximab, zolbetuximab), 43-14A, EPR 19202, or aGC182. In some embodiments, the CDR sequences of the antigen-binding domain that binds Claudin 18.2 have 100% identity with the CDR sequences of IMAB362 (claudiximab, zolbetuximab), 43-14A, EPR 19202, or aGC182, and the non-CDR (e.g., framework) sequences of the antigen-binding domain that binds Claudin 18.2 have at least 99% sequence identity with the non-CDR (e.g., framework) sequences of IMAB362 (claudiximab, zolbetuximab), 43-14A, EPR 19202, or aGC182. In some embodiments, the first polynucleotide encodes an antigen-binding domain comprising an amino acid sequence having at least 80% sequence identity with the amino acid sequence of SEQ ID NO: 55 (Claudin 18.2 Nanobody 1). In some embodiments, the first polynucleotide encodes an antigen-binding domain comprising an amino acid sequence having at least 85% sequence identity with the amino acid sequence of SEQ ID NO: 55 (Claudin 18.2 Nanobody 1). In some embodiments, the first polynucleotide encodes an antigen-binding domain comprising an amino acid sequence having at least 90% sequence identity with the amino acid sequence of SEQ ID NO: 55 (Claudin 18.2 Nanobody 1). In some embodiments, the first polynucleotide encodes an antigen-binding domain comprising an amino acid sequence having at least 95% sequence identity with the amino acid sequence of SEQ ID NO: 55 (Claudin 18.2 Nanobody 1). In some embodiments, the first polynucleotide encodes an antigen-binding domain comprising an amino acid sequence having at least 96% sequence identity with the amino acid sequence of SEQ ID NO: 55 (Claudin 18.2 Nanobody 1). In some embodiments, the first polynucleotide encodes an antigen-binding domain comprising an amino acid sequence having at least 97% sequence identity with the amino acid sequence of SEQ ID NO: 55 (Claudin 18.2 Nanobody 1). In some embodiments, the first polynucleotide encodes an antigen-binding domain comprising an amino acid sequence having at least 98% sequence identity with the amino acid sequence of SEQ ID NO: 55 (Claudin 18.2 Nanobody 1). In some embodiments, the first polynucleotide encodes an antigen-binding domain comprising an amino acid sequence having at least 99% sequence identity with the amino acid sequence of SEQ ID NO: 55 (Claudin 18.2 Nanobody 1). In some embodiments, the first polynucleotide encodes an antigen-binding domain comprising the amino acid sequence of SEQ ID NO: 55 (Claudin 18.2 Nanobody 1). In some embodiments, the first polynucleotide encodes an antigen-binding domain comprising an amino acid sequence comprising a CDR1 comprising SEQ ID NO: 57 (Claudin 18.2 Nanobody 1 Kabat CDR1), a CDR2 comprising SEQ ID NO: 58 (Claudin 18.2 Nanobody 1 Kabat CDR2), and a CDR3 comprising SEQ ID NO: 59 (Claudin 18.2 Nanobody 1 Kabat CDR3). In some embodiments, the first polynucleotide encodes an antigen-binding domain comprising an amino acid sequence comprising a CDR1 comprising SEQ ID NO: 60 (Claudin 18.2 Nanobody 1 IMGT CDR1), a CDR2 comprising SEQ ID NO: 61 (Claudin 18.2 Nanobody 1 IMGT CDR2), and a CDR3 comprising SEQ ID NO: 62 (Claudin 18.2 Nanobody 1 IMGT CDR3). In some embodiments, the CDR sequences of the antigen-binding domain that binds Claudin 18.2 have 100% identity with the CDR sequences of Claudin 18.2 Nanobody 1 (i.e., the first polynucleotide encodes an antigen-binding domain comprising an amino acid sequence comprising a CDR1, CDR2, and CDR3 each having 100% identity to the corresponding CDR in Claudin 18.2 Nanobody 1). In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 80% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 85% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 90% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 95% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 96% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 97% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 98% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 99% sequence identity with the non-CDR (e.g., framework) sequences of Claudin 18.2 Nanobody 1. In some embodiments, the first polynucleotide encodes an antigen-binding domain comprising an amino acid sequence having at least 80% sequence identity with the amino acid sequence of SEQ ID NO: 56 (Claudin 18.2 Nanobody 2). In some embodiments, the first polynucleotide encodes an antigen-binding domain comprising an amino acid sequence having at least 85% sequence identity with the amino acid sequence of SEQ ID NO: 56 (Claudin 18.2 Nanobody 2). In some embodiments, the first polynucleotide encodes an antigen-binding domain comprising an amino acid sequence having at least 90% sequence identity with the amino acid sequence of SEQ ID NO: 56 (Claudin 18.2 Nanobody 2). In some embodiments, the first polynucleotide encodes an antigen-binding domain comprising an amino acid sequence having at least 95% sequence identity with the amino acid sequence of SEQ ID NO: 56 (Claudin 18.2 Nanobody 2). In some embodiments, the first polynucleotide encodes an antigen-binding domain comprising an amino acid sequence having at least 96% sequence identity with the amino acid sequence of SEQ ID NO: 56 (Claudin 18.2 Nanobody 2). In some embodiments, the first polynucleotide encodes an antigen-binding domain comprising an amino acid sequence having at least 97% sequence identity with the amino acid sequence of SEQ ID NO: 56 (Claudin 18.2 Nanobody 2). In some embodiments, the first polynucleotide encodes an antigen-binding domain comprising an amino acid sequence having at least 98% sequence identity with the amino acid sequence of SEQ ID NO: 56 (Claudin 18.2 Nanobody 2). In some embodiments, the first polynucleotide encodes an antigen-binding domain comprising an amino acid sequence having at least 99% sequence identity with the amino acid sequence of SEQ ID NO: 56 (Claudin 18.2 Nanobody 2). In some embodiments, the first polynucleotide encodes an antigen-binding domain comprising the amino acid sequence of SEQ ID NO: 56 (Claudin 18.2 Nanobody 2). In some embodiments, the first polynucleotide encodes an antigen-binding domain comprising an amino acid sequence comprising a CDR1 comprising SEQ ID NO: 57 (Claudin 18.2 Nanobody 2 Kabat CDR1), a CDR2 comprising SEQ ID NO: 63 (Claudin 18.2 Nanobody 2 Kabat CDR2), and a CDR3 comprising SEQ ID NO: 59 (Claudin 18.2 Nanobody 2 Kabat CDR3). In some embodiments, the first polynucleotide encodes an antigen-binding domain comprising an amino acid sequence comprising a CDR1 comprising SEQ ID NO: 64 (Claudin 18.2 Nanobody 2 IMGT CDR1), a CDR2 comprising SEQ ID NO: 65 (Claudin 18.2 Nanobody 2 IMGT CDR2), and a CDR3 comprising SEQ ID NO: 62 (Claudin 18.2 Nanobody 2 IMGT CDR3). In some embodiments, the CDR sequences of the antigen-binding domain that binds Claudin 18.2 have 100% identity with the CDR sequences of Claudin 18.2 Nanobody 2 (i.e., the first polynucleotide encodes an antigen-binding domain comprising an amino acid sequence comprising a CDR1, CDR2, and CDR3 each having 100% identity to the corresponding CDR in Claudin 18.2 Nanobody 2). In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 80% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 85% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 90% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 95% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 96% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 97% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 98% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 99% sequence identity with the non-CDR (e.g., framework) sequences of Claudin 18.2 Nanobody 2. In some embodiments, the protein associated with the TCR complex is a CD3 protein, for example, a CD3 protein of a TCR complex on a T cell expressing the TAC. In some embodiments, the CD3 protein is a CD3γ protein, CD3δ protein and/or CD3ε protein. In some embodiments, the CD3 protein is a CD3ε protein. In some embodiments, binding of the CD3 protein induces activation of the T cell. In some embodiments, the antigen-binding domain that binds the protein associated with the TCR complex is a designed ankyrin repeat (DARPin) polypeptide, single chain variable fragment (scFv), single domain antibody, diabody, affibody, adnectin, affilin, phylomer; fynomer, affimer, peptide aptamer, knottin, centyrin, anticalin, or nanobody. In some embodiments, the antigen-binding domain that binds the protein associated with the TCR complex is derived from an antibody selected from UCHT1, OKT3, F6A, and L2K. In some embodiments, the antigen-binding domain that binds the protein associated with the TCR complex is a UCHT1 antigen-binding domain, for example, an scFv derived from UCHT1. In some embodiments, the UCHT1 antigen-binding domain comprises a Y to T mutation at a position corresponding to amino acid 182 of SEQ ID NO: 8 (Y182T). In some embodiments, the UCHT1 antigen-binding domain is a humanized variant of UCHT1 (huUCHT1), for example, a humanized variant of UCHT1 comprising a Y to T mutation at a position corresponding to amino acid 177 of SEQ ID NO: 34 (huUCHT1 (Y177T)). In some embodiments, the antigen-binding domain that binds the protein associated with the TCR complex comprises an amino acid sequence having at least 85% sequence identity with the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the antigen-binding domain that binds the protein associated with the TCR complex comprises an amino acid sequence having at least 90% sequence identity with the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the antigen-binding domain that binds the protein associated with the TCR complex comprises an amino acid sequence having at least 95% sequence identity with the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the antigen-binding domain that binds the protein associated with the TCR complex comprises an amino acid sequence having at least 96% sequence identity with the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the antigen-binding domain that binds the protein associated with the TCR complex comprises an amino acid sequence having at least 97% sequence identity with the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the antigen-binding domain that binds the protein associated with the TCR complex comprises an amino acid sequence having at least 98% sequence identity with the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the antigen-binding domain that binds the protein associated with the TCR complex comprises an amino acid sequence having at least 99% sequence identity with the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the antigen-binding domain that binds the protein associated with the TCR complex comprises the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T))). In some embodiments, the CDR sequences of the antigen-binding domain that binds the protein associated with the TCR complex have 100% identity with the CDR sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the antigen-binding domain that binds the protein associated with the TCR complex is an OKT3 antigen-binding domain. In some embodiments, the antigen-binding domain that binds the protein associated with the TCR complex comprises an amino acid sequence having at least 85% sequence identity with the amino acid sequence of SEQ ID NO: 16 (OKT3). In some embodiments, the antigen-binding domain that binds the protein associated with the TCR complex comprises an amino acid sequence having at least 90% sequence identity with the amino acid sequence of SEQ ID NO: 16 (OKT3). In some embodiments, the antigen-binding domain that binds the protein associated with the TCR complex comprises an amino acid sequence having at least 95% sequence identity with the amino acid sequence of SEQ ID NO: 16 (OKT3). In some embodiments, the antigen-binding domain that binds the protein associated with the TCR complex comprises an amino acid sequence having at least 96% sequence identity with the amino acid sequence of SEQ ID NO: 16 (OKT3). In some embodiments, the antigen-binding domain that binds the protein associated with the TCR complex comprises an amino acid sequence having at least 97% sequence identity with the amino acid sequence of SEQ ID NO: 16 (OKT3). In some embodiments, the antigen-binding domain that binds the protein associated with the TCR complex comprises an amino acid sequence having at least 98% sequence identity with the amino acid sequence of SEQ ID NO: 16 (OKT3). In some embodiments, the antigen-binding domain that binds the protein associated with the TCR complex comprises an amino acid sequence having at least 99% sequence identity with the amino acid sequence of SEQ ID NO: 16 (OKT3). In some embodiments, the antigen-binding domain that binds the protein associated with the TCR complex comprises the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 16 (OKT3)). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16

(OKT3), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 16 (OKT3). In some embodiments, the antigen-binding domain that binds the protein associated with the TCR complex is a F6A antigen-binding domain. In some embodiments, the antigen-binding domain that binds the protein associated with the TCR complex comprises an amino acid sequence having at least 85% sequence identity with the amino acid sequence of SEQ ID NO: 18 (F6A). In some embodiments, the antigen-binding domain that binds the protein associated with the TCR complex comprises an amino acid sequence having at least 90% sequence identity with the amino acid sequence of SEQ ID NO: 18 (F6A). In some embodiments, the antigen-binding domain that binds the protein associated with the TCR complex comprises an amino acid sequence having at least 95% sequence identity with the amino acid sequence of SEQ ID NO: 18 (F6A). In some embodiments, the antigen-binding domain that binds the protein associated with the TCR complex comprises an amino acid sequence having at least 96% sequence identity with the amino acid sequence of SEQ ID NO: 18 (F6A). In some embodiments, the antigen-binding domain that binds the protein associated with the TCR complex comprises an amino acid sequence having at least 97% sequence identity with the amino acid sequence of SEQ ID NO: 18 (F6A). In some embodiments, the antigen-binding domain that binds the protein associated with the TCR complex comprises an amino acid sequence having at least 98% sequence identity with the amino acid sequence of SEQ ID NO: 18 (F6A). In some embodiments, the antigen-binding domain that binds the protein associated with the TCR complex comprises an amino acid sequence having at least 99% sequence identity with the amino acid sequence of SEQ ID NO: 18 (F6A). In some embodiments, the antigen-binding domain that binds the protein associated with the TCR complex comprises the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 18 (F6A)). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 18 (F6A). In some embodiments, the antigen-binding domain that binds the protein associated with the TCR complex is a L2K antigen-binding domain. In some embodiments, the antigen-binding domain that binds the protein associated with the TCR complex comprises an amino acid sequence having at least 85% sequence identity with the amino acid sequence of SEQ ID NO: 20 (L2K). In some embodiments, the antigen-binding domain that binds the protein associated with the TCR complex comprises an amino acid sequence having at least 90% sequence identity with the amino acid sequence of SEQ ID NO: 20 (L2K). In some embodiments, the antigen-binding domain that binds the protein associated with the TCR complex comprises an amino acid sequence having at least 95% sequence identity with the amino acid sequence of SEQ ID NO: 20 (L2K). In some embodiments, the antigen-binding domain that binds the protein associated with the TCR complex comprises an amino acid sequence having at least 96% sequence identity with the amino acid sequence of SEQ ID NO: 20 (L2K). In some embodiments, the antigen-binding domain that binds the protein associated with the TCR complex comprises an amino acid sequence having at least 97% sequence identity with the amino acid sequence of SEQ ID NO: 20 (L2K). In some embodiments, the antigen-binding domain that binds the protein associated with the TCR complex comprises an amino acid sequence having at least 98% sequence identity with the amino acid sequence of SEQ ID NO: 20 (L2K). In some embodiments, the antigen-binding domain that binds the protein associated with the TCR complex comprises an amino acid sequence having at least 99% sequence identity with the amino acid sequence of SEQ ID NO: 20 (L2K). In some embodiments, the antigen-binding domain that binds the protein associated with the TCR complex comprises the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 20 (L2K)). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 20 (L2K). In some embodiments, the cytosolic domain is a CD4 cytosolic domain and the transmembrane domain is a CD4 transmembrane domain. In some embodiments, the cytosolic domain is a CD8 cytosolic domain and the transmembrane domain is a CD8 transmembrane domain. In some embodiments, the cytosolic and transmembrane domain comprise an amino acid sequence having at least 85% sequence identity with the amino acid sequence of SEQ ID NO: 12 (CD4 transmembrane and cytosolic domain). In some embodiments, the cytosolic and transmembrane domain comprise an amino acid sequence having at least 90% sequence identity with the amino acid sequence of SEQ ID NO: 12 (CD4 transmembrane and cytosolic domain). In some embodiments, the cytosolic and transmembrane domain comprise an amino acid sequence having at least 95% sequence identity with the amino acid sequence of SEQ ID NO: 12 (CD4 transmembrane and cytosolic domain). In some embodiments, the cytosolic and transmembrane domain comprise an amino acid sequence having at least 96% sequence identity with the amino acid sequence of SEQ ID NO: 12 (CD4 transmembrane and cytosolic domain). In some embodiments, the cytosolic and transmembrane domain comprise an amino acid sequence having at least 97% sequence identity with the amino acid sequence of SEQ ID NO: 12 (CD4 transmembrane and cytosolic domain). In some embodiments, the cytosolic and transmembrane domain comprise an amino acid sequence having at least 98% sequence identity with the amino acid sequence of SEQ ID NO: 12 (CD4 transmembrane and cytosolic domain). In some embodiments, the cytosolic and transmembrane domain comprise an amino acid sequence having at least 99% sequence identity with the amino acid sequence of SEQ ID NO: 12 (CD4 transmembrane and cytosolic domain). In some embodiments, the cytosolic and transmembrane domain comprise the amino acid sequence of SEQ ID NO: 12 (CD4 transmembrane and cytosolic domain). In some embodiments, the components encoded by the first, second, and/or third polynucleotides are connected in any suitable manner, such as in any suitable order and/or comprising any suitable linker(s). In some embodiments, the components encoded by (a), components encoded by (b), and components encoded by (c) are fused directly to each other, or joined by at least one linker. In some embodiments, the components encoded by (a) and the components encoded by (c) are fused to the components encoded by (b). In some embodiments, the components encoded by (b) and the components encoded by (c) are fused to the components encoded by (a). In some embodiments, at least one linker joins the components encoded by (a) to the components encoded by (b). In some embodiments, the at least one linker is a glycine and/or serine-rich linker, a large protein domain, a long helix structure, or a short helix structure. In some embodiments, the at least one linker comprises an amino acid sequence having at least 80% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 85% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 90% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 95% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 96% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 97% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 98% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 80% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the nucleic acid sequence does not encode a co-stimulatory domain and/or an activation domain. In some embodiments, the nucleic acid sequence further encodes a leader sequence. In some embodiments, the leader sequence comprises an amino acid sequence having at least 80% sequence identity with the amino acid sequence of SEQ ID NO: 2 (muIgG leader), SEQ ID NO: 38 (huIgG leader), or SEQ ID NO: 40 (huCD8a leader). In some embodiments, the leader sequence comprises an amino acid sequence having at least 85% sequence identity with the amino acid sequence of SEQ ID NO: 2 (muIgG leader), SEQ ID NO: 38 (huIgG leader), or SEQ ID NO: 40 (huCD8a leader). In some embodiments, the leader sequence comprises an amino acid sequence having at least 90% sequence identity with the amino acid sequence of SEQ ID NO: 2 (muIgG leader), SEQ ID NO: 38 (huIgG leader), or SEQ ID NO: 40 (huCD8a leader). In some embodiments, the leader sequence comprises an amino acid sequence having at least 95% sequence identity with the amino acid sequence of SEQ ID NO: 2 (muIgG leader), SEQ ID NO: 38 (huIgG leader), or SEQ ID NO: 40 (huCD8a leader). In some embodiments, the leader sequence comprises an amino acid sequence having at least 96% sequence identity with the amino acid sequence of SEQ ID NO: 2 (muIgG leader), SEQ ID NO: 38 (huIgG leader), or SEQ ID NO: 40 (huCD8a leader). In some embodiments, the leader sequence comprises an amino acid sequence having at least 97% sequence identity with the amino acid sequence of SEQ ID NO: 2 (muIgG leader), SEQ ID NO: 38 (huIgG leader), or SEQ ID NO: 40 (huCD8a leader). In some embodiments, the leader sequence comprises an amino acid sequence having at least 98% sequence identity with the amino acid sequence of SEQ ID NO: 2 (muIgG leader), SEQ ID NO: 38 (huIgG leader), or SEQ ID NO: 40 (huCD8a leader). In some embodiments, the leader sequence comprises an amino acid sequence having at least 99% sequence identity with the amino acid sequence of SEQ ID NO: 2 (muIgG leader), SEQ ID NO: 38 (huIgG leader), or SEQ ID NO: 40 (huCD8a leader). In some embodiments, the leader sequence comprises the amino acid sequence of SEQ ID NO: 2 (muIgG leader), SEQ ID NO: 38 (huIgG leader), or SEQ ID NO: 40 (huCD8a leader). In some embodiments, the nucleic acid comprises a sequence having at least 80%, at least 85%, at least 90%, at least 95%, at least 96%, at least 97%, at least 98%, at least 99%, or 100% sequence identity with the nucleic acid sequence of SEQ ID NO: 66, SEQ ID NO: 68, SEQ ID NO: 70, or SEQ ID NO: 72. In some embodiments, the Claudin 18.2-TAC polypeptide comprises an amino acid sequence having at least 80%, at least 85%, at least 90%, at least 95%, at least 96%, at least 97%, at least 98%, at least 99%, or 100% sequence identity with the amino acid sequence of SEQ ID NO: 67, SEQ ID NO: 69, SEQ ID NO: 71, or SEQ ID NO: 73.

Disclosed herein, in certain embodiments, are expression vectors comprising a nucleic acid disclosed herein (e.g., a nucleic acid encoding a Claudin 18.2-TAC disclosed herein). In some embodiments, the expression vector comprises a promoter functional in a mammalian cell. In some embodiments, the expression vector is a lentiviral vector, for example, a VSV-G pseudotyped lentiviral vector. In some embodiments, the expression vector is a γ retroviral vector, for example, a GALV pseudotyped γ-retroviral vector.

Disclosed herein, in certain embodiments, are Claudin 18.2 T cell-antigen couplers (TACs). In some embodiments, the Claudin 18.2-TAC comprises: (a) an antigen-binding domain that binds Claudin 18.2; (b) an antigen-binding domain that binds a protein associated with a TCR complex; and (c) a TCR co-receptor cytosolic domain and transmembrane domain. In some embodiments, the Claudin 18.2-TAC comprises, in order (e.g., from N-terminus to C-terminus): (a) an antigen-binding domain that binds Claudin 18.2; (b) an antigen-binding domain that binds a protein associated with a TCR complex; and (c) a TCR co-receptor cytosolic domain and transmembrane domain. In some embodiments, the antigen-binding domain that binds Claudin 18.2 is a designed ankyrin repeat (DARPin) polypeptide, single chain variable fragment (scFv), single domain antibody, diabody, affibody, adnectin, affilin, phylomer; fynomer, affimer, peptide aptamer, knottin, centyrin, anticalin, or nanobody. In some embodiments, the antigen-binding domain that binds Claudin 18.2 comprises an antigen-binding domain derived from an antibody selected from IMAB362 (claudiximab, zolbetuximab), 43-14A, EPR 19202, and aGC182. In some embodiments, the antigen-binding domain that binds Claudin 18.2 comprises an amino acid sequence having at least 80% sequence identity with the amino acid sequence of the antigen-binding domain(s) of IMAB362 (claudiximab, zolbetuximab), 43-14A, EPR 19202, or aGC182. In some embodiments, the antigen-binding domain that binds Claudin 18.2 comprises an amino acid sequence having at least 85% sequence identity with the amino acid sequence of the antigen-binding domain(s) of IMAB362 (claudiximab, zolbetuximab), 43-14A, EPR 19202, or aGC182. In some embodiments, the antigen-binding domain that binds Claudin 18.2 comprises an amino acid sequence having at least 90% sequence identity with the amino acid sequence of the antigen-binding domain(s) of IMAB362 (claudiximab, zolbetuximab), 43-14A, EPR 19202, or GC182. In some embodiments, the antigen-binding domain that binds Claudin 18.2 comprises an amino acid sequence having at least 95% sequence identity with the amino acid sequence of the antigen-binding domain(s) of IMAB362 (claudiximab, zolbetuximab), 43-14A, EPR 19202, or aGC182. In some embodiments, the antigen-binding domain that binds Claudin 18.2 comprises an amino acid sequence having at least 96% sequence identity with the amino acid sequence of the antigen-binding domain(s) of IMAB362 (claudiximab, zolbetuximab), 43-14A, EPR 19202, or aGC182. In some embodiments, the antigen-binding domain that binds Claudin 18.2 comprises an amino acid sequence having at least 97% sequence identity with the amino acid sequence of the antigen-binding domain(s) of IMAB362 (claudiximab, zolbetuximab), 43-14A, EPR 19202, or aGC182. In some embodiments, the antigen-binding domain that binds Claudin 18.2 comprises an amino acid sequence having at least 98% sequence identity with the amino acid sequence of the antigen-binding domain(s) of IMAB362 (claudiximab, zolbetuximab), 43-14A, EPR 19202, or aGC182. In some embodiments, the antigen-binding domain that binds Claudin 18.2 comprises an amino acid sequence having at least 99% sequence identity with the amino acid sequence of the antigen-binding domain(s) of IMAB362 (claudiximab, zolbetuximab), 43-14A, EPR 19202, or aGC182. In some embodiments, the antigen-binding domain that binds Claudin 18.2 comprises the amino acid sequence of the antigen-binding domain(s) of IMAB362 (claudiximab, zolbetuximab), 43-14A, EPR 19202, or aGC182. In some embodiments, the CDR sequences of the antigen-binding domain that binds Claudin 18.2 have 100% identity with the CDR sequences of IMAB362 (claudiximab, zolbetuximab), 43-14A, EPR 19202, or aGC182 (i.e., the antigen-binding domain that binds Claudin 18.2 comprises an amino acid sequence comprising a CDRH1, CDRH2, CDRH3, CDRL1, CDRL2, and CDRL3, each having 100% identity to the corresponding CDR in IMAB362 (claudiximab, zolbetuximab), 43-14A, EPR 19202, or aGC182). In some embodiments, the CDR sequences of the antigen-binding domain that binds Claudin 18.2 have 100% identity with the CDR sequences of IMAB362 (claudiximab, zolbetuximab), 43-14A, EPR 19202, or aGC182, and the non-CDR (e.g., framework) sequences of the antigen-binding domain that binds Claudin 18.2 have at least 80% sequence identity with the non-CDR (e.g., framework) sequences of IMAB362 (claudiximab, zolbetuximab), 43-14A, EPR 19202, or aGC182. In some embodiments, the CDR sequences of the antigen-binding domain that binds Claudin 18.2 have 100% identity with the CDR sequences of IMAB362 (claudiximab, zolbetuximab), 43-14A, EPR 19202, or aGC182, and the non-CDR (e.g., framework) sequences of the antigen-binding domain that binds Claudin 18.2 have at least 85% sequence identity with the non-CDR (e.g., framework) sequences of IMAB362 (claudiximab, zolbetuximab), 43-14A, EPR 19202, or aGC182. In some embodiments, the CDR sequences of the antigen-binding domain that binds Claudin 18.2 have 100% identity with the CDR sequences of IMAB362 (claudiximab, zolbetuximab), 43-14A, EPR 19202, or aGC182, and the non-CDR (e.g., framework) sequences of the antigen-binding domain that binds Claudin 18.2 have at least 90% sequence identity with the non-CDR (e.g., framework) sequences of IMAB362 (claudiximab, zolbetuximab), 43-14A, EPR 19202, or aGC182. In some embodiments, the CDR sequences of the antigen-binding domain that binds Claudin 18.2 have 100% identity with the CDR sequences of IMAB362 (claudiximab, zolbetuximab), 43-14A, EPR 19202, or aGC182, and the non-CDR (e.g., framework) sequences of the antigen-binding domain that binds Claudin 18.2 have at least 95% sequence identity with the non-CDR (e.g., framework) sequences of IMAB362 (claudiximab, zolbetuximab), 43-14A, EPR 19202, or aGC182. In some embodiments, the CDR sequences of the antigen-binding domain that binds Claudin 18.2 have 100% identity with the CDR sequences of IMAB362 (claudiximab, zolbetuximab), 43-14A, EPR 19202, or aGC182, and the non-CDR (e.g., framework) sequences of the antigen-binding domain that binds Claudin 18.2 have at least 96% sequence identity with the non-CDR (e.g., framework) sequences of IMAB362 (claudiximab, zolbetuximab), 43-14A, EPR 19202, or aGC182. In some embodiments, the CDR sequences of the antigen-binding domain that binds Claudin 18.2 have 100% identity with the CDR sequences of IMAB362 (claudiximab, zolbetuximab), 43-14A, EPR 19202, or aGC182, and the non-CDR (e.g., framework) sequences of the antigen-binding domain that binds Claudin 18.2 have at least 97% sequence identity with the non-CDR (e.g., framework) sequences of IMAB362 (claudiximab, zolbetuximab), 43-14A, EPR 19202, or aGC182. In some embodiments, the CDR sequences of the antigen-binding domain that binds Claudin 18.2 have 100% identity with the CDR sequences of IMAB362 (claudiximab, zolbetuximab), 43-14A, EPR 19202, or aGC182, and the non-CDR (e.g., framework) sequences of the antigen-binding domain that binds Claudin 18.2 have at least 98% sequence identity with the non-CDR (e.g., framework) sequences of IMAB362 (claudiximab, zolbetuximab), 43-14A, EPR 19202, or aGC182. In some embodiments, the CDR sequences of the antigen-binding domain that binds Claudin 18.2 have 100% identity with the CDR sequences of IMAB362 (claudiximab, zolbetuximab), 43-14A, EPR 19202, or aGC182, and the non-CDR (e.g., framework) sequences of the antigen-binding domain that binds Claudin 18.2 have at least 99% sequence identity with the non-CDR (e.g., framework) sequences of IMAB362 (claudiximab, zolbetuximab), 43-14A, EPR 19202, or aGC182. In some embodiments, the antigen-binding domain that binds Claudin 18.2 comprises an amino acid sequence having at least 80% sequence identity with the amino acid sequence of SEQ ID NO: 55 (Claudin 18.2 Nanobody 1). In some embodiments, the antigen-binding domain that binds Claudin 18.2 comprises an amino acid sequence having at least 85% sequence identity with the amino acid sequence of SEQ ID NO: 55 (Claudin 18.2 Nanobody 1). In some embodiments, the antigen-binding domain that binds Claudin 18.2 comprises an amino acid sequence having at least 90% sequence identity with the amino acid sequence of SEQ ID NO: 55 (Claudin 18.2 Nanobody 1). In some embodiments, the antigen-binding domain that binds Claudin 18.2 comprises an amino acid sequence having at least 95% sequence identity with the amino acid sequence of SEQ ID NO: 55 (Claudin 18.2 Nanobody 1). In some embodiments, the antigen-binding domain that binds Claudin 18.2 comprises an amino acid sequence having at least 96% sequence identity with the amino acid sequence of SEQ ID NO: 55 (Claudin 18.2 Nanobody 1). In some embodiments, the antigen-binding domain that binds Claudin 18.2 comprises an amino acid sequence having at least 97% sequence identity with the amino acid sequence of SEQ ID NO: 55 (Claudin 18.2 Nanobody 1). In some embodiments, the antigen-binding domain that binds Claudin 18.2 comprises an amino acid sequence having at least 98% sequence identity with the amino acid sequence of SEQ ID NO: 55 (Claudin 18.2 Nanobody 1). In some embodiments, the antigen-binding domain that binds Claudin 18.2 comprises an amino acid sequence having at least 99% sequence identity with the amino acid sequence of SEQ ID NO: 55 (Claudin 18.2 Nanobody 1). In some embodiments, the antigen-binding domain that binds Claudin 18.2 comprises the amino acid sequence of SEQ ID NO: 55 (Claudin 18.2 Nanobody 1). In some embodiments, the antigen-binding domain that binds Claudin 18.2 comprises an amino acid sequence comprising a CDR1 comprising SEQ ID NO: 57 (Claudin 18.2 Nanobody 1 Kabat CDR1), a CDR2 comprising SEQ ID NO: 58 (Claudin 18.2 Nanobody 1 Kabat CDR2), and a CDR3 comprising SEQ ID NO: 59 (Claudin 18.2 Nanobody 1 Kabat CDR3). In some embodiments, the antigen-binding domain that binds Claudin 18.2 comprises an amino acid sequence comprising a CDR1 comprising SEQ ID NO: 60 (Claudin 18.2 Nanobody 1 IMGT CDR1), a CDR2 comprising SEQ ID NO: 61 (Claudin 18.2 Nanobody 1 IMGT CDR1), and a CDR3 comprising SEQ ID NO: 62 (Claudin 18.2 Nanobody 1 IMGT CDR3). In some embodiments, the CDR sequences of the antigen-binding domain that binds Claudin 18.2 have 100% identity with the CDR sequences of Claudin 18.2 Nanobody 1 (i.e., the antigen-binding domain that binds Claudin 18.2 comprises an amino acid sequence comprising a CDR1, CDR2, and CDR3 each having 100% identity to the corresponding CDR in Claudin 18.2 Nanobody 1). In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 80% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 85% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 90% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 95% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 96% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 97% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 98% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 99% sequence identity with the non-CDR (e.g., framework) sequences of Claudin 18.2 Nanobody 1. In some embodiments, the antigen-binding domain that binds Claudin 18.2 comprises an amino acid sequence having at least 80% sequence identity with the amino acid sequence of SEQ ID NO: 56 (Claudin 18.2 Nanobody 2). In some embodiments, the antigen-binding domain that binds Claudin 18.2 comprises an amino acid sequence having at least 85% sequence identity with the amino acid sequence of SEQ ID NO: 56 (Claudin 18.2 Nanobody 2). In some embodiments, the antigen-binding domain that binds Claudin 18.2 comprises an amino acid sequence having at least 90% sequence identity with the amino acid sequence of SEQ ID NO: 56 (Claudin 18.2 Nanobody 2). In some embodiments, the antigen-binding domain that binds Claudin 18.2 comprises an amino acid sequence having at least 95% sequence identity with the amino acid sequence of SEQ ID NO: 56 (Claudin 18.2 Nanobody 2). In some embodiments, the antigen-binding domain that binds Claudin 18.2 comprises an amino acid sequence having at least 96% sequence identity with the amino acid sequence of SEQ ID NO: 56 (Claudin 18.2 Nanobody 2). In some embodiments, the antigen-binding domain that binds Claudin 18.2 comprises an amino acid sequence having at least 97% sequence identity with the amino acid sequence of SEQ ID NO: 56 (Claudin 18.2 Nanobody 2). In some embodiments, the antigen-binding domain that binds Claudin 18.2 comprises an amino acid sequence having at least 98% sequence identity with the amino acid sequence of SEQ ID NO: 56 (Claudin 18.2 Nanobody 2). In some embodiments, the antigen-binding domain that binds Claudin 18.2 comprises an amino acid sequence having at least 99% sequence identity with the amino acid sequence of SEQ ID NO: 56 (Claudin 18.2 Nanobody 2). In some embodiments, the antigen-binding domain that binds Claudin 18.2 comprises the amino acid sequence of SEQ ID NO: 56 (Claudin 18.2 Nanobody 2). In some embodiments, the antigen-binding domain that binds Claudin 18.2 comprises an amino acid sequence comprising a CDR1 comprising SEQ ID NO: 57 (Claudin 18.2 Nanobody 2 Kabat CDR1), a CDR2 comprising SEQ ID NO: 63 (Claudin 18.2 Nanobody 2 Kabat CDR2), and a CDR3 comprising SEQ ID NO: 59 (Claudin 18.2 Nanobody 2 Kabat CDR3). In some embodiments, the antigen-binding domain that binds Claudin 18.2 comprises an amino acid sequence comprising a CDR1 comprising SEQ ID NO: 64 (Claudin 18.2 Nanobody 2 IMGT CDR1), a CDR2 comprising SEQ ID NO: 65 (Claudin 18.2 Nanobody 2 IMGT CDR1), and a CDR3 comprising SEQ ID NO: 62 (Claudin 18.2 Nanobody 2 IMGT CDR3). In some embodiments, the CDR sequences of the antigen-binding domain that binds Claudin 18.2 have 100% identity with the CDR sequences of Claudin 18.2 Nanobody 2 (i.e., the antigen-binding domain that binds Claudin 18.2 comprises an amino acid sequence comprising a CDR1, CDR2, and CDR3 each having 100% identity to the corresponding CDR in Claudin 18.2 Nanobody 2). In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 80% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 85% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 90% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 95% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 96% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 97% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 98% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 99% sequence identity with the non-CDR (e.g., framework) sequences of Claudin 18.2 Nanobody 2. In some embodiments, the protein associated with the TCR complex is a CD3 protein, for example, a CD3 protein of a TCR complex on a T cell expressing the TAC. In some embodiments, the CD3 protein is a CD3γ protein, CD3δ protein and/or CDR protein. In some embodiments, the CD3 protein is a CDR protein. In some embodiments, binding of the CD3 protein induces activation of the T cell. In some embodiments, the antigen-binding domain that binds the protein associated with the TCR complex is a designed ankyrin repeat (DARPin) polypeptide, single chain variable fragment (scFv), single domain antibody, diabody, affibody, adnectin, affilin, phylomer; fynomer, affimer, peptide aptamer, knottin, centyrin, anticalin, or nanobody. In some embodiments, the antigen-binding domain that binds the protein associated with the TCR complex is derived from an antibody selected from UCHT1, OKT3, F6A, and L2K. In some embodiments, the antigen-binding domain that binds the protein associated with the TCR complex is a UCHT1 antigen-binding domain, for example, a UCHT1 single chain antibody. In some embodiments, the UCHT1 antigen-binding domain comprises a Y to T mutation at a position corresponding to amino acid 182 of SEQ ID NO: 8 (Y182T). In some embodiments, the UCHT1 antigen-binding domain is a humanized variant of UCHT1 (huUCHT1), for example, a humanized variant of UCHT1 comprising a Y to T mutation at a position corresponding to amino acid 177 of SEQ ID NO: 34 (huUCHT1 (Y177T)). In some embodiments, the antigen-binding domain that binds the protein associated with the TCR complex comprises an amino acid sequence having at least 85% sequence identity with the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the antigen-binding domain that binds the protein associated with the TCR complex comprises an amino acid sequence having at least 90% sequence identity with the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the antigen-binding domain that binds the protein associated with the TCR complex comprises an amino acid sequence having at least 95% sequence identity with the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the antigen-binding domain that binds the protein associated with the TCR complex comprises an amino acid sequence having at least 96% sequence identity with the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the antigen-binding domain that binds the protein associated with the TCR complex comprises an amino acid sequence having at least 97% sequence identity with the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the antigen-binding domain that binds the protein associated with the TCR complex comprises an amino acid sequence having at least 98% sequence identity with the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the antigen-binding domain that binds the protein associated with the TCR complex comprises an amino acid sequence having at least 99% sequence identity with the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the antigen-binding domain that binds the protein associated with the TCR complex comprises the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T))). In some embodiments, the CDR sequences of the antigen-binding domain that binds the protein associated with the TCR complex have 100% identity with the CDR sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 8 (UCHT1), SEQ ID NO: 44 (UCHT1 (Y182T)), SEQ ID NO: 34 (huUCHT1), or SEQ ID NO: 36 (huUCHT1 (Y177T)). In some embodiments, the antigen-binding domain that binds the protein associated with the TCR complex is an OKT3 antigen-binding domain. In some embodiments, the antigen-binding domain that binds the protein associated with the TCR complex comprises an amino acid sequence having at least 85% sequence identity with the amino acid sequence of SEQ ID NO: 16 (OKT3). In some embodiments, the antigen-binding domain that binds the protein associated with the TCR complex comprises an amino acid sequence having at least 90% sequence identity with the amino acid sequence of SEQ ID NO: 16 (OKT3). In some embodiments, the antigen-binding domain that binds the protein associated with the TCR complex comprises an amino acid sequence having at least 95% sequence identity with the amino acid sequence of SEQ ID NO: 16 (OKT3). In some embodiments, the antigen-binding domain that binds the protein associated with the TCR complex comprises an amino acid sequence having at least 96% sequence identity with the amino acid sequence of SEQ ID NO: 16 (OKT3). In some embodiments, the antigen-binding domain that binds the protein associated with the TCR complex comprises an amino acid sequence having at least 97% sequence identity with the amino acid sequence of SEQ ID NO: 16 (OKT3). In some embodiments, the antigen-binding domain that binds the protein associated with the TCR complex comprises an amino acid sequence having at least 98% sequence identity with the amino acid sequence of SEQ ID NO: 16 (OKT3). In some embodiments, the antigen-binding domain that binds the protein associated with the TCR complex comprises an amino acid sequence having at least 99% sequence identity with the amino acid sequence of SEQ ID NO: 16 (OKT3). In some embodiments, the antigen-binding domain that binds the protein associated with the TCR complex comprises the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 16 (OKT3)). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 16 (OKT3). In some embodiments, the antigen-binding domain that binds the protein associated with the TCR complex is a F6A antigen-binding domain. In some embodiments, the antigen-binding domain that binds the protein associated with the TCR complex comprises an amino acid sequence having at least 85% sequence identity with the amino acid sequence of SEQ ID NO: 18 (F6A). In some embodiments, the antigen-binding domain that binds the protein associated with the TCR complex comprises an amino acid sequence having at least 90% sequence identity with the amino acid sequence of SEQ ID NO: 18 (F6A). In some embodiments, the antigen-binding domain that binds the protein associated with the TCR complex comprises an amino acid sequence having at least 95% sequence identity with the amino acid sequence of SEQ ID NO: 18 (F6A). In some embodiments, the antigen-binding domain that binds the protein associated with the TCR complex comprises an amino acid sequence having at least 96% sequence identity with the amino acid sequence of SEQ ID NO: 18 (F6A). In some embodiments, the antigen-binding domain that binds the protein associated with the TCR complex comprises an amino acid sequence having at least 97% sequence identity with the amino acid sequence of SEQ ID NO: 18 (F6A). In some embodiments, the antigen-binding domain that binds the protein associated with the TCR complex comprises an amino acid sequence having at least 98% sequence identity with the amino acid sequence of SEQ ID NO: 18 (F6A). In some embodiments, the antigen-binding domain that binds the protein associated with the TCR complex comprises an amino acid sequence having at least 99% sequence identity with the amino acid sequence of SEQ ID NO: 18 (F6A). In some embodiments, the antigen-binding domain that binds the protein associated with the TCR complex comprises the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 18 (F6A)). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 18 (F6A). In some embodiments, the antigen-binding domain that binds the protein associated with the TCR complex is a L2K antigen-binding domain. In some embodiments, the antigen-binding domain that binds the protein associated with the TCR complex comprises an amino acid sequence having at least 85% sequence identity with the amino acid sequence of SEQ ID NO: 20 (L2K). In some embodiments, the antigen-binding domain that binds the protein associated with the TCR complex comprises an amino acid sequence having at least 90% sequence identity with the amino acid sequence of SEQ ID NO: 20 (L2K). In some embodiments, the antigen-binding domain that binds the protein associated with the TCR complex comprises an amino acid sequence having at least 95% sequence identity with the amino acid sequence of SEQ ID NO: 20 (L2K). In some embodiments, the antigen-binding domain that binds the protein associated with the TCR complex comprises an amino acid sequence having at least 96% sequence identity with the amino acid sequence of SEQ ID NO: 20 (L2K). In some embodiments, the antigen-binding domain that binds the protein associated with the TCR complex comprises an amino acid sequence having at least 97% sequence identity with the amino acid sequence of SEQ ID NO: 20 (L2K). In some embodiments, the antigen-binding domain that binds the protein associated with the TCR complex comprises an amino acid sequence having at least 98% sequence identity with the amino acid sequence of SEQ ID NO: 20 (L2K). In some embodiments, the antigen-binding domain that binds the protein associated with the TCR complex comprises an amino acid sequence having at least 99% sequence identity with the amino acid sequence of SEQ ID NO: 20 (L2K). In some embodiments, the antigen-binding domain that binds the protein associated with the TCR complex comprises the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 20 (L2K)). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 20 (L2K). In some embodiments, the cytosolic domain is a CD4 cytosolic domain and the transmembrane domain is a CD4 transmembrane domain. In some embodiments, the cytosolic domain is a CD8 cytosolic domain and the transmembrane domain is a CD8 transmembrane domain. In some embodiments, the cytosolic and transmembrane domain comprise an amino acid sequence having at least 85% sequence identity with SEQ ID NO: 12 (CD4 transmembrane and cytosolic domain). In some embodiments, the cytosolic and transmembrane domain comprise an amino acid sequence having at least 90% sequence identity with SEQ ID NO: 12 (CD4 transmembrane and cytosolic domain). In some embodiments, the cytosolic and transmembrane domain comprise an amino acid sequence having at least 95% sequence identity with SEQ ID NO: 12 (CD4 transmembrane and cytosolic domain). In some embodiments, the cytosolic and transmembrane domain comprise an amino acid sequence having at least 96% sequence identity with SEQ ID NO: 12 (CD4 transmembrane and cytosolic domain). In some embodiments, the cytosolic and transmembrane domain comprise an amino acid sequence having at least 97% sequence identity with SEQ ID NO: 12 (CD4 transmembrane and cytosolic domain). In some embodiments, the cytosolic and transmembrane domain comprise an amino acid sequence having at least 98% sequence identity with SEQ ID NO: 12 (CD4 transmembrane and cytosolic domain). In some embodiments, the cytosolic and transmembrane domain comprise an amino acid sequence having at least 99% sequence identity with SEQ ID NO: 12 (CD4 transmembrane and cytosolic domain). In some embodiments, the cytosolic and transmembrane domain comprise the amino acid sequence of SEQ ID NO: 12 (CD4 transmembrane and cytosolic domain). In some embodiments, the components of the Claudin 18.2-TAC are connected in any suitable manner, such as in any suitable order and/or comprising any suitable linker(s). In some embodiments, component (a), component (b), and component (c) are fused directly to each other, or joined by at least one linker. In some embodiments, component (a) and component (c) are fused to component (b). In some embodiments, component (b) and component (c) are fused to component (a). In some embodiments, at least one linker joins component (a) to component (b). In some embodiments, the at least one linker is a glycine and/or serine-rich linker, a large protein domain, a long helix structure, or a short helix structure. In some embodiments, the at least one linker comprises an amino acid sequence having at least 80% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 85% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 90% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 95% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 96% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 97% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 98% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 80% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the Claudin 18.2-TAC does not comprise a co-stimulatory domain and/or an activation domain. In some embodiments, the Claudin 18.2-TAC further comprises a leader sequence. In some embodiments, the leader sequence comprises an amino acid sequence having at least 80% sequence identity with the amino acid sequence of SEQ ID NO: 2 (muIgG leader), SEQ ID NO: 38 (huIgG leader), or SEQ ID NO: 40 (huCD8a leader). In some embodiments, the leader sequence comprises an amino acid sequence having at least 85% sequence identity with the amino acid sequence of SEQ ID NO: 2 (muIgG leader), SEQ ID NO: 38 (huIgG leader), or SEQ ID NO: 40 (huCD8a leader). In some embodiments, the leader sequence comprises an amino acid sequence having at least 90% sequence identity with the amino acid sequence of SEQ ID NO: 2 (muIgG leader), SEQ ID NO: 38 (huIgG leader), or SEQ ID NO: 40 (huCD8a leader). In some embodiments, the leader sequence comprises an amino acid sequence having at least 95% sequence identity with the amino acid sequence of SEQ ID NO: 2 (muIgG leader), SEQ ID NO: 38 (huIgG leader), or SEQ ID NO: 40 (huCD8a leader). In some embodiments, the leader sequence comprises an amino acid sequence having at least 96% sequence identity with the amino acid sequence of SEQ ID NO: 2 (muIgG leader), SEQ ID NO: 38 (huIgG leader), or SEQ ID NO: 40 (huCD8a leader). In some embodiments, the leader sequence comprises an amino acid sequence having at least 97% sequence identity with the amino acid sequence of SEQ ID NO: 2 (muIgG leader), SEQ ID NO: 38 (huIgG leader), or SEQ ID NO: 40 (huCD8a leader). In some embodiments, the leader sequence comprises an amino acid sequence having at least 98% sequence identity with the amino acid sequence of SEQ ID NO: 2 (muIgG leader), SEQ ID NO: 38 (huIgG leader), or SEQ ID NO: 40 (huCD8a leader). In some embodiments, the leader sequence comprises an amino acid sequence having at least 99% sequence identity with the amino acid sequence of SEQ ID NO: 2 (muIgG leader), SEQ ID NO: 38 (huIgG leader), or SEQ ID NO: 40 (huCD8a leader). In some embodiments, the leader sequence comprises the amino acid sequence of SEQ ID NO: 2 (muIgG leader), SEQ ID NO: 38 (huIgG leader), or SEQ ID NO: 40 (huCD8a leader). In some embodiments, the Claudin 18.2-TAC polypeptide comprises an amino acid sequence having at least 80%, at least 85%, at least 90%, at least 95%, at least 96%, at least 97%, at least 98%, at least 99%, or 100% sequence identity with the amino acid sequence of SEQ ID NO: 67. In some embodiments, the Claudin 18.2-TAC polypeptide comprises an amino acid sequence having at least 80%, at least 85%, at least 90%, at least 95%, at least 96%, at least 97%, at least 98%, at least 99%, or 100% sequence identity with the amino acid sequence of SEQ ID NO: 69. In some embodiments, the Claudin 18.2-TAC polypeptide comprises an amino acid sequence having at least 80%, at least 85%, at least 90%, at least 95%, at least 96%, at least 97%, at least 98%, at least 99%, or 100% sequence identity with the amino acid sequence of SEQ ID NO: 71. In some embodiments, the Claudin 18.2-TAC polypeptide comprises an amino acid sequence having at least 80%, at least 85%, at least 90%, at least 95%, at least 96%, at least 97%, at least 98%, at least 99%, or 100% sequence identity with the amino acid sequence of SEQ ID NO: 73.

Disclosed herein, in certain embodiments, are T cells comprising a nucleic acid disclosed herein, an expression vector disclosed herein, or a Claudin 18.2-TAC disclosed herein. In some embodiments, the T cell is a γδ T cell, e.g., a δ2 T cell, a δ1s T cell, or a γ9δ2 T cell.

Disclosed herein, in certain embodiments, are pharmaceutical compositions comprising a T cell disclosed herein, and a pharmaceutically acceptable excipient.

Disclosed herein, in certain embodiments, are methods of treating a Claudin 18.2-expressing cancer in an individual in need thereof, comprising administering to the individual a T cell or a pharmaceutical composition disclosed herein. In some embodiments, the cancer is a solid cancer or a liquid cancer. In some embodiments, the cancer is a pancreatic cancer (e.g., pancreatic adenocarcinoma, a gastric cancer (e.g., gastric adenocarcinoma), a signet ring cell carcinoma, a mucinous gastric cancer, a gastroesophageal cancer (e.g., gastroesophageal junction (GEJ) adenocarcinoma), an esophageal cancer, a cancer of the digestive system, an ovarian cancer, a mucinous ovarian cancer cell, or a lung cancer (e.g., non-small cell lung cancer).

Disclosed herein in certain embodiments, are conjugates comprising a T cell disclosed herein and a Claudin 18.2-expressing cancer cell. In some embodiments, the Claudin 18.2-TAC polypeptide is present on the surface of the T cell and the Claudin 18.2 is present on the surface of the cancer cell In some embodiments, the Claudin 18.2-TAC polypeptide is bound to the Claudin 18.2. In some embodiments, the cancer cell is a cell of a solid cancer. In some embodiments, the cancer cell is a pancreatic cancer cell, a gastric cancer cell, a signet ring cell carcinoma cell, a cancer of the digestive system, a mucinous gastric cancer cell, a gastroesophageal cancer cell, an esophageal cancer cell, an ovarian cancer cell, a mucinous ovarian cancer cell, a non-small cell lung cancer cell, or a lung cancer cell. In some embodiments, the cancer cell is a gastric cancer cell or a gastroesophageal cancer cell.

BRIEF DESCRIPTION OF THE DRAWINGS

The invention can be more completely understood with reference to the following drawings.

FIG. 2A depicts the overall cell count over time of T cells engineered to express indicated Claudin 18.2-TACs. FIG. 2B depicts the number of cell doublings over time of T cells engineered to express indicated Claudin 18.2-TACs. FIG. 2C depicts the percent viability over time of T cells engineered to express indicated Claudin 18.2-TACs.

FIGS. 5A and B depict binding of GFP-labeled Claudin 18.2 Nanobody 2 to indicated cells engineered to express Claudin 18.2 or control (FIG. 5A), binding of GFP-Claudin 18.2 Nanobody 2 fusion protein to a library of known membrane-anchored human proteins (FIG. 5B).

FIGS. 6A-6C depict assays demonstrating the activation of Claudin 18.2-TAC T cells after co-culture with target cells expressing Claudin 18.2 (top panels) or Claudin 18.1 (bottom panels). FIG. 6A shows confirmation of Claudin 18.2-TAC expression as measured by flow cytometry. FIG. 6B shows scatterplots of CD69 (vertical axes) staining vs TAC expression (horizontal axes) in engineered T cells exposed to cells expressing the indicated antigen. FIG. 6C shows normalized CD69% positivity in T cells expressing the indicated TACs and exposed to target cells expressing the indicated antigens.

FIG. 7 depicts cytotoxicity induced by T cells expressing the Claudin 18.2-TAC of SEQ ID NO: 69 or 73 following co-culture with KATO III cells engineered to express enhanced Luciferase (KATO IIIeLuc). NTD: non-transduced control cells. Effector cell:target cell (E:T) ratios that induced 50 percent killing of target cells (IC50) were calculated and the E:T ratio needed to reach half maximal cytotoxicity is shown.

FIG. 13 depicts markers that allow for an assessment of T cell activation, exhaustion and memory phenotype.

FIGS. 16A and 16B depict an in vitro assay showing cytotoxicity of target cells by T cells expressing the indicated Claudin 18.2-TACs. FIG. 16A depicts the normalized cytotoxicity at indicated effector:target (E:T) ratios. FIG. 16B depicts the measured $IC_{50}$ values of T cells expressing the indicated TACs.

FIG. 17A shows proliferation of cells as measured by flow cytometry-based detection of a cell tracking dye. FIG. 17B shows the measured division index (DI) of T cells expressing the indicated TACs.

FIG. 18A shows scatterplots of CD69 (vertical axes) staining vs TAC expression (horizontal axes) in engineered T cells exposed to indicated cell lines.

FIG. 18B shows normalized CD69% positivity in T cells expressing the indicated TACs and exposed to indicated target cells.

FIG. 19A depicts a schematic of the assay. FIG. 19B depicts graphs showing viability of indicated target cells following incubation with T cells expressing the indicated TACs.

FIG. 21A), overall survival (FIG. 21B), and relative change in body weight (FIG. 21C) for the indicated treatment groups. NT: Non treated animals (square); NTD: mice administered non-transduced control T cells (circle).

FIG. 25A depicts a schematic of the model.

FIG. 25B depicts measurement of tumor volumes over the course of the experiment following treatment with T cell expressing indicated TACs at indicated dosage levels.

FIGS. 26A-26B depict an in vivo murine model of the antitumor activity of Claudin 18.2-TAC T cells and different dosage levels. FIG. 26A depicts a schematic of the model. FIG. 26B depicts measurement of tumor volumes over the course of the experiment following treatment with T cell expressing indicated TACs at indicated dosage levels.

FIG. 27A depicts a schematic of the model. FIG. 27B depicts measurement of tumor flux over the course of the experiment following treatment with T cell expressing indicated TACs at indicated dosage levels.

FIGS. 28A-28B depict an in vivo murine re-challenge model of the antitumor activity of Claudin 18.2-TAC T cells in MHC-knockout mice. FIG. 28A depicts a schematic of the model. FIG. 28B depicts measurement of tumor volumes over the course of the experiment following treatment with T cell expressing indicated TACs over the course of the experiments, with rechallenge timepoints indicated.

DETAILED DESCRIPTION

Figure 1:
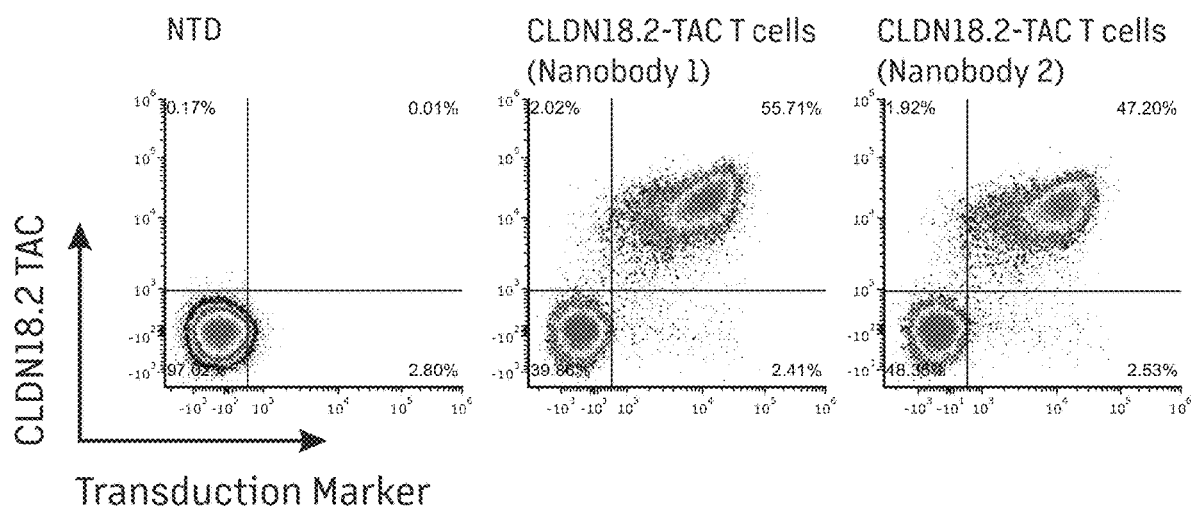
FIG. 1 depicts cell surface expression of the indicated TAC and an mStrawberry red fluorescence protein transduction marker in T cells. NTD: non-transduced control cells.

Cancer is a major health challenge. According to the American Cancer Society, more than one million people in the United States are diagnosed with cancer each year. While patients with early stage disease are sometimes treated effectively by conventional therapies (surgery, radiation, chemotherapy), few options are available to patients with advanced disease, and those options are typically palliative in nature.

Active immunotherapy seeks to employ the patient's immune system to clear tumors and offers an option to patients who have failed conventional therapies. Generally, this treatment involves infusing patients with large numbers of tumor-specific T cells. This approach has proven to be successful in early phase clinical trials for a number of diseases, including melanoma, myeloma, leukemia, lymphoma and synovial sarcoma. As a specific example, several clinical studies have demonstrated that immunotherapy with T cells are curative in patients with advanced melanoma, confirming the utility of this approach. Additionally, patients suffering from chronic lymphocytic leukemia (CLL) and acute lymphoblastic leukemia (ALL) have also been effectively treated and cured with T cell immunotherapy.

To this point, most engineered T cell therapies involving genetic modification of the T cells yield: (i) forced expression of T cell receptor (TCR); or (ii) a chimeric antigen receptor (CAR) specific for antigen targets on the tumor. To date, the chimeric antigen receptors used for engineering T cells consist of: (i) a targeting domain, usually a single-chain fragment variable (scFv); (ii) a transmembrane domain; and (iii) a cytosolic domain that contains signaling elements from the T cell receptor and associated proteins. Such chimeric antigen receptors have also been referred to as "T-body" or "Chimeric Immune Receptor" (CIR), but currently, most researchers use the term "CAR". One advantage of the CAR approach is that it allows any patient's immune cells to be targeted against any desirable target in a major histocompatibility complex (MHC) independent manner. This is appealing as MHC presentation is often defective in tumor cells.

CARs are considered in modular terms and scientists have spent considerable time investigating the influence of different cytoplasmic signaling domains on CAR function. Conventional CARs generally share two main components: (i) the CD3 zeta cytoplasmic domain, which contains immunotyrosine activation motifs (ITAMs) critical for T cell activation; and (ii) components of costimulatory receptors that trigger important survival pathways such as the Akt pathway.

The first-generation CARs employed a single signaling domain from either CD3ζ or FcεRIγ. Second-generation CARs combined the signaling domain of CD3ζ with the cytoplasmic domain of costimulatory receptors from either the CD28 or TNFR family of receptors. Most CAR-engineered T cells that are currently being tested in the clinic employ second-generation CARs where CD3ζ is coupled to the cytoplasmic domain of either CD28 or CD137. These second generation CARs have demonstrated anti-tumor activity in CD19-positive tumors. Third-generation CARs combined multiple costimulatory domains, but there is concern that third-generation CARs may lose antigen-specificity.

While CAR-engineered T cells have shown considerable promise in clinical application, they rely on a synthetic method for replacing the native activation signal that is provided by the T cell receptor (TCR). Since this synthetic receptor does not deliver all of the signaling components associated with the TCR (ex. ITAMs on CD3γ, CD3δ, CD3ε), it remains unclear whether the T cells are optimally activated by the CAR or how the CAR activation affects T cell differentiation (ex. progression to memory). Furthermore, since the CAR signaling domains are disconnected from their natural regulatory partners by the very nature of the CAR structure, there is an inherent risk that CARs may lead to a low-level of constitutive activation, which could result in off-target toxicities. Therefore, the synthetic nature of the prototypic CAR may disrupt canonical mechanisms that limit TCR activation, and may underpin the severe toxicity often associated with therapeutic doses of conventional CAR T cells.

Given these limitations, it is preferable to re-direct T cells to attack tumors via their natural TCR. An alternate chimeric receptor, termed a T cell Antigen Coupler (TAC or TAC) receptor, has been developed which employs a distinct biology to direct the T cell to attack tumors. While the CAR is a fully synthetic receptor that stitches together components of T cell receptor (TCR) signaling complex, the TAC receptor re-directs the TCR towards tumor targets and recapitulates the native TCR signaling structure. For example, in some embodiments, the TACs disclosed herein activate natural Major Histocompatibility complex (MHC) signaling through the T cell receptor (TCR), while retaining MHC-unrestricted targeting. Further, the TACs disclosed herein recruit the T Cell Receptor (TCR) in combination with co-receptor stimulation. Moreover, in some embodiments, TACs disclosed herein show enhanced activity and safety.

TACs are distinct from traditional CAR technology in that they include a second extracellular ligand that binds a protein associated with the TCR complex. Furthermore, TACs contain TCR co-receptor cytosolic domains as opposed to the TCR signaling domains used in CARs. The TCR co-receptor domains can facilitate T cell activation through endogenous TCR signaling as opposed to CARs, which function independently of the endogenous TCR. Instead, CARs typically function via their own synthetic activation domain (e.g., CD3z). This tonic signaling induced by CARs can lead to effector cell exhaustion. The structural differences between TACs and CARs results in molecules with different structural features and different functionality. For example, antigen-binding domains that are not functional in CARs may have satisfactory manufacturability or function in the context of a TAC.

Claudin 18.1 and 18.2 (CLDN18.1 and CLDN18.2) are highly conserved multi-membrane spanning proteins found in tight junctions. The extracellular domains of Claudin 18.1 and 18.2 include two prominent loops. Claudin 18.1 and 18.2 show significant divergence in the first extracellular loop but are otherwise identical. While Claudin 18.1 is broadly expressed in lung tissue, Claudin 18.2 is predominantly expressed in gastric tissues and therefore a target for treating gastric cancers.

Certain Terminology

The term "antigen-binding domain," refers to any substance or molecule that binds, directly or indirectly, to a target (e.g., Claudin 18.2). Antigen-binding domains include antibodies or fragments thereof, peptides, peptidomimetics, proteins, glycoproteins, proteoglycans, carbohydrates, lipids, nucleic acids, or small molecules that bind to a target.

As used herein, unless otherwise indicated, the term "antibody" is understood to mean an intact antibody (e.g., an intact monoclonal antibody), or a fragment thereof, such as a Fc fragment of an antibody (e.g., an Fc fragment of a monoclonal antibody), or an antigen-binding fragment of a monoclonal antibody (e.g., an antigen-binding fragment of a monoclonal antibody), including an intact antibody, antigen-binding fragment, or Fc fragment that has been modified, engineered, or chemically conjugated. In general, antibodies are multimeric proteins that contain four polypeptide chains. Two of the polypeptide chains are called immunoglobulin heavy chains (H chains), and two of the polypeptide chains are called immunoglobulin light chains (L chains). The immunoglobulin heavy and light chains are connected by an interchain disulfide bond. The immunoglobulin heavy chains are connected by interchain disulfide bonds. A light chain consists of one variable region (VL) and one constant region (CL). The heavy chain consists of one variable region (VH) and at least three constant regions (CH1, CH2 and CH3). The variable regions determine the binding specificity of the antibody. Each variable region contains three hypervariable regions known as complementarity determining regions (CDRs) flanked by four relatively conserved regions known as framework regions (FRs). The extent of the FRs and CDRs has been defined (Kabat, E. A., et al. (1991) Sequences of Proteins of Immunological Interest, Fifth Edition, U.S. Department of Health and Human Services, NIH Publication No. 91-3242; and Chothia, C. et al. (1987) J. Mol. Biol. 196:901-917). The three CDRs, referred to as CDR1, CDR2, and CDR3, contribute to the antibody binding specificity. Naturally occurring antibodies have been used as starting material for engineered antibodies, such as chimeric antibodies and humanized antibodies. Examples of antibody-based antigen-binding fragments include Fab, Fab', (Fab')2, Fv, single chain antibodies (e.g., scFv), minibodies, and diabodies. Examples of antibodies that have been modified or engineered include chimeric antibodies, humanized antibodies, and multispecific antibodies (e.g., bispecific antibodies). An example of a chemically conjugated antibody is an antibody conjugated to a toxin moiety.

The term "T cell" as used herein refers to a type of lymphocyte that plays a central role in cell-mediated immunity. T cells, also referred to as T lymphocytes, are distinguished from other lymphocytes, such as B cells and natural killer cells, by the presence of a T-cell receptor (TCR) on the cell surface. There are several subsets of T cells with distinct functions, including but not limited to, T helper cells, cytotoxic T cells, memory T cells, regulatory T cells and natural killer T cells.

The term "γδ T cell" or "gamma delta T cell" or "gd T cell" as used herein refers to any lymphocyte having a γδ T cell receptor (TCR) on its surface, including one γ-chain and one δ-chain.

The term "T cell antigen coupler" or TAC is used interchangeably with "trifunctional T cell antigen coupler" or Tri-TAC and refers to an engineered nucleic acid construct or polypeptide comprising (a) an antigen-binding domain that binds a target, (b) an antigen-binding domain that binds a protein associated with a T cell receptor (TCR) complex, and (c) a T cell receptor signaling domain.

The term "polynucleotide" and/or "nucleic acid sequence" and/or "nucleic acid" as used herein refers to a sequence of nucleoside or nucleotide monomers consisting of bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acids of the present disclosure may be isolated from biological organisms, formed by laboratory methods of genetic recombination or obtained by chemical synthesis or other known protocols for creating nucleic acids.

The term "isolated polynucleotide" or "isolated nucleic acid sequence" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e., sequences located at the 5' and 3' ends of the nucleic acid) from which the nucleic acid is derived. The term "nucleic acid" is intended to include DNA and RNA and is either double stranded or single stranded, and represents the sense or antisense strand. Further, the term "nucleic acid" includes the complementary nucleic acid sequences.

The term "recombinant nucleic acid" or "engineered nucleic acid" as used herein refers to a nucleic acid or polynucleotide that is not found in a biological organism. For example, recombinant nucleic acids may be formed by laboratory methods of genetic recombination (such as molecular cloning) to create sequences that would not otherwise be found in nature. Recombinant nucleic acids may also be created by chemical synthesis or other known protocols for creating nucleic acids.

The terms "peptide", "polypeptide," and "protein" as used herein mean a chain of amino acids. The term protein as used herein further means a large molecule comprising one or more chains of amino acids and, in some embodiments, is a fragment or domain of a protein or a full length protein. Furthermore, as used herein, the term protein either refers to a linear chain of amino acids or to a chain of amino acids that has been processed and folded into a functional protein. The protein structure is divided into four distinct levels: (1) primary structure—referring to the sequence of amino acids in the polypeptide chain, (2) secondary structure—referring to the regular local sub-structures on the polypeptide backbone chain, such as α-helix and β-sheets, (3) tertiary structure—referring to the three-dimensional structure if monomeric and multimeric protein molecules, and (4) quaternary structure—referring to the three-dimensional structure comprising the aggregation of two or more individual polypeptide chains that operate as a single functional unit. The use of peptide or polypeptide herein does not mean that the chain of amino acids is not also a protein (i.e., a chain of amino acids having a secondary, tertiary or quaternary structure).

The term "isolated polypeptide" refers to a polypeptide substantially free of cellular material or culture medium when produced by recombinant DNA techniques, or chemical precursors or other chemicals when chemically synthesized.

The term "vector" as used herein refers to a polynucleotide that is used to deliver a nucleic acid to the inside of a cell. In some embodiments, a vector is an expression vector comprising expression control sequences (for example, a promoter) operatively linked to a nucleic acid to be expressed in a cell. Vectors known in the art include, but are not limited to, plasmids, phages, cosmids and viruses.

The term "tumor antigen" or "tumor associated antigen" as used herein refers to an antigenic substance produced in tumor cells that triggers an immune response in a host (e.g., which is presented by MHC complexes). In some embodiments, a tumor antigen is on the surface of a tumor cell.

As used herein, the term "transmembrane and cytosolic domain" refers to a polypeptide that comprises a transmembrane domain and a cytosolic domain of a protein associated with the T cell receptor (TCR) complex. In some embodiments, such transmembrane and cytosolic domain may include, but is not limited to, protein domains that (a) associate with the lipid raft and/or (b) bind Lck.

A "TCR co-receptor" as used herein, refers to a molecule that assists the T cell receptor (TCR) in communicating with an antigen-presenting cell and may be considered part of the first signal that leads to the activation of the TCR. Examples of TCR co-receptors include, but are not limited to, CD4, LAG3, and CD8.

A "TCR co-stimulator" or "co-stimulatory domain" as used herein, refers to a molecule that enhances the response of a T cell to an antigen and may be considered as the second signal that leads to the activation of the TCR. Examples of TCR co-stimulators include, but are not limited to, ICOS, CD27, CD28, 4-1BB (CD 137), OX40 (CD134), CD30, CD40, lymphocyte fiction-associated antigen 1 (LFA-1), CD2, CD7, LIGHT, NKG2C, B7-H3, and a ligand that specifically binds CD83.

The terms "recipient", "individual", "subject", "host", and "patient", are used interchangeably herein and in some embodiments, refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is human. None of these terms require the supervision of medical personnel.

As used herein, the terms "treatment," "treating," and the like, in some embodiments, refer to administering an agent, or carrying out a procedure, for the purposes of obtaining an effect. The effect may be prophylactic in terms of completely or partially preventing a disease or symptom thereof and/or may be therapeutic in terms of affecting a partial or complete cure for a disease and/or symptoms of the disease. "Treatment," as used herein, may include treatment of a disease or disorder (e.g., cancer) in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. Treating may refer to any indicia of success in the treatment or amelioration or prevention of a cancer, including any objective or subjective parameter such as abatement; remission; diminishing of symptoms; or making the disease condition more tolerable to the patient; slowing in the rate of degeneration or decline; or making the final point of degeneration less debilitating. The treatment or amelioration of symptoms is based on one or more objective or subjective parameters; including the results of an examination by a physician. Accordingly, the term "treating" includes the administration of the compounds or agents of the present invention to prevent, delay, alleviate, arrest or inhibit development of the symptoms or conditions associated with diseases (e.g., cancer). The term "therapeutic effect" refers to the reduction, elimination, or prevention of the disease, symptoms of the disease, or side effects of the disease in the subject.

As used herein, singular forms "a", "and," and "the" include plural referents unless the context clearly indicates otherwise. Thus, for example, reference to "an antibody"

includes a plurality of antibodies and reference to "an antibody" in some embodiments includes multiple antibodies, and so forth.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes 91%, 92%, 93%, 94%, 95%, 95%, 96%, 97%, etc., as well as 91.1%, 91.2%, 91.3%, 91.4%, 91.5%, etc., 92.1%, 92.2%, 92.3%, 92.4%, 92.5%, etc., and so forth. In another example, reference to a range of 1-5,000 fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and so forth.

"About" a number, as used herein, refers to range including the number and ranging from 10% below that number to 10% above that number. "About" a range refers to 10% below the lower limit of the range, spanning to 10% above the upper limit of the range.

"Percent (%) identity" refers to the extent to which two sequences (nucleotide or amino acid) have the same residue at the same positions in an alignment. For example, "an amino acid sequence is X % identical to SEQ ID NO: Y" refers to % identity of the amino acid sequence to SEQ ID NO: Y and is elaborated as X % of residues in the amino acid sequence are identical to the residues of sequence disclosed in SEQ ID NO: Y. Generally, computer programs are employed for such calculations. Exemplary programs that compare and align pairs of sequences, include ALIGN (Myers and Miller, 1988), FASTA (Pearson and Lipman, 1988; Pearson, 1990) and gapped BLAST (Altschul et al., 1997), BLASTP, BLASTN, or GCG (Devereux et al., 1984).

As used herein, the term "selective binding" refers to the higher affinity with which a molecule (e.g., protein such as an antigen-binding domain of TAC) binds its target molecule (e.g., target antigen such as Claudin 18.2) over other molecules. Unless indicated otherwise, the terms "selective binding" and "specific binding" are used interchangeably herein.

T Cell-Antigen Couplers (TACs)

Disclosed herein, in certain embodiments, are nucleic acids encoding Claudin 18.2 T cell-antigen coupler (TAC) polypeptides. In some embodiments, the nucleic acids encoding the Claudin 18.2-TAC comprise: (a) a first polynucleotide encoding an antigen-binding domain that binds Claudin 18.2; (b) a second polynucleotide encoding an antigen-binding domain that binds the TCR complex; and (c) a third polynucleotide encoding a transmembrane domain and cytosolic domain. In some embodiments, the nucleic acids comprise, in order (e.g., from 5' to 3'): (a) the first polynucleotide; (b) the second polynucleotide; and (c) the third polynucleotide encoding a TCR co-receptor cytosolic domain and transmembrane domain. In some embodiments, the nucleic acids encoding the Claudin 18.2-TAC do not encode a co-stimulatory domain. In some embodiments, the nucleic acids encoding the Claudin 18.2-TAC do not encode a co-activation domain.

Further disclosed herein, in certain embodiments, are Claudin 18.2 T cell-antigen coupler (TAC) polypeptides. In some embodiments, the Claudin 18.2-TAC polypeptides comprise: (a) an antigen-binding domain that binds Claudin 18.2; (b) an antigen-binding domain that binds the TCR complex; and (c) a transmembrane domain and cytosolic domain. In some embodiments, the Claudin 18.2-TAC polypeptides comprise, in order (e.g., from N-terminus to C-terminus) (a) the antigen-binding domain that binds Claudin 18.2; (b) the antigen-binding domain that binds the TCR complex; and (c) the transmembrane domain and cytosolic domain. In some embodiments, the Claudin 18.2-TAC polypeptides do not include a co-stimulatory domain. In some embodiments, the Claudin 18.2-TAC polypeptides do not include a co-activation domain.

Further disclosed herein, in certain embodiments, are expression vectors comprising a nucleic acid encoding a Claudin 18.2-TAC polypeptide as described herein.

Further disclosed herein, in certain embodiments, are T cells comprising a nucleic acid encoding a Claudin 18.2-TAC polypeptide as described herein, T cells comprising an expression vector encoding a Claudin 18.2-TAC polypeptide as described herein, or T cells comprising a Claudin 18.2-TAC polypeptide as described herein.

Further disclosed herein, in certain embodiments, are methods of treating a cancer in an individual in need thereof, comprising administering to the individual a T cell comprising a Claudin 18.2 T cell-antigen coupler (TAC) polypeptide as described herein.

Claudin 18.2 Antigen-Binding Domain

In certain embodiments, the Claudin 18.2-TAC polypeptide comprises a Claudin 18.2 antigen-binding domain. In some embodiments, the Claudin 18.2 antigen-binding domain selectively binds Claudin 18.2. In some embodiments, the Claudin 18.2 antigen-binding domain binds to Claudin 18.2 on a target cell. In some embodiments, a target cell is a cell associated with a disease state, including, but not limited to, cancer. In some embodiments, a target cell is a tumor cell.

In some embodiments, the Claudin 18.2 antigen-binding domain is an antibody or a fragment thereof. In some embodiments, the Claudin 18.2 antigen-binding domain is selected from single chain antibodies (e.g., single-chain fragment variable antibodies (scFvs)), single domain antibodies (e.g., heavy-chain-only antibodies (VHH), shark heavy-chain-only antibodies (VNAR)), nanobodies, diabodies, minibodies, Fab fragments, Fab' fragments, F(ab')2 fragments, or Fv fragments that bind to Claudin 18.2.

In some embodiments, the Claudin 18.2 antigen-binding domain is selected from ankyrin repeat proteins (DARPins), affibodies, adnectins, affilins, phylomers, fynomers, affimers, peptide aptamers, lectins, knottins, centyrins, anticalins, peptides, peptidomimetics, proteins, glycoproteins, or proteoglycans that bind to Claudin 18.2, or naturally occurring ligands for Claudin 18.2. In some embodiments, the Claudin 18.2 antigen-binding domain is a non-protein compound that binds to Claudin 18.2, including but not limited to carbohydrates, lipids, nucleic acids, or small molecules.

In some embodiments, the Claudin 18.2 antigen-binding domain is a designed ankyrin repeat (DARPin) targeted to Claudin 18.2. In some embodiments, the Claudin 18.2 antigen-binding domain is a single-chain variable fragment (ScFv) targeted to Claudin 18.2. In some embodiments, the Claudin 18.2 antigen-binding domain is a nanobody targeted to Claudin 18.2.

In some embodiments, the Claudin 18.2 antigen-binding domain is of a nanobody referred to herein as Claudin 18.2 Nanobody 1 (having an amino acid sequence depicted in SEQ ID NO: 55). In some embodiments, the antigen-binding domain that binds Claudin 18.2 comprises an amino acid sequence having at least 80% sequence identity with the amino acid sequence of SEQ ID NO: 55 (Claudin 18.2 Nanobody 1). In some embodiments, the antigen-binding domain that binds Claudin 18.2 comprises an amino acid sequence having at least 85% sequence identity with the amino acid sequence of SEQ ID NO: 55 (Claudin 18.2 Nanobody 1). In some embodiments, the antigen-binding domain that binds Claudin 18.2 comprises an amino acid sequence having at least 90% sequence identity with the amino acid sequence of SEQ ID NO: 55 (Claudin 18.2 Nanobody 1). In some embodiments, the antigen-binding domain that binds Claudin 18.2 comprises an amino acid sequence having at least 95% sequence identity with the amino acid sequence of SEQ ID NO: 55 (Claudin 18.2 Nanobody 1). In some embodiments, the antigen-binding domain that binds Claudin 18.2 comprises an amino acid sequence having at least 96% sequence identity with the amino acid sequence of SEQ ID NO: 55 (Claudin 18.2 Nanobody 1). In some embodiments, the antigen-binding domain that binds Claudin 18.2 comprises an amino acid sequence having at least 97% sequence identity with the amino acid sequence of SEQ ID NO: 55 (Claudin 18.2 Nanobody 1). In some embodiments, the antigen-binding domain that binds Claudin 18.2 comprises an amino acid sequence having at least 98% sequence identity with the amino acid sequence of SEQ ID NO: 55 (Claudin 18.2 Nanobody 1). In some embodiments, the antigen-binding domain that binds Claudin 18.2 comprises an amino acid sequence having at least 99% sequence identity with the amino acid sequence of SEQ ID NO: 55 (Claudin 18.2 Nanobody 1). In some embodiments, the antigen-binding domain that binds Claudin 18.2 comprises the amino acid sequence of SEQ ID NO: 55 (Claudin 18.2 Nanobody 1). In some embodiments, the antigen-binding domain that binds Claudin 18.2 comprises an amino acid sequence comprising a CDR1 comprising SEQ ID NO: 57 (Claudin 18.2 Nanobody 1 Kabat CDR1), a CDR2 comprising SEQ ID NO: 58 (Claudin 18.2 Nanobody 1 Kabat CDR2), and a CDR3 comprising SEQ ID NO: 59 (Claudin 18.2 Nanobody 1 Kabat CDR3). In some embodiments, the antigen-binding domain that binds Claudin 18.2 comprises an amino acid sequence comprising a CDR1 comprising SEQ ID NO: 60 (Claudin 18.2 Nanobody 1 IMGT CDR1), a CDR2 comprising SEQ ID NO: 61 (Claudin 18.2 Nanobody 1 IMGT CDR2), and a CDR3 comprising SEQ ID NO: 62 (Claudin 18.2 Nanobody 1 IMGT CDR3). In some embodiments, the CDR sequences of the antigen-binding domain that binds Claudin 18.2 have 100% identity with the CDR sequences of Claudin 18.2 Nanobody 1 (i.e., the antigen-binding domain that binds Claudin 18.2 comprises an amino acid sequence comprising a CDR1, CDR2, and CDR3 each having 100% identity to the corresponding CDR in Claudin 18.2 Nanobody 1). In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 80% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 85% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 90% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 95% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 96% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 97% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 98% sequence identity with the non-CDR (e.g., framework) sequences of Claudin 18.2 Nanobody 1. In some embodiments, the CDR sequences of the antigen-binding domain that binds Claudin 18.2 have 100% identity with the CDR sequences of Claudin 18.2 Nanobody 1, and the non-CDR (e.g., framework) sequences of the antigen-binding domain that binds Claudin 18.2 have at least 99% sequence identity with the non-CDR (e.g., framework) sequences of Claudin 18.2 Nanobody 1.

In some embodiments, the Claudin 18.2 antigen-binding domain is of a nanobody referred to herein as Claudin 18.2 Nanobody 2 (having an amino acid sequence depicted in SEQ ID NO: 56). In some embodiments, the antigen-binding domain that binds Claudin 18.2 comprises an amino acid sequence having at least 80% sequence identity with the amino acid sequence of SEQ ID NO: 56 (Claudin 18.2 Nanobody 2). In some embodiments, the antigen-binding domain that binds Claudin 18.2 comprises an amino acid sequence having at least 85% sequence identity with the amino acid sequence of SEQ ID NO: 56 (Claudin 18.2 Nanobody 2). In some embodiments, the antigen-binding domain that binds Claudin 18.2 comprises an amino acid sequence having at least 90% sequence identity with the amino acid sequence of SEQ ID NO: 56 (Claudin 18.2 Nanobody 2). In some embodiments, the antigen-binding domain that binds Claudin 18.2 comprises an amino acid sequence having at least 95% sequence identity with the amino acid sequence of SEQ ID NO: 56 (Claudin 18.2 Nanobody 2). In some embodiments, the antigen-binding domain that binds Claudin 18.2 comprises an amino acid sequence having at least 96% sequence identity with the amino acid sequence of SEQ ID NO: 56 (Claudin 18.2 Nanobody 2). In some embodiments, the antigen-binding domain that binds Claudin 18.2 comprises an amino acid sequence having at least 97% sequence identity with the amino acid sequence of SEQ ID NO: 56 (Claudin 18.2 Nanobody 2). In some embodiments, the antigen-binding domain that binds Claudin 18.2 comprises an amino acid sequence having at least 98% sequence identity with the amino acid sequence of SEQ ID NO: 56 (Claudin 18.2 Nanobody 2). In some embodiments, the antigen-binding domain that binds Claudin 18.2 comprises an amino acid sequence having at least 99% sequence identity with the amino acid sequence of SEQ ID NO: 56 (Claudin 18.2 Nanobody 2). In some embodiments, the antigen-binding domain that binds Claudin 18.2 comprises the amino acid sequence of SEQ ID NO: 56 (Claudin 18.2 Nanobody 2). In some embodiments, the antigen-binding domain that binds Claudin 18.2 comprises an amino acid sequence comprising a CDR1 comprising SEQ ID NO: 57 (Claudin 18.2 Nanobody 2 Kabat CDR1), a CDR2 comprising SEQ ID NO: 63 (Claudin 18.2 Nanobody 2 Kabat CDR2), and a CDR3 comprising SEQ ID NO: 59 (Claudin 18.2 Nanobody 2 Kabat CDR3). In some embodiments, the antigen-binding domain that binds Claudin 18.2 comprises an amino acid sequence comprising a CDR1 comprising SEQ ID NO: 64 (Claudin 18.2 Nanobody 2 IMGT CDR1), a CDR2 comprising SEQ ID NO: 65 (Claudin 18.2 Nanobody 2 IMGT CDR2), and a CDR3 comprising SEQ ID NO: 62 (Claudin 18.2 Nanobody 2 IMGT CDR3). In some embodiments, the CDR sequences of the antigen-binding domain that binds Claudin 18.2 have 100% identity with the CDR sequences of Claudin 18.2 Nanobody 2 (i.e., the antigen-binding domain that binds Claudin 18.2 comprises an amino acid sequence comprising a CDR1, CDR2, and CDR3 each having 100% identity to the corresponding CDR in Claudin 18.2 Nanobody 2). In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 80% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 85% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 90% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 95% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 96% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 97% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 98% sequence identity with the non-CDR (e.g., framework) sequences of Claudin 18.2 Nanobody 2. In some embodiments, the CDR sequences of the antigen-binding domain that binds Claudin 18.2 have 100% identity with the CDR sequences of Claudin 18.2 Nanobody 2, and the non-CDR (e.g., framework) sequences of the antigen-binding domain that binds Claudin 18.2 have at least 99% sequence identity with the non-CDR (e.g., framework) sequences of Claudin 18.2 Nanobody 2.

In some embodiments, the Claudin 18.2 antigen-binding domain is of an antibody selected from IMAB362 (also known as claudiximab and zolbetuximab; having a heavy chain variable region depicted in SEQ ID NO: 48 and a light chain variable region depicted in SEQ ID NO: 49), 43-14A (available from Creative Biolabs, catalog no. HPAB-0120-YJ), EPR 19202 (available from Abcam, catalog no. ab222512), and aGC182. In some embodiments, the Claudin 18.2 antigen-binding domain comprises a humanized antigen-binding domain of an antibody selected from 43-14A and EPR 19202.

In some embodiments, the antigen-binding domain that binds Claudin 18.2 comprises an antigen-binding domain derived from IMAB362 (claudiximab, zolbetuximab). In some embodiments, the antigen-binding domain that binds Claudin 18.2 comprises an amino acid sequence having at least 80% sequence identity with the amino acid sequence of SEQ ID NO: 48 (IMAB362 heavy chain variable region) and an amino acid sequence having at least 80% sequence identity with the amino acid sequence of SEQ ID NO: 49 (IMAB362 light chain variable region). In some embodiments, the antigen-binding domain that binds Claudin 18.2 comprises an amino acid sequence having at least 85% sequence identity with the amino acid sequence of SEQ ID NO: 48 (IMAB362 heavy chain variable region) and an amino acid sequence having at least 85% sequence identity with the amino acid sequence of SEQ ID NO: 49 (IMAB362 light chain variable region). In some embodiments, the antigen-binding domain that binds Claudin 18.2 comprises an amino acid sequence having at least 90% sequence identity with the amino acid sequence of SEQ ID NO: 48 (IMAB362 heavy chain variable region) and an amino acid sequence having at least 90% sequence identity with the amino acid sequence of SEQ ID NO: 49 (IMAB362 light chain variable region). In some embodiments, the antigen-binding domain that binds Claudin 18.2 comprises an amino acid sequence having at least 95% sequence identity with the amino acid sequence of SEQ ID NO: 48 (IMAB362 heavy chain variable region) and an amino acid sequence having at least 95% sequence identity with the amino acid sequence of SEQ ID NO: 49 (IMAB362 light chain variable region). In some embodiments, the antigen-binding domain that binds Claudin 18.2 comprises an amino acid sequence having at least 96% sequence identity with the amino acid sequence of SEQ ID NO: 48 (IMAB362 heavy chain variable region) and an amino acid sequence having at least 96% sequence identity with the amino acid sequence of SEQ ID NO: 49 (IMAB362 light chain variable region). In some embodiments, the antigen-binding domain that binds Claudin 18.2 comprises an amino acid sequence having at least 97% sequence identity with the amino acid sequence of SEQ ID NO: 48 (IMAB362 heavy chain variable region) and an amino acid sequence having at least 97% sequence identity with the amino acid sequence of SEQ ID NO: 49 (IMAB362 light chain variable region). In some embodiments, the antigen-binding domain that binds Claudin 18.2 comprises an amino acid sequence having at least 98% sequence identity with the amino acid sequence of SEQ ID NO: 48 (IMAB362 heavy chain variable region) and an amino acid sequence having at least 98% sequence identity with the amino acid sequence of SEQ ID NO: 49 (IMAB362 light chain variable region). In some embodiments, the antigen-binding domain that binds Claudin 18.2 comprises an amino acid sequence having at least 99% sequence identity with the amino acid sequence of SEQ ID NO: 48 (IMAB362 heavy chain variable region) and an amino acid sequence having at least 99% sequence identity with the amino acid sequence of SEQ ID NO: 49 (IMAB362 light chain variable region). In some embodiments, the antigen-binding domain that binds Claudin 18.2 comprises the amino acid sequence of SEQ ID NO: 48 (IMAB362 heavy chain variable region) and the amino acid sequence of SEQ ID NO: 49 (IMAB362 light chain variable region). In some embodiments, the CDR sequences of the antigen-binding domain that binds Claudin 18.2 have 100% identity with the CDR sequences of IMAB362 (claudiximab, zolbetuximab) (i.e., the antigen-binding domain that binds Claudin 18.2 comprises an amino acid sequence comprising a CDRH1, CDRH2, CDRH3, CDRL1, CDRL2, and CDRL3, each having 100% identity to the corresponding CDR in IMAB362 (claudiximab, zolbetuximab). In some embodiments, the CDR sequences of the antigen-binding domain that binds Claudin 18.2 have 100% identity with the CDR sequences of IMAB362 (claudiximab, zolbetuximab), and the non-CDR (e.g., framework) sequences of the antigen-binding domain that binds Claudin 18.2 have at least 80% sequence identity with the non-CDR (e.g., framework) sequences of IMAB362 (claudiximab, zolbetuximab). In some embodiments, the CDR sequences of the antigen-binding domain that binds Claudin 18.2 have 100% identity with the CDR sequences of IMAB362 (claudiximab, zolbetuximab), and the non-CDR (e.g., framework) sequences of the antigen-binding domain that binds Claudin 18.2 have at least 85% sequence identity with the non-CDR (e.g., framework) sequences of IMAB362 (claudiximab, zolbetuximab). In some embodiments, the CDR sequences of the antigen-binding domain that binds Claudin 18.2 have 100% identity with the CDR sequences of IMAB362 (claudiximab, zolbetuximab), and the non-CDR (e.g., framework) sequences of the antigen-binding domain that binds Claudin 18.2 have at least 90% sequence identity with the non-CDR (e.g., framework) sequences of IMAB362 (claudiximab, zolbetuximab). In some embodiments, the CDR sequences of the antigen-binding domain that binds Claudin 18.2 have 100% identity with the CDR sequences of IMAB362 (claudiximab, zolbetuximab), and the non-CDR (e.g., framework) sequences of the antigen-binding domain that binds Claudin 18.2 have at least 95% sequence identity with the non-CDR (e.g., framework) sequences of IMAB362 (claudiximab, zolbetuximab). In some embodiments, the CDR sequences of the antigen-binding domain that binds Claudin 18.2 have 100% identity with the CDR sequences of IMAB362 (claudiximab, zolbetuximab), and the non-CDR (e.g., framework) sequences of the antigen-binding domain that binds Claudin 18.2 have at least 96% sequence identity with the non-CDR (e.g., framework) sequences of IMAB362 (claudiximab, zolbetuximab). In some embodiments, the CDR sequences of the antigen-binding domain that binds Claudin 18.2 have 100% identity with the CDR sequences of IMAB362 (claudiximab, zolbetuximab), and the non-CDR (e.g., framework) sequences of the antigen-binding domain that binds Claudin 18.2 have at least 97% sequence identity with the non-CDR (e.g., framework) sequences of IMAB362 (claudiximab, zolbetuximab). In some embodiments, the CDR sequences of the antigen-binding domain that binds Claudin 18.2 have 100% identity with the CDR sequences of IMAB362 (claudiximab, zolbetuximab), and the non-CDR (e.g., framework) sequences of the antigen-binding domain that binds Claudin 18.2 have at least 98% sequence identity with the non-CDR (e.g., framework) sequences of IMAB362 (claudiximab, zolbetuximab). In some embodiments, the CDR sequences of the antigen-binding domain that binds Claudin 18.2 have 100% identity with the CDR sequences of IMAB362 (claudiximab, zolbetuximab), and the non-CDR (e.g., framework) sequences of the antigen-binding domain that binds Claudin 18.2 have at least 99% sequence identity with the non-CDR (e.g., framework) sequences of IMAB362 (claudiximab, zolbetuximab).

In some embodiments, the antigen-binding domain that binds Claudin 18.2 comprises an antigen-binding domain derived from mouse anti-Claudin 18.2 recombinant antibody clone 43-14A. In some embodiments, the antigen-binding domain that binds Claudin 18.2 comprises an amino acid sequence having at least 80% sequence identity with the amino acid sequence of the antigen-binding domain(s) of 43-14A. In some embodiments, the antigen-binding domain that binds Claudin 18.2 comprises an amino acid sequence having at least 85% sequence identity with the amino acid sequence of the antigen-binding domain(s) of 43-14A. In some embodiments, the antigen-binding domain that binds Claudin 18.2 comprises an amino acid sequence having at least 90% sequence identity with the amino acid sequence of the antigen-binding domain(s) of 43-14A. In some embodiments, the antigen-binding domain that binds Claudin 18.2 comprises an amino acid sequence having at least 95% sequence identity with the amino acid sequence of the antigen-binding domain(s) of 43-14A. In some embodiments, the antigen-binding domain that binds Claudin 18.2 comprises an amino acid sequence having at least 96% sequence identity with the amino acid sequence of the antigen-binding domain(s) of 43-14A. In some embodiments, the antigen-binding domain that binds Claudin 18.2 comprises an amino acid sequence having at least 97% sequence identity with the amino acid sequence of the antigen-binding domain(s) of 43-14A. In some embodiments, the antigen-binding domain that binds Claudin 18.2 comprises an amino acid sequence having at least 98% sequence identity with the amino acid sequence of the antigen-binding domain(s) of 43-14A. In some embodiments, the antigen-binding domain that binds Claudin 18.2 comprises an amino acid sequence having at least 99% sequence identity with the amino acid sequence of the antigen-binding domain(s) of 43-14A. In some embodiments, the antigen-binding domain that binds Claudin 18.2 comprises the amino acid sequence of the antigen-binding domain(s) of 43-14A. In some embodiments, the CDR sequences of the antigen-binding domain that binds Claudin 18.2 have 100% identity with the CDR sequences of 43-14A (i.e., the antigen-binding domain that binds Claudin 18.2 comprises an amino acid sequence comprising a CDRH1, CDRH2, CDRH3, CDRL1, CDRL2, and CDRL3, each having 100% identity to the corresponding CDR in 43-14A. In some embodiments, the CDR sequences of the antigen-binding domain that binds Claudin 18.2 have 100% identity with the CDR sequences of 43-14A, and the non-CDR (e.g., framework) sequences of the antigen-binding domain that binds Claudin 18.2 have at least 80% sequence identity with the non-CDR (e.g., framework) sequences of 43-14A. In some embodiments, the CDR sequences of the antigen-binding domain that binds Claudin 18.2 have 100% identity with the CDR sequences of 43-14A, and the non-CDR (e.g., framework) sequences of the antigen-binding domain that binds Claudin 18.2 have at least 85% sequence identity with the non-CDR (e.g., framework) sequences of 43-14A. In some embodiments, the CDR sequences of the antigen-binding domain that binds Claudin 18.2 have 100% identity with the CDR sequences of 43-14A, and the non-CDR (e.g., framework) sequences of the antigen-binding domain that binds Claudin 18.2 have at least 90% sequence identity with the non-CDR (e.g., framework) sequences of 43-14A. In some embodiments, the CDR sequences of the antigen-binding domain that binds Claudin 18.2 have 100% identity with the CDR sequences of 43-14A, and the non-CDR (e.g., framework) sequences of the antigen-binding domain that binds Claudin 18.2 have at least 95% sequence identity with the non-CDR (e.g., framework) sequences of 43-14A. In some embodiments, the CDR sequences of the antigen-binding domain that binds Claudin 18.2 have 100% identity with the CDR sequences of 43-14A, and the non-CDR (e.g., framework) sequences of the antigen-binding domain that binds Claudin 18.2 have at least 96% sequence identity with the non-CDR (e.g., framework) sequences of 43-14A. In some embodiments, the CDR sequences of the antigen-binding domain that binds Claudin 18.2 have 100% identity with the CDR sequences of 43-14A, and the non-CDR (e.g., framework) sequences of the antigen-binding domain that binds Claudin 18.2 have at least 97% sequence identity with the non-CDR (e.g., framework) sequences of 43-14A. In some embodiments, the CDR sequences of the antigen-binding domain that binds Claudin 18.2 have 100% identity with the CDR sequences of 43-14A, and the non-CDR (e.g., framework) sequences of the antigen-binding domain that binds Claudin 18.2 have at least 98% sequence identity with the non-CDR (e.g., framework) sequences of 43-14A. In some embodiments, the CDR sequences of the antigen-binding domain that binds Claudin 18.2 have 100% identity with the CDR sequences of 43-14A, and the non-CDR (e.g., framework) sequences of the antigen-binding domain that binds Claudin 18.2 have at least 99% sequence identity with the non-CDR (e.g., framework) sequences of 43-14A.

In some embodiments, the antigen-binding domain that binds Claudin 18.2 comprises an antigen-binding domain derived from rabbit monoclonal antibody to Claudin 18.2 EPR 19202. In some embodiments, the antigen-binding domain that binds Claudin 18.2 comprises an amino acid sequence having at least 80% sequence identity with the amino acid sequence of the antigen-binding domain(s) of EPR 19202. In some embodiments, the antigen-binding domain that binds Claudin 18.2 comprises an amino acid sequence having at least 85% sequence identity with the amino acid sequence of the antigen-binding domain(s) of EPR 19202. In some embodiments, the antigen-binding domain that binds Claudin 18.2 comprises an amino acid sequence having at least 90% sequence identity with the amino acid sequence of the antigen-binding domain(s) of EPR 19202. In some embodiments, the antigen-binding domain that binds Claudin 18.2 comprises an amino acid sequence having at least 95% sequence identity with the amino acid sequence of the antigen-binding domain(s) of EPR 19202. In some embodiments, the antigen-binding domain that binds Claudin 18.2 comprises an amino acid sequence having at least 96% sequence identity with the amino acid sequence of the antigen-binding domain(s) of EPR 19202. In some embodiments, the antigen-binding domain that binds Claudin 18.2 comprises an amino acid sequence having at least 97% sequence identity with the amino acid sequence of the antigen-binding domain(s) of EPR 19202. In some embodiments, the antigen-binding domain that binds Claudin 18.2 comprises an amino acid sequence having at least 98% sequence identity with the amino acid sequence of the antigen-binding domain(s) of EPR 19202. In some embodiments, the antigen-binding domain that binds Claudin 18.2 comprises an amino acid sequence having at least 99% sequence identity with the amino acid sequence of the antigen-binding domain(s) of EPR 19202. In some embodiments, the antigen-binding domain that binds Claudin 18.2 comprises the amino acid sequence of the antigen-binding domain(s) of EPR 19202. In some embodiments, the CDR sequences of the antigen-binding domain that binds Claudin 18.2 have 100% identity with the CDR sequences of EPR 19202 (i.e., the antigen-binding domain that binds Claudin 18.2 comprises an amino acid sequence comprising a CDRH1, CDRH2, CDRH3, CDRL1, CDRL2, and CDRL3, each having 100% identity to the corresponding CDR in EPR 19202. In some embodiments, the CDR sequences of the antigen-binding domain that binds Claudin 18.2 have 100% identity with the CDR sequences of EPR 19202, and the non-CDR (e.g., framework) sequences of the antigen-binding domain that binds Claudin 18.2 have at least 80% sequence identity with the non-CDR (e.g., framework) sequences of EPR 19202. In some embodiments, the CDR sequences of the antigen-binding domain that binds Claudin 18.2 have 100% identity with the CDR sequences of EPR 19202, and the non-CDR (e.g., framework) sequences of the antigen-binding domain that binds Claudin 18.2 have at least 85% sequence identity with the non-CDR (e.g., framework) sequences of EPR 19202. In some embodiments, the CDR sequences of the antigen-binding domain that binds Claudin 18.2 have 100% identity with the CDR sequences of EPR 19202, and the non-CDR (e.g., framework) sequences of the antigen-binding domain that binds Claudin 18.2 have at least 90% sequence identity with the non-CDR (e.g., framework) sequences of EPR 19202. In some embodiments, the CDR sequences of the antigen-binding domain that binds Claudin 18.2 have 100% identity with the CDR sequences of EPR 19202, and the non-CDR (e.g., framework) sequences of the antigen-binding domain that binds Claudin 18.2 have at least 95% sequence identity with the non-CDR (e.g., framework) sequences of EPR 19202. In some embodiments, the CDR sequences of the antigen-binding domain that binds Claudin 18.2 have 100% identity with the CDR sequences of EPR 19202, and the non-CDR (e.g., framework) sequences of the antigen-binding domain that binds Claudin 18.2 have at least 96% sequence identity with the non-CDR (e.g., framework) sequences of EPR 19202. In some embodiments, the CDR sequences of the antigen-binding domain that binds Claudin 18.2 have 100% identity with the CDR sequences of EPR 19202, and the non-CDR (e.g., framework) sequences of the antigen-binding domain that binds Claudin 18.2 have at least 97% sequence identity with the non-CDR (e.g., framework) sequences of EPR 19202. In some embodiments, the CDR sequences of the antigen-binding domain that binds Claudin 18.2 have 100% identity with the CDR sequences of EPR 19202, and the non-CDR (e.g., framework) sequences of the antigen-binding domain that binds Claudin 18.2 have at least 98% sequence identity with the non-CDR (e.g., framework) sequences of EPR 19202. In some embodiments, the CDR sequences of the antigen-binding domain that binds Claudin 18.2 have 100% identity with the CDR sequences of EPR 19202, and the non-CDR (e.g., framework) sequences of the antigen-binding domain that binds Claudin 18.2 have at least 99% sequence identity with the non-CDR (e.g., framework) sequences of EPR 19202.

In some embodiments, the antigen-binding domain that binds Claudin 18.2 comprises an antigen-binding domain derived from monoclonal mouse anti-Claudin 18.2 antibody aGC182. In some embodiments, the antigen-binding domain that binds Claudin 18.2 comprises an amino acid sequence having at least 80% sequence identity with the amino acid sequence of the antigen-binding domain(s) of aGC182. In some embodiments, the antigen-binding domain that binds Claudin 18.2 comprises an amino acid sequence having at least 85% sequence identity with the amino acid sequence of the antigen-binding domain(s) of aGC182. In some embodiments, the antigen-binding domain that binds Claudin 18.2 comprises an amino acid sequence having at least 90% sequence identity with the amino acid sequence of the antigen-binding domain(s) of aGC182. In some embodiments, the antigen-binding domain that binds Claudin 18.2 comprises an amino acid sequence having at least 95% sequence identity with the amino acid sequence of the antigen-binding domain(s) of aGC182. In some embodiments, the antigen-binding domain that binds Claudin 18.2 comprises an amino acid sequence having at least 96% sequence identity with the amino acid sequence of the antigen-binding domain(s) of aGC182. In some embodiments, the antigen-binding domain that binds Claudin 18.2 comprises an amino acid sequence having at least 97% sequence identity with the amino acid sequence of the antigen-binding domain(s) of aGC182. In some embodiments, the antigen-binding domain that binds Claudin 18.2 comprises an amino acid sequence having at least 98% sequence identity with the amino acid sequence of the antigen-binding domain(s) of aGC182. In some embodiments, the antigen-binding domain that binds Claudin 18.2 comprises an amino acid sequence having at least 99% sequence identity with the amino acid sequence of the antigen-binding domain(s) of aGC182. In some embodiments, the antigen-binding domain that binds Claudin 18.2 comprises the amino acid sequence of the antigen-binding domain(s) of aGC182. In some embodiments, the CDR sequences of the antigen-binding domain that binds Claudin 18.2 have 100% identity with the CDR sequences of aGC182 (i.e., the antigen-binding domain that binds Claudin 18.2 comprises an amino acid sequence comprising a CDRH1, CDRH2, CDRH3, CDRL1, CDRL2, and CDRL3, each having 100% identity to the corresponding CDR in aGC182. In some embodiments, the CDR sequences of the antigen-binding domain that binds Claudin 18.2 have 100% identity with the CDR sequences of aGC182, and the non-CDR (e.g., framework) sequences of the antigen-binding domain that binds Claudin 18.2 have at least 80% sequence identity with the non-CDR (e.g., framework) sequences of aGC182. In some embodiments, the CDR sequences of the antigen-binding domain that binds Claudin 18.2 have 100% identity with the CDR sequences of aGC182, and the non-CDR (e.g., framework) sequences of the antigen-binding domain that binds Claudin 18.2 have at least 85% sequence identity with the non-CDR (e.g., framework) sequences of aGC182. In some embodiments, the CDR sequences of the antigen-binding domain that binds Claudin 18.2 have 100% identity with the CDR sequences of aGC182, and the non-CDR (e.g., framework) sequences of the antigen-binding domain that binds Claudin 18.2 have at least 90% sequence identity with the non-CDR (e.g., framework) sequences of aGC182. In some embodiments, the CDR sequences of the antigen-binding domain that binds Claudin 18.2 have 100% identity with the CDR sequences of aGC182, and the non-CDR (e.g., framework) sequences of the antigen-binding domain that binds Claudin 18.2 have at least 95% sequence identity with the non-CDR (e.g., framework) sequences of aGC182. In some embodiments, the CDR sequences of the antigen-binding domain that binds Claudin 18.2 have 100% identity with the CDR sequences of aGC182, and the non-CDR (e.g., framework) sequences of the antigen-binding domain that binds Claudin 18.2 have at least 96% sequence identity with the non-CDR (e.g., framework) sequences of aGC182. In some embodiments, the CDR sequences of the antigen-binding domain that binds Claudin 18.2 have 100% identity with the CDR sequences of aGC182, and the non-CDR (e.g., framework) sequences of the antigen-binding domain that binds Claudin 18.2 have at least 97% sequence identity with the non-CDR (e.g., framework) sequences of aGC182. In some embodiments, the CDR sequences of the antigen-binding domain that binds Claudin 18.2 have 100% identity with the CDR sequences of aGC182, and the non-CDR (e.g., framework) sequences of the antigen-binding domain that binds Claudin 18.2 have at least 98% sequence identity with the non-CDR (e.g., framework) sequences of aGC182. In some embodiments, the CDR sequences of the antigen-binding domain that binds Claudin 18.2 have 100% identity with the CDR sequences of aGC182, and the non-CDR (e.g., framework) sequences of the antigen-binding domain that binds Claudin 18.2 have at least 99% sequence identity with the non-CDR (e.g., framework) sequences of aGC182.

Amino acid sequences of exemplary antigen-binding domains that bind Claudin 18.2 are provided in Table 1.

TABLE 1

Table of Sequences

| SEQ ID NO | Description | Nucleotide/ Amino Acid |
|---|---|---|
| SEQ ID NO: 48 | IMAB362 Heavy Chain Variable Region | Amino Acid |
| SEQ ID NO: 49 | IMAB362 Light Chain Variable Region | Amino Acid |
| SEQ ID NO: 55 | Claudin 18.2 Nanobody 1 | Amino Acid |
| SEQ ID NO: 56 | Claudin 18.2 Nanobody 2 | Amino Acid |
| SEQ ID NO: 57 | Claudin 18.2 Nanobody 1 CDR1 (Kabat); Claudin 18.2 Nanobody 2 CDR1 (Kabat) | Amino Acid |
| SEQ ID NO: 58 | Claudin 18.2 Nanobody 1 CDR2 (Kabat) | Amino Acid |
| SEQ ID NO: 59 | Claudin 18.2 Nanobody 1 CDR3 (Kabat); Claudin 18.2 Nanobody 2 CDR3 (Kabat) | Amino Acid |
| SEQ ID NO: 60 | Claudin 18.2 Nanobody 1 CDR1 (IMGT) | Amino Acid |
| SEQ ID NO: 61 | Claudin 18.2 Nanobody 1 CDR2 (IMGT) | Amino Acid |
| SEQ ID NO: 62 | Claudin 18.2 Nanobody 1 CDR3 (IMGT); Claudin 18.2 Nanobody 2 CDR3 (IMGT) | Amino Acid |
| SEQ ID NO: 63 | Claudin 18.2 Nanobody 2 CDR2 (Kabat) | Amino Acid |
| SEQ ID NO: 64 | Claudin 18.2 Nanobody 2 CDR1 (IMGT) | Amino Acid |
| SEQ ID NO: 65 | Claudin 18.2 Nanobody 2 CDR2 (IMGT) | Amino Acid |

TCR Complex Protein Antigen-Binding Domain

In certain embodiments, the Claudin 18.2-TAC comprises an antigen-binding domain that binds a protein associated with the TCR complex. A "TCR complex protein antigen-binding domain," also referred to as a "TCR complex antigen-binding domain," "antigen-binding domain that binds the TCR complex," or "antigen-binding domain that binds a protein associated with the TCR complex," refers to any substance or molecule that binds, directly or indirectly, to a protein associated with a TCR complex. In some embodiments, the antigen-binding domain that binds a protein associated with a TCR complex selectively binds to a protein of the TCR. In some embodiments, the antigen-binding domain that binds a protein associated with a TCR complex comprises a substance that specifically binds to a protein of the TCR.

In some embodiments, the TCR complex protein antigen-binding domain is selected from antibodies or fragments thereof, for example, single chain antibodies (e.g., single-chain fragment variable antibodies (scFvs)), single domain antibodies (e.g., heavy-chain-only antibodies (VHH), shark heavy-chain-only antibodies (VNAR)), nanobodies, diabodies, minibodies, Fab fragments, Fab' fragments, F(ab')2 fragments, or Fv fragments that bind to a protein of the TCR. In some embodiments, the TCR complex protein antigen-binding domain is selected from ankyrin repeat proteins (DARPins), affibodies, adnectins, affilins, phylomers; fynomers, affimers, peptide aptamers, lectins, knottins, centyrins, anticalins, peptides, peptidomimetics, proteins, glycoproteins, or proteoglycans that bind to a protein of the TCR, or naturally occurring ligands for a protein of the TCR. In some embodiments, the TCR complex protein antigen-binding domain is a non-protein compound that binds to a protein of the TCR, including but not limited to carbohydrates, lipids, nucleic acids, or small molecules. In some embodiments, the TCR complex protein antigen-binding domain is a designed ankyrin repeat (DARPin) targeted to a protein of the TCR. In some embodiments, the TCR complex protein antigen-binding domain is a single-chain variable fragment (ScFv) targeted to a protein of the TCR. In some embodiments, the TCR complex protein antigen-binding domain is a nanobody targeted to a protein of the TCR.

Proteins associated with the TCR include, but are not limited to, the TCR alpha (α) chain, TCR beta (β) chain, TCR gamma (γ) chain, TCR delta (δ) chain, CD3γ chain, CD3δ chain and CD3ε chains. In some embodiments, an antigen-binding domain that binds a protein associated with the TCR complex is an antibody to the TCR alpha (α) chain, TCR beta (β) chain, TCR gamma (γ) chain, TCR delta (δ) chain, CD3γ chain, CD3δ chain and/or CD3ε chain. In some embodiments, the protein associated with a TCR complex is CD3. In some embodiments, the protein associated with a TCR complex is CD3ε. In some embodiments, the antigen-binding domain that binds CD3 is an antibody, for example, a single chain antibody, for example a single-chain variable fragment (scFv). Examples of CD3 antibodies, include, but are not limited to, UCHT1, OKT3, F6A, L2K, muromonab, otelixizumab, teplizumab, visilizumab, CD3-12, MEM-57, 4D10A6, CD3D, or TR66.

In some embodiments, the antigen-binding domain that binds the TCR complex is UCHT1, or a variant thereof. In some embodiments, the UCHT1 antigen-binding domain is encoded by SEQ ID NO: 7. In some embodiments, the UCHT1 antigen-binding domain comprises SEQ ID NO: 8. In some embodiments, the UCHT1 antigen-binding domain is mutated. In some embodiments, the UCHT1 antigen-binding domain comprises a Y to T mutation at a position corresponding to amino acid 182 of SEQ ID NO: 8 (Y182T). In some embodiments, the UCHT1 (Y182T) antigen-binding domain is encoded by SEQ ID NO: 43. In some embodiments, the UCHT1 (Y182T) antigen-binding domain comprises SEQ ID NO: 44. In some embodiments, the antigen-binding domain that binds the TCR complex is a humanized UCHT1 (huUCHT1). In some embodiments, the huUCHT1 antigen-binding domain is encoded by SEQ ID NO: 33. In some embodiments, the huUCHT1 antigen-binding domain comprises SEQ ID NO: 34. In some embodiments, the huUCHT1 has a Y to T mutation at a position corresponding to amino acid 177 of SEQ ID NO: 34 (Y177T). In some embodiments, the huUCHT1 (Y177T) antigen-binding domain is encoded by SEQ ID NO: 35. In some embodiments, the huUCHT1 antigen-binding domain comprises SEQ ID NO: 36.

In some embodiments, the polynucleotide encoding the antigen-binding domain that binds the protein associated with the TCR complex comprises a nucleotide sequence having at least 70% sequence identity with the nucleotide sequence of SEQ ID NO: 7 (UCHT1). In some embodiments, the polynucleotide encoding the antigen-binding domain that binds the protein associated with the TCR complex comprises a nucleotide sequence having at least 75% sequence identity with the nucleotide sequence of SEQ ID NO: 7 (UCHT1). In some embodiments, the polynucleotide encoding the antigen-binding domain that binds the protein associated with the TCR complex comprises a nucleotide sequence having at least 80% sequence identity with the nucleotide sequence of SEQ ID NO: 7 (UCHT1). In some embodiments, the polynucleotide encoding the antigen-binding domain that binds the protein associated with the TCR complex comprises a nucleotide sequence having at least 85% sequence identity with the nucleotide sequence of SEQ ID NO: 7 (UCHT1). In some embodiments, the polynucleotide encoding the antigen-binding domain that binds the protein associated with the TCR complex comprises a nucleotide sequence having at least 90% sequence identity with the nucleotide sequence of SEQ ID NO: 7 (UCHT1). In some embodiments, the polynucleotide encoding the antigen-binding domain that binds the protein associated with the TCR complex comprises a nucleotide sequence having at least 95% sequence identity with the nucleotide sequence of SEQ ID NO: 7 (UCHT1). In some embodiments, the polynucleotide encoding the antigen-binding domain that binds the protein associated with the TCR complex comprises a nucleotide sequence having at least 96% sequence identity with the nucleotide sequence of SEQ ID NO: 7 (UCHT1). In some embodiments, the polynucleotide encoding the antigen-binding domain that binds the protein associated with the TCR complex comprises a nucleotide sequence having at least 97% sequence identity with the nucleotide sequence of SEQ ID NO: 7 (UCHT1). In some embodiments, the polynucleotide encoding the antigen-binding domain that binds the protein associated with the TCR complex comprises a nucleotide sequence having at least 98% sequence identity with the nucleotide sequence of SEQ ID NO: 7 (UCHT1). In some embodiments, the polynucleotide encoding the antigen-binding domain that binds the protein associated with the TCR complex comprises a nucleotide sequence having at least 99% sequence identity with the nucleotide sequence of SEQ ID NO: 7 (UCHT1). In some embodiments, the polynucleotide encoding the antigen-binding domain that binds the protein associated with the TCR complex comprises the nucleotide sequence of SEQ ID NO: 7 (UCHT1).

In some embodiments, the antigen-binding domain that binds the protein associated with the TCR complex comprises an amino acid sequence having at least 70% sequence identity with the amino acid sequence of SEQ ID NO: 8 (UCHT1). In some embodiments, the antigen-binding domain that binds the protein associated with the TCR complex comprises an amino acid sequence having at least 75% sequence identity with the amino acid sequence of SEQ ID NO: 8 (UCHT1). In some embodiments, the antigen-binding domain that binds the protein associated with the TCR complex comprises an amino acid sequence having at least 80% sequence identity with the amino acid sequence of SEQ ID NO: 8 (UCHT1). In some embodiments, the antigen-binding domain that binds the protein associated with the TCR complex comprises an amino acid sequence having at least 85% sequence identity with the amino acid sequence of SEQ ID NO: 8 (UCHT1). In some embodiments, the antigen-binding domain that binds the protein associated with the TCR complex comprises an amino acid sequence having at least 90% sequence identity with the amino acid sequence of SEQ ID NO: 8 (UCHT1). In some embodiments, the antigen-binding domain that binds the protein associated with the TCR complex comprises an amino acid sequence having at least 95% sequence identity with the amino acid sequence of SEQ ID NO: 8 (UCHT1). In some embodiments, the antigen-binding domain that binds the protein associated with the TCR complex comprises an amino acid sequence having at least 96% sequence identity with the amino acid sequence of SEQ ID NO: 8 (UCHT1). In some embodiments, the antigen-binding domain that binds the protein associated with the TCR complex comprises an amino acid sequence having at least 97% sequence identity with the amino acid sequence of SEQ ID NO: 8 (UCHT1). In some embodiments, the antigen-binding domain that binds the protein associated with the TCR complex comprises an amino acid sequence having at least 98% sequence identity with the amino acid sequence of SEQ ID NO: 8 (UCHT1). In some embodiments, the antigen-binding domain that binds the protein associated with the TCR complex comprises an amino acid sequence having at least 99% sequence identity with the amino acid sequence of SEQ ID NO: 8 (UCHT1). In some embodiments, the antigen-binding domain that binds the protein associated with the TCR complex comprises the amino acid sequence of SEQ ID NO: 8 (UCHT1). In some embodiments, the CDR sequences of the antigen-binding domain that binds the protein associated with the TCR complex have 100% identity with the CDR sequences of the amino acid sequence of SEQ ID NO: 8 (UCHT1) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 8 (UCHT1). In some embodiments, the CDR sequences of the antigen-binding domain that binds the protein associated with the TCR complex have 100% identity with the CDR sequences of the amino acid sequence of SEQ ID NO: 8 (UCHT1), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 8 (UCHT1). In some embodiments, the CDR sequences of the antigen-binding domain that binds the protein associated with the TCR complex have 100% identity with the CDR sequences of the amino acid sequence of SEQ ID NO: 8 (UCHT1), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 8 (UCHT1). In some embodiments, the CDR sequences of the antigen-binding domain that binds the protein associated with the TCR complex have 100% identity with the CDR sequences of the amino acid sequence of SEQ ID NO: 8 (UCHT1), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 8 (UCHT1). In some embodiments, the CDR sequences of the antigen-binding domain that binds the protein associated with the TCR complex have 100% identity with the CDR sequences of the amino acid sequence of SEQ ID NO: 8 (UCHT1), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 8 (UCHT1). In some embodiments, the CDR sequences of the antigen-binding domain that binds the protein associated with the TCR complex have 100% identity with the CDR sequences of the amino acid sequence of SEQ ID NO: 8 (UCHT1), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 8 (UCHT1). In some embodiments, the CDR sequences of the antigen-binding domain that binds the protein associated with the TCR complex have 100% identity with the CDR sequences of the amino acid sequence of SEQ ID NO: 8 (UCHT1), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 8 (UCHT1). In some embodiments, the CDR sequences of the antigen-binding domain that binds the protein associated with the TCR complex have 100% identity with the CDR sequences of the amino acid sequence of SEQ ID NO: 8 (UCHT1), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 8 (UCHT1). In some embodiments, the CDR sequences of the antigen-binding domain that binds the protein associated with the TCR complex have 100% identity with the CDR sequences of the amino acid sequence of SEQ ID NO: 8 (UCHT1), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 8 (UCHT1).

In some embodiments, the polynucleotide encoding the antigen-binding domain that binds the protein associated with the TCR complex comprises a nucleotide sequence having at least 70% sequence identity with the nucleotide sequence of SEQ ID NO: 43 (UCHT1 (Y182T)). In some embodiments, the polynucleotide encoding the antigen-binding domain that binds the protein associated with the TCR complex comprises a nucleotide sequence having at least 75% sequence identity with the nucleotide sequence of SEQ ID NO: 43 (UCHT1 (Y182T)). In some embodiments, the polynucleotide encoding the antigen-binding domain that binds the protein associated with the TCR complex comprises a nucleotide sequence having at least 80% sequence identity with the nucleotide sequence of SEQ ID NO: 43 (UCHT1 (Y182T)). In some embodiments, the polynucleotide encoding the antigen-binding domain that binds the protein associated with the TCR complex comprises a nucleotide sequence having at least 85% sequence identity with the nucleotide sequence of SEQ ID NO: 43 (UCHT1 (Y182T)). In some embodiments, the polynucleotide encoding the antigen-binding domain that binds the protein associated with the TCR complex comprises a nucleotide sequence having at least 90% sequence identity with the nucleotide sequence of SEQ ID NO: 43 (UCHT1 (Y182T)). In some embodiments, the polynucleotide encoding the antigen-binding domain that binds the protein associated with the TCR complex comprises a nucleotide sequence having at least 95% sequence identity with the nucleotide sequence of SEQ ID NO: 43 (UCHT1 (Y182T)). In some embodiments, the polynucleotide encoding the antigen-binding domain that binds the protein associated with the TCR complex comprises a nucleotide sequence having at least 96% sequence identity with the nucleotide sequence of SEQ ID NO: 43 (UCHT1 (Y182T)). In some embodiments, the polynucleotide encoding the antigen-binding domain that binds the protein associated with the TCR complex comprises a nucleotide sequence having at least 97% sequence identity with the nucleotide sequence of SEQ ID NO: 43 (UCHT1 (Y182T)). In some embodiments, the polynucleotide encoding the antigen-binding domain that binds the protein associated with the TCR complex comprises a nucleotide sequence having at least 98% sequence identity with the nucleotide sequence of SEQ ID NO: 43 (UCHT1 (Y182T)). In some embodiments, the polynucleotide encoding the antigen-binding domain that binds the protein associated with the TCR complex comprises a nucleotide sequence having at least 99% sequence identity with the nucleotide sequence of SEQ ID NO: 43 (UCHT1 (Y182T)). In some embodiments, the polynucleotide encoding the antigen-binding domain that binds the protein associated with the TCR complex comprises the nucleotide sequence of SEQ ID NO: 43 (UCHT1 (Y182T)).

In some embodiments, the antigen-binding domain that binds the protein associated with the TCR complex comprises an amino acid sequence having at least 70% sequence identity with the amino acid sequence of SEQ ID NO: 44 (UCHT1 (Y182T)). In some embodiments, the antigen-binding domain that binds the protein associated with the TCR complex comprises an amino acid sequence having at least 75% sequence identity with the amino acid sequence of SEQ ID NO: 44 (UCHT1 (Y182T)). In some embodiments, the antigen-binding domain that binds the protein associated with the TCR complex comprises an amino acid sequence having at least 80% sequence identity with the amino acid sequence of SEQ ID NO: 44 (UCHT1 (Y182T)). In some embodiments, the antigen-binding domain that binds the protein associated with the TCR complex comprises an amino acid sequence having at least 85% sequence identity with the amino acid sequence of SEQ ID NO: 44 (UCHT1 (Y182T)). In some embodiments, the antigen-binding domain that binds the protein associated with the TCR complex comprises an amino acid sequence having at least 90% sequence identity with the amino acid sequence of SEQ ID NO: 44 (UCHT1 (Y182T)). In some embodiments, the antigen-binding domain that binds the protein associated with the TCR complex comprises an amino acid sequence having at least 95% sequence identity with the amino acid sequence of SEQ ID NO: 44 (UCHT1 (Y182T)). In some embodiments, the antigen-binding domain that binds the protein associated with the TCR complex comprises an amino acid sequence having at least 96% sequence identity with the amino acid sequence of SEQ ID NO: 44 (UCHT1 (Y182T)). In some embodiments, the antigen-binding domain that binds the protein associated with the TCR complex comprises an amino acid sequence having at least 97% sequence identity with the amino acid sequence of SEQ ID NO: 44 (UCHT1 (Y182T)). In some embodiments, the antigen-binding domain that binds the protein associated with the TCR complex comprises an amino acid sequence having at least 98% sequence identity with the amino acid sequence of SEQ ID NO: 44 (UCHT1 (Y182T)). In some embodiments, the antigen-binding domain that binds the protein associated with the TCR complex comprises an amino acid sequence having at least 99% sequence identity with the amino acid sequence of SEQ ID NO: 44 (UCHT1 (Y182T)). In some embodiments, the antigen-binding domain that binds the protein associated with the TCR complex comprises the amino acid sequence of SEQ ID NO: 44 (UCHT1 (Y182T)). In some embodiments, the CDR sequences of the antigen-binding domain that binds the protein associated with the TCR complex have 100% identity with the CDR sequences of the amino acid sequence of SEQ ID NO: 44 (UCHT1 (Y182T)) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 44 (UCHT1 (Y182T)). In some embodiments, the CDR sequences of the antigen-binding domain that binds the protein associated with the TCR complex have 100% identity with the CDR sequences of the amino acid sequence of SEQ ID NO: 44 (UCHT1 (Y182T)), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 44 (UCHT1 (Y182T)). In some embodiments, the CDR sequences of the antigen-binding domain that binds the protein associated with the TCR complex have 100% identity with the CDR sequences of the amino acid sequence of SEQ ID NO: 44 (UCHT1 (Y182T)), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 44 (UCHT1 (Y182T)). In some embodiments, the CDR sequences of the antigen-binding domain that binds the protein associated with the TCR complex have 100% identity with the CDR sequences of the amino acid sequence of SEQ ID NO: 44 (UCHT1 (Y182T)), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 44 (UCHT1 (Y182T)). In some embodiments, the CDR sequences of the antigen-binding domain that binds the protein associated with the TCR complex have 100% identity with the CDR sequences of the amino acid sequence of SEQ ID NO: 44 (UCHT1 (Y182T)), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 44 (UCHT1 (Y182T)). In some embodiments, the CDR sequences of the antigen-binding domain that binds the protein associated with the TCR complex have 100% identity with the CDR sequences of the amino acid sequence of SEQ ID NO: 44 (UCHT1 (Y182T)), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 44 (UCHT1 (Y182T)). In some embodiments, the CDR sequences of the antigen-binding domain that binds the protein associated with the TCR complex have 100% identity with the CDR sequences of the amino acid sequence of SEQ ID NO: 44 (UCHT1 (Y182T)), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 44 (UCHT1 (Y182T)). In some embodiments, the CDR sequences of the antigen-binding domain that binds the protein associated with the TCR complex have 100% identity with the CDR sequences of the amino acid sequence of SEQ ID NO: 44 (UCHT1 (Y182T)), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 44 (UCHT1 (Y182T)). In some embodiments, the CDR sequences of the antigen-binding domain that binds the protein associated with the TCR complex have 100% identity with the CDR sequences of the amino acid sequence of SEQ ID NO: 44 (UCHT1 (Y182T)), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 44 (UCHT1 (Y182T)).

In some embodiments, the polynucleotide encoding the antigen-binding domain that binds the protein associated with the TCR complex comprises a nucleotide sequence having at least 70% sequence identity with the nucleotide sequence of SEQ ID NO: 33 (huUCHT1). In some embodiments, the polynucleotide encoding the antigen-binding domain that binds the protein associated with the TCR complex comprises a nucleotide sequence having at least 75% sequence identity with the nucleotide sequence of SEQ ID NO: 33 (huUCHT1). In some embodiments, the polynucleotide encoding the antigen-binding domain that binds the protein associated with the TCR complex comprises a nucleotide sequence having at least 80% sequence identity with the nucleotide sequence of SEQ ID NO: 33 (huUCHT1). In some embodiments, the polynucleotide encoding the antigen-binding domain that binds the protein associated with the TCR complex comprises a nucleotide sequence having at least 85% sequence identity with the nucleotide sequence of SEQ ID NO: 33 (huUCHT1). In some embodiments, the polynucleotide encoding the antigen-binding domain that binds the protein associated with the TCR complex comprises a nucleotide sequence having at least 90% sequence identity with the nucleotide sequence of SEQ ID NO: 33 (huUCHT1). In some embodiments, the polynucleotide encoding the antigen-binding domain that binds the protein associated with the TCR complex comprises a nucleotide sequence having at least 95% sequence identity with the nucleotide sequence of SEQ ID NO: 33 (huUCHT1). In some embodiments, the polynucleotide encoding the antigen-binding domain that binds the protein associated with the TCR complex comprises a nucleotide sequence having at least 96% sequence identity with the nucleotide sequence of SEQ ID NO: 33 (huUCHT1). In some embodiments, the polynucleotide encoding the antigen-binding domain that binds the protein associated with the TCR complex comprises a nucleotide sequence having at least 97% sequence identity with the nucleotide sequence of SEQ ID NO: 33 (huUCHT1). In some embodiments, the polynucleotide encoding the antigen-binding domain that binds the protein associated with the TCR complex comprises a nucleotide sequence having at least 98% sequence identity with the nucleotide sequence of SEQ ID NO: 33 (huUCHT1). In some embodiments, the polynucleotide encoding the antigen-binding domain that binds the protein associated with the TCR complex comprises a nucleotide sequence having at least 99% sequence identity with the nucleotide sequence of SEQ ID NO: 33 (huUCHT1). In some embodiments, the polynucleotide encoding the antigen-binding domain that binds the protein associated with the TCR complex comprises the nucleotide sequence of SEQ ID NO: 33 (huUCHT1).

In some embodiments, the antigen-binding domain that binds the protein associated with the TCR complex comprises an amino acid sequence having at least 70% sequence identity with the amino acid sequence of SEQ ID NO: 34 (huUCHT1). In some embodiments, the antigen-binding domain that binds the protein associated with the TCR complex comprises an amino acid sequence having at least 75% sequence identity with the amino acid sequence of SEQ ID NO: 34 (huUCHT1). In some embodiments, the antigen-binding domain that binds the protein associated with the TCR complex comprises an amino acid sequence having at least 80% sequence identity with the amino acid sequence of SEQ ID NO: 34 (huUCHT1). In some embodiments, the antigen-binding domain that binds the protein associated with the TCR complex comprises an amino acid sequence having at least 85% sequence identity with the amino acid sequence of SEQ ID NO: 34 (huUCHT1). In some embodiments, the antigen-binding domain that binds the protein associated with the TCR complex comprises an amino acid sequence having at least 90% sequence identity with the amino acid sequence of SEQ ID NO: 34 (huUCHT1). In some embodiments, the antigen-binding domain that binds the protein associated with the TCR complex comprises an amino acid sequence having at least 95% sequence identity with the amino acid sequence of SEQ ID NO: 34 (huUCHT1). In some embodiments, the antigen-binding domain that binds the protein associated with the TCR complex comprises an amino acid sequence having at least 96% sequence identity with the amino acid sequence of SEQ ID NO: 34 (huUCHT1). In some embodiments, the antigen-binding domain that binds the protein associated with the TCR complex comprises an amino acid sequence having at least 97% sequence identity with the amino acid sequence of SEQ ID NO: 34 (huUCHT1). In some embodiments, the antigen-binding domain that binds the protein associated with the TCR complex comprises an amino acid sequence having at least 98% sequence identity with the amino acid sequence of SEQ ID NO: 34 (huUCHT1). In some embodiments, the antigen-binding domain that binds the protein associated with the TCR complex comprises an amino acid sequence having at least 99% sequence identity with the amino acid sequence of SEQ ID NO: 34 (huUCHT1). In some embodiments, the antigen-binding domain that binds the protein associated with the TCR complex comprises the amino acid sequence of SEQ ID NO: 34 (huUCHT1). In some embodiments, the CDR sequences of the antigen-binding domain that binds the protein associated with the TCR complex have 100% identity with the CDR sequences of the amino acid sequence of SEQ ID NO: 34 (huUCHT1) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 34 (huUCHT1). In some embodiments, the CDR sequences of the antigen-binding domain that binds the protein associated with the TCR complex have 100% identity with the CDR sequences of the amino acid sequence of SEQ ID NO: 34 (huUCHT1), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 34 (huUCHT1). In some embodiments, the CDR sequences of the antigen-binding domain that binds the protein associated with the TCR complex have 100% identity with the CDR sequences of the amino acid sequence of SEQ ID NO: 34 (huUCHT1), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 34 (huUCHT1). In some embodiments, the CDR sequences of the antigen-binding domain that binds the protein associated with the TCR complex have 100% identity with the CDR sequences of the amino acid sequence of SEQ ID NO: 34 (huUCHT1), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 34 (huUCHT1). In some embodiments, the CDR sequences of the antigen-binding domain that binds the protein associated with the TCR complex have 100% identity with the CDR sequences of the amino acid sequence of SEQ ID NO: 34 (huUCHT1), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 34 (huUCHT1). In some embodiments, the CDR sequences of the antigen-binding domain that binds the protein associated with the TCR complex have 100% identity with the CDR sequences of the amino acid sequence of SEQ ID NO: 34 (huUCHT1), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 34 (huUCHT1). In some embodiments, the CDR sequences of the antigen-binding domain that binds the protein associated with the TCR complex have 100% identity with the CDR sequences of the amino acid sequence of SEQ ID NO: 34 (huUCHT1), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 34 (huUCHT1). In some embodiments, the CDR sequences of the antigen-binding domain that binds the protein associated with the TCR complex have 100% identity with the CDR sequences of the amino acid sequence of SEQ ID NO: 34 (huUCHT1), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 34 (huUCHT1). In some embodiments, the CDR sequences of the antigen-binding domain that binds the protein associated with the TCR complex have 100% identity with the CDR sequences of the amino acid sequence of SEQ ID NO: 34 (huUCHT1), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 34 (huUCHT1).

In some embodiments, the polynucleotide encoding the antigen-binding domain that binds the protein associated with the TCR complex comprises a nucleotide sequence having at least 70% sequence identity with the nucleotide sequence of SEQ ID NO: 35 (huUCHT1 (Y177T)). In some embodiments, the polynucleotide encoding the antigen-binding domain that binds the protein associated with the TCR complex comprises a nucleotide sequence having at least 75% sequence identity with the nucleotide sequence of SEQ ID NO: 35 (huUCHT1 (Y177T)). In some embodiments, the polynucleotide encoding the antigen-binding domain that binds the protein associated with the TCR complex comprises a nucleotide sequence having at least 80% sequence identity with the nucleotide sequence of SEQ ID NO: 35 (huUCHT1 (Y177T)). In some embodiments, the polynucleotide encoding the antigen-binding domain that binds the protein associated with the TCR complex comprises a nucleotide sequence having at least 85% sequence identity with the nucleotide sequence of SEQ ID NO: 35 (huUCHT1 (Y177T)). In some embodiments, the polynucleotide encoding the antigen-binding domain that binds the protein associated with the TCR complex comprises a nucleotide sequence having at least 90% sequence identity with the nucleotide sequence of SEQ ID NO: 35 (huUCHT1 (Y177T)). In some embodiments, the polynucleotide encoding the antigen-binding domain that binds the protein associated with the TCR complex comprises a nucleotide sequence having at least 95% sequence identity with the nucleotide sequence of SEQ ID NO: 35 (huUCHT1 (Y177T)). In some embodiments, the polynucleotide encoding the antigen-binding domain that binds the protein associated with the TCR complex comprises a nucleotide sequence having at least 96% sequence identity with the nucleotide sequence of SEQ ID NO: 35 (huUCHT1 (Y177T)). In some embodiments, the polynucleotide encoding the antigen-binding domain that binds the protein associated with the TCR complex comprises a nucleotide sequence having at least 97% sequence identity with the nucleotide sequence of SEQ ID NO: 35 (huUCHT1 (Y177T)). In some embodiments, the polynucleotide encoding the antigen-binding domain that binds the protein associated with the TCR complex comprises a nucleotide sequence having at least 98% sequence identity with the nucleotide sequence of SEQ ID NO: 35 (huUCHT1 (Y177T)). In some embodiments, the polynucleotide encoding the antigen-binding domain that binds the protein associated with the TCR complex comprises a nucleotide sequence having at least 99% sequence identity with the nucleotide sequence of SEQ ID NO: 35 (huUCHT1 (Y177T)). In some embodiments, the polynucleotide encoding the antigen-binding domain that binds the protein associated with the TCR complex comprises the nucleotide sequence of SEQ ID NO: 35 (huUCHT1 (Y177T)).

In some embodiments, the antigen-binding domain that binds the protein associated with the TCR complex comprises an amino acid sequence having at least 70% sequence identity with the amino acid sequence of SEQ ID NO: 36 (huUCHT1 (Y177T)). In some embodiments, the antigen-binding domain that binds the protein associated with the TCR complex comprises an amino acid sequence having at least 75% sequence identity with the amino acid sequence of SEQ ID NO: 36 (huUCHT1 (Y177T)). In some embodiments, the antigen-binding domain that binds the protein associated with the TCR complex comprises an amino acid sequence having at least 80% sequence identity with the amino acid sequence of SEQ ID NO: 36 (huUCHT1 (Y177T)). In some embodiments, the antigen-binding domain that binds the protein associated with the TCR complex comprises an amino acid sequence having at least 85% sequence identity with the amino acid sequence of SEQ ID NO: 36 (huUCHT1 (Y177T)). In some embodiments, the antigen-binding domain that binds the protein associated with the TCR complex comprises an amino acid sequence having at least 90% sequence identity with the amino acid sequence of SEQ ID NO: 36 (huUCHT1 (Y177T)). In some embodiments, the antigen-binding domain that binds the protein associated with the TCR complex comprises an amino acid sequence having at least 95% sequence identity with the amino acid sequence of SEQ ID NO: 36 (huUCHT1 (Y177T)). In some embodiments, the antigen-binding domain that binds the protein associated with the TCR complex comprises an amino acid sequence having at least 96% sequence identity with the amino acid sequence of SEQ ID NO: 36 (huUCHT1 (Y177T)). In some embodiments, the antigen-binding domain that binds the protein associated with the TCR complex comprises an amino acid sequence having at least 97% sequence identity with the amino acid sequence of SEQ ID NO: 36 (huUCHT1 (Y177T)). In some embodiments, the antigen-binding domain that binds the protein associated with the TCR complex comprises an amino acid sequence having at least 98% sequence identity with the amino acid sequence of SEQ ID NO: 36 (huUCHT1 (Y177T)). In some embodiments, the antigen-binding domain that binds the protein associated with the TCR complex comprises an amino acid sequence having at least 99% sequence identity with the amino acid sequence of SEQ ID NO: 36 (huUCHT1 (Y177T)). In some embodiments, the antigen-binding domain that binds the protein associated with the TCR complex comprises the amino acid sequence of SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 36 (huUCHT1 (Y177T)) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 36 (huUCHT1 (Y177T)), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 36 (huUCHT1 (Y177T)), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 36 (huUCHT1 (Y177T)), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 36 (huUCHT1 (Y177T)), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 36 (huUCHT1 (Y177T)), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 36 (huUCHT1 (Y177T)), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 36 (huUCHT1 (Y177T)), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 36 (huUCHT1 (Y177T)). In some embodiments, the CDR sequences of the antigen-binding domain that binds the protein associated with the TCR complex have 100% identity with the CDR sequences of the amino acid sequence of SEQ ID NO: 36 (huUCHT1 (Y177T)), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 36 (huUCHT1 (Y177T)).

In some embodiments, the antigen-binding domain that binds to the protein associated with the TCR complex is OKT3. In some embodiments, the murine OKT3 antigen-binding domain is encoded by SEQ ID NO: 15. In some embodiments, the OKT3 antigen-binding domain comprises SEQ ID NO: 16.

In some embodiments, the polynucleotide encoding the antigen-binding domain that binds the protein associated with the TCR complex comprises a nucleotide sequence having at least 70% sequence identity with the nucleotide sequence of SEQ ID NO: 15 (OKT3). In some embodiments, the polynucleotide encoding the antigen-binding domain that binds the protein associated with the TCR complex comprises a nucleotide sequence having at least 75% sequence identity with the nucleotide sequence of SEQ ID NO: 15 (OKT3). In some embodiments, the polynucleotide encoding the antigen-binding domain that binds the protein associated with the TCR complex comprises a nucleotide sequence having at least 80% sequence identity with the nucleotide sequence of SEQ ID NO: 15 (OKT3). In some embodiments, the polynucleotide encoding the antigen-binding domain that binds the protein associated with the TCR complex comprises a nucleotide sequence having at least 85% sequence identity with the nucleotide sequence of SEQ ID NO: 15 (OKT3). In some embodiments, the polynucleotide encoding the antigen-binding domain that binds the protein associated with the TCR complex comprises a nucleotide sequence having at least 90% sequence identity with the nucleotide sequence of SEQ ID NO: 15 (OKT3). In some embodiments, the polynucleotide encoding the antigen-binding domain that binds the protein associated with the TCR complex comprises a nucleotide sequence having at least 95% sequence identity with the nucleotide sequence of SEQ ID NO: 15 (OKT3). In some embodiments, the polynucleotide encoding the antigen-binding domain that binds the protein associated with the TCR complex comprises a nucleotide sequence having at least 96% sequence identity with the nucleotide sequence of SEQ ID NO: 15 (OKT3). In some embodiments, the polynucleotide encoding the antigen-binding domain that binds the protein associated with the TCR complex comprises a nucleotide sequence having at least 97% sequence identity with the nucleotide sequence of SEQ ID NO: 15 (OKT3). In some embodiments, the polynucleotide encoding the antigen-binding domain that binds the protein associated with the TCR complex comprises a nucleotide sequence having at least 98% sequence identity with the nucleotide sequence of SEQ ID NO: 15 (OKT3). In some embodiments, the polynucleotide encoding the antigen-binding domain that binds the protein associated with the TCR complex comprises a nucleotide sequence having at least 99% sequence identity with the nucleotide sequence of SEQ ID NO: 15 (OKT3). In some embodiments, the polynucleotide encoding the antigen-binding domain that binds the protein associated with the TCR complex comprises the nucleotide sequence of SEQ ID NO: 15 (OKT3).

In some embodiments, the antigen-binding domain that binds the protein associated with the TCR complex comprises an amino acid sequence having at least 70% sequence identity with the amino acid sequence of SEQ ID NO: 16 (OKT3). In some embodiments, the antigen-binding domain that binds the protein associated with the TCR complex comprises an amino acid sequence having at least 75% sequence identity with the amino acid sequence of SEQ ID NO: 16 (OKT3). In some embodiments, the antigen-binding domain that binds the protein associated with the TCR complex comprises an amino acid sequence having at least 80% sequence identity with the amino acid sequence of SEQ ID NO: 16 (OKT3). In some embodiments, the antigen-binding domain that binds the protein associated with the TCR complex comprises an amino acid sequence having at least 85% sequence identity with the amino acid sequence of SEQ ID NO: 16 (OKT3). In some embodiments, the antigen-binding domain that binds the protein associated with the TCR complex comprises an amino acid sequence having at least 90% sequence identity with the amino acid sequence of SEQ ID NO: 16 (OKT3). In some embodiments, the antigen-binding domain that binds the protein associated with the TCR complex comprises an amino acid sequence having at least 95% sequence identity with the amino acid sequence of SEQ ID NO: 16 (OKT3). In some embodiments, the antigen-binding domain that binds the protein associated with the TCR complex comprises an amino acid sequence having at least 96% sequence identity with the amino acid sequence of SEQ ID NO: 16 (OKT3). In some embodiments, the antigen-binding domain that binds the protein associated with the TCR complex comprises an amino acid sequence having at least 97% sequence identity with the amino acid sequence of SEQ ID NO: 16 (OKT3). In some embodiments, the antigen-binding domain that binds the protein associated with the TCR complex comprises an amino acid sequence having at least 98% sequence identity with the amino acid sequence of SEQ ID NO: 16 (OKT3). In some embodiments, the antigen-binding domain that binds the protein associated with the TCR complex comprises an amino acid sequence having at least 99% sequence identity with the amino acid sequence of SEQ ID NO: 16 (OKT3). In some embodiments, the antigen-binding domain that binds the protein associated with the TCR complex comprises the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 16 (OKT3). In some embodiments, the CDR sequences of the antigen-binding domain that binds the protein associated with the TCR complex have 100% identity with the CDR sequences of the amino acid sequence of SEQ ID NO: 16 (OKT3), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 16 (OKT3).

In some embodiments, the antigen-binding domain that binds to the protein associated with the TCR complex is F6A. In some embodiments, the murine F6A antigen-binding domain is encoded by SEQ ID NO: 17. In some embodiments, the F6A antigen-binding domain comprises SEQ ID NO: 18.

In some embodiments, the polynucleotide encoding the antigen-binding domain that binds the protein associated with the TCR complex comprises a nucleotide sequence having at least 70% sequence identity with the nucleotide sequence of SEQ ID NO: 17 (F6A). In some embodiments, the polynucleotide encoding the antigen-binding domain that binds the protein associated with the TCR complex comprises a nucleotide sequence having at least 75% sequence identity with the nucleotide sequence of SEQ ID NO: 17 (F6A). In some embodiments, the polynucleotide encoding the antigen-binding domain that binds the protein associated with the TCR complex comprises a nucleotide sequence having at least 80% sequence identity with the nucleotide sequence of SEQ ID NO: 17 (F6A). In some embodiments, the polynucleotide encoding the antigen-binding domain that binds the protein associated with the TCR complex comprises a nucleotide sequence having at least 85% sequence identity with the nucleotide sequence of SEQ ID NO: 17 (F6A). In some embodiments, the polynucleotide encoding the antigen-binding domain that binds the protein associated with the TCR complex comprises a nucleotide sequence having at least 90% sequence identity with the nucleotide sequence of SEQ ID NO: 17 (F6A). In some embodiments, the polynucleotide encoding the antigen-binding domain that binds the protein associated with the TCR complex comprises a nucleotide sequence having at least 95% sequence identity with the nucleotide sequence of SEQ ID NO: 17 (F6A). In some embodiments, the polynucleotide encoding the antigen-binding domain that binds the protein associated with the TCR complex comprises a nucleotide sequence having at least 96% sequence identity with the nucleotide sequence of SEQ ID NO: 17 (F6A). In some embodiments, the polynucleotide encoding the antigen-binding domain that binds the protein associated with the TCR complex comprises a nucleotide sequence having at least 97% sequence identity with the nucleotide sequence of SEQ ID NO: 17 (F6A). In some embodiments, the polynucleotide encoding the antigen-binding domain that binds the protein associated with the TCR complex comprises a nucleotide sequence having at least 98% sequence identity with the nucleotide sequence of SEQ ID NO: 17 (F6A). In some embodiments, the polynucleotide encoding the antigen-binding domain that binds the protein associated with the TCR complex comprises a nucleotide sequence having at least 99% sequence identity with the nucleotide sequence of SEQ ID NO: 17 (F6A). In some embodiments, the polynucleotide encoding the antigen-binding domain that binds the protein associated with the TCR complex comprises the nucleotide sequence of SEQ ID NO: 17 (F6A).

In some embodiments, the antigen-binding domain that binds the protein associated with the TCR complex comprises an amino acid sequence having at least 70% sequence identity with the amino acid sequence of SEQ ID NO: 18 (F6A). In some embodiments, the antigen-binding domain that binds the protein associated with the TCR complex comprises an amino acid sequence having at least 75% sequence identity with the amino acid sequence of SEQ ID NO: 18 (F6A). In some embodiments, the antigen-binding domain that binds the protein associated with the TCR complex comprises an amino acid sequence having at least 80% sequence identity with the amino acid sequence of SEQ ID NO: 18 (F6A). In some embodiments, the antigen-binding domain that binds the protein associated with the TCR complex comprises an amino acid sequence having at least 85% sequence identity with the amino acid sequence of SEQ ID NO: 18 (F6A). In some embodiments, the antigen-binding domain that binds the protein associated with the TCR complex comprises an amino acid sequence having at least 90% sequence identity with the amino acid sequence of SEQ ID NO: 18 (F6A). In some embodiments, the antigen-binding domain that binds the protein associated with the TCR complex comprises an amino acid sequence having at least 95% sequence identity with the amino acid sequence of SEQ ID NO: 18 (F6A). In some embodiments, the antigen-binding domain that binds the protein associated with the TCR complex comprises an amino acid sequence having at least 96% sequence identity with the amino acid sequence of SEQ ID NO: 18 (F6A). In some embodiments, the antigen-binding domain that binds the protein associated with the TCR complex comprises an amino acid sequence having at least 97% sequence identity with the amino acid sequence of SEQ ID NO: 18 (F6A). In some embodiments, the antigen-binding domain that binds the protein associated with the TCR complex comprises an amino acid sequence having at least 98% sequence identity with the amino acid sequence of SEQ ID NO: 18 (F6A). In some embodiments, the antigen-binding domain that binds the protein associated with the TCR complex comprises an amino acid sequence having at least 99% sequence identity with the amino acid sequence of SEQ ID NO: 18 (F6A). In some embodiments, the antigen-binding domain that binds the protein associated with the TCR complex comprises the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 18 (F6A). In some embodiments, the CDR sequences of the antigen-binding domain that binds the protein associated with the TCR complex have 100% identity with the CDR sequences of the amino acid sequence of SEQ ID NO: 18 (F6A), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 18 (F6A).

In some embodiments, the antigen-binding domain that binds to the protein associated with the TCR complex is L2K. In some embodiments, the murine L2K antigen-binding domain is encoded by SEQ ID NO: 19. In some embodiments, the L2K antigen-binding domain comprises SEQ ID NO: 20.

In some embodiments, the polynucleotide encoding the antigen-binding domain that binds the protein associated with the TCR complex comprises a nucleotide sequence having at least 70% sequence identity with the nucleotide sequence of SEQ ID NO: 19 (L2K). In some embodiments, the polynucleotide encoding the antigen-binding domain that binds the protein associated with the TCR complex comprises a nucleotide sequence having at least 75% sequence identity with the nucleotide sequence of SEQ ID NO: 19 (L2K). In some embodiments, the polynucleotide encoding the antigen-binding domain that binds the protein associated with the TCR complex comprises a nucleotide sequence having at least 80% sequence identity with the nucleotide sequence of SEQ ID NO: 19 (L2K). In some embodiments, the polynucleotide encoding the antigen-binding domain that binds the protein associated with the TCR complex comprises a nucleotide sequence having at least 85% sequence identity with the nucleotide sequence of SEQ ID NO: 19 (L2K). In some embodiments, the polynucleotide encoding the antigen-binding domain that binds the protein associated with the TCR complex comprises a nucleotide sequence having at least 90% sequence identity with the nucleotide sequence of SEQ ID NO: 19 (L2K). In some embodiments, the polynucleotide encoding the antigen-binding domain that binds the protein associated with the TCR complex comprises a nucleotide sequence having at least 95% sequence identity with the nucleotide sequence of SEQ ID NO: 19 (L2K). In some embodiments, the polynucleotide encoding the antigen-binding domain that binds the protein associated with the TCR complex comprises a nucleotide sequence having at least 96% sequence identity with the nucleotide sequence of SEQ ID NO: 19 (L2K). In some embodiments, the polynucleotide encoding the antigen-binding domain that binds the protein associated with the TCR complex comprises a nucleotide sequence having at least 97% sequence identity with the nucleotide sequence of SEQ ID NO: 19 (L2K). In some embodiments, the polynucleotide encoding the antigen-binding domain that binds the protein associated with the TCR complex comprises a nucleotide sequence having at least 98% sequence identity with the nucleotide sequence of SEQ ID NO: 19 (L2K). In some embodiments, the polynucleotide encoding the antigen-binding domain that binds the protein associated with the TCR complex comprises a nucleotide sequence having at least 99% sequence identity with the nucleotide sequence of SEQ ID NO: 19 (L2K). In some embodiments, the polynucleotide encoding the antigen-binding domain that binds the protein associated with the TCR complex comprises the nucleotide sequence of SEQ ID NO: 19 (L2K).

In some embodiments, the antigen-binding domain that binds the protein associated with the TCR complex comprises an amino acid sequence having at least 70% sequence identity with the amino acid sequence of SEQ ID NO: 20 (L2K). In some embodiments, the antigen-binding domain that binds the protein associated with the TCR complex comprises an amino acid sequence having at least 75% sequence identity with the amino acid sequence of SEQ ID NO: 20 (L2K). In some embodiments, the antigen-binding domain that binds the protein associated with the TCR complex comprises an amino acid sequence having at least 80% sequence identity with the amino acid sequence of SEQ ID NO: 20 (L2K). In some embodiments, the antigen-binding domain that binds the protein associated with the TCR complex comprises an amino acid sequence having at least 85% sequence identity with the amino acid sequence of SEQ ID NO: 20 (L2K). In some embodiments, the antigen-binding domain that binds the protein associated with the TCR complex comprises an amino acid sequence having at least 90% sequence identity with the amino acid sequence of SEQ ID NO: 20 (L2K). In some embodiments, the antigen-binding domain that binds the protein associated with the TCR complex comprises an amino acid sequence having at least 95% sequence identity with the amino acid sequence of SEQ ID NO: 20 (L2K). In some embodiments, the antigen-binding domain that binds the protein associated with the TCR complex comprises an amino acid sequence having at least 96% sequence identity with the amino acid sequence of SEQ ID NO: 20 (L2K). In some embodiments, the antigen-binding domain that binds the protein associated with the TCR complex comprises an amino acid sequence having at least 97% sequence identity with the amino acid sequence of SEQ ID NO: 20 (L2K). In some embodiments, the antigen-binding domain that binds the protein associated with the TCR complex comprises an amino acid sequence having at least 98% sequence identity with the amino acid sequence of SEQ ID NO: 20 (L2K). In some embodiments, the antigen-binding domain that binds the protein associated with the TCR complex comprises an amino acid sequence having at least 99% sequence identity with the amino acid sequence of SEQ ID NO: 20 (L2K). In some embodiments, the antigen-binding domain that binds the protein associated with the TCR complex comprises the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 20 (L2K). In some embodiments, the CDR sequences of the antigen-binding domain that binds the protein associated with the TCR complex have 100% identity with the CDR sequences of the amino acid sequence of SEQ ID NO: 20 (L2K), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 20 (L2K).

Amino acid and nucleotide sequences of exemplary antigen-binding domains that bind a protein associated with the TCR complex are provided in Table 2.

TABLE 2

Table of Sequences

| SEQ ID NO | Description | Nucleotide/Amino Acid |
|---|---|---|
| SEQ ID NO: 7 | UCHT1[1] | Nucleotide |
| SEQ ID NO: 8 | UCHT1[2] | Amino Acid |
| SEQ ID NO: 15 | OKT3 | Nucleotide |
| SEQ ID NO: 16 | OKT3 | Amino Acid |
| SEQ ID NO: 17 | F6A | Nucleotide |
| SEQ ID NO: 18 | F6A | Amino Acid |

TABLE 2-continued

Table of Sequences

| SEQ ID NO | Description | Nucleotide/Amino Acid |
|---|---|---|
| SEQ ID NO: 19 | L2K | Nucleotide |
| SEQ ID NO: 20 | L2K | Amino Acid |
| SEQ ID NO: 33 | huUCHT1 | Nucleotide |
| SEQ ID NO: 34 | huUCHT1 | Amino Acid |
| SEQ ID NO: 35 | huUCHT1 (Y177T) | Nucleotide |
| SEQ ID NO: 36 | huUCHT1 (Y177T) | Amino Acid |
| SEQ ID NO: 43 | UCHT1 (Y182T) | Nucleotide |
| SEQ ID NO: 44 | UCHT1 (Y182T) | Amino Acid |

[1]Light chain, nucleotides 1-324; Linker, nucleotides 325-387; Heavy chain, nucleotides 388-750
[2]Light chain, amino acids 1-108; Linker, amino acids 109-128; Heavy chain, amino acids 129-250

Transmembrane Domain and Cytosolic Domain

In some embodiments, a Claudin 18.2 T cell antigen coupler polypeptide comprises a T cell receptor signaling domain polypeptide. In some embodiments, a Claudin 18.2 T cell antigen coupler polypeptide comprises a transmembrane domain of a TCR signaling domain. In some embodiments, a Claudin 18.2 T cell antigen coupler polypeptide comprises a cytosolic domain of a TCR signaling domain polypeptide. In some embodiments, a Claudin 18.2 T cell antigen coupler polypeptide comprises a transmembrane domain and a cytosolic domain of a TCR signaling domain polypeptide.

In some embodiments, the T cell receptor signaling domain polypeptide comprises a TCR co-receptor domain. In some embodiments, the TCR signaling domain polypeptide comprises a transmembrane domain and/or a cytosolic domain of a TCR co-receptor. In some embodiments, the TCR co-receptor is CD4, CD8, LAGS, or a chimeric variation thereof.

In some embodiments, the TCR co-receptor is CD4. In some embodiments, the Claudin 18.2-TAC comprises a transmembrane domain and a cytosolic domain of a CD4 co-receptor. In some embodiments, the polynucleotide encoding the cytosolic and transmembrane domain comprises a nucleotide sequence having at least 70% sequence identity with the nucleotide sequence of SEQ ID NO: 11 (CD4 transmembrane and cytosolic domain). In some embodiments, the polynucleotide encoding the cytosolic and transmembrane domain comprises a nucleotide sequence having at least 75% sequence identity with the nucleotide sequence of SEQ ID NO: 11 (CD4 transmembrane and cytosolic domain). In some embodiments, the polynucleotide encoding the cytosolic and transmembrane domain comprises a nucleotide sequence having at least 80% sequence identity with the nucleotide sequence of SEQ ID NO: 11 (CD4 transmembrane and cytosolic domain). In some embodiments, the polynucleotide encoding the cytosolic and transmembrane domain comprises a nucleotide sequence having at least 85% sequence identity with the nucleotide sequence of SEQ ID NO: 11 (CD4 transmembrane and cytosolic domain). In some embodiments, the polynucleotide encoding the cytosolic and transmembrane domain comprises a nucleotide sequence having at least 90% sequence identity with the nucleotide sequence of SEQ ID NO: 11 (CD4 transmembrane and cytosolic domain). In some embodiments, the polynucleotide encoding the cytosolic and transmembrane domain comprises a nucleotide sequence having at least 95% sequence identity with the nucleotide sequence of SEQ ID NO: 11 (CD4 transmembrane and cytosolic domain). In some embodiments, the polynucleotide encoding the cytosolic and transmembrane domain comprises a nucleotide sequence having at least 96% sequence identity with the nucleotide sequence of SEQ ID NO: 11 (CD4 transmembrane and cytosolic domain). In some embodiments, the polynucleotide encoding the cytosolic and transmembrane domain comprises a nucleotide sequence having at least 97% sequence identity with the nucleotide sequence of SEQ ID NO: 11 (CD4 transmembrane and cytosolic domain). In some embodiments, the polynucleotide encoding the cytosolic and transmembrane domain comprises a nucleotide sequence having at least 98% sequence identity with the nucleotide sequence of SEQ ID NO: 11 (CD4 transmembrane and cytosolic domain). In some embodiments, the polynucleotide encoding the cytosolic and transmembrane domain comprises a nucleotide sequence having at least 99% sequence identity with the nucleotide sequence of SEQ ID NO: 11 (CD4 transmembrane and cytosolic domain). In some embodiments, the polynucleotide encoding the cytosolic and transmembrane domain comprises the nucleotide sequence of SEQ ID NO: 11 (CD4 transmembrane and cytosolic domain). In some embodiments, the cytosolic and transmembrane domain comprise an amino acid sequence having at least 70% sequence identity with the amino acid sequence of SEQ ID NO: 12 (CD4 transmembrane and cytosolic domain). In some embodiments, the cytosolic and transmembrane domain comprise an amino acid sequence having at least 75% sequence identity with the amino acid sequence of SEQ ID NO: 12 (CD4 transmembrane and cytosolic domain). In some embodiments, the cytosolic and transmembrane domain comprise an amino acid sequence having at least 80% sequence identity with the amino acid sequence of SEQ ID NO: 12 (CD4 transmembrane and cytosolic domain). In some embodiments, the cytosolic and transmembrane domain comprise an amino acid sequence having at least 85% sequence identity with the amino acid sequence of SEQ ID NO: 12 (CD4 transmembrane and cytosolic domain). In some embodiments, the cytosolic and transmembrane domain comprise an amino acid sequence having at least 90% sequence identity with the amino acid sequence of SEQ ID NO: 12 (CD4 transmembrane and cytosolic domain). In some embodiments, the cytosolic and transmembrane domain comprise an amino acid sequence having at least 95% sequence identity with the amino acid sequence of SEQ ID NO: 12 (CD4 transmembrane and cytosolic domain). In some embodiments, the cytosolic and transmembrane domain comprise an amino acid sequence having at least 96% sequence identity with the amino acid sequence of SEQ ID NO: 12 (CD4 transmembrane and cytosolic domain). In some embodiments, the cytosolic and transmembrane domain comprise an amino acid sequence having at least 97% sequence identity with the amino acid sequence of SEQ ID NO: 12 (CD4 transmembrane and cytosolic domain). In some embodiments, the cytosolic and transmembrane domain comprise an amino acid sequence having at least 98% sequence identity with the amino acid sequence of SEQ ID NO: 12 (CD4 transmembrane and cytosolic domain). In some embodiments, the cytosolic and transmembrane domain comprise an amino acid sequence having at least 99% sequence identity with the amino acid sequence of SEQ ID NO: 12 (CD4 transmembrane and cytosolic domain). In some embodiments, the cytosolic and transmembrane domain comprise the amino acid sequence of SEQ ID NO: 12 (CD4 transmembrane and cytosolic domain).

In some embodiments, the TCR co-receptor is CD8. In some embodiments, the TCR co-receptor is CD8α. In some embodiments, the polynucleotide encoding the cytosolic and transmembrane domain comprises a nucleotide sequence having at least 70% sequence identity with the nucleotide sequence of SEQ ID NO: 27 (CD8 transmembrane and cytosolic domain). In some embodiments, the polynucleotide encoding the cytosolic and transmembrane domain comprises a nucleotide sequence having at least 75% sequence identity with the nucleotide sequence of SEQ ID NO: 27 (CD8 transmembrane and cytosolic domain). In some embodiments, the polynucleotide encoding the cytosolic and transmembrane domain comprises a nucleotide sequence having at least 80% sequence identity with the nucleotide sequence of SEQ ID NO: 27 (CD8 transmembrane and cytosolic domain). In some embodiments, the polynucleotide encoding the cytosolic and transmembrane domain comprises a nucleotide sequence having at least 85% sequence identity with the nucleotide sequence of SEQ ID NO: 27 (CD8 transmembrane and cytosolic domain). In some embodiments, the polynucleotide encoding the cytosolic and transmembrane domain comprises a nucleotide sequence having at least 90% sequence identity with the nucleotide sequence of SEQ ID NO: 27 (CD8 transmembrane and cytosolic domain). In some embodiments, the polynucleotide encoding the cytosolic and transmembrane domain comprises a nucleotide sequence having at least 95% sequence identity with the nucleotide sequence of SEQ ID NO: 27 (CD8 transmembrane and cytosolic domain). In some embodiments, the polynucleotide encoding the cytosolic and transmembrane domain comprises a nucleotide sequence having at least 96% sequence identity with the nucleotide sequence of SEQ ID NO: 27 (CD8 transmembrane and cytosolic domain). In some embodiments, the polynucleotide encoding the cytosolic and transmembrane domain comprises a nucleotide sequence having at least 97% sequence identity with the nucleotide sequence of SEQ ID NO: 27 (CD8 transmembrane and cytosolic domain). In some embodiments, the polynucleotide encoding the cytosolic and transmembrane domain comprises a nucleotide sequence having at least 98% sequence identity with the nucleotide sequence of SEQ ID NO: 27 (CD8 transmembrane and cytosolic domain). In some embodiments, the polynucleotide encoding the cytosolic and transmembrane domain comprises a nucleotide sequence having at least 99% sequence identity with the nucleotide sequence of SEQ ID NO: 27 (CD8 transmembrane and cytosolic domain). In some embodiments, the polynucleotide encoding the cytosolic and transmembrane domain comprises the nucleotide sequence of SEQ ID NO: 27 (CD8 transmembrane and cytosolic domain). In some embodiments, the cytosolic and transmembrane domain comprise an amino acid sequence having at least 70% sequence identity with the amino acid sequence of SEQ ID NO: 28 (CD8 transmembrane and cytosolic domain). In some embodiments, the cytosolic and transmembrane domain comprise an amino acid sequence having at least 75% sequence identity with the amino acid sequence of SEQ ID NO: 28 (CD8 transmembrane and cytosolic domain). In some embodiments, the cytosolic and transmembrane domain comprise an amino acid sequence having at least 80% sequence identity with the amino acid sequence of SEQ ID NO: 28 (CD8 transmembrane and cytosolic domain). In some embodiments, the cytosolic and transmembrane domain comprise an amino acid sequence having at least 85% sequence identity with the amino acid sequence of SEQ ID NO: 28 (CD8 transmembrane and cytosolic domain). In some embodiments, the cytosolic and transmembrane domain comprise an amino acid sequence having at least 90% sequence identity with the amino acid sequence of SEQ ID NO: 28 (CD8 transmembrane and cytosolic domain). In some embodiments, the cytosolic and transmembrane domain comprise an amino acid sequence having at least 95% sequence identity with the amino acid sequence of SEQ ID NO: 28 (CD8 transmembrane and cytosolic domain). In some embodiments, the cytosolic and transmembrane domain comprise an amino acid sequence having at least 96% sequence identity with the amino acid sequence of SEQ ID NO: 28 (CD8 transmembrane and cytosolic domain). In some embodiments, the cytosolic and transmembrane domain comprise an amino acid sequence having at least 97% sequence identity with the amino acid sequence of SEQ ID NO: 28 (CD8 transmembrane and cytosolic domain). In some embodiments, the cytosolic and transmembrane domain comprise an amino acid sequence having at least 98% sequence identity with the amino acid sequence of SEQ ID NO: 28 (CD8 transmembrane and cytosolic domain). In some embodiments, the cytosolic and transmembrane domain comprise an amino acid sequence having at least 99% sequence identity with the amino acid sequence of SEQ ID NO: 28 (CD8 transmembrane and cytosolic domain). In some embodiments, the cytosolic and transmembrane domain comprise the amino acid sequence of SEQ ID NO: 28 (CD8 transmembrane and cytosolic domain).

In some embodiments, the TCR signaling domain polypeptide comprises a chimera of sequences or domains from co-receptors. In some embodiments, the TCR signaling domain polypeptide comprises a chimera of CD8α and CD8β, wherein the CD8α arginine rich region is replaced with the CD8β arginine rich region (CD8α+R(β) chimera). In some embodiments, the polynucleotide encoding the cytosolic and transmembrane domain comprises a nucleotide sequence having at least 70% sequence identity with the nucleotide sequence of SEQ ID NO: 29 (CD8α+R(β) chimera). In some embodiments, the polynucleotide encoding the cytosolic and transmembrane domain comprises a nucleotide sequence having at least 75% sequence identity with the nucleotide sequence of SEQ ID NO: 29 (CD8α+R(β) chimera). In some embodiments, the polynucleotide encoding the cytosolic and transmembrane domain comprises a nucleotide sequence having at least 80% sequence identity with the nucleotide sequence of SEQ ID NO: 29 (CD8α+R(β) chimera). In some embodiments, the polynucleotide encoding the cytosolic and transmembrane domain comprises a nucleotide sequence having at least 85% sequence identity with the nucleotide sequence of SEQ ID NO: 29 (CD8α+R(β) chimera). In some embodiments, the polynucleotide encoding the cytosolic and transmembrane domain comprises a nucleotide sequence having at least 90% sequence identity with the nucleotide sequence of SEQ ID NO: 29 (CD8α+R(β) chimera). In some embodiments, the polynucleotide encoding the cytosolic and transmembrane domain comprises a nucleotide sequence having at least 95% sequence identity with the nucleotide sequence of SEQ ID NO: 29 (CD8α+R(β) chimera). In some embodiments, the polynucleotide encoding the cytosolic and transmembrane domain comprises a nucleotide sequence having at least 96% sequence identity with the nucleotide sequence of SEQ ID NO: 29 (CD8α+R(β) chimera). In some embodiments, the polynucleotide encoding the cytosolic and transmembrane domain comprises a nucleotide sequence having at least 97% sequence identity with the nucleotide sequence of SEQ ID NO: 29 (CD8α+R(β) chimera). In some embodiments, the polynucleotide encoding the cytosolic and transmembrane domain comprises a nucleotide sequence having at least 98% sequence identity with the nucleotide sequence of SEQ ID NO: 29 (CD8α+R(β) chimera). In some embodiments, the polynucleotide encoding the cytosolic and transmembrane domain comprises a nucleotide sequence having at least 99% sequence identity with the nucleotide sequence of SEQ ID NO: 29 (CD8α+R(β) chimera). In some embodiments, the polynucleotide encoding the cytosolic and transmembrane domain comprises the nucleotide sequence of SEQ ID NO: 29 (CD8α+R(β) chimera). In some embodiments, the cytosolic and transmembrane domain comprise an amino acid sequence having at least 70% sequence identity with the amino acid sequence of SEQ ID NO: 30 (CD8α+R(β) chimera). In some embodiments, the cytosolic and transmembrane domain comprise an amino acid sequence having at least 75% sequence identity with the amino acid sequence of SEQ ID NO: 30 (CD8α+R(β) chimera). In some embodiments, the cytosolic and transmembrane domain comprise an amino acid sequence having at least 80% sequence identity with the amino acid sequence of SEQ ID NO: 30 (CD8α+R(β) chimera). In some embodiments, the cytosolic and transmembrane domain comprise an amino acid sequence having at least 85% sequence identity with the amino acid sequence of SEQ ID NO: 30 (CD8α+R(β) chimera). In some embodiments, the cytosolic and transmembrane domain comprise an amino acid sequence having at least 90% sequence identity with the amino acid sequence of SEQ ID NO: 30 (CD8α+R(β) chimera). In some embodiments, the cytosolic and transmembrane domain comprise an amino acid sequence having at least 95% sequence identity with the amino acid sequence of SEQ ID NO: 30 (CD8α+R(β) chimera). In some embodiments, the cytosolic and transmembrane domain comprise an amino acid sequence having at least 96% sequence identity with the amino acid sequence of SEQ ID NO: 30 (CD8α+R(β) chimera). In some embodiments, the cytosolic and transmembrane domain comprise an amino acid sequence having at least 97% sequence identity with the amino acid sequence of SEQ ID NO: 30 (CD8α+R(β) chimera). In some embodiments, the cytosolic and transmembrane domain comprise an amino acid sequence having at least 98% sequence identity with the amino acid sequence of SEQ ID NO: 30 (CD8α+R(β) chimera). In some embodiments, the cytosolic and transmembrane domain comprise an amino acid sequence having at least 99% sequence identity with the amino acid sequence of SEQ ID NO: 30 (CD8α+R(β) chimera). In some embodiments, the cytosolic and transmembrane domain comprise the amino acid sequence of SEQ ID NO: 30 (CD8α+R(β) chimera).

In some embodiments, the TCR signaling domain polypeptide comprises a chimera of CD8α and CD8β, where the CD8α CXCP domain, which contains an Lck binding motif, is appended to the C-terminus of the CD8β cytosolic domain (CD8β+Lck chimera). In some embodiments, the polynucleotide encoding the cytosolic and transmembrane domain comprises a nucleotide sequence having at least 70% sequence identity with the nucleotide sequence of SEQ ID NO: 31 (CD8β+Lck chimera). In some embodiments, the polynucleotide encoding the cytosolic and transmembrane domain comprises a nucleotide sequence having at least 75% sequence identity with the nucleotide sequence of SEQ ID NO: 31 (CD8β+Lck chimera). In some embodiments, the polynucleotide encoding the cytosolic and transmembrane domain comprises a nucleotide sequence having at least 80% sequence identity with the nucleotide sequence of SEQ ID NO: 31 (CD8β+Lck chimera). In some embodiments, the polynucleotide encoding the cytosolic and transmembrane domain comprises a nucleotide sequence having at least 85% sequence identity with the nucleotide sequence of SEQ ID NO: 31 (CD8β+Lck chimera). In some embodiments, the polynucleotide encoding the cytosolic and transmembrane domain comprises a nucleotide sequence having at least 90% sequence identity with the nucleotide sequence of SEQ ID NO: 31 (CD8β+Lck chimera). In some embodiments, the polynucleotide encoding the cytosolic and transmembrane domain comprises a nucleotide sequence having at least 95% sequence identity with the nucleotide sequence of SEQ ID NO: 31 (CD8β+Lck chimera). In some embodiments, the polynucleotide encoding the cytosolic and transmembrane domain comprises a nucleotide sequence having at least 96% sequence identity with the nucleotide sequence of SEQ ID NO: 31 (CD8β+Lck chimera). In some embodiments, the polynucleotide encoding the cytosolic and transmembrane domain comprises a nucleotide sequence having at least 97% sequence identity with the nucleotide sequence of SEQ ID NO: 31 (CD8β+Lck chimera). In some embodiments, the polynucleotide encoding the cytosolic and transmembrane domain comprises a nucleotide sequence having at least 98% sequence identity with the nucleotide sequence of SEQ ID NO: 31 (CD8β+Lck chimera). In some embodiments, the polynucleotide encoding the cytosolic and transmembrane domain comprises a nucleotide sequence having at least 99% sequence identity with the nucleotide sequence of SEQ ID NO: 31 (CD8β+Lck chimera). In some embodiments, the polynucleotide encoding the cytosolic and transmembrane domain comprises the nucleotide sequence of SEQ ID NO: 31 (CD8β+Lck chimera). In some embodiments, the cytosolic and transmembrane domain comprise an amino acid sequence having at least 70% sequence identity with the amino acid sequence of SEQ ID NO: 32 (CD8β+Lck chimera). In some embodiments, the cytosolic and transmembrane domain comprise an amino acid sequence having at least 75% sequence identity with the amino acid sequence of SEQ ID NO: 32 (CD8β+Lck chimera). In some embodiments, the cytosolic and transmembrane domain comprise an amino acid sequence having at least 80% sequence identity with the amino acid sequence of SEQ ID NO: 32 (CD8β+Lck chimera). In some embodiments, the cytosolic and transmembrane domain comprise an amino acid sequence having at least 85% sequence identity with the amino acid sequence of SEQ ID NO: 32 (CD8β+Lck chimera). In some embodiments, the cytosolic and transmembrane domain comprise an amino acid sequence having at least 90% sequence identity with the amino acid sequence of SEQ ID NO: 32 (CD8β+Lck chimera). In some embodiments, the cytosolic and transmembrane domain comprise an amino acid sequence having at least 95% sequence identity with the amino acid sequence of SEQ ID NO: 32 (CD8β+Lck chimera). In some embodiments, the cytosolic and transmembrane domain comprise an amino acid sequence having at least 96% sequence identity with the amino acid sequence of SEQ ID NO: 32 (CD8β+Lck chimera). In some embodiments, the cytosolic and transmembrane domain comprise an amino acid sequence having at least 97% sequence identity with the amino acid sequence of SEQ ID NO: 32 (CD8β+Lck chimera). In some embodiments, the cytosolic and transmembrane domain comprise an amino acid sequence having at least 98% sequence identity with the amino acid sequence of SEQ ID NO: 32 (CD8β+Lck chimera). In some embodiments, the cytosolic and transmembrane domain comprise an amino acid sequence having at least 99% sequence identity with the amino acid sequence of SEQ ID NO: 32 (CD8β+Lck chimera). In some embodiments, the cytosolic and transmembrane domain comprise the amino acid sequence of SEQ ID NO: 32 (CD8β+Lck chimera).

In some embodiments, the TCR signaling domain polypeptide includes both a cytosolic domain and a transmembrane domain of a TCR co-receptor protein. In some embodiments, the cytosolic domain and transmembrane domain are from the same co-receptor or from different co-receptors.

Amino acid and nucleotide sequences of exemplary transmembrane and cytosolic domains are provided in Table 3.

TABLE 3

Table of Sequences

| SEQ ID NO | Description | Nucleotide/Amino Acid |
| --- | --- | --- |
| SEQ ID NO: 11 | CD4 Domain[1] | Nucleotide |
| SEQ ID NO: 12 | CD4 Domain[2] | Amino Acid |
| SEQ ID NO: 27 | CD8α Domain | Nucleotide |
| SEQ ID NO: 28 | CD8α Domain | Amino Acid |
| SEQ ID NO: 29 | CD8α + R(β) Domain | Nucleotide |
| SEQ ID NO: 30 | CD8α + R(β) Domain | Amino Acid |
| SEQ ID NO: 31 | CD8α + Lck Domain | Nucleotide |
| SEQ ID NO: 32 | CD8α + Lck Domain | Amino Acid |

[1]Extracellular linker, nucleotides 1-66; Transmembrane domain, nucleotides 67-132; Cytosolic domain, nucleotides 133-254
[2]Extracellular linker, amino acids 1-22; Transmembrane domain, amino acids 23-44; Cytosolic domain, amino acids 45-84

Configurations, Linkers, and Connectors

In some embodiments, a nucleic acid disclosed herein is in an order of (1) a first polynucleotide encoding an antigen-binding domain that binds Claudin 18.2; (2) a second polynucleotide encoding an antigen-binding domain that binds a TCR complex; (3) a third polynucleotide encoding a transmembrane domain and a cytosolic domain. In some embodiments, a nucleic acid disclosed herein is in an order of (1) a first polynucleotide encoding an antigen-binding domain that binds Claudin 18.2; (2) a second polynucleotide encoding an antigen-binding domain that binds a TCR complex; (3) a third polynucleotide encoding a transmembrane domain and a cytosolic domain, wherein the order is 5' end to 3' end. In some embodiments, a nucleic acid disclosed herein is in an order of (1) a first polynucleotide encoding an antigen-binding domain that binds Claudin 18.2; (2) a second polynucleotide encoding an antigen-binding domain that binds a TCR complex; (3) a third polynucleotide encoding a transmembrane domain and a cytosolic domain, wherein the order is 3' end to 5' end. In some embodiments, a nucleic acid described herein is in an order of (1) a first polynucleotide encoding an antigen-binding domain that binds a TCR complex; (2) a second polynucleotide encoding an antigen-binding domain that binds Claudin 18.2; (3) a third polynucleotide encoding a transmembrane domain and a cytosolic domain. In some embodiments, a nucleic acid described herein is in an order of (1) a first polynucleotide encoding an antigen-binding domain that binds a TCR complex; (2) a second polynucleotide encoding an antigen-binding domain that binds Claudin 18.2; (3) a third polynucleotide encoding a transmembrane domain and a cytosolic domain, wherein the order is 5' end to 3' end. In some embodiments, a nucleic acid described herein is in an order of (1) a first polynucleotide encoding an antigen-binding domain that binds a TCR complex; (2) a second polynucleotide encoding an antigen-binding domain that binds Claudin 18.2; (3) a third polynucleotide encoding a transmembrane domain and a cytosolic domain, wherein the order is 3' end to 5' end.

In some embodiments, a Claudin 18.2-TAC polypeptide disclosed herein is in an order of (1) an antigen-binding domain that binds Claudin 18.2; (2) an antigen-binding domain that binds a TCR complex; (3) a transmembrane domain and a cytosolic domain, wherein the order is N-terminus to C-terminus. In some embodiments, a Claudin 18.2-TAC polypeptide disclosed herein is in an order of (1) an antigen-binding domain that binds Claudin 18.2; (2) an antigen-binding domain that binds a TCR complex; (3) a transmembrane domain and a cytosolic domain, wherein the order is C-terminus to N-terminus. In some embodiments, a Claudin 18.2-TAC polypeptide described herein is in an order of (1) an antigen-binding domain that binds a TCR complex; (2) an antigen-binding domain that binds Claudin 18.2; (3) a transmembrane domain and a cytosolic domain, wherein the order is N-terminus to C-terminus. In some embodiments, a Claudin 18.2-TAC polypeptide described herein is in an order of (1) an antigen-binding domain that binds a TCR complex; (2) an antigen-binding domain that binds Claudin 18.2; (3) a transmembrane domain and a cytosolic domain, wherein the order is C-terminus to N-terminus.

In some embodiments, the antigen-binding domain that binds Claudin 18.2, the antigen-binding domain that binds the TCR complex, and/or the transmembrane domain and cytosolic domain are directly fused. For example, the antigen-binding domain that binds Claudin 18.2 and the transmembrane domain and cytosolic domain are both fused to the antigen-binding domain that binds the TCR complex. In some embodiments, the antigen-binding domain that binds Claudin 18.2, the antigen-binding domain that binds the TCR complex, and/or the transmembrane domain and cytosolic domain are joined by at least one linker. In some embodiments, the antigen-binding domain that binds Claudin 18.2 and the antigen-binding domain that binds the TCR complex are directly fused, and joined to the transmembrane domain and cytosolic domain by a linker. In some embodiments, the antigen-binding domain that binds the TCR complex and the transmembrane domain and cytosolic domain are directly fused, and joined to the antigen-binding domain that binds Claudin 18.2 by a linker.

In some embodiments, the linker is a peptide linker. In some embodiments, the peptide linker comprises 1 to 40 amino acids. In some embodiments, the peptide linker comprises 1 to 30 amino acids. In some embodiments, the peptide linker comprises 1 to 15 amino acids. In some embodiments, the peptide linker comprises 1 to 10 amino acids. In some embodiments, the peptide linker comprises 1 to 6 amino acids. In some embodiments, the peptide linker comprises 30 to 40 amino acids. In some embodiments, the peptide linker comprises 32 to 36 amino acids. In some embodiments, the peptide linker comprises 5 to 30 amino acids. In some embodiments, the peptide linker comprises 5 amino acids. In some embodiments, the peptide linker comprises 10 amino acids. In some embodiments, the peptide linker comprises 15 amino acids. In some embodiments, the peptide linker comprises 20 amino acids. In some embodiments, the peptide linker comprises 25 amino acids. In some embodiments, the peptide linker comprises 30 amino acids. In some embodiments, the peptide linker comprises a glycine and/or serine-rich linker.

In some embodiments, the at least one linker comprises an amino acid sequence having at least 80% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 85% identity with the amino acid sequence of SEQ ID NO:

6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 90% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 95% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 96% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 97% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 98% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises an amino acid sequence having at least 80% identity with the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker). In some embodiments, the at least one linker comprises the amino acid sequence of SEQ ID NO: 6 ((G4S)4-based linker), SEQ ID NO: 10 (G4S-based linker), SEQ ID NO: 14 (CD4 based linker), SEQ ID NO: 22 (short helix connector), SEQ ID NO: 24 (long helix connector), SEQ ID NO: 26 (large domain connector), SEQ ID NO: 41 (flexible connector), SEQ ID NO: 45 (G4S flexible linker), or SEQ ID NO: 46 (G4S3 flexible linker).

In some embodiments, the peptide linker that joins the antigen-binding domain that binds Claudin 18.2 to the antigen-binding domain that binds a TCR complex (e.g., UCHT1) is known as the connector to distinguish this protein domain from other linkers in the TAC. The connector may be of any size. In some embodiments, the connector between the antigen-binding domain that binds a TCR complex and the antigen-binding domain that binds Claudin 18.2 is a short helix comprising SEQ ID NO: 22. In some embodiments, the connector between the antigen-binding domain that binds a TCR complex and the antigen-binding domain that binds Claudin 18.2 is a short helix encoded by SEQ ID NO: 21. In some embodiments, the connector between the antigen-binding domain that binds a TCR complex and the antigen-binding domain that binds Claudin 18.2 is a long helix comprising SEQ ID NO: 24. In some embodiments, the connector between the antigen-binding domain that binds a TCR complex and the antigen-binding domain that binds Claudin 18.2 is a long helix encoded by SEQ ID NO: 23. In some embodiments, the connector between the antigen-binding domain that binds a TCR complex and the antigen-binding domain that binds Claudin 18.2 is a large domain comprising SEQ ID NO: 26. In some embodiments, the connector between the antigen-binding domain that binds a TCR complex and the antigen-binding domain that binds Claudin 18.2 is a large domain encoded by SEQ ID NO: 25.

In some embodiments, a nucleic acid or TAC disclosed herein comprises a leader sequence. In some embodiments, the leader sequence is encoded by a nucleotide sequence having at least 80% sequence identity with the nucleotide sequence of SEQ ID NO: 1 (muIgG leader), SEQ ID NO: 37 (huIgG leader), or SEQ ID NO: 39 (huCD8α leader). In some embodiments, the leader sequence is encoded by a nucleotide sequence having at least 85% sequence identity with the nucleotide sequence of SEQ ID NO: 1 (muIgG leader), SEQ ID NO: 37 (huIgG leader), or SEQ ID NO: 39 (huCD8α leader). In some embodiments, the leader sequence is encoded by a nucleotide sequence having at least 90% sequence identity with the nucleotide sequence of SEQ ID NO: 1 (muIgG leader), SEQ ID NO: 37 (huIgG leader), or SEQ ID NO: 39 (huCD8α leader). In some embodiments, the leader sequence is encoded by a nucleotide sequence having at least 95% sequence identity with the nucleotide sequence of SEQ ID NO: 1 (muIgG leader), SEQ ID NO: 37 (huIgG leader), or SEQ ID NO: 39 (huCD8α leader). In some embodiments, the leader sequence is encoded by a nucleotide sequence having at least 96% sequence identity with the nucleotide sequence of SEQ ID NO: 1 (muIgG leader), SEQ ID NO: 37 (huIgG leader), or SEQ ID NO: 39 (huCD8α leader). In some embodiments, the leader sequence is encoded by a nucleotide sequence having at least 97% sequence identity with the nucleotide sequence of SEQ ID NO: 1 (muIgG leader), SEQ ID NO: 37 (huIgG leader), or SEQ ID NO: 39 (huCD8α leader). In some embodiments, the leader sequence is encoded by a nucleotide sequence having at least 98% sequence identity with the nucleotide sequence of SEQ ID NO: 1 (muIgG leader), SEQ ID NO: 37 (huIgG leader), or SEQ ID NO: 39 (huCD8α leader). In some embodiments, the leader sequence is encoded by a nucleotide sequence having at least 99% sequence identity with the nucleotide sequence of SEQ ID NO: 1 (muIgG leader), SEQ ID NO: 37 (huIgG leader), or SEQ ID NO: 39 (huCD8α leader). In some embodiments, the leader sequence comprises the nucleotide sequence of SEQ ID NO: 1 (muIgG leader), SEQ ID NO: 37 (huIgG leader), or SEQ ID NO: 39 (huCD8α leader).

In some embodiments, a nucleic acid or TAC disclosed herein comprises a leader sequence. In some embodiments, the leader sequence comprises an amino acid sequence having at least 80% sequence identity with the amino acid sequence of SEQ ID NO: 2 (muIgG leader), SEQ ID NO: 38 (huIgG leader), or SEQ ID NO: 40 (huCD8α leader). In some embodiments, the leader sequence comprises an amino acid sequence having at least 85% sequence identity with the amino acid sequence of SEQ ID NO: 2 (muIgG leader), SEQ ID NO: 38 (huIgG leader), or SEQ ID NO: 40 (huCD8α leader). In some embodiments, the leader sequence comprises an amino acid sequence having at least 90% sequence identity with the amino acid sequence of SEQ ID NO: 2 (muIgG leader), SEQ ID NO: 38 (huIgG leader), or SEQ ID NO: 40 (huCD8α leader). In some embodiments, the leader sequence comprises an amino acid sequence having at least 95% sequence identity with the amino acid sequence of SEQ ID NO: 2 (muIgG leader), SEQ ID NO: 38 (huIgG leader), or SEQ ID NO: 40 (huCD8α leader). In some embodiments, the leader sequence comprises an amino acid sequence having at least 96% sequence identity with the amino acid sequence of SEQ ID NO: 2 (muIgG leader), SEQ ID NO: 38 (huIgG leader), or SEQ ID NO: 40 (huCD8α leader). In some embodiments, the leader sequence comprises an amino acid sequence having at least 97% sequence identity with the amino acid sequence of SEQ ID NO: 2 (muIgG leader), SEQ ID NO: 38 (huIgG leader), or SEQ ID NO: 40 (huCD8α leader). In some embodiments, the leader sequence comprises an amino acid sequence having at least 98% sequence identity with the amino acid sequence of SEQ ID NO: 2 (muIgG leader), SEQ ID NO: 38 (huIgG leader), or SEQ ID NO: 40 (huCD8α leader). In some embodiments, the leader sequence comprises an amino acid sequence having at least 99% sequence identity with the amino acid sequence of SEQ ID NO: 2 (muIgG leader), SEQ ID NO: 38 (huIgG leader), or SEQ ID NO: 40 (huCD8α leader). In some embodiments, the leader sequence comprises the amino acid sequence of SEQ ID NO: 2 (muIgG leader), SEQ ID NO: 38 (huIgG leader), or SEQ ID NO: 40 (huCD8α leader).

Amino acid and nucleotide sequences of exemplary linkers, connectors, and leader sequences are provided in Table 4.

TABLE 4

Table of Sequences

| SEQ ID NO | Description | Nucleotide/Amino Acid |
|---|---|---|
| SEQ ID NO: 1 | muIgG leader (secretion signal) | Nucleotide |
| SEQ ID NO: 2 | muIgG leader (secretion signal) | Amino Acid |
| SEQ ID NO: 3 | Myc Tag | Nucleotide |
| SEQ ID NO: 4 | Myc Tag | Amino Acid |
| SEQ ID NO: 5 | (G4S)4-based linker | Nucleotide |
| SEQ ID NO: 6 | (G4S)4-based linker | Amino Acid |
| SEQ ID NO: 9 | G4S-based linker | Nucleotide |
| SEQ ID NO: 10 | G4S-based linker | Amino Acid |
| SEQ ID NO: 13 | CD4 based linker | Nucleotide |
| SEQ ID NO: 14 | CD4 based linker | Amino Acid |
| SEQ ID NO: 21 | Short Helix connector | Nucleotide |
| SEQ ID NO: 22 | Short Helix connector | Amino Acid |
| SEQ ID NO: 23 | Long Helix connector | Nucleotide |
| SEQ ID NO: 24 | Long Helix connector | Amino Acid |
| SEQ ID NO: 25 | Large domain connector | Nucleotide |
| SEQ ID NO: 26 | Large domain connector | Amino Acid |
| SEQ ID NO: 37 | huIgG leader | Nucleotide |
| SEQ ID NO: 38 | huIgG leader | Amino Acid |
| SEQ ID NO: 39 | huCD8a leader | Nucleotide |
| SEQ ID NO: 40 | huCD8a leader | Amino Acid |
| SEQ ID NO: 41 | Flexible Connector | Amino Acid |
| SEQ ID NO: 42 | Flexible Connector | Nucleotide |
| SEQ ID NO: 45 | G4S flexible linker | Amino Acid |
| SEQ ID NO: 54 | G4S flexible linker | Nucleotide |

TABLE 4-continued

Table of Sequences

| SEQ ID NO | Description | Nucleotide/Amino Acid |
|---|---|---|
| SEQ ID NO: 46 | G4S3 flexible linker | Amino Acid |
| SEQ ID NO: 47 | G4S3 flexible linker | Nucleotide |

Specific TACs

Disclosed herein, in certain embodiments, are Claudin 18.2-TAC polypeptides comprising (a) an antigen-binding domain that binds Claudin 18.2, (b) a single-chain antibody (scFv) that binds CD3ε, and (c) a transmembrane and cytosolic domain of the CD4 co-receptor. In some embodiments, the Claudin 18.2-TAC polypeptides comprise (a) an antigen-binding domain that binds Claudin 18.2, (b) UCHT1, and (c) a transmembrane and cytosolic domain of the CD4 co-receptor. In some embodiments, the Claudin 18.2-TAC polypeptides comprise (a) an antigen-binding domain that binds Claudin 18.2, (b) UCHT1 (Y182T), and (c) a transmembrane and cytosolic domain of the CD4 co-receptor. In some embodiments, the Claudin 18.2-TAC polypeptides comprise (a) an antigen-binding domain that binds Claudin 18.2, (b) huUCHT1, and (c) a transmembrane and cytosolic domain of the CD4 co-receptor. In some embodiments, the Claudin 18.2-TAC polypeptides comprise (a) an antigen-binding domain that binds Claudin 18.2, (b) huUCHT1 (Y177T), and (c) a transmembrane and cytosolic domain of the CD4 co-receptor. In some embodiments, the Claudin 18.2-TAC polypeptides comprise (a) an antigen-binding domain that binds Claudin 18.2, (b) OKT3, and (c) a transmembrane and cytosolic domain of the CD4 co-receptor. In some embodiments, the Claudin 18.2-TAC polypeptides comprise (a) an antigen-binding domain that binds Claudin 18.2, (b) F6A, and (c) a transmembrane and cytosolic domain of the CD4 co-receptor. In some embodiments, the Claudin 18.2-TAC polypeptides comprise (a) an antigen-binding domain that binds Claudin 18.2, (b) L2K, and (c) a transmembrane and cytosolic domain of the CD4 co-receptor.

Disclosed herein, in certain embodiments, are Claudin 18.2-TAC polypeptides comprising (a) a DARPin that binds Claudin 18.2, (b) UCHT1, and (c) a transmembrane and cytosolic domain of the CD4 co-receptor. In some embodiments, the Claudin 18.2-TAC polypeptides comprise (a) a DARPin that binds Claudin 18.2, (b) UCHT1 (Y182T), and (c) a transmembrane and cytosolic domain of the CD4 co-receptor. In some embodiments, the Claudin 18.2-TAC polypeptides comprise (a) a DARPin that binds Claudin 18.2, (b) huUCHT1, and (c) a transmembrane and cytosolic domain of the CD4 co-receptor. In some embodiments, the Claudin 18.2-TAC polypeptides comprise (a) a DARPin that binds Claudin 18.2, (b) huUCHT1 (Y177T), and (c) a transmembrane and cytosolic domain of the CD4 co-receptor. In some embodiments, the Claudin 18.2-TAC polypeptides comprise (a) a DARPin that binds Claudin 18.2, (b) OKT3, and (c) a transmembrane and cytosolic domain of the CD4 co-receptor. In some embodiments, the Claudin 18.2-TAC polypeptides comprise (a) a DARPin that binds Claudin 18.2, (b) F6A, and (c) a transmembrane and cytosolic domain of the CD4 co-receptor. In some embodiments, the Claudin 18.2-TAC polypeptides comprise (a) a DARPin that binds Claudin 18.2, (b) L2K, and (c) a transmembrane and cytosolic domain of the CD4 co-receptor.

Disclosed herein, in certain embodiments, are Claudin 18.2-TACs comprising (a) a scFv that binds Claudin 18.2, (b) UCHT1, and (c) a transmembrane and cytosolic domain of the CD4 co-receptor. In some embodiments, the Claudin 18.2-TAC polypeptides comprise (a) a scFv that binds Claudin 18.2, (b) UCHT1 (Y182T), and (c) a transmembrane and cytosolic domain of the CD4 co-receptor. In some embodiments, the Claudin 18.2-TAC polypeptides comprise (a) a scFv that binds Claudin 18.2, (b) huUCHT1, and (c) a transmembrane and cytosolic domain of the CD4 co-receptor. In some embodiments, the Claudin 18.2-TAC polypeptides comprise (a) a scFv that binds Claudin 18.2, (b) huUCHT1 (Y177T), and (c) a transmembrane and cytosolic domain of the CD4 co-receptor. In some embodiments, the Claudin 18.2-TAC polypeptides comprise (a) a scFv that binds Claudin 18.2, (b) OKT3, and (c) a transmembrane and cytosolic domain of the CD4 co-receptor. In some embodiments, the Claudin 18.2-TAC polypeptides comprise (a) a scFv that binds Claudin 18.2, (b) F6A, and (c) a transmembrane and cytosolic domain of the CD4 co-receptor. In some embodiments, the Claudin 18.2-TAC polypeptides comprise (a) a scFv that binds Claudin 18.2, (b) L2K, and (c) a transmembrane and cytosolic domain of the CD4 co-receptor.

Disclosed herein, in certain embodiments, are Claudin 18.2-TACs comprising (a) a nanobody that binds Claudin 18.2, (b) UCHT1, and (c) a transmembrane and cytosolic domain of the CD4 co-receptor. In some embodiments, the Claudin 18.2-TAC polypeptides comprise (a) a nanobody that binds Claudin 18.2, (b) UCHT1 (Y182T), and (c) a transmembrane and cytosolic domain of the CD4 co-receptor. In some embodiments, the Claudin 18.2-TAC polypeptides comprise (a) a nanobody that binds Claudin 18.2, (b) huUCHT1, and (c) a transmembrane and cytosolic domain of the CD4 co-receptor. In some embodiments, the Claudin 18.2-TAC polypeptides comprise (a) a nanobody that binds Claudin 18.2, (b) huUCHT1 (Y177T), and (c) a transmembrane and cytosolic domain of the CD4 co-receptor. In some embodiments, the Claudin 18.2-TAC polypeptides comprise (a) a nanobody that binds Claudin 18.2, (b) OKT3, and (c) a transmembrane and cytosolic domain of the CD4 co-receptor. In some embodiments, the Claudin 18.2-TAC polypeptides comprise (a) a nanobody that binds Claudin 18.2, (b) F6A, and (c) a transmembrane and cytosolic domain of the CD4 co-receptor. In some embodiments, the Claudin 18.2-TAC polypeptides comprise (a) a nanobody that binds Claudin 18.2, (b) L2K, and (c) a transmembrane and cytosolic domain of the CD4 co-receptor.

Disclosed herein, in certain embodiments, are Claudin 18.2-TACs comprising (a) an antigen-binding domain that binds Claudin 18.2, (b) a single-chain antibody (scFv) that binds CD3ε, and (c) a transmembrane and cytosolic domain of the CD8 co-receptor. In some embodiments, the Claudin 18.2-TAC polypeptides comprise (a) an antigen-binding domain that binds Claudin 18.2, (b) UCHT1, and (c) a transmembrane and cytosolic domain of the CD8 co-receptor. In some embodiments, the Claudin 18.2-TAC polypeptides comprise (a) an antigen-binding domain that binds Claudin 18.2, (b) UCHT1 (Y182T), and (c) a transmembrane and cytosolic domain of the CD8 co-receptor. In some embodiments, the Claudin 18.2-TAC polypeptides comprise (a) an antigen-binding domain that binds Claudin 18.2, (b) huUCHT1, and (c) a transmembrane and cytosolic domain of the CD8 co-receptor. In some embodiments, the Claudin 18.2-TAC polypeptides comprise (a) an antigen-binding domain that binds Claudin 18.2, (b) huUCHT1 (Y177T), and (c) a transmembrane and cytosolic domain of the CD8 co-receptor. In some embodiments, the Claudin 18.2-TAC polypeptides comprise (a) an antigen-binding domain that binds Claudin 18.2, (b) OKT3, and (c) a transmembrane and cytosolic domain of the CD8 co-receptor. In some embodiments, the Claudin 18.2-TAC polypeptides comprise (a) an antigen-binding domain that binds Claudin 18.2, (b) F6A, and (c) a transmembrane and cytosolic domain of the CD8 co-receptor. In some embodiments, the Claudin 18.2-TAC polypeptides comprise (a) an antigen-binding domain that binds Claudin 18.2, (b) L2K, and (c) a transmembrane and cytosolic domain of the CD8 co-receptor.

Disclosed herein, in certain embodiments, are Claudin 18.2-TACs comprising (a) a DARPin that binds Claudin 18.2, (b) UCHT1, and (c) a transmembrane and cytosolic domain of the CD4 co-receptor. In some embodiments, the Claudin 18.2-TAC polypeptides comprise (a) a DARPin that binds Claudin 18.2, (b) UCHT1 (Y182T), and (c) a transmembrane and cytosolic domain of the CD8 co-receptor. In some embodiments, the Claudin 18.2-TAC polypeptides comprise (a) a DARPin that binds Claudin 18.2, (b) huUCHT1, and (c) a transmembrane and cytosolic domain of the CD8 co-receptor. In some embodiments, the Claudin 18.2-TAC polypeptides comprise (a) a DARPin that binds Claudin 18.2, (b) huUCHT1 (Y177T), and (c) a transmembrane and cytosolic domain of the CD8 co-receptor. In some embodiments, the Claudin 18.2-TAC polypeptides comprise (a) a DARPin that binds Claudin 18.2, (b) OKT3, and (c) a transmembrane and cytosolic domain of the CD8 co-receptor. In some embodiments, the Claudin 18.2-TAC polypeptides comprise (a) a DARPin that binds Claudin 18.2, (b) F6A, and (c) a transmembrane and cytosolic domain of the CD8 co-receptor. In some embodiments, the Claudin 18.2-TAC polypeptides comprise (a) a DARPin that binds Claudin 18.2, (b) L2K, and (c) a transmembrane and cytosolic domain of the CD8 co-receptor.

Disclosed herein, in certain embodiments, are Claudin 18.2-TACs comprising (a) a scFv that binds Claudin 18.2, (b) UCHT1, and (c) a transmembrane and cytosolic domain of the CD8 co-receptor. In some embodiments, the Claudin 18.2-TAC polypeptides comprise (a) a scFv that binds Claudin 18.2, (b) UCHT1 (Y182T), and (c) a transmembrane and cytosolic domain of the CD8 co-receptor. In some embodiments, the Claudin 18.2-TAC polypeptides comprise (a) a scFv that binds Claudin 18.2, (b) huUCHT1, and (c) a transmembrane and cytosolic domain of the CD8 co-receptor. In some embodiments, the Claudin 18.2-TAC polypeptides comprise (a) a scFv that binds Claudin 18.2, (b) huUCHT1 (Y177T), and (c) a transmembrane and cytosolic domain of the CD8 co-receptor. In some embodiments, the Claudin 18.2-TAC polypeptides comprise (a) a scFv that binds Claudin 18.2, (b) OKT3, and (c) a transmembrane and cytosolic domain of the CD8 co-receptor. In some embodiments, the TAC polypeptides comprise (a) a scFv that binds Claudin 18.2, (b) F6A, and (c) a transmembrane and cytosolic domain of the CD8 co-receptor. In some embodiments, the Claudin 18.2-TAC polypeptides comprise (a) a scFv that binds Claudin 18.2, (b) L2K, and (c) a transmembrane and cytosolic domain of the CD8 co-receptor.

Disclosed herein, in certain embodiments, are Claudin 18.2-TACs comprising (a) a nanobody that binds Claudin 18.2, (b) UCHT1, and (c) a transmembrane and cytosolic domain of the CD8 co-receptor. In some embodiments, the Claudin 18.2-TAC polypeptides comprise (a) a nanobody that binds Claudin 18.2, (b) UCHT1 (Y182T), and (c) a transmembrane and cytosolic domain of the CD8 co-receptor. In some embodiments, the Claudin 18.2-TAC polypeptides comprise (a) a nanobody that binds Claudin 18.2, (b) huUCHT1, and (c) a transmembrane and cytosolic domain of the CD8 co-receptor. In some embodiments, the Claudin 18.2-TAC polypeptides comprise (a) a nanobody that binds Claudin 18.2, (b) huUCHT1 (Y177T), and (c) a transmembrane and cytosolic domain of the CD8 co-receptor. In some embodiments, the Claudin 18.2-TAC polypeptides comprise (a) a nanobody that binds Claudin 18.2, (b) OKT3, and (c) a transmembrane and cytosolic domain of the CD8 co-receptor. In some embodiments, the TAC polypeptides comprise (a) a nanobody that binds Claudin 18.2, (b) F6A, and (c) a transmembrane and cytosolic domain of the CD8 co-receptor. In some embodiments, the Claudin 18.2-TAC polypeptides comprise (a) a nanobody that binds Claudin 18.2, (b) L2K, and (c) a transmembrane and cytosolic domain of the CD8 co-receptor.

In certain instances, the Claudin 18.2-TAC polypeptides draw CD3 and TCR into lipid raft regions of the membrane, and brings Lck into the proximity of the TCR, similar to natural MHC binding.

In some embodiments, the Claudin 18.2-TAC comprises (from N- to C-terminus): (a) a myc tag, (b) a (G4S)4-based linker, (c) a humanized variant of UCHT1 (huUCHT1), (d) a G4S-based linker, and (e) a CD4 transmembrane and cytosolic domain.

For example, in some embodiments, the polynucleotide encoding the Claudin 18.2-TAC comprises a nucleotide sequence encoding an antigen-binding domain that binds Claudin 18.2 and a nucleotide sequence having at least 70% sequence identity with the nucleotide sequence of SEQ ID NO: 50 (Scaffold 1). In some embodiments, the polynucleotide encoding the Claudin 18.2-TAC comprises a nucleotide sequence encoding an antigen-binding domain that binds Claudin 18.2 and a nucleotide sequence having at least 75% sequence identity with the nucleotide sequence of SEQ ID NO: 50 (Scaffold 1). In some embodiments, the polynucleotide encoding the Claudin 18.2-TAC comprises a nucleotide sequence encoding an antigen-binding domain that binds Claudin 18.2 and a nucleotide sequence having at least 80% sequence identity with the nucleotide sequence of SEQ ID NO: 50 (Scaffold 1). In some embodiments, the polynucleotide encoding the Claudin 18.2-TAC comprises a nucleotide sequence encoding an antigen-binding domain that binds Claudin 18.2 and a nucleotide sequence having at least 85% sequence identity with the nucleotide sequence of SEQ ID NO: 50 (Scaffold 1). In some embodiments, the polynucleotide encoding the Claudin 18.2-TAC comprises a nucleotide sequence encoding an antigen-binding domain that binds Claudin 18.2 and a nucleotide sequence having at least 90% sequence identity with the nucleotide sequence of SEQ ID NO: 50 (Scaffold 1). In some embodiments, the polynucleotide encoding the Claudin 18.2-TAC comprises a nucleotide sequence encoding an antigen-binding domain that binds Claudin 18.2 and a nucleotide sequence having at least 95% sequence identity with the nucleotide sequence of SEQ ID NO: 50 (Scaffold 1). In some embodiments, the polynucleotide encoding the Claudin 18.2-TAC comprises a nucleotide sequence encoding an antigen-binding domain that binds Claudin 18.2 and a nucleotide sequence having at least 96% sequence identity with the nucleotide sequence of SEQ ID NO: 50 (Scaffold 1). In some embodiments, the polynucleotide encoding the Claudin 18.2-TAC comprises a nucleotide sequence encoding an antigen-binding domain that binds Claudin 18.2 and a nucleotide sequence having at least 97% sequence identity with the nucleotide sequence of SEQ ID NO: 50 (Scaffold 1). In some embodiments, the polynucleotide encoding the Claudin 18.2-TAC comprises a nucleotide sequence encoding an antigen-binding domain that binds Claudin 18.2 and a nucleotide sequence having at least 98% sequence identity with the nucleotide sequence of SEQ ID NO: 50 (Scaffold 1). In some embodiments, the polynucleotide encoding the Claudin 18.2-TAC comprises a nucleotide sequence encoding an antigen-binding domain that binds Claudin 18.2 and a nucleotide sequence having at least 99% sequence identity with the nucleotide sequence of SEQ ID NO: 50 (Scaffold 1). In some embodiments, the polynucleotide encoding the Claudin 18.2-TAC comprises a nucleotide sequence encoding an antigen-binding domain that binds Claudin 18.2 and the nucleotide sequence of SEQ ID NO: 50 (Scaffold 1).

In some embodiments, the Claudin 18.2-TAC comprises an antigen-binding domain that binds Claudin 18.2 and an amino acid sequence having at least 70% sequence identity with the amino acid sequence of SEQ ID NO: 51 (Scaffold 1). In some embodiments, the Claudin 18.2-TAC comprises an antigen-binding domain that binds Claudin 18.2 and an amino acid sequence having at least 75% sequence identity with the amino acid sequence of SEQ ID NO: 51 (Scaffold 1). In some embodiments, the Claudin 18.2-TAC comprises an antigen-binding domain that binds Claudin 18.2 and an amino acid sequence having at least 80% sequence identity with the amino acid sequence of SEQ ID NO: 51 (Scaffold 1). In some embodiments, the Claudin 18.2-TAC comprises an antigen-binding domain that binds Claudin 18.2 and an amino acid sequence having at least 85% sequence identity with the amino acid sequence of SEQ ID NO: 51 (Scaffold 1). In some embodiments, the Claudin 18.2-TAC comprises an antigen-binding domain that binds Claudin 18.2 and an amino acid sequence having at least 90% sequence identity with the amino acid sequence of SEQ ID NO: 51 (Scaffold 1). In some embodiments, the Claudin 18.2-TAC comprises an antigen-binding domain that binds Claudin 18.2 and an amino acid sequence having at least 95% sequence identity with the amino acid sequence of SEQ ID NO: 51 (Scaffold 1). In some embodiments, the Claudin 18.2-TAC comprises an antigen-binding domain that binds Claudin 18.2 and an amino acid sequence having at least 96% sequence identity with the amino acid sequence of SEQ ID NO: 51 (Scaffold 1). In some embodiments, the Claudin 18.2-TAC comprises an antigen-binding domain that binds Claudin 18.2 and an amino acid sequence having at least 97% sequence identity with the amino acid sequence of SEQ ID NO: 51 (Scaffold 1). In some embodiments, the Claudin 18.2-TAC comprises an antigen-binding domain that binds Claudin 18.2 and an amino acid sequence having at least 98% sequence identity with the amino acid sequence of SEQ ID NO: 51 (Scaffold 1). In some embodiments, the Claudin 18.2-TAC comprises an antigen-binding domain that binds Claudin 18.2 and an amino acid sequence having at least 99% sequence identity with the amino acid sequence of SEQ ID NO: 51 (Scaffold 1). In some embodiments, the Claudin 18.2-TAC comprises an antigen-binding domain that binds Claudin 18.2 and the amino acid sequence of SEQ ID NO: 51 (Scaffold 1).

In some embodiments, the Claudin 18.2-TAC comprises (from N- to C-terminus): (a) a myc tag, (b) a (G4S)4-based linker, (c) a humanized variant of UCHT1 comprising a Y to T mutation at a position corresponding to amino acid 177 of SEQ ID NO: 34 (huUCHT1 (Y177T)), (d) a G4S-based linker, and (e) a CD4 transmembrane and cytosolic domain.

For example, in some embodiments, the polynucleotide encoding the Claudin 18.2-TAC comprises a nucleotide sequence encoding an antigen-binding domain that binds Claudin 18.2 and a nucleotide sequence having at least 70% sequence identity with the nucleotide sequence of SEQ ID NO: 52 (Scaffold 2). In some embodiments, the polynucleotide encoding the Claudin 18.2-TAC comprises a nucleotide sequence encoding an antigen-binding domain that binds Claudin 18.2 and a nucleotide sequence having at least 75% sequence identity with the nucleotide sequence of SEQ ID NO: 52 (Scaffold 2). In some embodiments, the polynucleotide encoding the Claudin 18.2-TAC comprises a nucleotide sequence encoding an antigen-binding domain that binds Claudin 18.2 and a nucleotide sequence having at least 80% sequence identity with the nucleotide sequence of SEQ ID NO: 52 (Scaffold 2). In some embodiments, the polynucleotide encoding the Claudin 18.2-TAC comprises a nucleotide sequence encoding an antigen-binding domain that binds Claudin 18.2 and a nucleotide sequence having at least 85% sequence identity with the nucleotide sequence of SEQ ID NO: 52 (Scaffold 2). In some embodiments, the polynucleotide encoding the Claudin 18.2-TAC comprises a nucleotide sequence encoding an antigen-binding domain that binds Claudin 18.2 and a nucleotide sequence having at least 90% sequence identity with the nucleotide sequence of SEQ ID NO: 52 (Scaffold 2). In some embodiments, the polynucleotide encoding the Claudin 18.2-TAC comprises a nucleotide sequence encoding an antigen-binding domain that binds Claudin 18.2 and a nucleotide sequence having at least 95% sequence identity with the nucleotide sequence of SEQ ID NO: 52 (Scaffold 2). In some embodiments, the polynucleotide encoding the Claudin 18.2-TAC comprises a nucleotide sequence encoding an antigen-binding domain that binds Claudin 18.2 and a nucleotide sequence having at least 96% sequence identity with the nucleotide sequence of SEQ ID NO: 52 (Scaffold 2). In some embodiments, the polynucleotide encoding the Claudin 18.2-TAC comprises a nucleotide sequence encoding an antigen-binding domain that binds Claudin 18.2 and a nucleotide sequence having at least 97% sequence identity with the nucleotide sequence of SEQ ID NO: 52 (Scaffold 2). In some embodiments, the polynucleotide encoding the Claudin 18.2-TAC comprises a nucleotide sequence encoding an antigen-binding domain that binds Claudin 18.2 and a nucleotide sequence having at least 98% sequence identity with the nucleotide sequence of SEQ ID NO: 52 (Scaffold 2). In some embodiments, the polynucleotide encoding the Claudin 18.2-TAC comprises a nucleotide sequence encoding an antigen-binding domain that binds Claudin 18.2 and a nucleotide sequence having at least 99% sequence identity with the nucleotide sequence of SEQ ID NO: 52 (Scaffold 2). In some embodiments, the polynucleotide encoding the Claudin 18.2-TAC comprises a nucleotide sequence encoding an antigen-binding domain that binds Claudin 18.2 and the nucleotide sequence of SEQ ID NO: 52 (Scaffold 2).

In some embodiments, the Claudin 18.2-TAC comprises an amino acid sequence having at least 70% sequence identity with the amino acid sequence of SEQ ID NO: 53 (Scaffold 2). In some embodiments, the Claudin 18.2-TAC comprises an antigen-binding domain that binds Claudin 18.2 and an amino acid sequence having at least 75% sequence identity with the amino acid sequence of SEQ ID NO: 53 (Scaffold 2). In some embodiments, the Claudin 18.2-TAC comprises an antigen-binding domain that binds Claudin 18.2 and an amino acid sequence having at least 80% sequence identity with the amino acid sequence of SEQ ID NO: 53 (Scaffold 2). In some embodiments, the Claudin 18.2-TAC comprises an antigen-binding domain that binds Claudin 18.2 and an amino acid sequence having at least 85% sequence identity with the amino acid sequence of SEQ ID NO: 53 (Scaffold 2). In some embodiments, the Claudin 18.2-TAC comprises an antigen-binding domain that binds Claudin 18.2 and an amino acid sequence having at least 90% sequence identity with the amino acid sequence of SEQ ID NO: 53 (Scaffold 2). In some embodiments, the Claudin 18.2-TAC comprises an antigen-binding domain that binds Claudin 18.2 and an amino acid sequence having at least 95% sequence identity with the amino acid sequence of SEQ ID NO: 53 (Scaffold 2). In some embodiments, the Claudin 18.2-TAC comprises an antigen-binding domain that binds Claudin 18.2 and an amino acid sequence having at least 96% sequence identity with the amino acid sequence of SEQ ID NO: 53 (Scaffold 2). In some embodiments, the Claudin 18.2-TAC comprises an antigen-binding domain that binds Claudin 18.2 and an amino acid sequence having at least 97% sequence identity with the amino acid sequence of SEQ ID NO: 53 (Scaffold 2). In some embodiments, the Claudin 18.2-TAC comprises an antigen-binding domain that binds Claudin 18.2 and an amino acid sequence having at least 98% sequence identity with the amino acid sequence of SEQ ID NO: 53 (Scaffold 2). In some embodiments, the Claudin 18.2-TAC comprises an antigen-binding domain that binds Claudin 18.2 and an amino acid sequence having at least 99% sequence identity with the amino acid sequence of SEQ ID NO: 53 (Scaffold 2). In some embodiments, the Claudin 18.2-TAC comprises an antigen-binding domain that binds Claudin 18.2 and the amino acid sequence of SEQ ID NO: 53 (Scaffold 2).

Amino acid and nucleotide sequences of exemplary TACs scaffolds are provided in Table 5.

TABLE 5

Table of Sequences

| SEQ ID NO | Description | Nucleotide/ Amino Acid |
|---|---|---|
| SEQ ID NO: 50 | Scaffold 1 (Myc tag - (G4S)4-based linker - huUCHT1 - G4S-based linker - CD4) | Nucleotide |
| SEQ ID NO: 51 | Scaffold 1 (Myc tag - (G4S)4-based linker - huUCHT1 - G4S-based linker - CD4) | Amino Acid |
| SEQ ID NO: 52 | Scaffold 2 (Myc tag - (G4S)4-based linker - huUCHT1 (Y177T) - G4S-based linker - CD4) | Nucleotide |
| SEQ ID NO: 53 | Scaffold 2 (Myc tag - (G4S)4-based linker - huUCHT1 (Y177T) - G4S-based linker - CD4) | Amino Acid |

In some embodiments, the Claudin 18.2-TAC comprises (from N- to C-terminus): (a) a CD8α leader, (b) Claudin 18.2 Nanobody 1 (SEQ ID NO: 55), (c) a myc tag, (d) a (G4S)4-based linker, (e) a humanized variant of UCHT1, (d) a G4S-based linker, and (e) a CD4 transmembrane and cytosolic domain.

In some embodiments, the polynucleotide encoding the Claudin 18.2-TAC comprises a nucleotide sequence having at least 70% sequence identity with the nucleotide sequence of SEQ ID NO: 66 (Nanobody 1/huUCHT1 Scaffold). In some embodiments, the polynucleotide encoding the Claudin 18.2-TAC comprises a nucleotide sequence having at least 75% sequence identity with the nucleotide sequence of SEQ ID NO: 66 (Nanobody 1/huUCHT1 Scaffold). In some embodiments, the polynucleotide encoding the Claudin 18.2-TAC comprises a nucleotide sequence having at least 80% sequence identity with the nucleotide sequence of SEQ ID NO: 66 (Nanobody 1/huUCHT1 Scaffold). In some embodiments, the polynucleotide encoding the Claudin 18.2-TAC comprises a nucleotide sequence having at least 85% sequence identity with the nucleotide sequence of SEQ ID NO: 66 (Nanobody 1/huUCHT1 Scaffold). In some embodiments, the polynucleotide encoding the Claudin 18.2-TAC comprises a nucleotide sequence having at least 90% sequence identity with the nucleotide sequence of SEQ ID NO: 66 (Nanobody 1/huUCHT1 Scaffold). In some embodiments, the polynucleotide encoding the Claudin 18.2-TAC comprises a nucleotide sequence having at least 95% sequence identity with the nucleotide sequence of SEQ ID NO: 66 (Nanobody 1/huUCHT1 Scaffold). In some embodiments, the polynucleotide encoding the Claudin 18.2-TAC comprises a nucleotide sequence having at least 96% sequence identity with the nucleotide sequence of SEQ ID NO: 66 (Nanobody 1/huUCHT1 Scaffold). In some embodiments, the polynucleotide encoding the Claudin 18.2-TAC comprises a nucleotide sequence having at least 97% sequence identity with the nucleotide sequence of SEQ ID NO: 66 (Nanobody 1/huUCHT1 Scaffold). In some embodiments, the polynucleotide encoding the Claudin 18.2-TAC comprises a nucleotide sequence having at least 98% sequence identity with the nucleotide sequence of SEQ ID NO: 66 (Nanobody 1/huUCHT1 Scaffold). In some embodiments, the polynucleotide encoding the Claudin 18.2-TAC comprises a nucleotide sequence having at least 99% sequence identity with the nucleotide sequence of SEQ ID NO: 66 (Nanobody 1/huUCHT1 Scaffold). In some embodiments, the polynucleotide encoding the Claudin 18.2-TAC comprises the nucleotide sequence of SEQ ID NO: 66 (Nanobody 1/huUCHT1 Scaffold).

In some embodiments, the Claudin 18.2-TAC comprises an amino acid sequence having at least 70% sequence identity with the amino acid sequence of SEQ ID NO: 67 (Nanobody 1/huUCHT1 Scaffold). In some embodiments, the Claudin 18.2-TAC comprises an amino acid sequence having at least 75% sequence identity with the amino acid sequence of SEQ ID NO: 67 (Nanobody 1/huUCHT1 Scaffold). In some embodiments, the Claudin 18.2-TAC comprises an amino acid sequence having at least 80% sequence identity with the amino acid sequence of SEQ ID NO: 67 (Nanobody 1/huUCHT1 Scaffold). In some embodiments, the Claudin 18.2-TAC comprises an amino acid sequence having at least 85% sequence identity with the amino acid sequence of SEQ ID NO: 67 (Nanobody 1/huUCHT1 Scaffold). In some embodiments, the Claudin 18.2-TAC comprises an amino acid sequence having at least 90% sequence identity with the amino acid sequence of SEQ ID NO: 67 (Nanobody 1/huUCHT1 Scaffold). In some embodiments, the Claudin 18.2-TAC comprises an amino acid sequence having at least 95% sequence identity with the amino acid sequence of SEQ ID NO: 67 (Nanobody 1/huUCHT1 Scaffold). In some embodiments, the Claudin 18.2-TAC comprises an amino acid sequence having at least 96% sequence identity with the amino acid sequence of SEQ ID NO: 67 (Nanobody 1/huUCHT1 Scaffold). In some embodiments, the Claudin 18.2-TAC comprises an amino acid sequence having at least 97% sequence identity with the amino acid sequence of SEQ ID NO: 67 (Nanobody 1/huUCHT1 Scaffold). In some embodiments, the Claudin 18.2-TAC comprises an amino acid sequence having at least 98% sequence identity with the amino acid sequence of SEQ ID NO: 67 (Nanobody 1/huUCHT1 Scaffold). In some embodiments, the Claudin 18.2-TAC comprises an amino acid sequence having at least 99% sequence identity with the amino acid sequence of SEQ ID NO: 67 (Nanobody 1/huUCHT1 Scaffold). In some embodiments, the Claudin 18.2-TAC comprises the amino acid sequence of SEQ ID NO: 67 (Nanobody 1/huUCHT1 Scaffold).

In some embodiments, the Claudin 18.2-TAC comprises (from N- to C-terminus): (a) a CD8a leader, (b) Claudin 18.2 Nanobody 1 (SEQ ID NO: 55), (c) a myc tag, (d) a (G4S)4-based linker, (e) a humanized variant of UCHT1 comprising a Y to T mutation at a position corresponding to amino acid 177 of SEQ ID NO: 34 (huUCHT1 (Y177T)), (d) a G4S-based linker, and (e) a CD4 transmembrane and cytosolic domain.

In some embodiments, the polynucleotide encoding the Claudin 18.2-TAC comprises a nucleotide sequence having at least 70% sequence identity with the nucleotide sequence of SEQ ID NO: 68 (Nanobody 1/huUCHT1 Y177T Scaffold). In some embodiments, the polynucleotide encoding the Claudin 18.2-TAC comprises a nucleotide sequence having at least 75% sequence identity with the nucleotide sequence of SEQ ID NO: 68 (Nanobody 1/huUCHT1 Y177T Scaffold). In some embodiments, the polynucleotide encoding the Claudin 18.2-TAC comprises a nucleotide sequence having at least 80% sequence identity with the nucleotide sequence of SEQ ID NO: 68 (Nanobody 1/huUCHT1 Y177T Scaffold). In some embodiments, the polynucleotide encoding the Claudin 18.2-TAC comprises a nucleotide sequence having at least 85% sequence identity with the nucleotide sequence of SEQ ID NO: 68 (Nanobody 1/huUCHT1 Y177T Scaffold). In some embodiments, the polynucleotide encoding the Claudin 18.2-TAC comprises a nucleotide sequence having at least 90% sequence identity with the nucleotide sequence of SEQ ID NO: 68 (Nanobody 1/huUCHT1 Y177T Scaffold). In some embodiments, the polynucleotide encoding the Claudin 18.2-TAC comprises a nucleotide sequence having at least 95% sequence identity with the nucleotide sequence of SEQ ID NO: 68 (Nanobody 1/huUCHT1 Y177T Scaffold). In some embodiments, the polynucleotide encoding the Claudin 18.2-TAC comprises a nucleotide sequence having at least 96% sequence identity with the nucleotide sequence of SEQ ID NO: 68 (Nanobody 1/huUCHT1 Y177T Scaffold). In some embodiments, the polynucleotide encoding the Claudin 18.2-TAC comprises a nucleotide sequence having at least 97% sequence identity with the nucleotide sequence of SEQ ID NO: 68 (Nanobody 1/huUCHT1 Y177T Scaffold). In some embodiments, the polynucleotide encoding the Claudin 18.2-TAC comprises a nucleotide sequence having at least 98% sequence identity with the nucleotide sequence of SEQ ID NO: 68 (Nanobody 1/huUCHT1 Y177T Scaffold). In some embodiments, the polynucleotide encoding the Claudin 18.2-TAC comprises a nucleotide sequence having at least 99% sequence identity with the nucleotide sequence of SEQ ID NO: 68 (Nanobody 1/huUCHT1 Y177T Scaffold). In some embodiments, the polynucleotide encoding the Claudin 18.2-TAC comprises the nucleotide sequence of SEQ ID NO: 68 (Nanobody 1/huUCHT1 Y177T Scaffold).

In some embodiments, the polynucleotide encoding the Claudin 18.2-TAC comprises a nucleotide sequence having at least 70% sequence identity with the nucleotide sequence of SEQ ID NO: 74 (Nanobody 1/huUCHT1 Y177T Scaffold). In some embodiments, the polynucleotide encoding the Claudin 18.2-TAC comprises a nucleotide sequence having at least 75% sequence identity with the nucleotide sequence of SEQ ID NO: 74 (Nanobody 1/huUCHT1 Y177T Scaffold). In some embodiments, the polynucleotide encoding the Claudin 18.2-TAC comprises a nucleotide sequence having at least 80% sequence identity with the nucleotide sequence of SEQ ID NO: 74 (Nanobody 1/huUCHT1 Y177T Scaffold). In some embodiments, the polynucleotide encoding the Claudin 18.2-TAC comprises a nucleotide sequence having at least 85% sequence identity with the nucleotide sequence of SEQ ID NO: 74 (Nanobody 1/huUCHT1 Y177T Scaffold). In some embodiments, the polynucleotide encoding the Claudin 18.2-TAC comprises a nucleotide sequence having at least 90% sequence identity with the nucleotide sequence of SEQ ID NO: 74 (Nanobody 1/huUCHT1 Y177T Scaffold). In some embodiments, the polynucleotide encoding the Claudin 18.2-TAC comprises a nucleotide sequence having at least 95% sequence identity with the nucleotide sequence of SEQ ID NO: 74 (Nanobody 1/huUCHT1 Y177T Scaffold). In some embodiments, the polynucleotide encoding the Claudin 18.2-TAC comprises a nucleotide sequence having at least 96% sequence identity with the nucleotide sequence of SEQ ID NO: 74 (Nanobody 1/huUCHT1 Y177T Scaffold). In some embodiments, the polynucleotide encoding the Claudin 18.2-TAC comprises a nucleotide sequence having at least 97% sequence identity with the nucleotide sequence of SEQ ID NO: 74 (Nanobody 1/huUCHT1 Y177T Scaffold). In some embodiments, the polynucleotide encoding the Claudin 18.2-TAC comprises a nucleotide sequence having at least 98% sequence identity with the nucleotide sequence of SEQ ID NO: 74 (Nanobody 1/huUCHT1 Y177T Scaffold). In some embodiments, the polynucleotide encoding the Claudin 18.2-TAC comprises a nucleotide sequence having at least 99% sequence identity with the nucleotide sequence of SEQ ID NO: 74 (Nanobody 1/huUCHT1 Y177T Scaffold). In some embodiments, the polynucleotide encoding the Claudin 18.2-TAC comprises the nucleotide sequence of SEQ ID NO: 74 (Nanobody 1/huUCHT1 Y177T Scaffold).

In some embodiments, the Claudin 18.2-TAC comprises an amino acid sequence having at least 70% sequence identity with the amino acid sequence of SEQ ID NO: 69 (Nanobody 1/huUCHT1 Y177T Scaffold). In some embodiments, the Claudin 18.2-TAC comprises an amino acid sequence having at least 75% sequence identity with the amino acid sequence of SEQ ID NO: 69 (Nanobody 1/huUCHT1 Y177T Scaffold). In some embodiments, the Claudin 18.2-TAC comprises an amino acid sequence having at least 80% sequence identity with the amino acid sequence of SEQ ID NO: 69 (Nanobody 1/huUCHT1 Y177T Scaffold). In some embodiments, the Claudin 18.2-TAC comprises an amino acid sequence having at least 85% sequence identity with the amino acid sequence of SEQ ID NO: 69 (Nanobody 1/huUCHT1 Y177T Scaffold). In some embodiments, the Claudin 18.2-TAC comprises an amino acid sequence having at least 90% sequence identity with the amino acid sequence of SEQ ID NO: 69 (Nanobody 1/huUCHT1 Y177T Scaffold). In some embodiments, the Claudin 18.2-TAC comprises an amino acid sequence having at least 95% sequence identity with the amino acid sequence of SEQ ID NO: 69 (Nanobody 1/huUCHT1 Y177T Scaffold). In some embodiments, the Claudin 18.2-TAC comprises an amino acid sequence having at least 96% sequence identity with the amino acid sequence of SEQ ID NO: 69 (Nanobody 1/huUCHT1 Y177T Scaffold). In some embodiments, the Claudin 18.2-TAC comprises an amino acid sequence having at least 97% sequence identity with the amino acid sequence of SEQ ID NO: 69 (Nanobody 1/huUCHT1 Y177T Scaffold). In some embodiments, the Claudin 18.2-TAC comprises an amino acid sequence having at least 98% sequence identity with the amino acid sequence of SEQ ID NO: 69 (Nanobody 1/huUCHT1 Y177T Scaffold). In some embodiments, the Claudin 18.2-TAC comprises an amino acid sequence having at least 99% sequence identity with the amino acid sequence of SEQ ID NO: 69 (Nanobody 1/huUCHT1 Y177T Scaffold). In some embodiments, the Claudin 18.2-TAC comprises the amino acid sequence of SEQ ID NO: 69 (Nanobody 1/huUCHT1 Y177T Scaffold).

In some embodiments, the Claudin 18.2-TAC comprises from N- to C-terminus): (a) a CD8a leader, (b) Claudin 18.2 Nanobody 2 (SEQ ID NO: 56), (c) a myc tag, (d) a (G4S)4-based linker, (e) a humanized variant of UCHT1, (d) a G4S-based linker, and (e) a CD4 transmembrane and cytosolic domain.

In some embodiments, the polynucleotide encoding the Claudin 18.2-TAC comprises a nucleotide sequence having at least 70% sequence identity with the nucleotide sequence of SEQ ID NO: 70 (Nanobody 2/huUCHT1 Scaffold). In some embodiments, the polynucleotide encoding the Claudin 18.2-TAC comprises a nucleotide sequence having at least 75% sequence identity with the nucleotide sequence of SEQ ID NO: 70 (Nanobody 2/huUCHT1 Scaffold). In some embodiments, the polynucleotide encoding the Claudin 18.2-TAC comprises a nucleotide sequence having at least 80% sequence identity with the nucleotide sequence of SEQ ID NO: 70 (Nanobody 2/huUCHT1 Scaffold). In some embodiments, the polynucleotide encoding the Claudin 18.2-TAC comprises a nucleotide sequence having at least 85% sequence identity with the nucleotide sequence of SEQ ID NO: 70 (Nanobody 2/huUCHT1 Scaffold). In some embodiments, the polynucleotide encoding the Claudin 18.2-TAC comprises a nucleotide sequence having at least 90% sequence identity with the nucleotide sequence of SEQ ID NO: 70 (Nanobody 2/huUCHT1 Scaffold). In some embodiments, the polynucleotide encoding the Claudin 18.2-TAC comprises a nucleotide sequence having at least 95% sequence identity with the nucleotide sequence of SEQ ID NO: 70 (Nanobody 2/huUCHT1 Scaffold). In some embodiments, the polynucleotide encoding the Claudin 18.2-TAC comprises a nucleotide sequence having at least 96% sequence identity with the nucleotide sequence of SEQ ID NO: 70 (Nanobody 2/huUCHT1 Scaffold). In some embodiments, the polynucleotide encoding the Claudin 18.2-TAC comprises a nucleotide sequence having at least 97% sequence identity with the nucleotide sequence of SEQ ID NO: 70 (Nanobody 2/huUCHT1 Scaffold). In some embodiments, the polynucleotide encoding the Claudin 18.2-TAC comprises a nucleotide sequence having at least 98% sequence identity with the nucleotide sequence of SEQ ID NO: 70 (Nanobody 2/huUCHT1 Scaffold). In some embodiments, the polynucleotide encoding the Claudin 18.2-TAC comprises a nucleotide sequence having at least 99% sequence identity with the nucleotide sequence of SEQ ID NO: 70 (Nanobody 2/huUCHT1 Scaffold). In some embodiments, the polynucleotide encoding the Claudin 18.2-TAC comprises the nucleotide sequence of SEQ ID NO: 70 (Nanobody 2/huUCHT1 Scaffold).

In some embodiments, the Claudin 18.2-TAC comprises an amino acid sequence having at least 70% sequence identity with the amino acid sequence of SEQ ID NO: 71 (Nanobody 2/huUCHT1 Scaffold). In some embodiments, the Claudin 18.2-TAC comprises an amino acid sequence having at least 75% sequence identity with the amino acid sequence of SEQ ID NO: 71 (Nanobody 2/huUCHT1 Scaffold). In some embodiments, the Claudin 18.2-TAC comprises an amino acid sequence having at least 80% sequence identity with the amino acid sequence of SEQ ID NO: 71 (Nanobody 2/huUCHT1 Scaffold). In some embodiments, the Claudin 18.2-TAC comprises an amino acid sequence having at least 85% sequence identity with the amino acid sequence of SEQ ID NO: 71 (Nanobody 2/huUCHT1 Scaffold). In some embodiments, the Claudin 18.2-TAC comprises an amino acid sequence having at least 90% sequence identity with the amino acid sequence of SEQ ID NO: 71 (Nanobody 2/huUCHT1 Scaffold). In some embodiments, the Claudin 18.2-TAC comprises an amino acid sequence having at least 95% sequence identity with the amino acid sequence of SEQ ID NO: 71 (Nanobody 2/huUCHT1 Scaffold). In some embodiments, the Claudin 18.2-TAC comprises an amino acid sequence having at least 96% sequence identity with the amino acid sequence of SEQ ID NO: 71 (Nanobody 2/huUCHT1 Scaffold). In some embodiments, the Claudin 18.2-TAC comprises an amino acid sequence having at least 97% sequence identity with the amino acid sequence of SEQ ID NO: 71 (Nanobody 2/huUCHT1 Scaffold). In some embodiments, the Claudin 18.2-TAC comprises an amino acid sequence having at least 98% sequence identity with the amino acid sequence of SEQ ID NO: 71 (Nanobody 2/huUCHT1 Scaffold). In some embodiments, the Claudin 18.2-TAC comprises an amino acid sequence having at least 99% sequence identity with the amino acid sequence of SEQ ID NO: 71 (Nanobody 2/huUCHT1 Scaffold). In some embodiments, the Claudin 18.2-TAC comprises the amino acid sequence of SEQ ID NO: 71 (Nanobody 2/huUCHT1 Scaffold).

In some embodiments, the Claudin 18.2-TAC comprises (from N- to C-terminus): (a) a CD8a leader, (b) Claudin 18.2 Nanobody 2 (SEQ ID NO: 56), (c) a myc tag, (d) a (G4S)4-based linker, (e) a humanized variant of UCHT1 comprising a Y to T mutation at a position corresponding to amino acid 177 of SEQ ID NO: 34 (huUCHT1 (Y177T)), (d) a G4S-based linker, and (e) a CD4 transmembrane and cytosolic domain.

In some embodiments, the polynucleotide encoding the Claudin 18.2-TAC comprises a nucleotide sequence having at least 70% sequence identity with the nucleotide sequence of SEQ ID NO: 72 (Nanobody 2/huUCHT1 Y177T Scaffold). In some embodiments, the polynucleotide encoding the Claudin 18.2-TAC comprises a nucleotide sequence having at least 75% sequence identity with the nucleotide sequence of SEQ ID NO: 72 (Nanobody 2/huUCHT1 Y177T Scaffold). In some embodiments, the polynucleotide encoding the Claudin 18.2-TAC comprises a nucleotide sequence having at least 80% sequence identity with the nucleotide sequence of SEQ ID NO: 72 (Nanobody 2/huUCHT1 Y177T Scaffold). In some embodiments, the polynucleotide encoding the Claudin 18.2-TAC comprises a nucleotide sequence having at least 85% sequence identity with the nucleotide sequence of SEQ ID NO: 72 (Nanobody 2/huUCHT1 Y177T Scaffold). In some embodiments, the polynucleotide encoding the Claudin 18.2-TAC comprises a nucleotide sequence having at least 90% sequence identity with the nucleotide sequence of SEQ ID NO: 72 (Nanobody 2/huUCHT1 Y177T Scaffold). In some embodiments, the polynucleotide encoding the Claudin 18.2-TAC comprises a nucleotide sequence having at least 95% sequence identity with the nucleotide sequence of SEQ ID NO: 72 (Nanobody 2/huUCHT1 Y177T Scaffold). In some embodiments, the polynucleotide encoding the Claudin 18.2-TAC comprises a nucleotide sequence having at least 96% sequence identity with the nucleotide sequence of SEQ ID NO: 72 (Nanobody 2/huUCHT1 Y177T Scaffold). In some embodiments, the polynucleotide encoding the Claudin 18.2-TAC comprises a nucleotide sequence having at least 97% sequence identity with the nucleotide sequence of SEQ ID NO: 72 (Nanobody 2/huUCHT1 Y177T Scaffold). In some embodiments, the polynucleotide encoding the Claudin 18.2-TAC comprises a nucleotide sequence having at least 98% sequence identity with the nucleotide sequence of SEQ ID NO: 72 (Nanobody 2/huUCHT1 Y177T Scaffold). In some embodiments, the polynucleotide encoding the Claudin 18.2-TAC comprises a nucleotide sequence having at least 99% sequence identity with the nucleotide sequence of SEQ ID NO: 72 (Nanobody 2/huUCHT1 Y177T Scaffold). In some embodiments, the polynucleotide encoding the Claudin 18.2-TAC comprises the nucleotide sequence of SEQ ID NO: 72 (Nanobody 2/huUCHT1 Y177T Scaffold).

In some embodiments, the polynucleotide encoding the Claudin 18.2-TAC comprises a nucleotide sequence having at least 70% sequence identity with the nucleotide sequence of SEQ ID NO: 75 (Nanobody 2/huUCHT1 Y177T Scaffold). In some embodiments, the polynucleotide encoding the Claudin 18.2-TAC comprises a nucleotide sequence having at least 75% sequence identity with the nucleotide sequence of SEQ ID NO: 75 (Nanobody 2/huUCHT1 Y177T Scaffold). In some embodiments, the polynucleotide encoding the Claudin 18.2-TAC comprises a nucleotide sequence having at least 80% sequence identity with the nucleotide sequence of SEQ ID NO: 75 (Nanobody 2/huUCHT1 Y177T Scaffold). In some embodiments, the polynucleotide encoding the Claudin 18.2-TAC comprises a nucleotide sequence having at least 85% sequence identity with the nucleotide sequence of SEQ ID NO: 75 (Nanobody 2/huUCHT1 Y177T Scaffold). In some embodiments, the polynucleotide encoding the Claudin 18.2-TAC comprises a nucleotide sequence having at least 90% sequence identity with the nucleotide sequence of SEQ ID NO: 75 (Nanobody 2/huUCHT1 Y177T Scaffold). In some embodiments, the polynucleotide encoding the Claudin 18.2-TAC comprises a nucleotide sequence having at least 95% sequence identity with the nucleotide sequence of SEQ ID NO: 75 (Nanobody 2/huUCHT1 Y177T Scaffold). In some embodiments, the polynucleotide encoding the Claudin 18.2-TAC comprises a nucleotide sequence having at least 96% sequence identity with the nucleotide sequence of SEQ ID NO: 75 (Nanobody 2/huUCHT1 Y177T Scaffold). In some embodiments, the polynucleotide encoding the Claudin 18.2-TAC comprises a nucleotide sequence having at least 97% sequence identity with the nucleotide sequence of SEQ ID NO: 75 (Nanobody 2/huUCHT1 Y177T Scaffold). In some embodiments, the polynucleotide encoding the Claudin 18.2-TAC comprises a nucleotide sequence having at least 98% sequence identity with the nucleotide sequence of SEQ ID NO: 75 (Nanobody 2/huUCHT1 Y177T Scaffold). In some embodiments, the polynucleotide encoding the Claudin 18.2-TAC comprises a nucleotide sequence having at least 99% sequence identity with the nucleotide sequence of SEQ ID NO: 75 (Nanobody 2/huUCHT1 Y177T Scaffold). In some embodiments, the polynucleotide encoding the Claudin 18.2-TAC comprises the nucleotide sequence of SEQ ID NO: 75 (Nanobody 2/huUCHT1 Y177T Scaffold).

In some embodiments, the Claudin 18.2-TAC comprises an amino acid sequence having at least 70% sequence identity with the amino acid sequence of SEQ ID NO: 73 (Nanobody 2/huUCHT1 Y177T Scaffold). In some embodiments, the Claudin 18.2-TAC comprises an amino acid sequence having at least 75% sequence identity with the amino acid sequence of SEQ ID NO: 73 (Nanobody 2/huUCHT1 Y177T Scaffold). In some embodiments, the Claudin 18.2-TAC comprises an amino acid sequence having at least 80% sequence identity with the amino acid sequence of SEQ ID NO: 73 (Nanobody 2/huUCHT1 Y177T Scaffold). In some embodiments, the Claudin 18.2-TAC comprises an amino acid sequence having at least 85% sequence identity with the amino acid sequence of SEQ ID NO: 73 (Nanobody 2/huUCHT1 Y177T Scaffold). In some embodiments, the Claudin 18.2-TAC comprises an amino acid sequence having at least 90% sequence identity with the amino acid sequence of SEQ ID NO: 73 (Nanobody 2/huUCHT1 Y177T Scaffold). In some embodiments, the Claudin 18.2-TAC comprises an amino acid sequence having at least 95% sequence identity with the amino acid sequence of SEQ ID NO: 73 (Nanobody 2/huUCHT1 Y177T Scaffold). In some embodiments, the Claudin 18.2-TAC comprises an amino acid sequence having at least 96% sequence identity with the amino acid sequence of SEQ ID NO: 73 (Nanobody 2/huUCHT1 Y177T Scaffold). In some embodiments, the Claudin 18.2-TAC comprises an amino acid sequence having at least 97% sequence identity with the amino acid sequence of SEQ ID NO: 73 (Nanobody 2/huUCHT1 Y177T Scaffold). In some embodiments, the Claudin 18.2-TAC comprises an amino acid sequence having at least 98% sequence identity with the amino acid sequence of SEQ ID NO: 73 (Nanobody 2/huUCHT1 Y177T Scaffold). In some embodiments, the Claudin 18.2-TAC comprises an amino acid sequence having at least 99% sequence identity with the amino acid sequence of SEQ ID NO: 73 (Nanobody 2/huUCHT1 Y177T Scaffold). In some embodiments, the Claudin 18.2-TAC comprises the amino acid sequence of SEQ ID NO: 73 (Nanobody 2/huUCHT1 Y177T Scaffold).

Amino acid and nucleotide sequences of exemplary Claudin 18.2-TACs are provided in Table 6

TABLE 6

Table of Sequences

| SEQ ID NO | Description | Nucleotide/ Amino Acid |
|---|---|---|
| SEQ ID NO: 66 | Nanobody 1/huUCHT1 Scaffold (huCD8a leader - Claudin 18.2 Nanobody 1 - Myc tag - (G4S)4-based linker - huUCHT1 - G4S-based linker - CD4) | Nucleotide |
| SEQ ID NO: 67 | Nanobody 1/huUCHT1 Scaffold (huCD8a leader - Claudin 18.2 Nanobody 1 - Myc tag - (G4S)4-based linker - huUCHT1 - G4S-based linker - CD4) | Amino Acid |
| SEQ ID NO: 68 | Nanobody 1/huUCHT1 Y177T Scaffold (huCD8a leader - Claudin 18.2 Nanobody 1 - Myc tag - (G4S)4-based linker - huUCHT1 (Y177T) - G4S-based linker - CD4) | Nucleotide |
| SEQ ID NO: 69 | Nanobody 1/huUCHT1 Y177T Scaffold (huCD8a leader - Claudin 18.2 Nanobody 1 - Myc tag - (G4S)4-based linker - huUCHT1 (Y177T) - G4S-based linker - CD4) | Amino Acid |
| SEQ ID NO: 70 | Nanobody 2/huUCHT1 Scaffold (huCD8a leader - Claudin 18.2 Nanobody 2 - Myc tag - (G4S)4-based linker - huUCHT1 - G4S-based linker - CD4) | Nucleotide |
| SEQ ID NO: 71 | Nanobody 2/huUCHT1 Scaffold (huCD8a leader - Claudin 18.2 Nanobody 2 - Myc tag - (G4S)4-based linker - huUCHT1 - G4S-based linker - CD4) | Amino Acid |
| SEQ ID NO: 72 | Nanobody 2/huUCHT1 Y177T Scaffold (huCD8a leader - Claudin 18.2 Nanobody 2 - Myc tag - (G4S)4-based linker - huUCHT1 (Y177T) - G4S-based linker - CD4) | Nucleotide |
| SEQ ID NO: 73 | Nanobody 2/huUCHT1 Y177T Scaffold (huCD8a leader - Claudin 18.2 Nanobody 2 - Myc tag - (G4S)4-based linker - huUCHT1 (Y177T) - G4S-based linker - CD4) | Amino Acid |
| SEQ ID NO: 74 | Nanobody 1/huUCHT1 Y177T Scaffold (huCD8a leader - Claudin 18.2 Nanobody 1 - Myc tag - (G4S)4-based linker - huUCHT1 (Y177T) - G4S-based linker - CD4) | Nucleotide |
| SEQ ID NO: 75 | Nanobody 2/huUCHT1 Y177T Scaffold (huCD8a leader - Claudin 18.2 Nanobody 2 - Myc tag - (G4S)4-based linker - huUCHT1 (Y177T) - G4S-based linker - CD4) | Nucleotide |

Vector Constructs

Disclosed herein, in certain embodiments, are vectors comprising a Claudin 18.2-TAC nucleic acid sequence as disclosed herein. In some embodiments, the vectors further comprise a promoter. In some embodiments, the promoter is functional in a mammalian cell. Promoters, regions of DNA that initiate transcription of a particular nucleic acid sequence, are well known in the art. A "promoter functional in a mammalian cell" refers to a promoter that drives expression of the associated nucleic acid sequence in a mammalian cell. A promoter that drives expression of a nucleic acid sequence is referred to as being "operably connected" to the nucleic acid sequence.

A variety of delivery vectors and expression vehicles are employed to introduce nucleic acids described herein into a cell.

Disclosed herein, in certain embodiments, are vectors comprising:
  a. a first polynucleotide encoding an antigen-binding domain that binds Claudin 18.2;
  b. a second polynucleotide encoding an antigen-binding domain that binds a protein associated with a TCR complex;
  c. a third polynucleotide encoding a T cell receptor signaling domain polypeptide; and
  d. a promoter that is functional in a mammalian cell.

In some embodiments, the first polynucleotide and third polynucleotide are fused to the second polynucleotide and the coding sequence is operably connected to the promoter. In some embodiments, the second polynucleotide and third polynucleotide are fused to the first polynucleotide and the coding sequence is operably connected to the promoter. In some embodiments, the vector is designed for expression in mammalian cells. In some embodiments, the vector is a viral vector. In some embodiments, the viral vector is a retroviral vector.

In some embodiments, vectors that are useful comprise vectors derived from retroviruses, lentiviruses, Murine Stem Cell Viruses (MSCV), pox viruses, adenoviruses, and adeno-associated viruses. Other delivery vectors that are useful comprise vectors derived from herpes simplex viruses, transposons, vaccinia viruses, human papilloma virus, Simian immunodeficiency viruses, HTLV, human foamy virus and variants thereof. Further vectors that are useful comprise vectors derived from spumaviruses, mammalian type B retroviruses, mammalian type C retroviruses, avian type C retroviruses, mammalian type D retroviruses and HTLV/BLV type retroviruses. Examples of lentiviral vectors useful in the disclosed compositions and methods are a pCCL4 vector, a pLVX vector (e.g., pLVX-IRES-ZsGreen1 Vector, Cat. No. 632187, Takara Bio) and a pCDH vector (e.g., pCDH-CMV-MCS cDNA Single Promoter Cloning and Expression Lentivector, Cat. No. CD500B-1, System Bio). One example of a γ-retroviral vector useful in the disclosed compositions and methods is a pRetroQ vector (e.g., pRetroQ-DsRed Monomer-N1 Vector, Cat. No. 632507, Takara Bio).

Pharmaceutical Compositions

Disclosed herein, in certain embodiments, are pharmaceutical compositions comprising an engineered T cell disclosed herein (transduced with and/or expressing a Claudin 18.2-TAC polypeptide), and a pharmaceutically acceptable carrier. Pharmaceutically acceptable carriers include, but are not limited to, buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); or preservatives. In some embodiments, the engineered T cells are formulated for intravenous administration.

Pharmaceutical compositions are administered in a manner appropriate to the disease to be treated (or prevented). The quantity and frequency of administration is determined by such factors as the condition of the patient, and the type and severity of the patient's disease, although appropriate dosages are determined by clinical trials. When "an immunologically effective amount," "an anti-tumor effective amount," "a tumor-inhibiting effective amount," or "therapeutic amount" is indicated, the precise amount of the compositions of the present invention to be administered is determined by a physician with consideration of individual differences in age, weight, tumor size, extent of infection or metastasis, and condition of the patient (subject).

In some embodiments, the engineered T cells and/or pharmaceutical compositions described herein are administered at a dosage of $10^1$ to $10^{15}$ cells per kg body weight, $10^4$ to $10^9$ cells per kg body weight, optionally $10^5$ to $10^8$ cells per kg body weight, $10^6$ to $10^7$ cells per kg body weight or $10^5$ to $10^6$ cells per kg body weight, including all integer values within those ranges. In some embodiments, the modified T cells and/or pharmaceutical compositions described herein are administered at a dosage of greater than $10^1$ cells per kg body weight. In some embodiments, the modified T cells and/or pharmaceutical compositions described herein are administered at a dosage of less than $10^{15}$ cells per kg body weight.

In some embodiments, the engineered T cells and/or pharmaceutical compositions described herein are administered at a dosage of $0.5 \times 10^6$ cells, $2 \times 10^6$ cells, $4 \times 10^6$ cells, $5 \times 10^6$ cells, $1.2 \times 10^7$ cells, $2 \times 10^7$ cells, $5 \times 10^7$ cells, $2 \times 10^8$ cells, $5 \times 10^8$ cells, $2 \times 10^9$ cells, $0.5$-$2000 \times 10^6$ cells, $0.5$-$2 \times 10^6$ cells, $0.5$-$2 \times 10^7$ cells, $0.5$-$2 \times 10^8$ cells, or $0.5$-$2 \times 10^9$ cells, including all integer values within those ranges.

Also disclosed herein are pharmaceutical compositions comprising engineered/modified and unmodified T cells, or comprising different populations of engineered/modified T cells with or without unmodified T cells. One of ordinary skill in the art would understand that a therapeutic quantity of engineered/modified T cells need not be homogenous in nature.

In some embodiments, T cell compositions are administered multiple times at these dosages. In some embodiments, the dosage is administered a single time or multiple times, for example daily, weekly, biweekly, or monthly, hourly, or is administered upon recurrence, relapse or progression of the cancer being treated. The cells, in some embodiments, are administered by using infusion techniques that are commonly known in immunotherapy (see, e.g., Rosenberg et al., New Eng. J. of Med. 319:1676, 1988).

In some embodiments, the pharmaceutical composition is substantially free of, e.g., there are no detectable levels of a contaminant, e.g., selected from the group consisting of endotoxin, *mycoplasma*, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium a fungus, *mycoplasma*, IL-2, and IL-7.

In some embodiments, the modified/engineered T cells and/or pharmaceutical compositions are administered by methods including, but not limited to, aerosol inhalation, injection, infusion, ingestion, transfusion, implantation or transplantation. The modified T cells and/or pharmaceutical compositions may be administered to a subject transarterially, subcutaneously, intradermally, intratumorally, intranodally, intramedullary, intramuscularly, by intravenous (i.v.) injection, by intravenous (i.v.) infusion, or intraperitoneally. The modified/engineered T cells and/or pharmaceutical compositions thereof may be administered to a patient by intradermal or subcutaneous injection. The modified/engineered T cells and/or pharmaceutical compositions thereof may be administered by i.v. injection. The modified/engineered T cells and/or pharmaceutical compositions thereof may be injected directly into a tumor, lymph node, or site of infection.

A pharmaceutical composition may be prepared by known methods for the preparation of pharmaceutically acceptable compositions that are administered to subjects, such that an effective quantity of the T cells is combined in a mixture with a pharmaceutically acceptable carrier. Suitable carriers are described, for example, in Remington's Pharmaceutical Sciences (Remington's Pharmaceutical Sciences, $20^{th}$ ed., Mack Publishing Company, Easton, Pa., USA, 2000). On this basis, the compositions may include, albeit not exclusively, solutions of the substances in association with one or more pharmaceutically acceptable carriers or diluents, and contained in buffered solutions with a suitable pH and iso-osmotic with the physiological fluids.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, N-(1(2,3-dioleyloxy)propyl)N,N,N-trimethylammonium chloride (DOTMA), diolesylphosphotidyl-ethanolamine (DOPE), and liposomes. In some embodiments, such compositions contain a therapeutically effective amount of the compound, together with a suitable amount of carrier so as to provide the form for direct administration to the patient.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions.

A pharmaceutical composition disclosed herein may be formulated into a variety of forms and administered by a number of different means. A pharmaceutical formulation may be administered orally, rectally, or parenterally, in formulations containing conventionally acceptable carriers, adjuvants, and vehicles as desired. The term "parenteral" as used herein includes subcutaneous, intravenous, intramuscular, or intrasternal injection and infusion techniques. Administration includes injection or infusion, including intra-arterial, intracardiac, intracerebroventricular, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration. In some exemplary embodiments, a route of administration is via an injection such as an intramuscular, intravenous, subcutaneous, or intraperitoneal injection.

Liquid formulations include an oral formulation, an intravenous formulation, an intranasal formulation, an ocular formulation, an otic formulation, an aerosol, and the like. In certain embodiments, a combination of various formulations is administered. In certain embodiments a composition is formulated for an extended release profile.

Methods of Treatment and Use

Disclosed herein, in certain embodiments, are methods of using engineered T cells disclosed herein in the treatment of a Claudin 18.2-expressing cancer in an individual in need thereof.

In some embodiments, an antigen-binding domain that binds Claudin 18.2 of a TAC polypeptide disclosed herein binds to Claudin 18.2 on a tumor cell. In some embodiments, an antigen-binding domain that binds Claudin 18.2 of a TAC polypeptide disclosed herein selectively binds to Claudin 18.2 on a tumor cell. In some embodiments, an antigen-binding domain that binds Claudin 18.2 of a TAC polypeptide disclosed herein specifically binds to Claudin 18.2 on a tumor cell.

Disclosed herein, in certain embodiments, are methods of treating a cancer expressing Claudin 18.2 in an individual in need thereof, comprising administering to the individual an engineered T cell disclosed herein or a pharmaceutical composition comprising an engineered T cell disclosed herein.

Further disclosed herein is use of an engineered T cell disclosed herein in the preparation of a medicament to treat cancer expressing Claudin 18.2 in an individual in need thereof. Additionally disclosed herein in certain embodiments is the use of an engineered T cell disclosed herein or a pharmaceutical composition disclosed herein to treat a cancer expressing Claudin 18.2 in an individual in need thereof.

In some embodiments, the engineered T cells disclosed herein are part of a combination therapy. In some embodiments, effectiveness of a therapy disclosed herein is assessed multiple times. In some embodiments, patients are stratified based on a response to a treatment disclosed herein. In some embodiments, an effectiveness of treatment determines entrance into a trial.

In some embodiments, the engineered T cells disclosed herein are administered in combination with a lymphodepleting therapy, or are administered to a subject who has received a lymphodepleting therapy. Examples of lymphodepleting therapies include nonmyeloablative lymphodepleting chemotherapy, myeloablative lymphodepleting chemotherapy, fludarabine, cyclophosphamide, corticosteroids, alemtuzumab, total body irradiation (TBI), and any combination thereof.

Cancers that may be treated with engineered T cells disclosed herein include any form of neoplastic disease. In some embodiments, cancers that are treated include, but are not limited to, a pancreatic cancer (e.g., pancreatic adenocarcinoma, a gastric cancer (e.g., gastric adenocarcinoma), a gastroesophageal cancer (e.g., gastroesophageal junction (GEJ) adenocarcinoma), an esophageal cancer, an ovarian cancer, or a lung cancer (e.g., non-small cell lung cancer).

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1—Manufacturing of Claudin 18.2-TAC T Cells

This example was designed to test the manufacturability of nanobody-based Claudin 18.2-TACs. Previous versions of TACs have used either scFv or DARPin antigen-binding domains.

T cells were engineered to express a Claudin 18.2 T cell-antigen coupler (TAC) including (i) Claudin 18.2 Nanobody 1 (including SEQ ID NO: 57 (Kabat CDR1), SEQ ID NO: 58 (Kabat CDR2), and SEQ ID NO: 59 (Kabat CDR3)), or Claudin 18.2 Nanobody 2 (including SEQ ID NO: 57 (Kabat CDR1), SEQ ID NO: 63 (Kabat CDR2), and SEQ ID NO: 59 (Kabat CDR3)), (ii) an huUCHT1 or huUCHT1 (Y177T) antigen-binding domain that binds CD3, and (iii) a CD4 cytosolic and transmembrane domain: Nanobody 1/huUCHT1 Scaffold (SEQ ID NO: 67), Nanobody 1/huUCHT1 (Y177T) (SEQ ID NO:69), Nanobody 2/huUCHT1 Scaffold (SEQ ID NO: 71), or Nanobody 2/huUCHT1 (Y177T) (SEQ ID NO: 73).

In one experiment, two of the Claudin 18.2-TACs (SEQ ID NOs: 67 or 71) were expressed by a lentiviral vector, which co-expressed mStrawberry red fluorescence protein as a transduction marker. Results are shown in FIG. 1 and depict surface expression of the Claudin 18.2-TACs. Non-transduced control cells (NTD) were used as a negative control.

In another experiment, Claudin 18.2-TAC T cells were produced using a commercial pilot grade lentivector and. Claudin 18.2-TAC T cells were produced from CD4/CD8+ selected peripheral blood lymphocytes which were activated with CD3/CD28/CD2 and IL-2 and IL-7, followed by pilot grade lentiviral transduction.

Figure 2A:
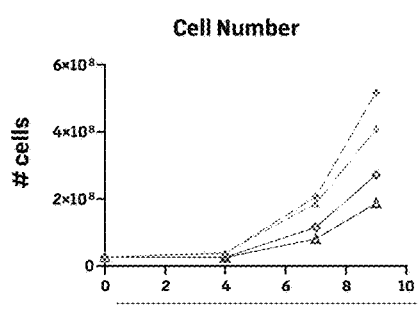
FIGS. 2A-2C depict the assessment of Claudin 18.2-TAC T cell manufacturing.
Figure 2B:
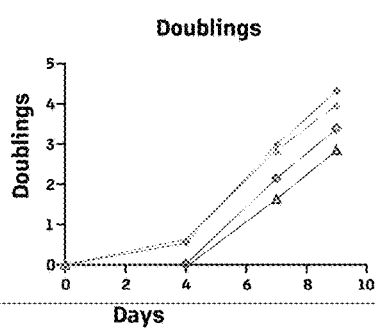
Figure 2C:
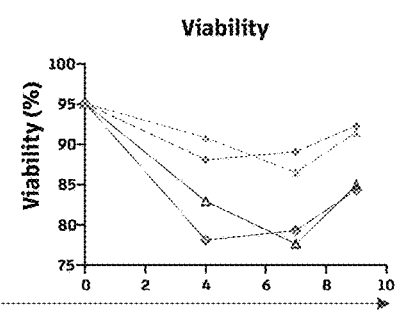

During the transduction and growth period, viable cells were counted at days 4, 7 and 9. The number of cells (FIG. 2A), cell doublings (FIG. 2B), and viability (FIG. 2C) are shown. Claudin 18.2-TAC Nanobody 1 (SEQ ID NO:67) (open diamonds) Claudin 18.2-TAC Nanobody 1/Y177T (SEQ ID NO:69) (closed diamonds), Claudin 18.2-TAC Nanobody 2 (SEQ ID NO:71) (open triangles), and Claudin 18.2-TAC Nanobody 2/Y177T (SEQ ID NO:73) (closed triangles) T cells are shown. T cells engineered with Nanobody 1 and 2 in the context of the Claudin 18.2-TAC huUCHT1 Y177T scaffold (SEQ ID NOs: 69 an 73, respectively) showed the preferred manufacturing properties, showing higher levels of viability and cell expansion relative to T cells engineered with the Nanobody 1 and 2 in the context of the Claudin 18.2-TAC scaffold (SEQ ID NOs: 67 and 71, respectively).

In another experiment, Claudin 18.2-TAC T cells were produced using a research grade lentivector. CLDN18.2-TAC T cells were produced from CD4/CD8+ selected peripheral blood lymphocytes which were activated overnight with CD3/CD28/CD2 and IL-2 and IL-7, followed by research grade lentiviral transduction at MOI 10 in G-Rex well plates for 8 days.

Figure 3:
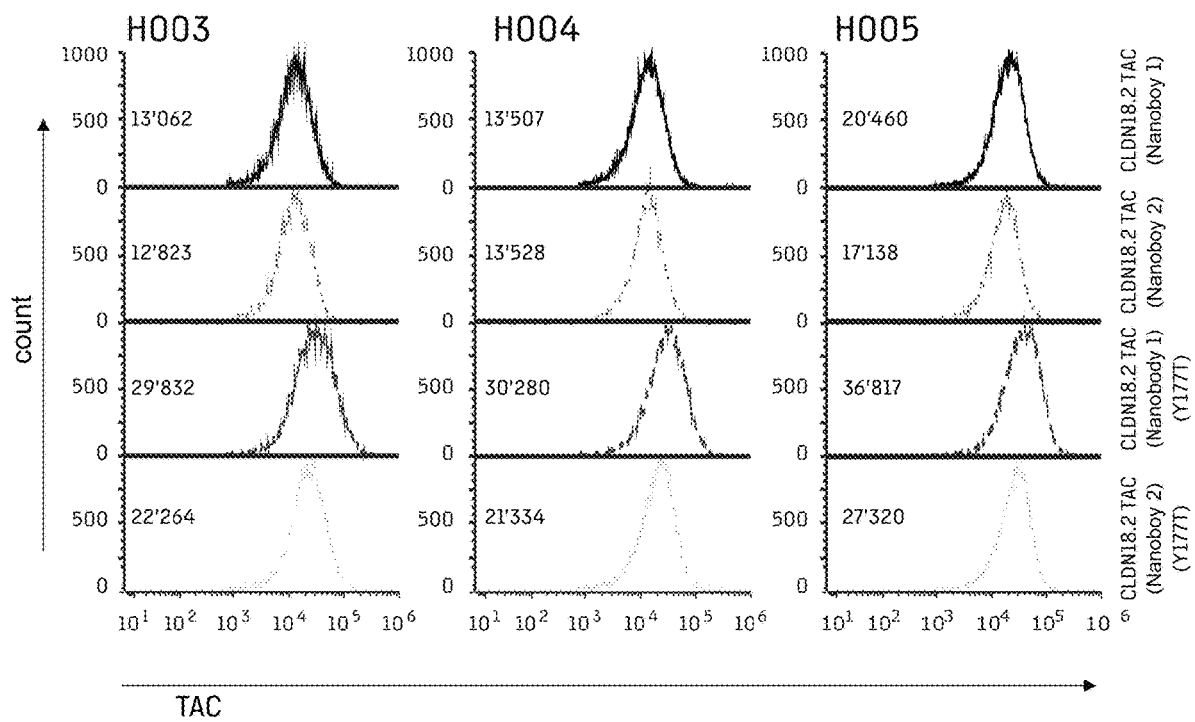
FIG. 3 depicts histograms of expression of indicated Claudin 18.2-TACs in T cells from indicated donors as measured by flow cytometry.

T cells were produced from 3 separate donors. After 8 days, all T cells were collected and stained for surface TAC expression. Histograms showing the TAC expression are overlayed with each of the T cell constructs per donor. Median fluorescent intensity (MFI) values for the Claudin 18.2-TAC constructs are shown alongside their respective histograms (FIG. 3). T cells engineered with Nanobody 1 and 2 in the context of the huUCHT1 Y177T scaffold (SEQ ID NOs: 69 and 73, respectively) showed higher TAC surface expression compared to T cells engineered with Nanobody 1 and 2 in the context of the huUCHT1 scaffold (SEQ ID NOs: 67 and 71, respectively). This effect was consistent across all three donors tested.

Figure 4:
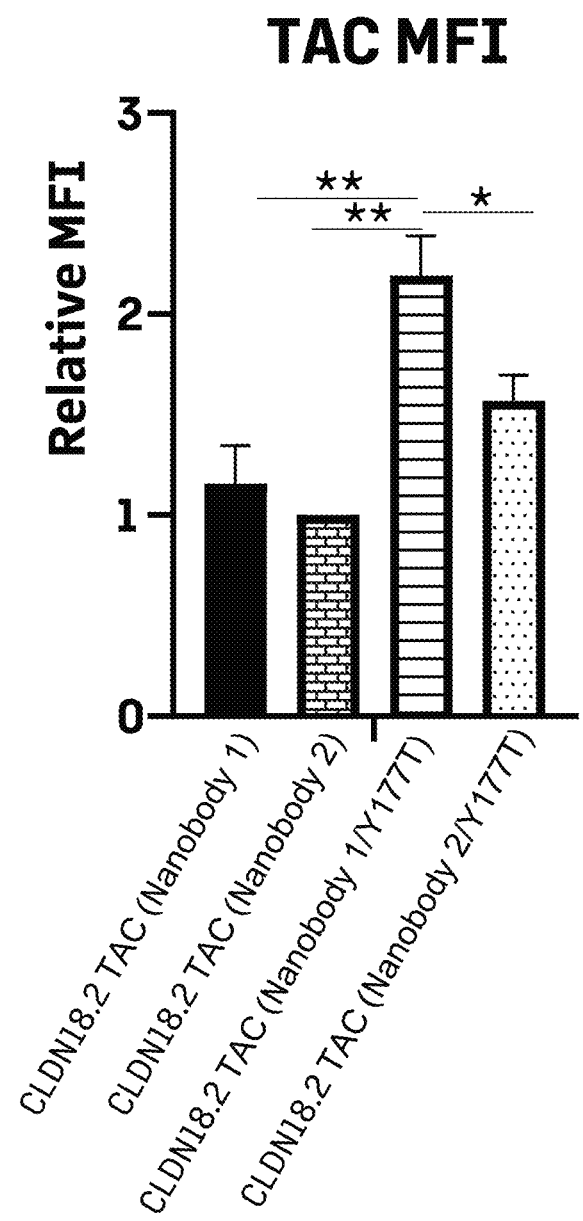
FIG. 4 depicts the relative expression of indicated Claudin 18.2-TACs in T cells as measured by flow cytometry.

In another experiment, the TAC surface expression of T cells engineered with either Claudin 18.2 T cell-antigen coupler (TAC) (SEQ ID NOs: 69 and 73) or its next generation scaffold (huUCHT1 Y177T) (SEQ ID NOs: 67 and 71), including Claudin 18.2 Nanobody 1 (SEQ ID NOs: 67 and 69) or Nanobody 2 (SEQ ID NOs: 71 and 73) produced using either of the above-described manufacturing methods were compared (FIG. 4). The Claudin 18.2-TAC MFI was calculated as a fraction of a relevant positive control TAC. The relative MFI values demonstrated that the Y177T scaffold of both Nanobody 1 and 2 showed enhanced surface expression, with Claudin 18.2-TAC Nanobody 1/Y177T (SEQ ID NO:69) T cells significantly showing the highest TAC surface expression.

These results show that T cells can be engineered to express any of the four tested Claudin 18.2-TACs. Furthermore, these results show for the first time that TACs comprising a nanobody-based antigen-binding domain can be effectively manufactured.

Example 2—Specificity of Claudin 18.2-TAC T Cells for Claudin 18.2 Relative to Claudin 18.1

The binding specificity of the Claudin 18.2 binder (Claudin Nanobody 2, SEQ ID NO: 56) used in exemplary Claudin 18.2-TACs was assessed using a recombinant protein comprising the Claudin 18.2 binding domain fused to GFP. The purified protein was then tested for its ability to bind to Claudin 18.2-expressing human HEK or avian QT6 cells. As shown in FIG. 5A, the Claudin 18.2-binding domain of SEQ ID NO:56 was able to bind the Claudin 18.2-engineered target cells but not to non-engineered control HEK and QT6 cells. The fusion protein showed concentration dependent binding to Claudin 18.2-engineered cells but not vector only control cells.

Claudin 18.2 Nanobody 2 (SEQ ID NO: 56) was further tested for potential binding against other proteins using a protein array encompassing over 6000 human membrane proteins, collectively representing ~94% of membrane-anchored human proteins. The Claudin 18.2 binder-GFP fusion protein bound Claudin 18.2 and no other surface protein. This demonstrates that the binding domain (SEQ ID NO: 56) used in Claudin 18.2-TAC is specific for Claudin 18.2 (FIG. 5B).

To further assess the specificity of the Claudin 18.2 Nanobody 2 when used in the TAC molecule expressed by T cells, Claudin 18.2 T cell-antigen coupler (TAC) T cells were engineered as described in Example 1 using a Claudin 18.2-TAC including Nanobody 2/huUCHT1 Y177T Scaffold (SEQ ID NO: 73) and assayed for specificity for Claudin 18.2 positive target cells. Specificity was also evaluated in target cells expressing Claudin 18.1, a close homolog of Claudin 18.2 and result of alternative splicing of the Claudin 18 transcript.

In another experiment, T cells were engineered to express a Claudin 18.2 T cell-antigen coupler (TAC) including (i) Claudin 18.2 Nanobody 1 (including SEQ ID NO: 57 (Kabat CDR1), SEQ ID NO: 58 (Kabat CDR2), and SEQ ID NO: 59 (Kabat CDR3)), or Claudin 18.2 Nanobody 2 (including SEQ ID NO: 57 (Kabat CDR1), SEQ ID NO: 63 (Kabat CDR2), and SEQ ID NO: 59 (Kabat CDR3)), (ii) an huUCHT1 or huUCHT1 (Y177T) antigen-binding domain that binds CD3, and (iii) a CD4 cytosolic and transmembrane domain: Nanobody 1/huUCHT1 Scaffold (SEQ ID NO: 67), Nanobody 1/huUCHT1 (Y177T) (SEQ ID NO:69), Nanobody 2/huUCHT1 Scaffold (SEQ ID NO: 71), or Nanobody 2/huUCHT1 (Y177T) (SEQ ID NO: 73).

N87 gastric cancer cells engineered to overexpress either Claudin 18.1 or 18.2 T cells expressing the Claudin 18.2-TAC. The expression of both Claudin 18.2 and Claudin 18.1 was tested via flow cytometry, and the respective histograms are shown (FIG. 6A). To assess the activity of T cells expressing the Claudin 18.2-TAC of SEQ ID NO: 73, T cells were co-cultured at a 1:1 ratio with N87-CLDN18.1 and N87-CLDN18.2 target cells. Following the 4 hour co-culture, T cells were harvested and analyzed by flow cytometry for the expression of CD69 in T cells expressing Claudin 18.2-TAC (SEQ ID NO: 73) (identified by fluorescent protein transduction marker).

As shown in FIG. 6B, T cells expressing Claudin 18.2-TAC (SEQ ID NO: 73) were successfully activated when co-cultured with Claudin 18.2 but not Claudin 18.1 positive target cells, indicating that Claudin 18.2-TAC T cells do not cross-react with Claudin 18.1 expressing cells. Neither T cells alone nor NTD negative controls lead to CD69 up regulation (data not shown). When stimulated with Claudin 18.2-expressing tumor cells, non-transduced T cells in the Claudin 18.2-TAC T cell product also show upregulation of CD69.

FIG. 6C shows the combined results of Claudin 18.2-TAC Nanobody 1/huUCHT1 (SEQ ID NO: 67) (open diamonds), Claudin 18.2-TAC Nanobody 1/huUCHT1 Y177T (SEQ ID NO: 69) (closed diamonds), Claudin 18.2-TAC Nanobody 2/huUCHT1 (SEQ ID NO: 71) (open triangles), and Claudin 18.2-TAC Nanobody 2/Y177T (SEQ ID NO: 73) (closed triangles) in co-culture with either Claudin 18.1 or 18.2-engineered N87 cells. Since N87 cells naturally express the HER2 oncoprotein, CD69 upregulation was normalized to CD69 expression observed with the HER2-TAC T cell positive control co-cultured with N87 cells. Data represents the average of 3 different experiments with TAC-T cells derived from three different donors. Positive control HER2-TAC T cells are shown as closed grey circles, while NTD (non-transduced) negative control T cells are shown as closed black circles. T cells expressing Claudin 18.2-TAC were successfully activated when co-cultured with Claudin 18.2 but not Claudin 18.1-positive target cells or non-engineered N87 tumor cells, indicating that Claudin 18.2-TAC T cells do not cross-react with Claudin-18.1-expressing cells. NTD negative controls do not show upregulation of CD69. When stimulated with Claudin 18.2-expressing tumor cells, non-transduced T cells in the Claudin 18.2-TAC T cell product also show upregulation of CD69.

Example 3—Cytokine Release by Claudin 18.2-TAC T Cells Following Antigen-Specific Activation Claudin 18.2 T cell-antigen coupler (TAC) T cells are engineered as described in Example 1 and assayed for in vitro activity.

The Claudin 18.2-TAC T cells are assayed for pro-inflammatory cytokine release following co-culture with Claudin 18.2 and Claudin 18.1 positive target cells. T cells and target cells are co-cultured for 4-24 hours. It is expected that pro-inflammatory cytokines, such as TNFa and INFg, are detected following co-culture of Claudin 18.2-TAC T cells with Claudin 18.2 positive target cells, but not with Claudin 18.1 positive target cells.

The Claudin 18.2-TAC T cells are also assayed for in vitro proliferation following co-culture with Claudin 18.2 and Claudin 18.1 positive target cells. Claudin 18.2-TAC cells are labeled with a fluorescent marker and then co-cultured with mitomycin C treated target cells. After several days of culture, T cell proliferation is analyzed. It is expected that Claudin 18.2-TAC T cells only show proliferation when cultured with Claudin 18.2 positive target cells, and not with Claudin 18.1 positive target cells.

Example 4—In Vitro Cytotoxicity of Claudin 18.2-TAC T Cells

T cells were engineered to express a Claudin 18.2 T cell-antigen coupler (TAC) including (i) Claudin 18.2 Nanobody 1 (including SEQ ID NO: 57 (Kabat CDR1), SEQ ID NO: 58 (Kabat CDR2), and SEQ ID NO: 59 (Kabat CDR3)), or Claudin 18.2 Nanobody 2 (including SEQ ID NO: 57 (Kabat CDR1), SEQ ID NO: 63 (Kabat CDR2), and SEQ ID NO: 59 (Kabat CDR3)), (ii) a UCHT1 antigen-binding domain that binds CD3, and (iii) a CD4 cytosolic and transmembrane domain: Nanobody 1/huUCHT1 Scaffold (SEQ ID NO: 67) or Nanobody 2/huUCHT1 Y177T Scaffold (SEQ ID NO: 71). KATO III cells, naturally expressing Claudin 18.2, were engineered to express enhanced Luciferase (eLuc) to yield a KATO III$^{eLuc}$ cell line. T cells expressing either Claudin 18.2-TAC (SEQ ID NO: 67 or 71) were co-cultured with KATO III$^{eLuc}$ for 30 hours. At the end of the co-culture the viability of the KATO III$^{eLuc}$ cells was assessed by measuring luminescence relative to an untreated control. Results are shown in FIG. 7. As depicted, Claudin 18.2-TAC T cells engineered to express either the Claudin 18.2-TAC of SEQ ID NO: 67 (Nanobody 1/huUCHT1 Scaffold); or the Claudin 18.2-TAC of SEQ ID NO: 71 (Nanobody 2/huUCHT1 Scaffold), but not non-transduced control T cells (NTD), were able to efficiently engage and kill KATO III$^{eLuc}$ cells.

Example 5—In Vitro Cytotoxicity of Claudin 18.2-TAC T Cells

Figure 8:
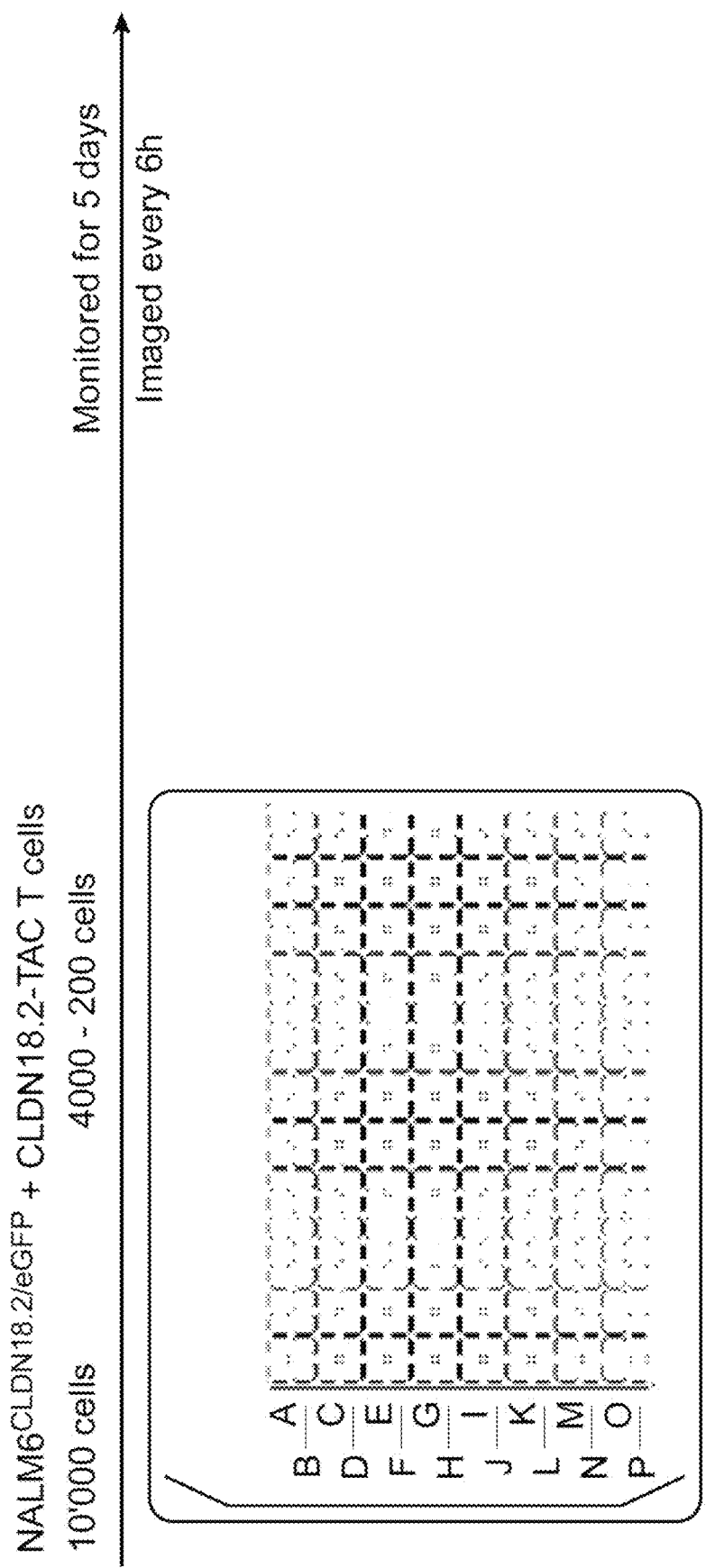
FIG. 8 is a schematic of an in vitro cytotoxicity assay described in Example 3.

T cells were engineered to express a Claudin 18.2 T cell-antigen coupler (TAC) including (i) Claudin 18.2 Nanobody 1 (including SEQ ID NO: 57 (Kabat CDR1), SEQ ID NO: 58 (Kabat CDR2), and SEQ ID NO: 59 (Kabat CDR3)), or Claudin 18.2 Nanobody 2 (including SEQ ID NO: 57 (Kabat CDR1), SEQ ID NO: 63 (Kabat CDR2), and SEQ ID NO: 59 (Kabat CDR3)), (ii) a UCHT1 antigen-binding domain that binds CD3, and (iii) a CD4 cytosolic and transmembrane domain: Nanobody 1/huUCHT1 Scaffold (SEQ ID NO: 67) or Nanobody 2/huUCHT1 Scaffold (SEQ ID NO: 71). NALM6 cells were engineered to express eGFP (NALM6$^{eGFP}$) or eGFP and Claudin 18.2 (NALM6$^{CLDN18.2/eGFP}$). T cells expressing either Claudin 18.2-TAC (SEQ ID NO: 67 or 71) were co-cultured with NALM6$^{CLDN18.2/eGFP}$ or NALM6$^{eGFP}$ cells. Non-transduced (NTD) T cells were used as negative control. Since NALM6 tumor cells naturally express the CD19 antigen, CD19-TAC T cells were used as a positive control. The cell culture was monitored using a Cytation instrument. Cells were cultured for 5 days, and each well was imaged every 6 hours. All experiments were performed in triplicate. A schematic of the experiment is depicted in FIG. 8.

Figure 9:
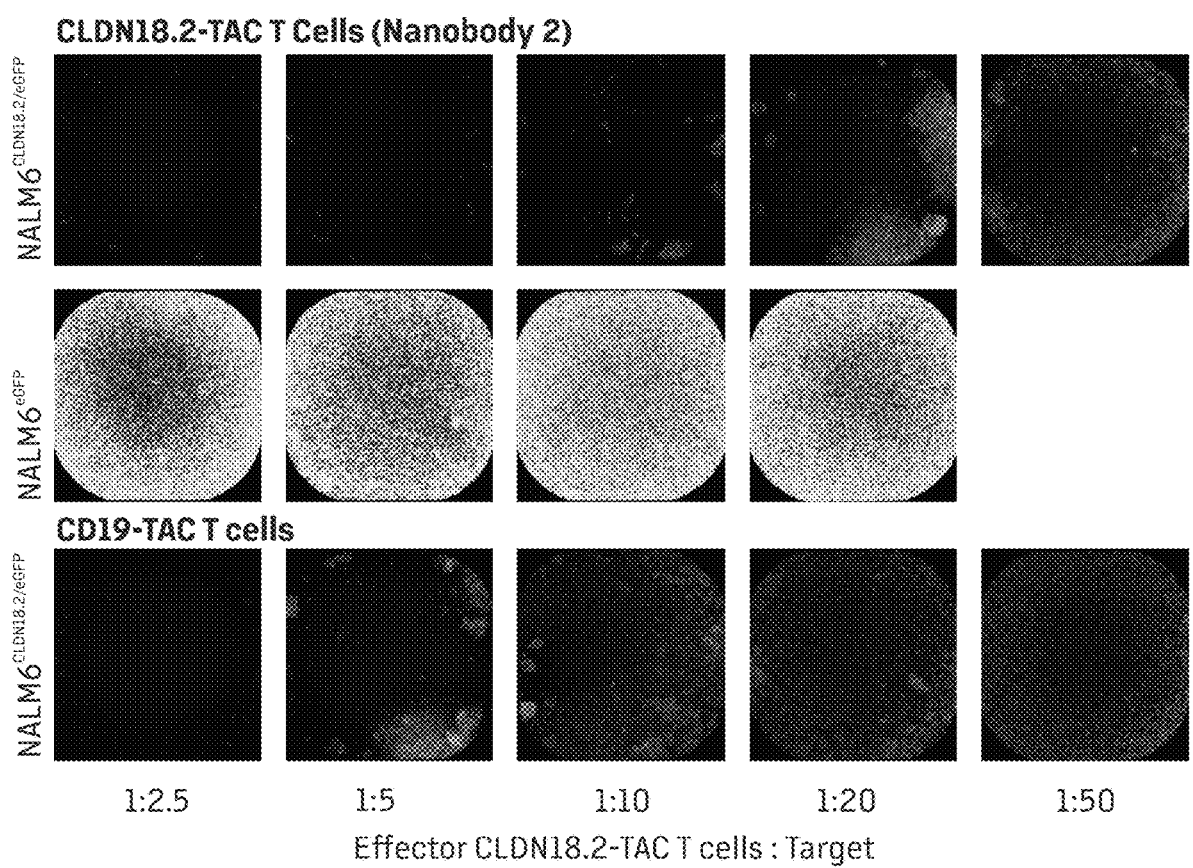
FIG. 9 depicts representative images of co-cultures of the indicated effector cell (TAC T cell) and target cell (NALM6CLDN18.2/eGFP or NALM6eGFP cells) at different E:T ratios after 5 days of co-culture.

FIG. 9 depicts images of co-cultures at different E:T ratios after 5 days of co-culture. T cells expressing the Claudin 18.2-TAC of SEQ ID NO: 71, when co-cultured with NALM6$^{eGFP}$ cells, did not control tumor cell growth. However, when T cells expressing the Claudin 18.2-TAC of SEQ ID NO: 71 were co-cultured with NALM6$^{CLDN18.2/eGFP}$ cells, tumor cell growth was controlled at or above an E:T ratio of 1:20 (500 Claudin 18.2-TAC T cells:10,000 target cells). By comparison, CD19-TAC T cells, which are known to be cytotoxic towards NALM6 cells, controlled tumor cell growth at or above an E:T ratio of 1:5 (2000 CD19-TAC T cells:10,000 target cells).

Figure 10:
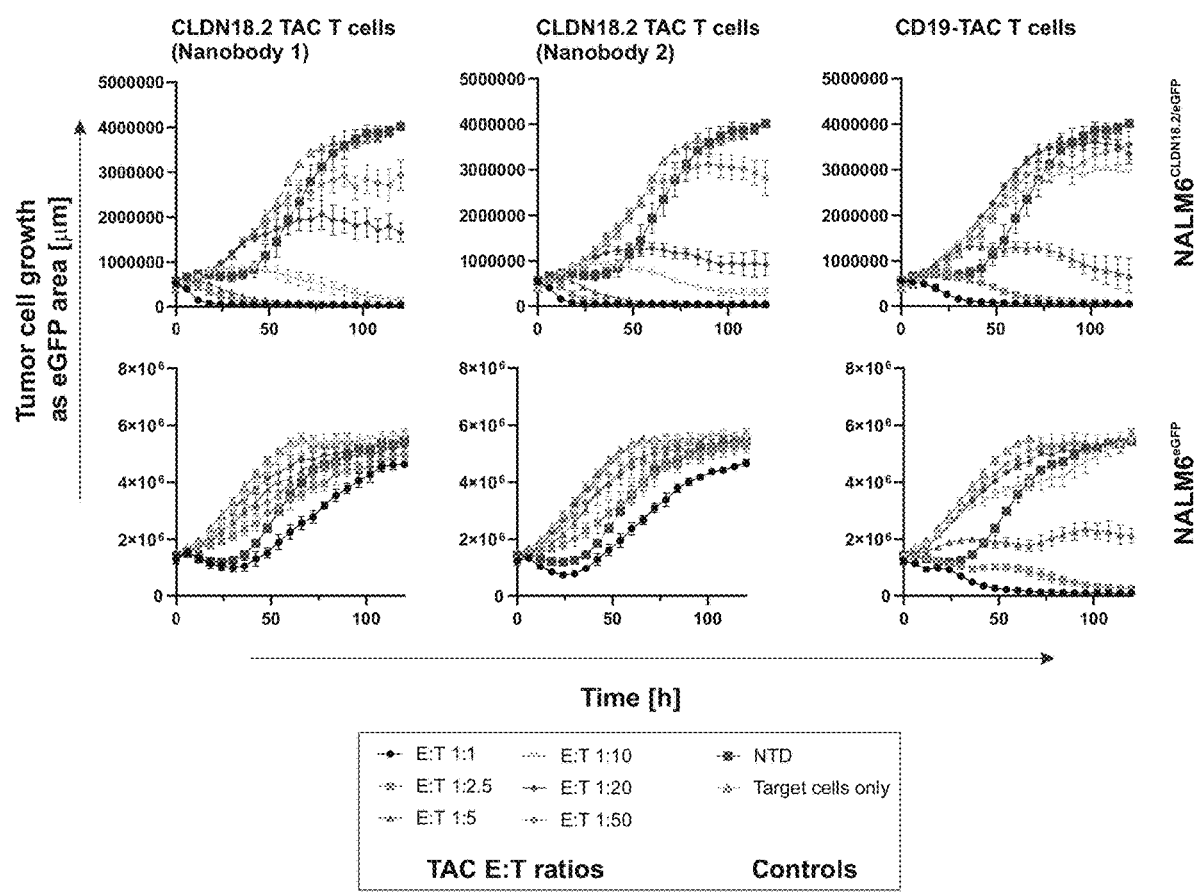
FIG. 10 depicts a quantitative analysis of tumor cell growth as measured by eGFP area for co-cultures of the indicated effector cell (TAC T cell) and target cell (NALM6CLDN18.2/eGFP or NALM6eGFP cells) at different E:T ratios. NTD: non-transduced control cells.

FIG. 10 depicts a quantitative analysis of tumor cell growth as a function of eGFP area. Tumor cells alone grew exponentially. NTD T cells, used at a 1:1 E:T ratio, caused a brief delay in NALM6$^{eGFP}$/NALM6$^{CLDN18.2/eGFP}$ growth, but ultimately but did not control tumor cell growth. T cells expressing the Claudin 18.2-TAC of SEQ ID NO: 67 or 71 did not control NALM6$^{eGFP}$ cell growth. However, when T cells engineered to express either the Claudin 18.2-TAC of SEQ ID NO: 67 (Nanobody 1/huUCHT Scaffold) or the TAC of SEQ ID NO:71 (Nanobody 2/huUCHT1 Scaffold TAC) were co-cultured with NALM6$^{CLDN18.2/eGFP}$ cells, there was significant control of tumor cell growth that was superior to that of CD19-TAC T cells.

Figure 11:
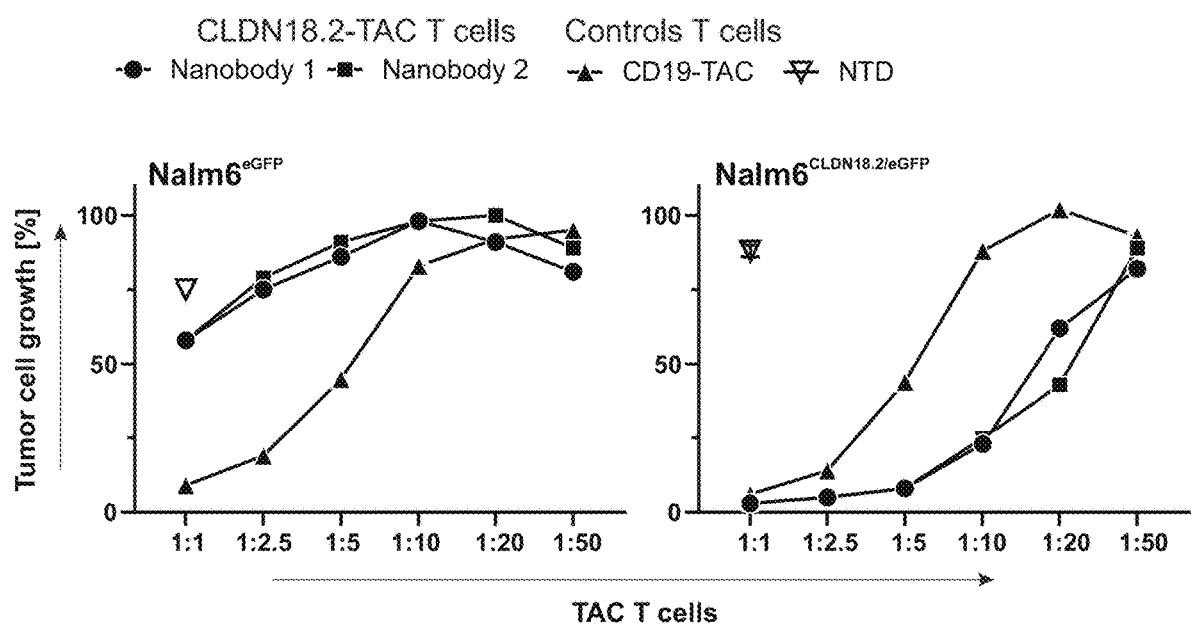
FIG. 11 depicts an area under the curve (AUC) analysis of the cytotoxicity results shown in FIG. 10.
Figure 12:
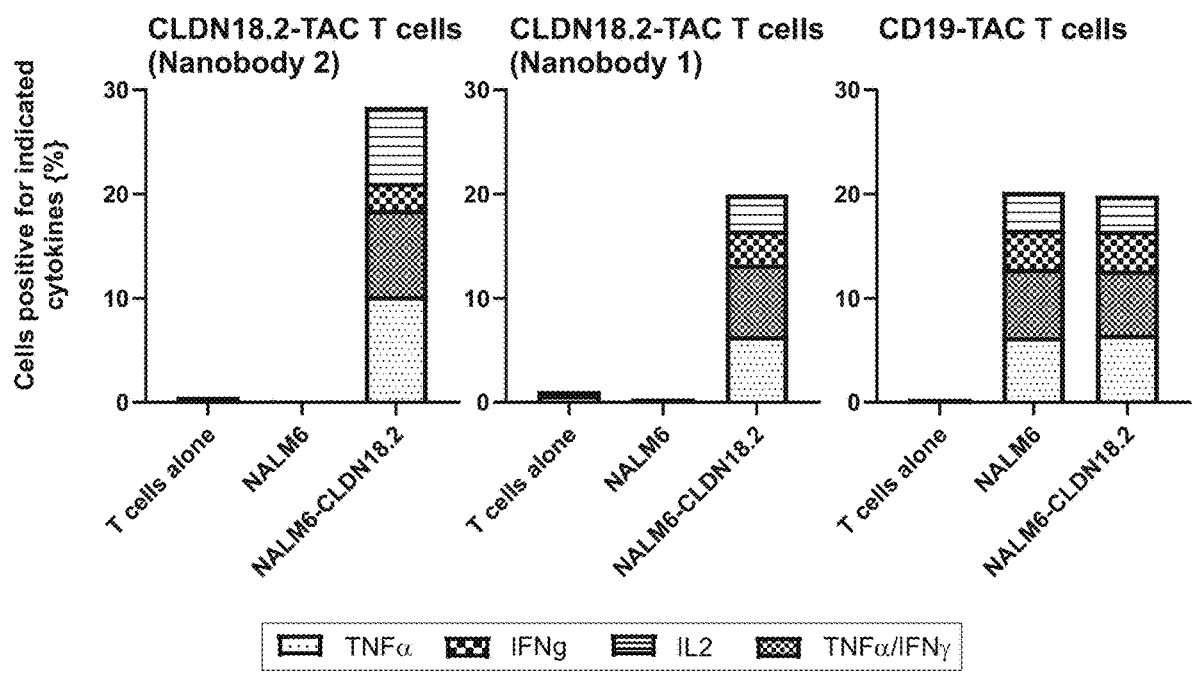
FIG. 12 depicts IFNg, TNFa, and IL2 production, as measured by flow cytometry, following co-culture of the indicated effector cell (TAC T cell) and target cell (NALM6CLDN18.2 or NALM6eGFP cells). Indicated effector cell (TAC T cell) cytokine production in the absence of any target cells is shown as a control.

FIG. 11 depicts an area under the curve (AUC) analysis of the cytotoxicity results shown in FIG. 10. AUC was plotted against E:T ratio. The time course of target cells alone was used to normalize all data to 100%. When the TAC of SEQ ID NO: 67 (Nanobody 1/huUCHT1 Scaffold); or the TAC of SEQ ID NO: 71 (Nanobody 2/huUCHT1 Scaffold) were co-cultured with NALM6$^{eGFP}$, a limited effect on tumor cell growth was observed at high E:T ratios, comparable to the NTD control. However, in cultures with NALM6$^{CLDN18.2/eGFP}$ both Claudin 18.2-TAC constructs showed significant tumor control with roughly equal efficiency, which was superior to that of CD19-TAC T cells Example 6—In Vitro Cytokine Production by Claudin 18.2-TAC T Cells T cells were engineered to express a Claudin 18.2 T cell-antigen coupler (TAC) including (i) Claudin 18.2 Nanobody 1 (including SEQ ID NO: 57 (Kabat CDR1), SEQ ID NO: 58 (Kabat CDR2), and SEQ ID NO: 59 (Kabat CDR3)), or Claudin 18.2 Nanobody 2 (including SEQ ID NO: 57 (Kabat CDR1), SEQ ID NO: 63 (Kabat CDR2), and SEQ ID NO: 59 (Kabat CDR3)), (ii) a UCHT1 antigen-binding domain that binds CD3, and (iii) a CD4 cytosolic and transmembrane domain: Nanobody 1/huUCHT1 Scaffold (SEQ ID NO: 67) or Nanobody 2/huUCHT1 Scaffold (SEQ ID NO: 71). NALM6 cells were engineered to express Claudin 18.2 (NALM6$^{CLDN18.2}$) T cells expressing either Claudin 18.2-TAC (SEQ ID NO: 67 or 71) were co-cultured with NALM6$^{CLDN18.2}$ cells, NALM6 cells, or no target cells. Non-transduced (NTD) T cells were used as negative control. CD19-TAC T cells were used as a positive control. Cells were stained for IFNγ, TNFα, and IL2, and analyzed by flow cytometry. Results are shown in FIG. 12. Both Claudin 18.2-TAC T cell variants showed cytokine production in the presence but not in the absence of Claudin 18.2-expressing target cells, with qualitatively superior cytokine production observed in the presence of the Claudin 18.2-TAC of SEQ ID NO: 71 compared to the Claudin 18.2-TAC of SEQ ID NO: 67. Activation of Claudin 18.2-TAC T cell variants was similar or superior to that of CD19-TAC T cells. There was no indication of auto-activation.

Example 7—Phenotypic Characterization of Claudin 18.2-TAC T Cells

Figure 14:
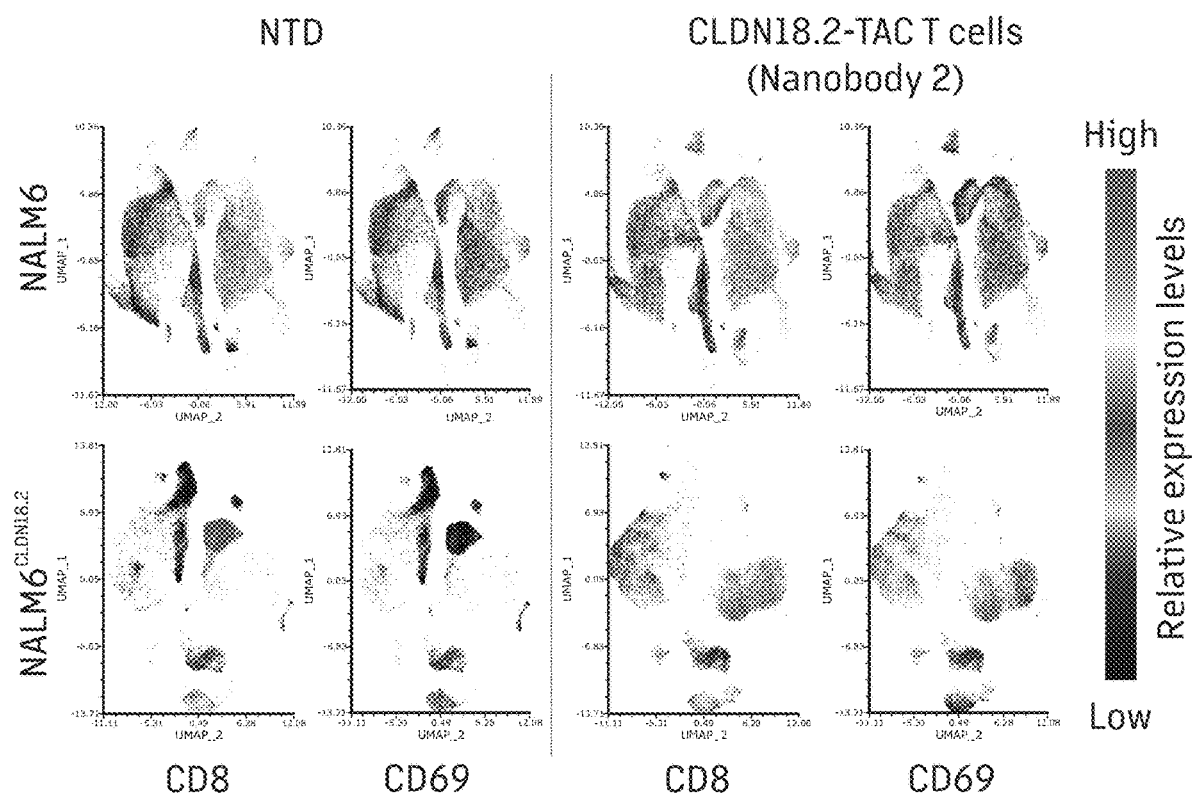
FIG. 14 depicts the results of a 16 parameter UMAP analysis highlighting CD8 and CD69 expression following co-culture of Claudin 18.2-TAC T cells or non-transduced (NTD) control cells with NALM6eGFP or NALM6CLDN18.2/eGFP cells. Colors indicate the relative abundance of the illustrated markers.

T cells were engineered to express a Claudin 18.2 T cell-antigen coupler (TAC) including (i) Claudin 18.2 Nanobody 2 (including SEQ ID NO: 57 (Kabat CDR1), SEQ ID NO: 63 (Kabat CDR2), and SEQ ID NO: 59 (Kabat CDR3)), (ii) a UCHT1 antigen-binding domain that binds CD3, and (iii) a CD4 cytosolic and transmembrane domain: Nanobody 2/huUCHT1 Y177T Scaffold (SEQ ID NO: 73). NALM6 cells were engineered to express eGFP (NALM6$^{eGFP}$) or eGFP and Claudin 18.2 (NALM6$^{CLDN18.2/eGFP}$). T cells expressing the Claudin 18.2-TAC or non-transduced (NTD) control cells were co-cultured with NALM6$^{eGFP}$ or NALM6$^{CLDN18.2/eGFP}$ cells and analyzed for the 16 markers depicted in FIG. 13. These markers allow an assessment of T cell activation, exhaustion and memory phenotype. Cells were analyzed and clustered using the UMAP algorithm. Results are shown in FIG. 14. Expression of CD8 and CD69 is shown, with shades indicating the relative abundance of the illustrated markers. The data shows similar patterns of expression of all surface markers analyzed on Claudin 18.2-TAC T cell products and NTD cells cultured with NALM6 cells. However, when cultured with Claudin 18.2-expressing NALM6 cells, Claudin 18.2-TAC T cell products (but not NTD cells) become activated as indicated by upregulation of CD69. Claudin 18.2-TAC T cell products retain similar memory phenotypes to the NTD controls even post activation (data not shown). Together, this data demonstrates that Claudin 18.2-TAC T cell products do not exhibit tonic signaling and are activated only in the presence of the Claudin 18.2 antigen.

Example 8—In Vitro Activity of Claudin 18.2-TAC T Cells

Figure 15:
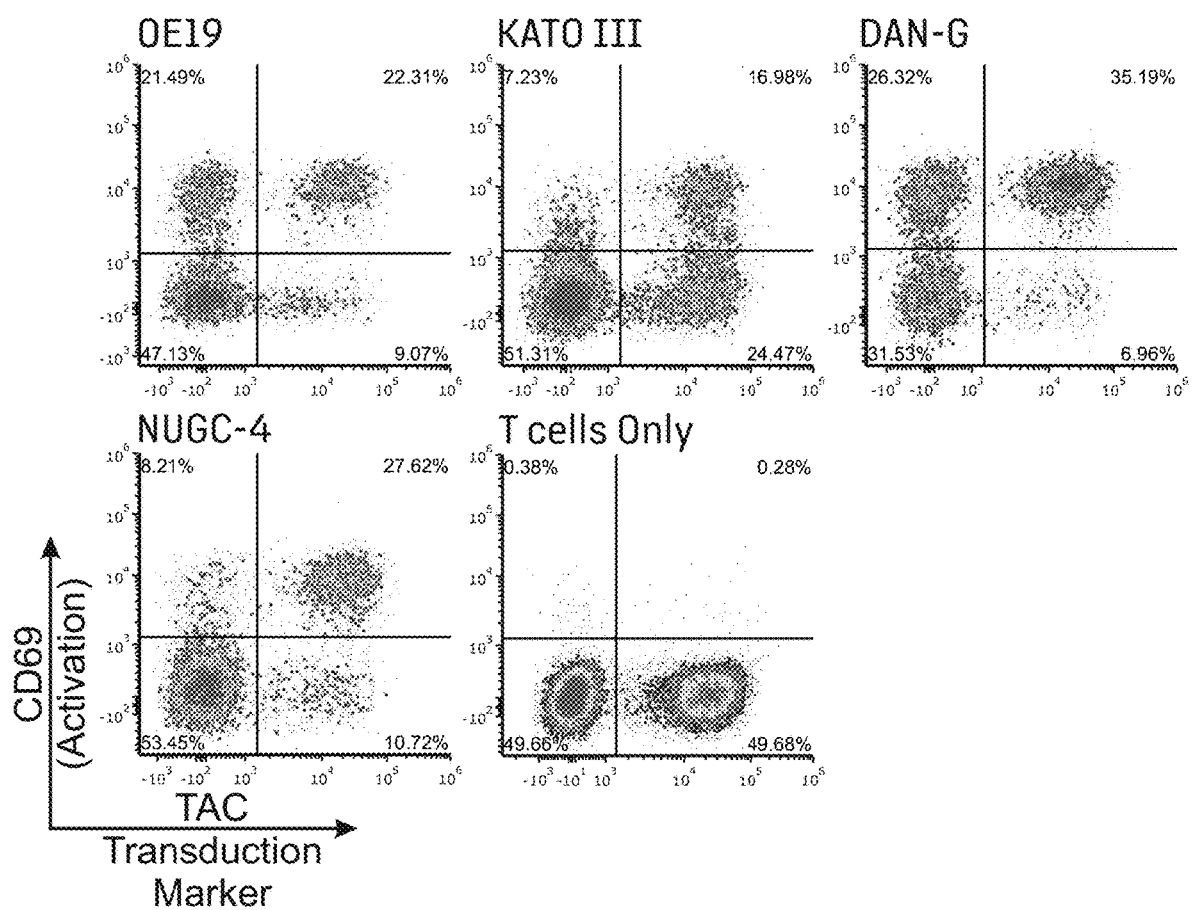
FIG. 15 depicts flow cytometry plots of CD69 staining (vertical axis) and Claudin 18.2-TAC transduction (horizontal axis) of CLDN18.9-TAC T cells co-cultured with indicated Claudin 18.2-expressing cell lines.

In one experiment, T cells were engineered to express a Claudin 18.2 T cell-antigen coupler (TAC) including (i) Claudin 18.2 Nanobody 2 (including SEQ ID NO: 57 (Kabat CDR1), SEQ ID NO: 63 (Kabat CDR2), and SEQ ID NO: 59 (Kabat CDR3)), (ii) a UCHT1 antigen-binding domain that binds CD3, and (iii) a CD4 cytosolic and transmembrane domain: Nanobody 2/huUCHT1 Y177T Scaffold (SEQ ID NO: 73). T cells expressing the Claudin 18.2-TAC (SEQ ID NO: 73) were co-cultured at a 1:1 ratio with a variety of tumor cell lines naturally expressing Claudin 18.2 (OE19, NUGC-4 [gastric adenocarcinoma], KATO III [gastric carcinoma], DAN-G [pancreatic adenocarcinoma]). Following the 4 hour co-culture, Claudin 18.2-TAC-expressing T cells (identified by fluorescent protein transduction marker) were harvested and analyzed for CD69 surface expression (early activation marker) by flow cytometry. As shown in FIG. 15, T cells expressing the Claudin 18.2-TAC of SEQ ID NO: 73 were successfully activated when co-cultured by all Claudin 18.2 positive target cells but not with Claudin 18.2 negative control cells (data not shown). Neither NTD negative controls (data not shown) nor T cells alone showed activation. When stimulated with Claudin 18.2-expressing tumor cells, non-transduced T cells in the Claudin 18.2-TAC (SEQ ID NO: 73) T cell product also show upregulation of CD69.

In another experiment, T cells were engineered to express a Claudin 18.2 T cell-antigen coupler (TAC) including (i) Claudin 18.2 Nanobody 1 (including SEQ ID NO: 57 (Kabat CDR1), SEQ ID NO: 58 (Kabat CDR2), and SEQ ID NO: 59 (Kabat CDR3)), or Claudin 18.2 Nanobody 2 (including SEQ ID NO: 57 (Kabat CDR1), SEQ ID NO: 63 (Kabat CDR2), and SEQ ID NO: 59 (Kabat CDR3)), (ii) an huUCHT1 or huUCHT1 (Y177T) antigen-binding domain that binds CD3, and (iii) a CD4 cytosolic and transmembrane domain: Nanobody 1/huUCHT1 Scaffold (SEQ ID NO: 67), Nanobody 1/huUCHT1 (Y177T) (SEQ ID NO:69), Nanobody 2/huUCHT1 Scaffold (SEQ ID NO: 71), or Nanobody 2/huUCHT1 (Y177T) (SEQ ID NO: 73). Claudin 18.2-TAC T cells were co-cultured at E:T ratios 1:1, 1:2.5, 1:5, 1:10, 1:20, 1:50 and 1:100 with 1×10$^4$ NALM6$^{CLDN18.2GFPeLuc}$ target cells/well in a cell imaging reader. Photos were captured every 8 hours for 5 days. The area of GFP-expressing cells is calculated for each time point and E:T ratio. From these values, the area under the curve (AUC) for each of the Claudin 18.2-TAC T cells was calculated and plotted, representing target cell killing at each E:T ratio.

FIG. 16A shows exemplary results of Claudin 18.2-TAC Nanobody 1/huUCHT1 (SEQ ID NO:67) (open diamonds), Claudin 18.2-TAC NA3SH1/huUCHT1 Y177T (SEQ ID NO:69) (closed diamonds), Claudin 18.2-TAC Nanobody 2/huUCHT1 (SEQ ID NO:71) (open triangles), and Claudin 18.2-TAC Nanobody 2/huUCHT1 Y177T (SEQ ID NO:73) (closed triangles) in co-culture with NALM6$^{CLDN18.2/eGFP}$. Data shown demonstrate the different levels of target cell killing dependent on the used E:T ratios. NTD and target cells alone are shown as negative controls. The IC$_{50}$ was calculated from individual AUC curves derived from the averaged values of 2 different cytotoxicity assays with product manufactured from two different donors. IC$_{50}$ value represents the E:T ratio at which 50% of target killing is observed after a 5-day co-culture (FIG. 16B). The graph shows that the TAC constructs containing Nanobody 1 Nanobody 1 (SEQ ID NO:67) have a higher level of cytotoxicity compared to Nanobody 2 (hVH6) variants.

Figure 17A:
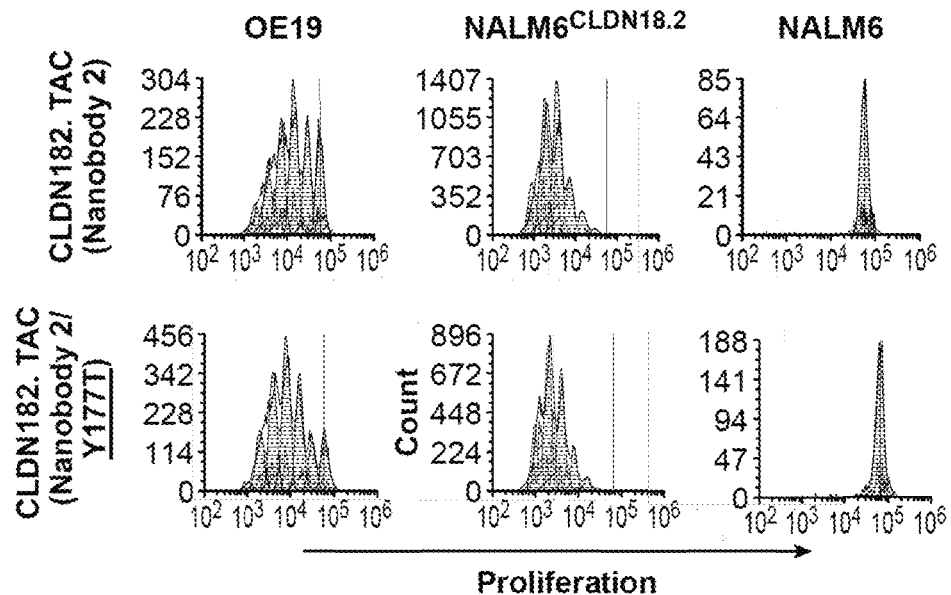
FIGS. 17A and 17B depict an assessment of the proliferation of Claudin 18.2-TAC-expressing T cells.
Figure 17B:
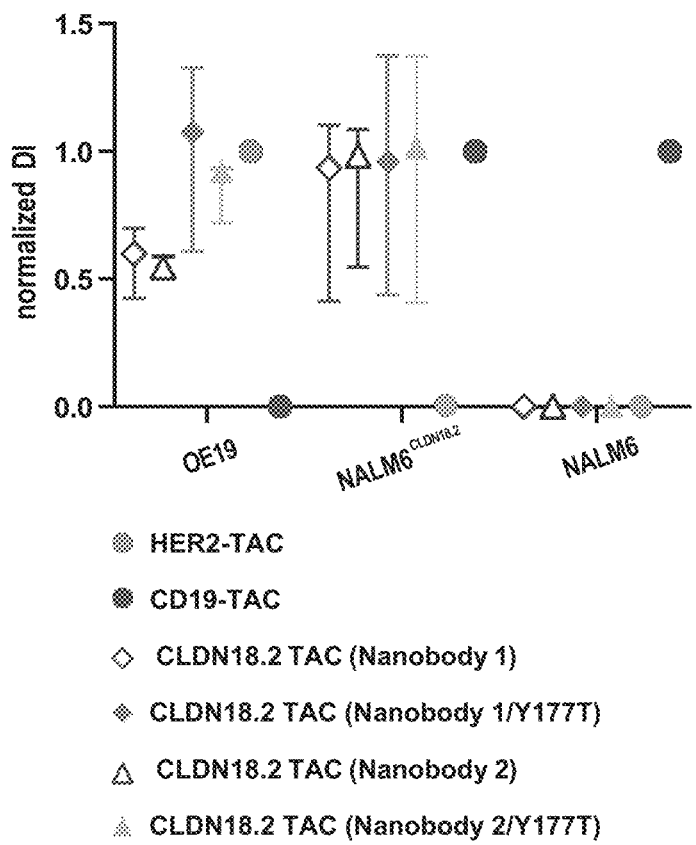

In another experiment, T cells were engineered to express a Claudin 18.2 T cell-antigen coupler (TAC) including (i) Claudin 18.2 Nanobody 1 (including SEQ ID NO: 57 (Kabat CDR1), SEQ ID NO: 58 (Kabat CDR2), and SEQ ID NO: 59 (Kabat CDR3)), or Claudin 18.2 Nanobody 2 (including SEQ ID NO: 57 (Kabat CDR1), SEQ ID NO: 63 (Kabat CDR2), and SEQ ID NO: 59 (Kabat CDR3)), (ii) an huUCHT1 or huUCHT1 (Y177T) antigen-binding domain that binds CD3, and (iii) a CD4 cytosolic and transmembrane domain: Nanobody 1/huUCHT1 Scaffold (SEQ ID NO: 67), Nanobody 1/huUCHT1 (Y177T) (SEQ ID NO:69), Nanobody 2/huUCHT1 Scaffold (SEQ ID NO: 71), or Nanobody 2/huUCHT1 (Y177T) (SEQ ID NO: 73). Proliferation of T cells engineered with Claudin 18.2-TAC variants, co-cultured in a 1:3 E:T ratio for 4 days with either OE19, NALM6$^{CLDN18.2}$ or NALM6 target cell lines, was evaluated. NALM6$^{CLDN18.2}$ is a leukemic cell line that was engineered to overexpress Claudin 18.2, and OE19 is a gastroesophageal cancer cell line naturally expressing Claudin 18.2. The parental NALM6 cell line lacks any Claudin 18.2 expression and was used as a negative control. Target cells were preincubated with mitomycin, whereas T cells were loaded with cell tracing (CTV) dye prior to co-culture. After 4 days, T cells were analyzed by flow cytometry for CTV staining, which can track T cell divisions. Representative histogram flow plots showing CTV dye dilution in Claudin 18.2-TAC Nanobody 2 (SEQ ID NO:71) and Claudin 18.2-TAC Nanobody 2/Y177T (SEQ ID NO:73) T cells after co-culture with the various target cells (FIG. 17A). The data show that both Claudin 18.2-TAC T cell cultures proliferate upon co-culture with Claudin 18.2 target cell lines, OE19 and NALM6$^{CLDN18.2}$, but not the Claudin 18.2 negative NALM6 cell line. The division index (DI), a measure of proliferation, from all Claudin 18.2-TAC T cells was averaged across 3 separate donors, and normalized to their respective positive controls (i.e., HER2-TAC T for OE19 and CD19-TAC T for NALM6$^{CLDN18.2}$ and NALM6) (FIG. 17B). When co-cultured with OE19, T cells engineered with the TAC huUCHT1 Y177T scaffold comprising either Nanobody 1 or 2 showed enhanced proliferation when compared to T cells engineered with the TAC scaffold of either Nanobody 1 or 2. When co-cultured with NALM6$^{CLDN18.2}$, T cells engineered with the huUCHT1 Y177T scaffold of either Nanobody 1 or 2 showed similar proliferation when compared to T cells engineered with the TAC scaffold of either Nanobody 1 or 2. No proliferation was observed against Claudin 18.2 negative control cells.

Figure 18A:
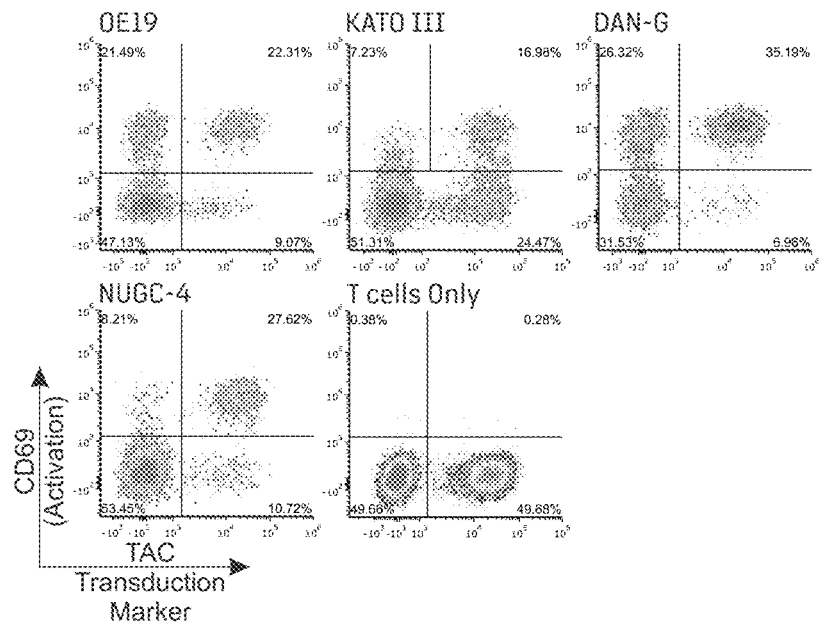
FIGS. 18A and 18B depict an assessment of the activation of T cells expressing the indicated Claudin 18.2-TACs.
Figure 18B:
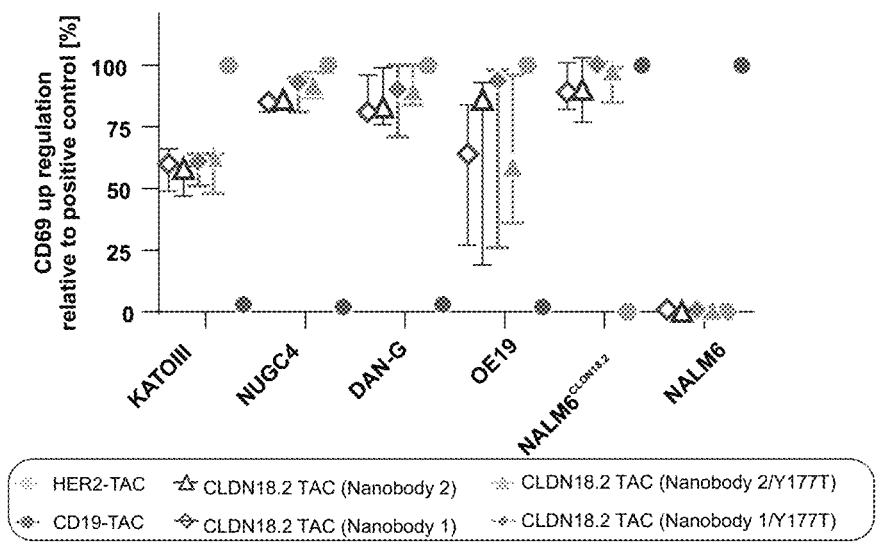

In another example, T cells were engineered to express a Claudin 18.2 T cell-antigen coupler (TAC) including (i) Claudin 18.2 Nanobody 1 (including SEQ ID NO: 57 (Kabat CDR1), SEQ ID NO: 58 (Kabat CDR2), and SEQ ID NO: 59 (Kabat CDR3)), or Claudin 18.2 Nanobody 2 (including SEQ ID NO: 57 (Kabat CDR1), SEQ ID NO: 63 (Kabat CDR2), and SEQ ID NO: 59 (Kabat CDR3)), (ii) an huUCHT1 or huUCHT1 (Y177T) antigen-binding domain that binds CD3, and (iii) a CD4 cytosolic and transmembrane domain: Nanobody 1/huUCHT1 Scaffold (SEQ ID NO: 67), Nanobody 1/huUCHT1 (Y177T) (SEQ ID NO:69), Nanobody 2/huUCHT1 Scaffold (SEQ ID NO: 71), or Nanobody 2/huUCHT1 (Y177T) (SEQ ID NO: 73). T cell activation was measured as a function of the upregulation of the early T cell activation marker CD69. T cells engineered with Claudin 18.2-TAC variants were co-cultured at a 1:1 ratio with a variety of tumor cell lines naturally expressing Claudin 18.2, such as OE19 (gastroesophageal carcinoma), NUGC-4 and KATO III (both gastric adenocarcinoma), and DAN-G (pancreatic adenocarcinoma). In addition, a co-culture with NALM6 cells engineered to overexpress Claudin 18.2 was used. Following a 4-hour co-culture, Claudin 18.2-TAC-expressing T cells were harvested and analyzed for CD69 surface expression by flow cytometry. FIG. 18A shows representative flow plots of T cells engineered with Claudin 18.2-TAC Nanobody 2/huUCHT1 Y177T (SEQ ID NO:73). CD69 expression is shown relative to the fluorescent protein transduction marker. T cell activation is evident for each Claudin 18.2-TAC T cell product as shown by CD69 upregulation, which was also observed for a fraction of non-transduced T cells in Claudin 18.2-TAC T cell products. No CD69 expression was observed in Claudin 18.2-TAC T cell products cultured in the absence of target cells (T cells alone). FIG. 18B shows the average of 3 independent co-culture experiments. The cultures included T cells engineered with Claudin 18.2 T cell-antigen coupler (TAC) or its next-generation scaffold (huUCHT1 Y177T) comprising Claudin 18.2 Nanobody 1 or Nanobody 2, derived from the manufacturing of 3 different donors. The resulting CD69 expression was normalized to the HER2-TAC (OE19, NUGC-4, KATO III, DAN-G) or CD19-TAC (NALM6) positive controls. T cells engineered with Claudin 18.2 T cell-antigen coupler (TAC) or its next generation scaffold (huUCHT1 Y177T) including Claudin 18.2 Nanobody 1 and 2 were activated by all Claudin 18.2 expressing cell lines, the engineered NALM6$^{CLDN18.2}$ control, but not the NALM6 negative control. This data demonstrates that T cells engineered with Claudin 18.2-TAC are able to identify and react against a broad range of target cells, including tumor cells naturally expressing Claudin 18.2.

Figure 19A:
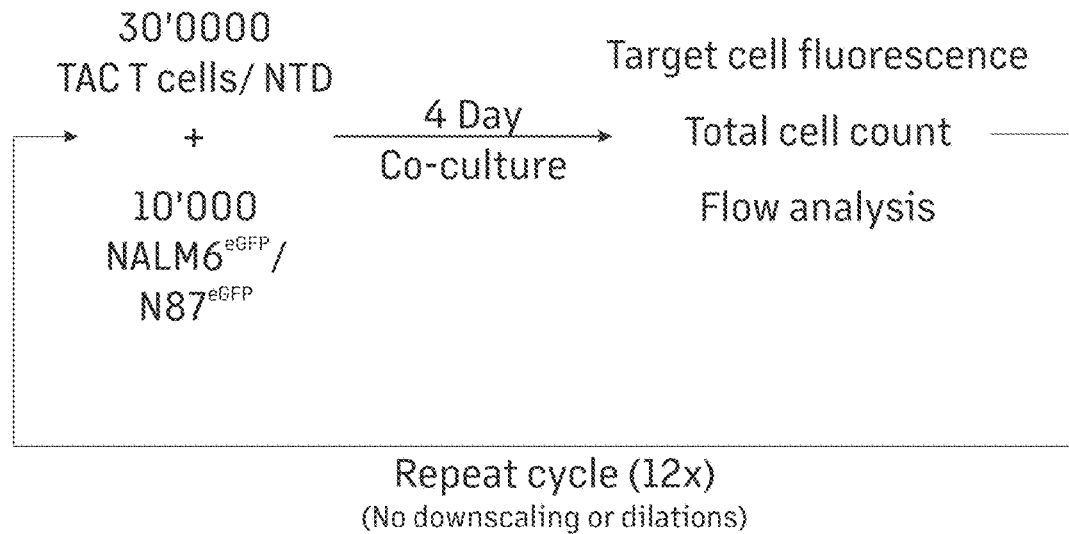
FIGS. 19A and 19B depict an assay testing repeated stimulation of TAC-expressing T cells.
Figure 19B:
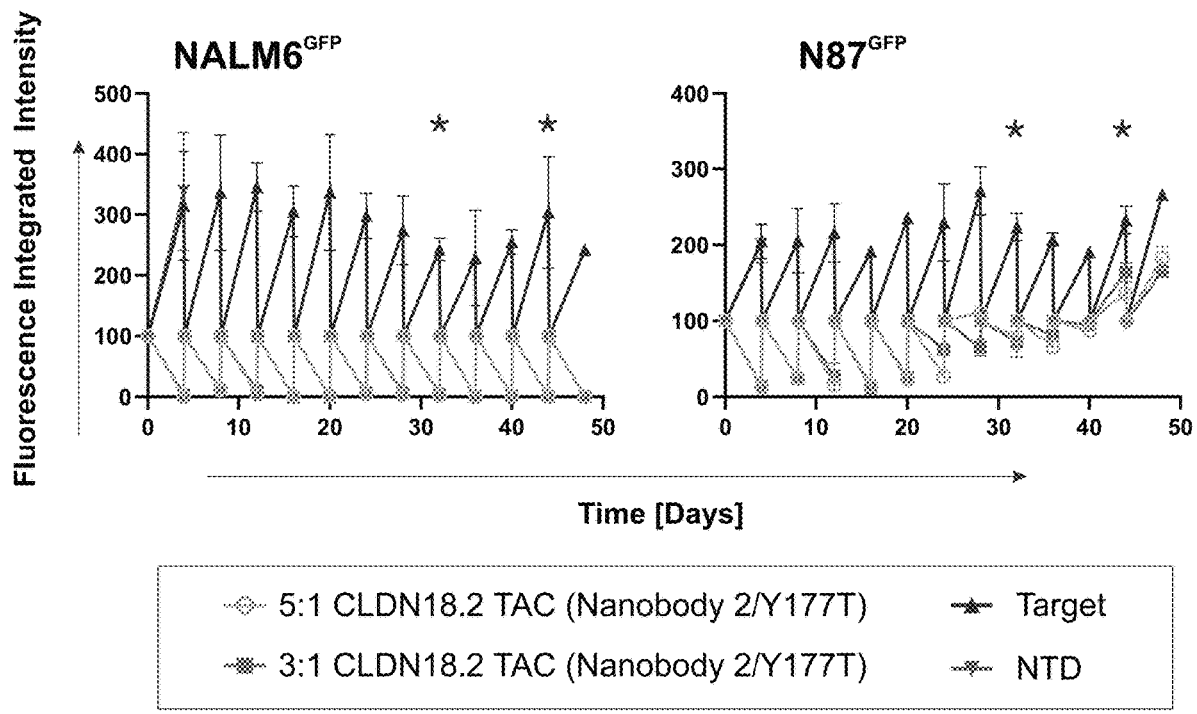

In another experiment, T cells were engineered to express a Claudin 18.2 T cell-antigen coupler (TAC) including (i) Claudin 18.2 Nanobody 2 (including SEQ ID NO: 57 (Kabat CDR1), SEQ ID NO: 63 (Kabat CDR2), and SEQ ID NO: 59 (Kabat CDR3)), (ii) an huUCHT1 (Y177T) antigen-binding domain that binds CD3, and (iii) a CD4 cytosolic and transmembrane domain: or Nanobody 2/huUCHT1 (Y177T) (SEQ ID NO: 73). The ability of the Claudin 18.2-TAC to retain sustained cytotoxicity was evaluated. The experimental schematic is shown in FIG. 19A. Claudin 18.2-TAC T cells were co-cultured with NALM6$^{CLDN18.2/eGFP}$ or N87$^{CLDN18.2/eGFP}$ cells at E:T ratios of 3:1 and 5:1 (total T cells:target cells) for 4 days. Target cell fluorescence was monitored using a Cytation instrument on D0 and D4. Each assay condition was set up in triplicates in a 48-well tissue culture dish. On D4, total cell counts were performed on the T cells which were carried forward into fresh co-cultures with new target cells while maintaining the same E:T ratios. Surplus T cells were subjected to flow cytometry analysis. Twelve successive 4-day rounds of co-culture were performed. Non-transduced (NTD) T cells were included in the first round as negative controls. Quantitative analysis of tumor cell growth as a function of eGFP integrated intensity is shown. The fluorescence signal captured on D4 of each round was normalized to D0 of that round (FIG. 19B). Tumor cells alone grew out uncontrolled in each round as expected. NALM6$^{CLDN18.2/eGFP}$ cells co-cultured with Claudin 18.2-TAC (Nanobody 2/Y177T) T cells were successfully cleared in each of the 12 rounds. Growth of N87$^{CLDN18.2/eGFP}$ cells co-cultured with Claudin 18.2-TAC T cells was controlled in the first 5 rounds, with the degree of control lessening in later rounds. Asterisks indicate time points when some of the 48 wells needed to be combined to retain the desired E:T ratios.

Example 9—In Vivo Activity of Claudin 18.2-TAC T Cells

T cells were engineered to express a Claudin 18.2 T cell-antigen coupler (TAC) including Claudin 18.2 Nanobody 2 (including SEQ ID NO: 57 (Kabat CDR1), SEQ ID NO: 63 (Kabat CDR2), and SEQ ID NO: 59 (Kabat CDR3)), (ii) a UCHT1 antigen-binding domain that binds CD3, and (iii) a CD4 cytosolic and transmembrane domain: Nanobody 2/huUCHT1 Y177T Scaffold (SEQ ID NO: 73).

In one experiment, NSG mice were inoculated with 5×10$^5$ NALM6$^{CLDN18.2/eLuc}$ tumor cells. Four days after engraftment, mice were treated with a single intravenous dose of T cells expressing the Claudin 18.2-TAC of SEQ ID NO: 73. Non-treated (NT) mice and mice treated with non-transduced T cells (NTD) were used as negative controls. Mice were dosed with 4×10$^6$ TAC T cells or an equivalent number of NTD cells that matches the total T cell dose used for TAC T cells. Total luminescence was measured weekly.

Figure 20:
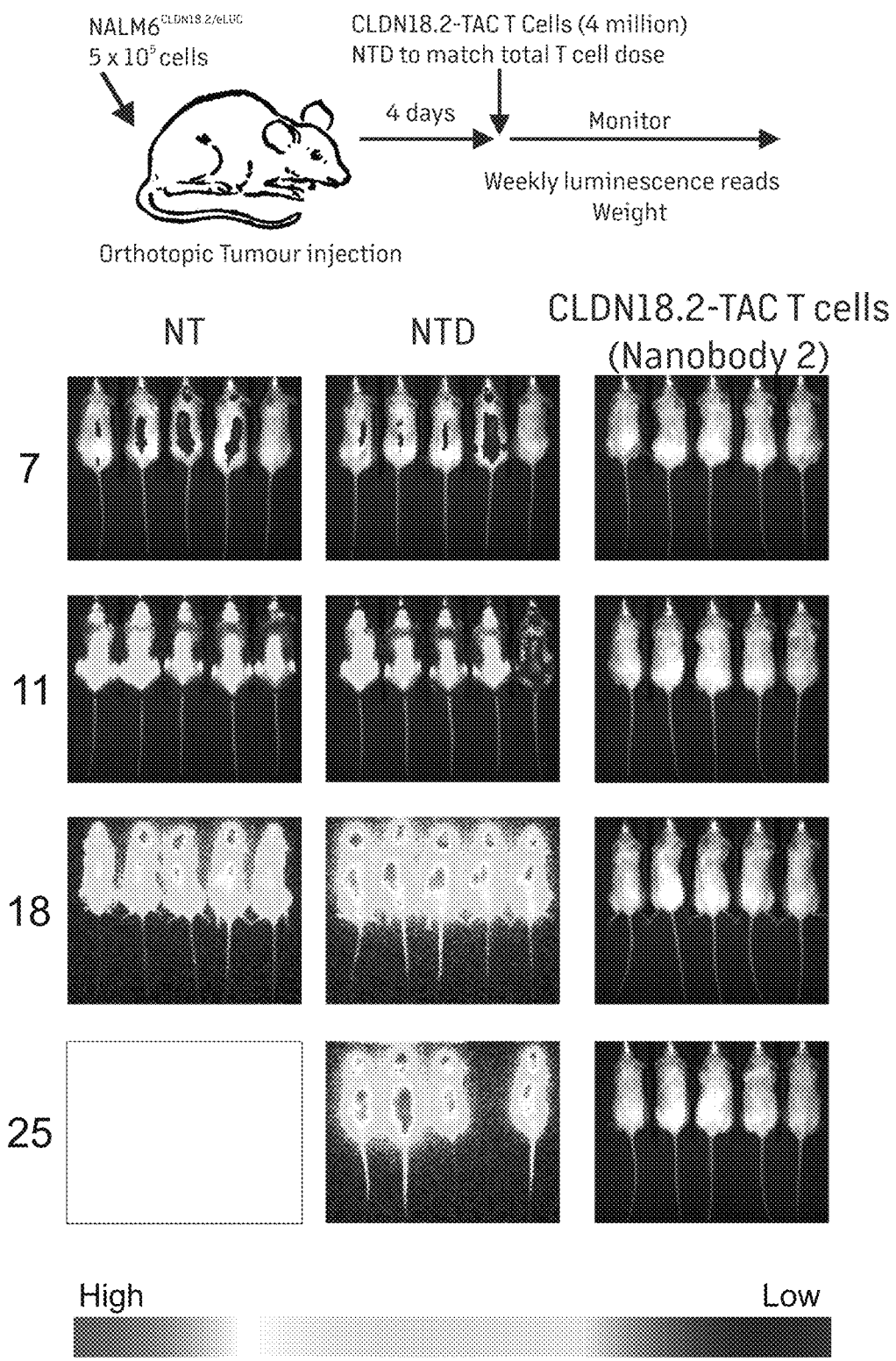
FIG. 20 depicts a schematic of in vivo murine experiments described in Example 9 (top) and resulting total flux (photons/second) as the sum of the dorsal and ventral reads for the indicated treatment groups (bottom).

The resulting total flux (photons/second) as the sum of the dorsal and ventral reads is shown in FIG. 20. Complete tumor rejection was achieved in all animals treated with T cells expressing the Claudin 18.2-TAC of SEQ ID NO: 73 during the 30 day study duration. Negative controls did not show any tumor control. No TAC associated toxicity was observed.

Figure 21A:
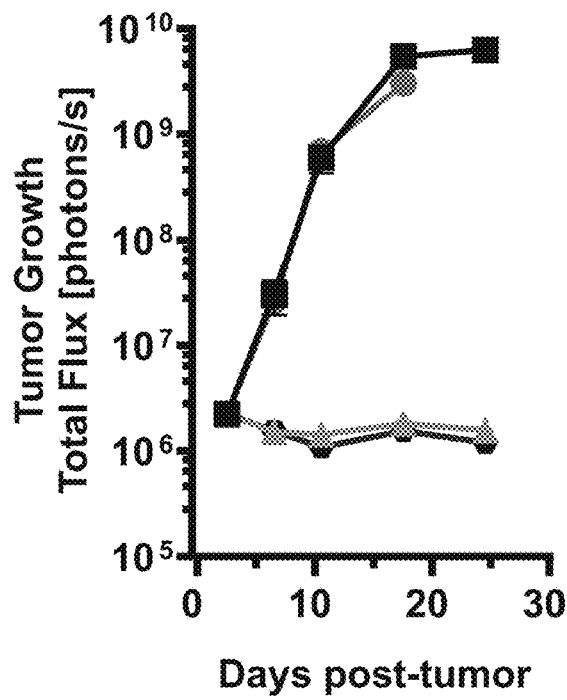
FIGS. 21A-21C depict luminescence (total flux.
Figure 21B:
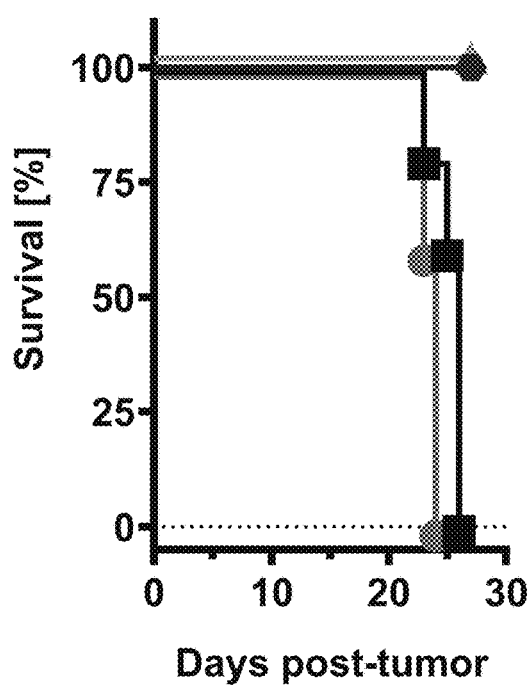
Figure 21C:
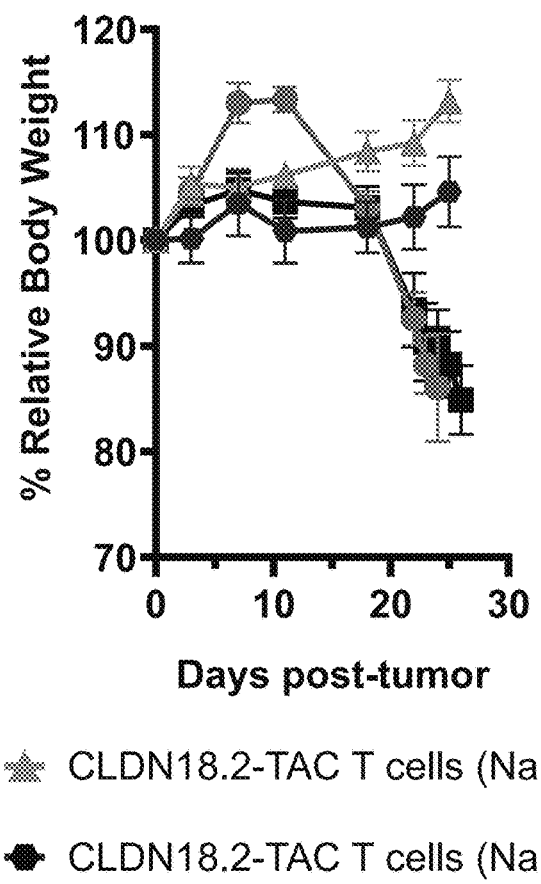

The amount of luminescence presented as total flux is shown in FIG. 21A. Overall survival is shown in FIG. 21B. Relative change in body weight, as a means to assess toxicity, is shown in FIG. 21C. Non treated animals (NT) or mice administered non-transduced control T cells (NTD) showed no tumor control. All of these animals reached endpoint within the 30-day period and showed tumor induced weight drops as early as day 20 post tumor inoculation. In contrast, all animals treated with T cells expressing the Claudin 18.2-TAC of SEQ ID NO: 73 showed complete tumor control, survived the 30-day study period, and lacked signs of toxicity.

Figure 22:
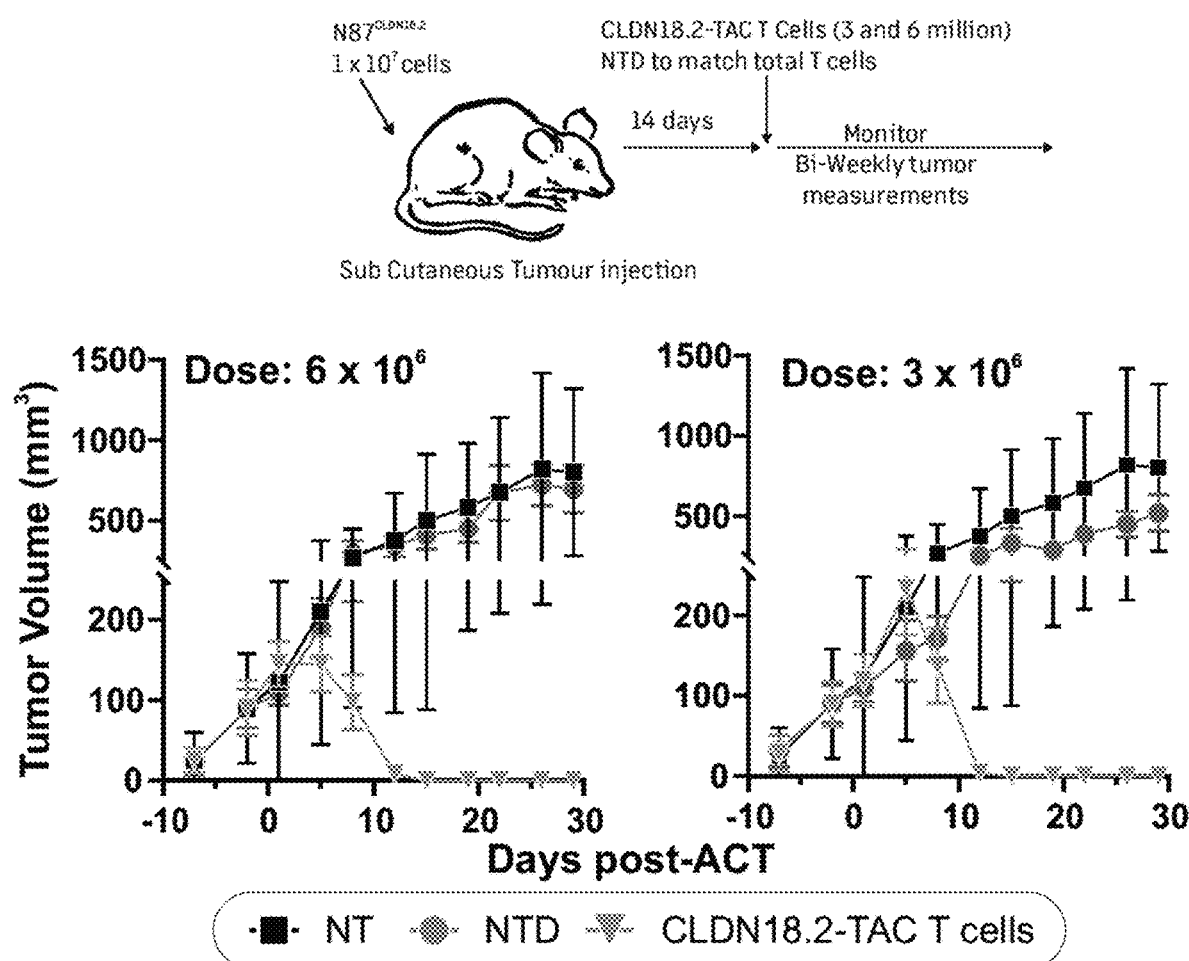
FIG. 22 depicts a schematic of in vivo murine model of the antitumor activity of Claudin 18.2-TAC T cells and tumor volumes over time in response to indicated dosages.

In another experiment, NSG mice were inoculated with $1\times10^7$ N87$^{CLDN18.2}$ tumor cells (FIG. 22, top panel). Fourteen days after engraftment, mice were treated with a single dose of either 3 or $6\times10^6$ T cells expressing the Claudin 18.2-TAC of SEQ ID NO: 73. The negative controls include non-treated (NT) mice or mice treated with non-transduced T cells (NTD). Tumor volume was measured bi-weekly, and the resulting tumor volume is shown in FIG. 22, bottom panels. Complete tumor rejection was achieved in all animals treated with T cells expressing the Claudin 18.2-TAC of SEQ ID NO: 73. Neither NTD nor NT controls showed tumor regression.

Figure 23:
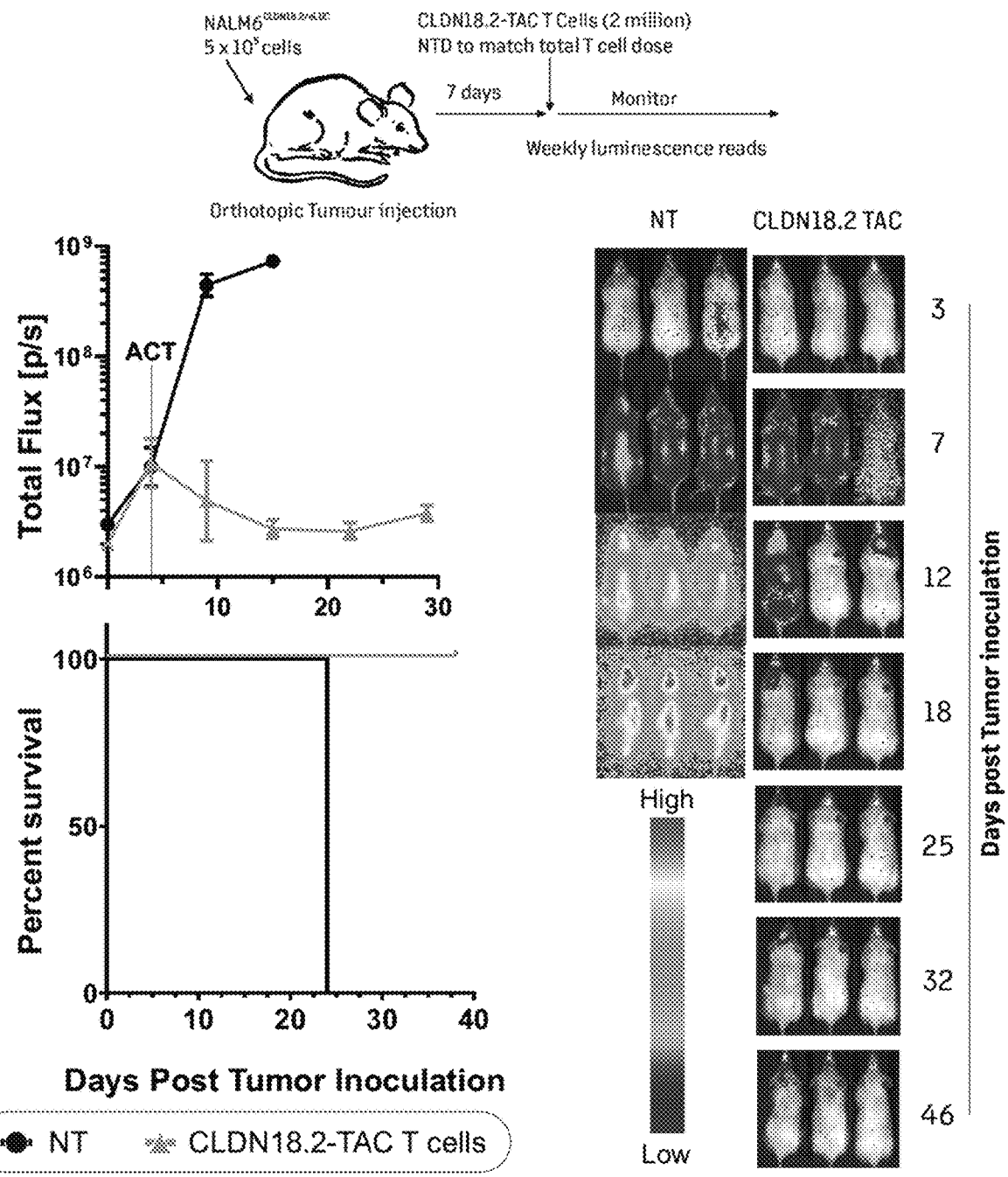
FIG. 23 depicts a schematic of an in vivo murine model of the antitumor activity of Claudin 18.2-TAC T cells (top panel), luminescence (total flux; center-left panel), overall survival (bottom-left panel), and whole body scans of mice in the indicated treatment groups over the treatment course (right panel).

In another experiment, mice were inoculated with $5\times10^5$ NALM6$^{CLDN18.2/eLuc}$ tumor cells (FIG. 23, top panel). Seven days after engraftment, mice were treated with a single dose of T cells expressing the Claudin 18.2-TAC of SEQ ID NO: 73. Non-treated (NT) mice are shown. At this dose level non-transduced T cells (NTD) were not included as negative control as they showed no response when given at a $4\times10^6$ dose (data not shown). Mice were dosed with $2\times10^6$ TAC T cells. Total luminescence was measured weekly, and the resulting total flux (photons/second) as the sum of the dorsal and ventral reads is shown in FIG. 23, center-left panel. The luminescence images are shown (FIG. 23, right panel). T cells expressing the Claudin 18.2-TAC of SEQ ID NO: 73 were able to induce complete tumor regression, while NTD controls had no impact (data not shown). Survival curves are shown, demonstrating the survival of mice treated with T cells expressing the Claudin 18.2-TAC of SEQ ID NO: 73 (FIG. 23, bottom-left panel).

Figure 24:
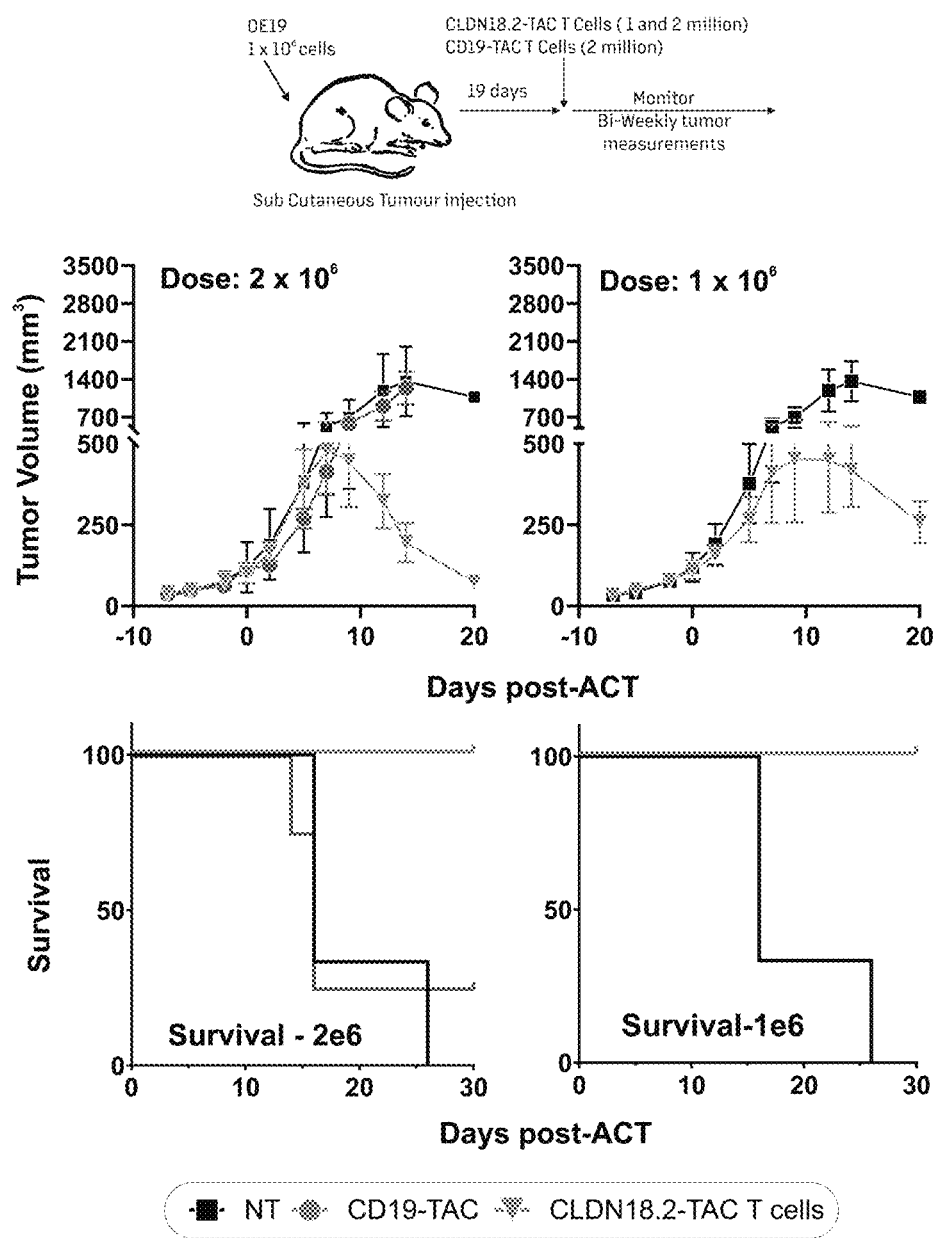
FIG. 24 depict a schematic of an in vivo murine model of the antitumor activity of Claudin 18.2-TAC T cells (top panel), tumor volumes over time in response to indicated dosages (center panels), and overall survival (bottom panels).

In another experiment, NSG mice were inoculated with $1\times10^6$ OE19 tumor cells which naturally expresses Claudin 18.2 (FIG. 24, top panel). Nineteen days after engraftment of tumor cells, mice were treated with a single dose of either 1 or $2\times10^6$ T cells expressing the Claudin 18.2-TAC of SEQ ID NO: 73. The negative controls include non-treated (NT) mice or mice treated with non-transduced T cells (NTD). Tumor volume was measured bi-weekly, and the resulting tumor volume is shown in FIG. 24, center panels. Complete tumor rejection was achieved in all animals treated T cells expressing the Claudin 18.2-TAC of SEQ ID NO: 73, whereas control animals showed tumor outgrowth. Survival curves of treated and control mice are shown in FIG. 24, bottom panels, demonstrating the survival mice treated with T cells expressing the Claudin 18.2-TAC of SEQ ID NO: 73.

Figure 25A:
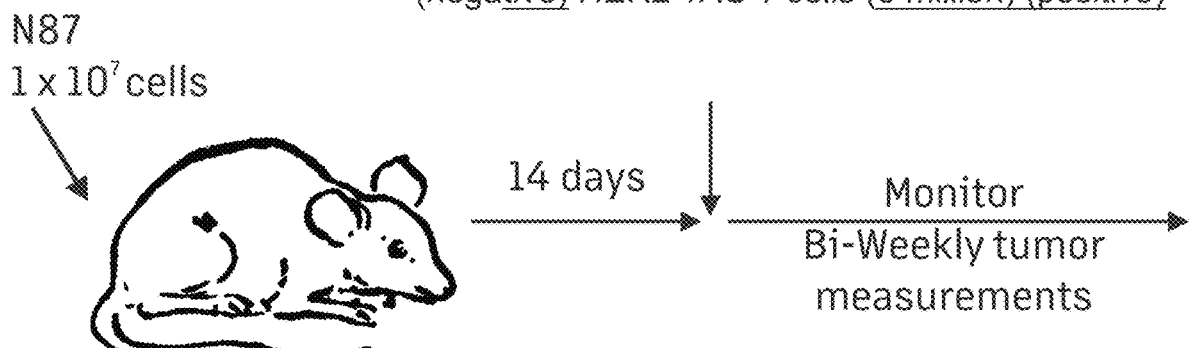
FIGS. 25A-25B depict an in vivo murine model of the antitumor activity of Claudin 18.2-TAC T cells and different dosage levels.
Figure 25B:
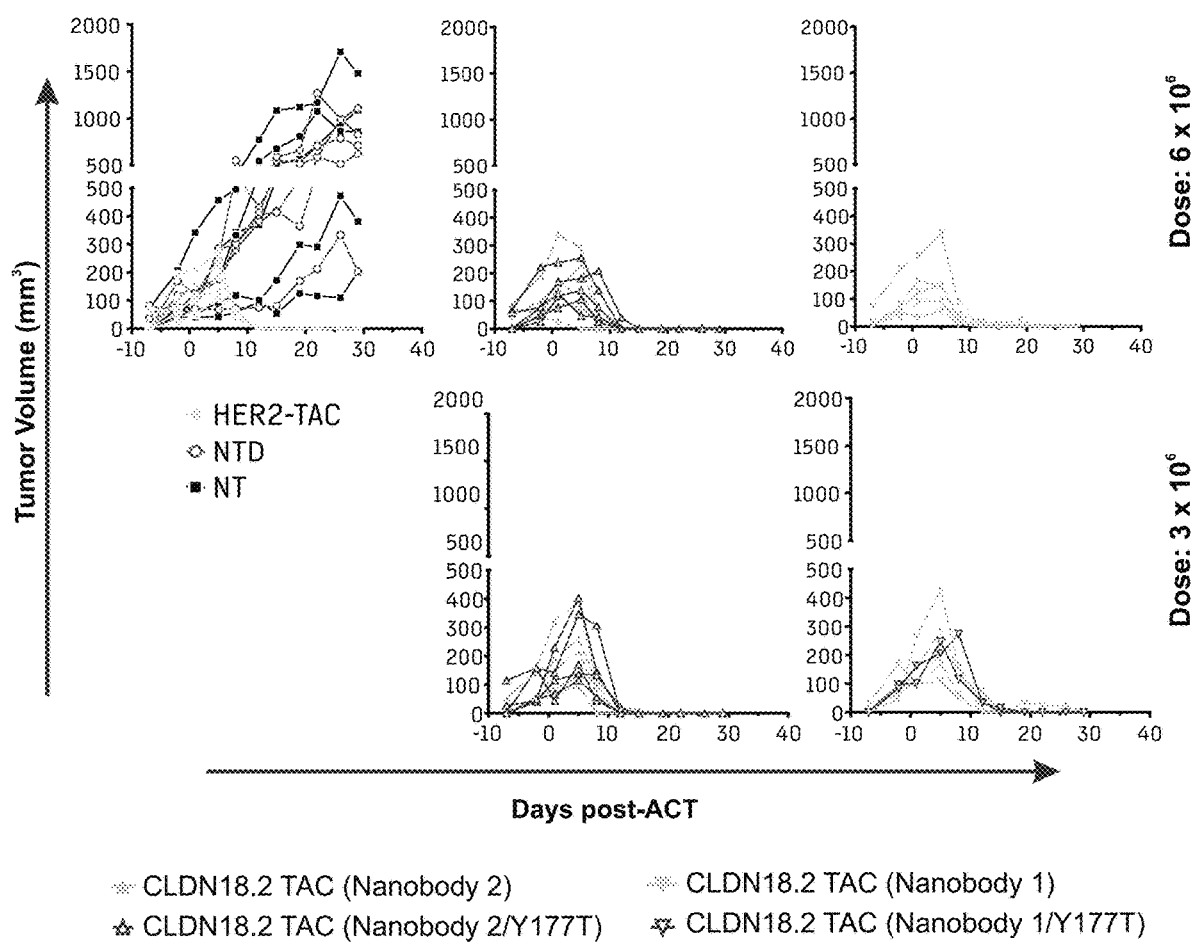

In one example, T cells were engineered to express a Claudin 18.2 T cell-antigen coupler (TAC) including (i) Claudin 18.2 Nanobody 1 (including SEQ ID NO: 57 (Kabat CDR1), SEQ ID NO: 58 (Kabat CDR2), and SEQ ID NO: 59 (Kabat CDR3)), or Claudin 18.2 Nanobody 2 (including SEQ ID NO: 57 (Kabat CDR1), SEQ ID NO: 63 (Kabat CDR2), and SEQ ID NO: 59 (Kabat CDR3)), (ii) an huUCHT1 or huUCHT1 (Y177T) antigen-binding domain that binds CD3, and (iii) a CD4 cytosolic and transmembrane domain: Nanobody 1/huUCHT1 Scaffold (SEQ ID NO: 67), Nanobody 1/huUCHT1 (Y177T) (SEQ ID NO:69), Nanobody 2/huUCHT1 Scaffold (SEQ ID NO: 71), or Nanobody 2/huUCHT1 (Y177T) (SEQ ID NO: 73). NSG mice were inoculated with $1\times10^7$ N87$^{CLDN18.2}$ tumor cells and then treated with CLDN18.2 TAC T cells. The experimental schematic is shown in FIG. 25A. Fourteen days after engraftment, mice were treated with a single dose of either 3 or $6\times10^6$ T cells engineered with Claudin 18.2 T cell-antigen coupler (TAC) and its next-generation scaffold (huUCHT1 Y177T) comprising Claudin 18.2 Nanobody 1 or Nanobody 2. The negative controls include non-treated (NT) mice or mice treated with non-transduced T cells (NTD). HER2-TAC T cells were used as positive control. Tumor volume was measured bi-weekly. Tumor volumes of mice treated with Claudin 18.2-TAC Nanobody (SEQ ID NO: 67) (closed inverted triangle), Claudin 18.2-TAC Nanobody 1/Y177T (SEQ ID NO: 69) (open inverted triangle), Claudin 18.2-TAC Nanobody 2 (SEQ ID NO:71) (closed triangles), and Claudin 18.2-TAC Nanobody 2/Y177T (SEQ ID NO: 73) (open triangles) are shown (FIG. 25B). Non-treated control mice are shown (closed square). As negative controls, mice treated with non-transduced (open circles) and, as positive controls, mice treated with HER2-TAC (closed circle) are shown. Complete tumor rejection was achieved in all animals treated with T cells expressing the Claudin 18.2-TAC receptors. Neither NTD nor NT controls showed tumor regression. The HER2-Tac positive control induced tumor regression similar to the Claudin 18.2-TAC variants.

Figure 26A:
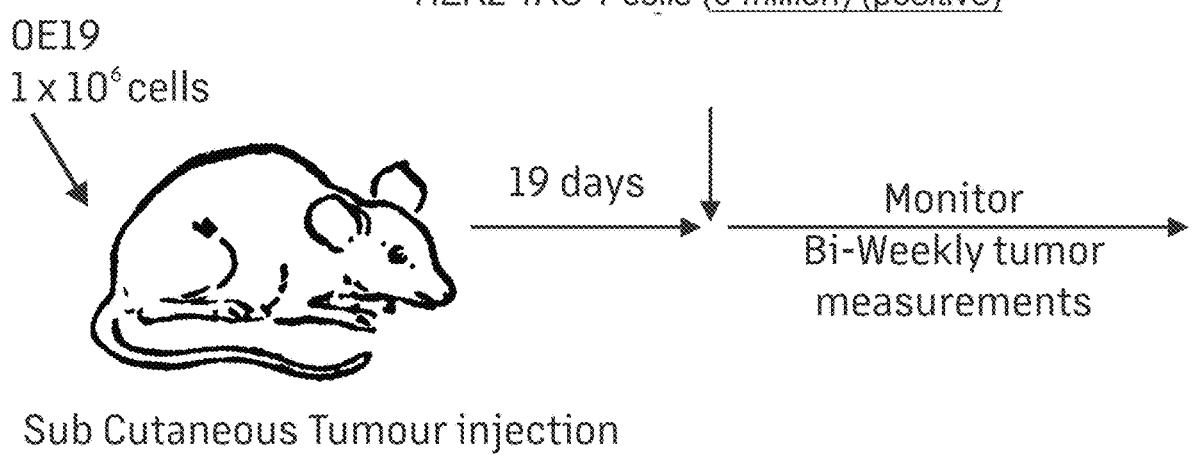

In another experiment, T cells were engineered to express a Claudin 18.2 T cell-antigen coupler (TAC) including (i) Claudin 18.2 Nanobody 1 (including SEQ ID NO: 57 (Kabat CDR1), SEQ ID NO: 58 (Kabat CDR2), and SEQ ID NO: 59 (Kabat CDR3)), or Claudin 18.2 Nanobody 2 (including SEQ ID NO: 57 (Kabat CDR1), SEQ ID NO: 63 (Kabat CDR2), and SEQ ID NO: 59 (Kabat CDR3)), (ii) an huUCHT1 or huUCHT1 (Y177T) antigen-binding domain that binds CD3, and (iii) a CD4 cytosolic and transmembrane domain: Nanobody 1/huUCHT1 Scaffold (SEQ ID NO: 67), Nanobody 1/huUCHT1 (Y177T) (SEQ ID NO:69), Nanobody 2/huUCHT1 Scaffold (SEQ ID NO: 71), or Nanobody 2/huUCHT1 (Y177T) (SEQ ID NO: 73). NSG mice were inoculated with $1\times10^6$ OE19 tumor cells subcutaneously and then treated with subtherapeutic doses of Claudin 18.2-TAC T cells. The experimental schematic is shown in FIG. 26A. Nineteen days after engraftment, mice were treated with a single intravenous dose of either 1 or $2\times10^6$ T cells engineered with Claudin 18.2 T cell-antigen coupler (TAC) and its next-generation scaffold (huUCHT1 Y177T) comprising Claudin 18.2 Nanobody 1 and 2. Non-treated (NT) mice and mice treated with non-transduced T cells (NTD) were used as negative controls. As additional negative controls, mice were treated with $2\times10^6$ CD19-TAC T cells and, as positive controls, mice were treated with $6\times10^6$ HER2-TAC T cells. Tumor volume was measured biweekly. Tumor volume of mice treated with Claudin 18.2-TAC Nanobody 1 (SEQ ID NO:67) (closed inverted triangle), Claudin 18.2-TAC Nanobody 1/Y177T (SEQ ID NO:69) (open inverted triangle), Claudin 18.2-TAC Nanobody 2 (SEQ ID NO:71) (closed triangles), and Claudin 18.2-TAC Nanobody 2/Y177T (SEQ ID NO:71 (open triangles) are shown (FIG. 26B). Control groups are shown. NTD are represented by open circles; NT are represented by closed black squares. Mice treated with CD19-TAC T cells are represented by grey closed circles, and those treated with HER2-TAC T cells are represented by small light grey closed circles. Claudin 18.2-TAC Nanobody 2/Y177T (SEQ ID NO:71) T cells showed complete tumor clearance or significant tumor regression at both $1\times10^6$ and $2\times10^6$ doses. Claudin 18.2-TAC Nanobody 1/Y177T (SEQ ID NO:69) showed complete tumor clearance at the $2\times10^6$ dose. With the $1\times10^6$ dose, Claudin 18.2-TAC Nanobody 1/Y177T (SEQ ID NO:69) showed total tumor clearance or significant tumor regression in 60% of treated mice, and tumor control in the remaining 40%. At the $2\times10^6$ dose level Claudin 18.2-TAC Nanobody 2 (SEQ ID NO:71) showed tumor clearance in 40% of mice and some level of tumor control in the remaining 60%. At the 2×10⁶ dose level Claudin 18.2-TAC Nanobody 1 (SEQ ID NO:67) showed complete tumor clearance or significant tumor regression in 40% mice, while the remaining 60% showed tumor outgrowth. At the 1×10⁶ treatment dose level, Claudin 18.2-TAC Nanobody 1 (SEQ ID NO:67) treated mice failed to show any tumor control. Mice treated with the HER2-TAC T cell positive control achieved complete tumor clearance.

Figure 27A:
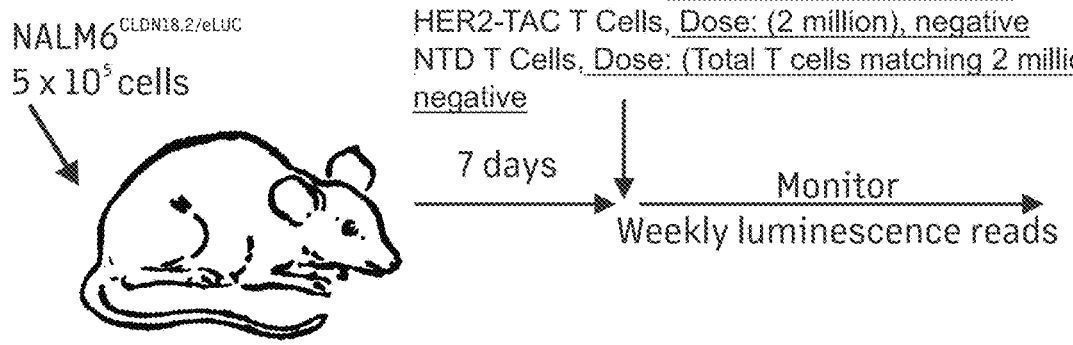
FIGS. 27A-27B depict an in vivo murine model of the antitumor activity of Claudin 18.2-TAC T cells and different dosage levels.
Figure 27B:
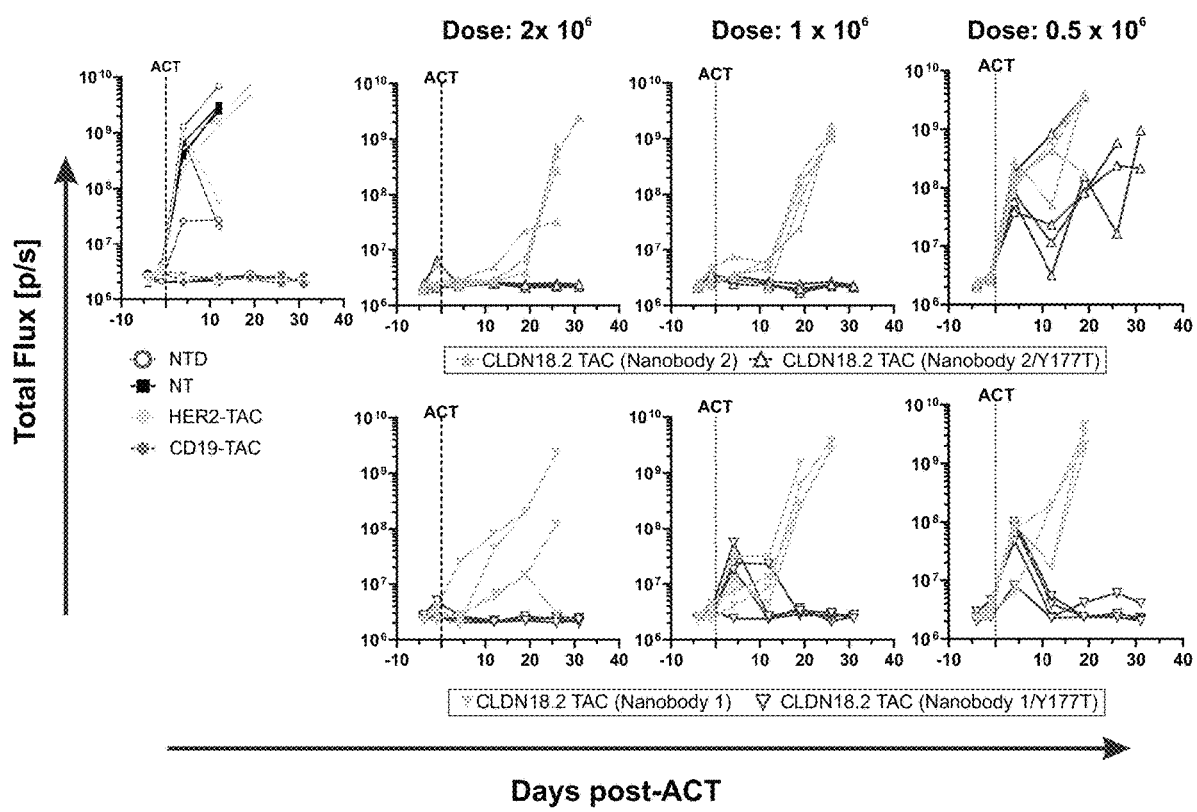

In another experiment, T cells were engineered to express a Claudin 18.2 T cell-antigen coupler (TAC) including (i) Claudin 18.2 Nanobody 1 (including SEQ ID NO: 57 (Kabat CDR1), SEQ ID NO: 58 (Kabat CDR2), and SEQ ID NO: 59 (Kabat CDR3)), or Claudin 18.2 Nanobody 2 (including SEQ ID NO: 57 (Kabat CDR1), SEQ ID NO: 63 (Kabat CDR2), and SEQ ID NO: 59 (Kabat CDR3)), (ii) an huUCHT1 or huUCHT1 (Y177T) antigen-binding domain that binds CD3, and (iii) a CD4 cytosolic and transmembrane domain: Nanobody 1/huUCHT1 Scaffold (SEQ ID NO: 67), Nanobody 1/huUCHT1 (Y177T) (SEQ ID NO:69), Nanobody 2/huUCHT1 Scaffold (SEQ ID NO: 71), or Nanobody 2/huUCHT1 (Y177T) (SEQ ID NO: 73). NSG mice were inoculated with 5×10⁵ NALM6$^{CLDN18.2/eLuc}$ tumor cells intravenously and then treated with Claudin 18.2-TAC T cells. The experimental schematic is shown in FIG. 27A. Seven days after engraftment, mice were treated with a single intravenous dose of 1 or 0.5, 1 or 2×10⁶ T cells engineered with Claudin 18.2 T cell-antigen coupler (TAC) and its next-generation scaffold (TAC, Y177T) comprising Claudin 18.2 Nanobody 1 and 2. Non-treated (NT) mice and mice treated with non-transduced T cells (NTD) were used as negative controls. As negative controls, mice were treated with 2×10⁶ HER2-TAC T cells and, as positive controls, mice were treated with 4×10⁶ CD19-TAC T cells. Tumor growth was measured weekly by total luminescence. The resulting total flux (photons/second) as the sum of the dorsal and ventral reads are shown. Mice were treated with Claudin 18.2-TAC Nanobody 1 (SEQ ID NO:67) (closed inverted triangle), Claudin 18.2-TAC Nanobody 1/Y177T (SEQ ID NO:69) (open inverted triangle), Claudin 18.2-TAC Nanobody 2 (SEQ ID NO:71) (closed triangles), and Claudin 18.2-TAC Nanobody 2/Y177T (SEQ ID NO:71) (open triangles) are shown (FIG. 27B). NTD are represented by open circles; NT are represented by closed squares. Mice treated with CD19-TAC T cells are represented by grey closed circles, and animals treated with HER2-TAC T cells are represented by closed hexagon. At the 2×10⁶ and 1×10⁶ dose levels, both Claudin 18.2-TAC Nanobody 1/Y177T (SEQ ID NO:69) and Claudin 18.2-TAC Nanobody 2/Y177T (SEQ ID NO:71) T treated groups showed complete tumor clearance, whereas Claudin 18.2-TAC Nanobody 1 (SEQ ID NO:67) and Claudin 18.2-TAC Nanobody 2 (SEQ ID NO:71) T cells showed tumor outgrowth. At the 0.5×10⁶ dose level, Claudin 18.2-TAC Nanobody 1/Y177T (SEQ ID NO:69) treated mice showed complete tumor clearance or significant tumor regression. Claudin 18.2-TAC Nanobody 1/Y177T (SEQ ID NO:69) treated animals showed some tumor regression and control, but ultimately tumors did grow out. In Claudin 18.2-TAC Nanobody 1 (SEQ ID NO:67) and Claudin 18.2-TAC Nanobody 2 (SEQ ID NO:71) treated animals tumors grew out. Animals treated with CD19-TAC T cells as positive control showed complete tumor clearance. Neither NTD, NT nor HER2-TAC T negative controls showed tumor any regression.

Figure 28A:
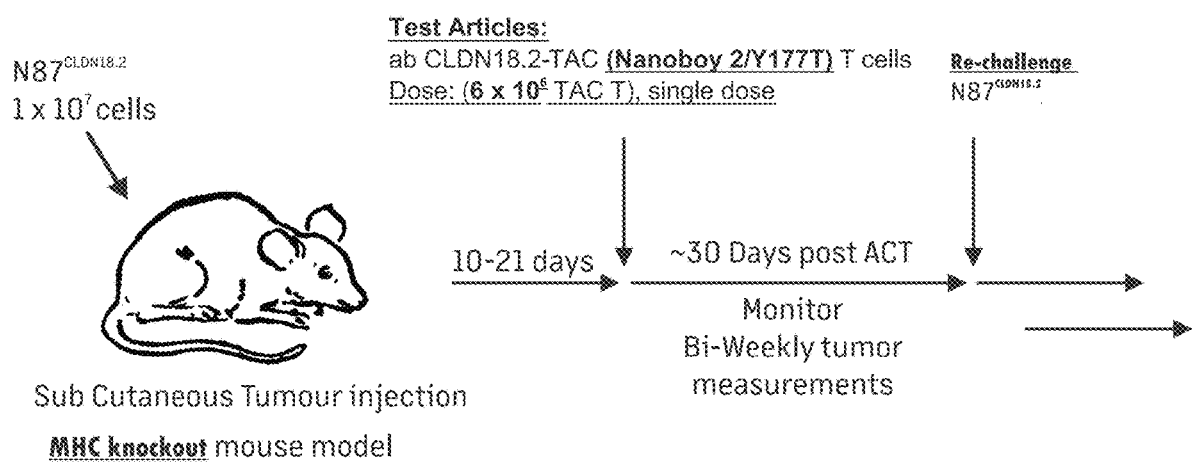

In another experiment, T cells were engineered to express a Claudin 18.2 T cell-antigen coupler (TAC) including (i) Claudin 18.2 Nanobody 1 (including SEQ ID NO: 57 (Kabat CDR1), SEQ ID NO: 58 (Kabat CDR2), and SEQ ID NO: 59 (Kabat CDR3)), or Claudin 18.2 Nanobody 2 (including SEQ ID NO: 57 (Kabat CDR1), SEQ ID NO: 63 (Kabat CDR2), and SEQ ID NO: 59 (Kabat CDR3)), (ii) an huUCHT1 or huUCHT1 (Y177T) antigen-binding domain that binds CD3, and (iii) a CD4 cytosolic and transmembrane domain: Nanobody 1/huUCHT1 Scaffold (SEQ ID NO: 67), Nanobody 1/huUCHT1 (Y177T) (SEQ ID NO:69), Nanobody 2/huUCHT1 Scaffold (SEQ ID NO: 71), or Nanobody 2/huUCHT1 (Y177T) (SEQ ID NO: 73). NSG-MHC I/II double knock-out (DKO) mutant mice were inoculated with 1×10⁷ NCI-N87$^{CLDN18.2}$ tumor cells subcutaneously and then treated with Claudin 18.2-TAC T cells (FIG. 14). NSG-MHC I/II DKO were chosen as they lack MHC I/II and, thus, are less likely to cause any T cell driven xenoreactivity against mouse tissue which can result in GvHD and make persistence data challenging to interpret. The experimental schematic is shown in FIG. 28A. Ten to twenty-one days after engraftment, mice were treated with a single intravenous dose of 6×10⁶ Claudin 18.2-TAC Nanobody 2/Y177T (SEQ ID NO:71) T cells. Non-treated (NT) mice and mice treated with non-transduced T cells (NTD) were used as negative controls. Tumor volume was monitored biweekly. After 30 days post-ACT or about 14 days post initial tumor clearance, mice were re-challenged with 1×10⁷ NCI-N87$^{CLDN18.2}$ tumor cells injected subcutaneously in the opposite flank. Tumors were monitored biweekly. The resulting tumor volumes are shown in FIG. 28B. Non-treated negative control mice challenged with either the first (group 1) or second (group 2) N87$^{CLDN18.2}$ tumor challenge showed complete outgrowth in both cases. The NTD control group showed initial tumor outgrowth. Two out of 4 mice showed tumor regression 20 days post ACT. However, only one mouse ultimately cleared the tumor while the second mice showed tumor outgrowth. Upon rechallenge of these mice, only 1 of 4 mice was resistant to the N87$^{CLDN18.2}$ re-challenge, in agreement with some level of alloreactivity. In contrast, mice treated with Claudin 18.2-TAC Nanobody 2/Y177T (SEQ ID NO:71) T cells showed rapid and complete tumor clearance following ACT. Following the rechallenge, all mice remained protected and were able to clear all tumors. Thus, the experiment demonstrates that Claudin 18.2-TAC Nanobody 2/Y177T (SEQ ID NO:71)-expressing T cells can persist in vivo.

Example 10—Comparison of In Vitro Activities of T Cells Expressing Different Claudin 18.2-TACs A first population of T cells is engineered to express a first Claudin 18.2 T cell-antigen coupler (TAC) including (i) Claudin 18.2 Nanobody 2 (including SEQ ID NO: 57 (Kabat CDR1), SEQ ID NO: 63 (Kabat CDR2), and SEQ ID NO: 59 (Kabat CDR3)), (ii) an huUCHT1 (Y177T) antigen-binding domain that binds CD3 (SEQ ID NO: 36), and (iii) a CD4 cytosolic and transmembrane domain (SEQ ID NO: 12). A second population of T cells is engineered to express a second Claudin 18.2 T cell-antigen coupler (TAC) including (i) a scFv-based Claudin 18.2-binding domain, (ii) an huUCHT1 (Y177T) antigen-binding domain that binds CD3 (SEQ ID NO: 36), and (iii) a CD4 cytosolic and transmembrane domain (SEQ ID NO: 12).

Target cells that naturally express Claudin 18.2 are engineered to express enhanced Luciferase (eLuc).

T cells expressing the first Claudin 18.2-TAC are compared to those expressing the second Claudin 18.2 TAC. TAC T cells are co-cultured with the eLuc-expressing target cells for 30 hours. At the end of the co-culture the viability of the eLuc-expressing target cells is assessed by measuring luminescence relative to an untreated control. Results are analyzed to compare the relative activities of the two populations of T cells.

What is claimed is:

1. A Claudin 18.2 T cell-antigen coupler (TAC) polypeptide, comprising:
   (a) an extracellular Claudin 18.2-single antigen-binding domain of heavy chain-only antibodies (VHH) comprising a CDR1 having the amino acid sequence of SEQ ID NO: 57, a CDR2 having the amino acid sequence of SEQ ID NO: 63, and a CDR3 having the amino acid sequence of SEQ ID NO: 59;
   (b) an extracellular CD3 binding domain consisting of an amino acid sequence 100% identical to SEQ ID NO: 36; and
   (c) a T cell co-receptor cytosolic domain polypeptide comprising a CD4 cytosolic domain and aCD4 transmembrane domain and consisting of an amino acid sequence 100% identical to SEQ ID NO: 12;
   wherein component (a), component (b), and component (c) are fused directly to each other, or joined by at least one linker.

2. The Claudin 18.2-TAC polypeptide of claim 1, wherein the Claudin 18.2-binding domain comprises an amino acid sequence having at least 80% sequence identity to SEQ ID NO: 56.

3. The Claudin 18.2-TAC polypeptide of claim 1, wherein the Claudin 18.2-binding domain comprises an amino acid sequence having at least 90% sequence identity to SEQ ID NO: 56.

4. The Claudin 18.2-TAC polypeptide of claim 1, wherein the Claudin 18.2-binding domain comprises the amino acid sequence of SEQ ID NO: 56.

5. The Claudin 18.2-TAC polypeptide of claim 1, wherein the Claudin 18.2-TAC polypeptide comprises an amino acid sequence having at least 80% sequence identity with the amino acid sequence of SEQ ID NO: 73.

6. The Claudin 18.2-TAC polypeptide of claim 1, wherein the Claudin 18.2-TAC polypeptide comprises an amino acid sequence having at least 90% sequence identity with the amino acid sequence of SEQ ID NO: 73.

7. The Claudin 18.2-TAC polypeptide of claim 1, wherein the Claudin 18.2-TAC polypeptide comprises an amino acid sequence having the amino acid sequence of SEQ ID NO: 73.

8. The Claudin 18.2-TAC polypeptide of claim 1, wherein component (a) and component (c) are fused to component (b) or wherein component (b) and component (c) are fused to component (a).

9. The Claudin 18.2-TAC polypeptide of claim 1, wherein the Claudin 18.2-TAC does not comprise a co-stimulatory domain or an activation domain.

10. A nucleic acid encoding the Claudin 18.2-TAC polypeptide of claim 1.

11. The nucleic acid claim 10, wherein the nucleic acid comprises a sequence having at least 80% sequence identity with the nucleic acid sequence of SEQ ID NO: 72.

12. An expression vector comprising the nucleic acid of claim 11.

13. A engineered T cell comprising the expression vector of claim 12, wherein the Claudin 18.2 polypeptide is expressed by the engineered T cell.

14. The T cell of claim 13, where the T cell is a γδ T cell.

15. A pharmaceutical composition comprising the T cell of claim 13, and a pharmaceutically acceptable excipient.

16. A method of providing a cancer immunotherapy for treating a Claudin 18.2-expressing cancer in an individual in need thereof, comprising administering to the individual the pharmaceutical composition of claim 15, wherein an antigen binding antibody fragment of the Claudin 18.2-TAC polypeptide binds to a Claudin 18.2 antigen expressed by the cancer, wherein administration of the γδ T cell results in a reduction in cancer cells in the subject.

17. The method of claim 16, wherein the cancer is a solid cancer.

18. The method of claim 16, wherein the cancer is a pancreatic cancer, a gastric cancer, a signet ring cell carcinoma, a mucinous gastric cancer, a gastroesophageal cancer, an esophageal cancer, a digestive system cancer, an ovarian cancer, a mucinous ovarian cancer, a non-small cell lung cancer, or a lung cancer.

* * * * *

```
                             SEQUENCE LISTING

<160> NUMBER OF SEQ ID NOS: 75

<210> SEQ ID NO 1
<211> LENGTH: 1542
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atggctctgc ctgtgacagc tctgttgctg cctctggctc tgctgctgca tgctgctaga      60
cctcaggtgc agctggttga atctggcgga ggacttgttc agcctggcgg ctctctgaga     120
ctgtcttgtg ccgccagcgg cagcatcttc aatatccccg tgatgggctg gtacagacag     180
gcccctggaa agcagagaga gctggttgcc ggaatctcta ccgcggcac cacaaattac      240 ggcgacagcg tgaagggcag attcaccatc agccgggaca acgccaagaa caccgtgtac     300
ctgcagatga acagcctgaa gcctgaggac accgccgtgt actactgcaa tgtgctggtg     360
gtgtctggca tcggcagcac actggaagtt tggggccagg gcacactggt cacagtgtct     420
agcgagcaga agctgatctc cgaggaagat ctgaatccag gcgaggcgg aggaagtggc     480 ggcggaggta gcggaggtgg tggaagcgga ggcggcggat ctggatctat ggatatccag     540
atgacccagt ccccgagctc cctgtccgcc tctgtgggcg ataggggtcac catcacctgc     600 cgtgccagtc aggacatccg taattatctg aactggtatc aacagaaacc aggaaaagct     660
ccgaaactac tgatttacta tacctcccgc ctggagtctg gagtcccttc tcgcttctct     720
ggttctggtt ctgggacgga ttacactctg accatcagca gtctgcaacc ggaagacttc     780
gcaacttatt actgtcagca aggtaatact ctgccgtgga cgttcggaca gggcaccaag     840
gtggagatca aaggcggcgg cggaagtgga ggaggaggct caggcggagg agggagcgag     900
gttcagctgg tggagtctgg cggtggcctg gtgcagccag ggggctcact ccgtttgtcc     960
tgtgcagctt ctggctactc ctttaccggc tacactatga actgggtgcg tcaggcccca    1020
ggtaagggcc tggaatgggt tgcactgatt aatccttata aggtgttag tacctacaac    1080 cagaagttca ggaccgtttt cactataagc gtagataaat ccaaaaacac agcctacctg    1140
caaatgaaca gcctgcgtgc tgaggacact gccgtctatt attgtgctag aagcggatac    1200
tacggcgata gtgactggta ttttgacgtg tggggtcaag aaccctggt caccgtctcc    1260 tcgacatcag gtggtggcgg atctctggaa tctggccagg tgctgctgga atccaacatc    1320
aaggtgctgc ccacctggtc tacccagtt cagcctatgg ctctgattgt gcttggcgga    1380
gttgccggcc tgctgctgtt tatcggcctg ggcatcttct tttgcgtgcg gtgcagacat    1440
cggcggagac aggctgagag aatgagccag atcaagcggc tgctgagcga aagaaaacc    1500 tgtcagtgcc ctcaccggtt ccagaaaaca tgcagcccca tc                      1542

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 2

Met Asp Phe Gln Val Gln Ile Phe Ser Phe Leu Leu Ile Ser Ala Ser
1               5                   10                  15

Val Ile

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gaacagaaac tgattagcga agaagacctg                                          30

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Gln Lys Leu Ile Ser Glu Glu Asp Leu
1               5                   10

<210> SEQ ID NO 5
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aaccccgggg gaggaggagg gagcggggga ggaggcagcg gcggggggagg ctctggagga        60 ggagggagcg gatcc                                                          75

<210> SEQ ID NO 6
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Pro Gly Gly Gly Gly Gly Ser Gly Gly Gly Gly Ser Gly Gly Gly
1               5                   10                  15

Gly Ser Gly Gly Gly Gly Ser Gly Ser
            20                  25

<210> SEQ ID NO 7
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atggacatcc agatgactca gaccacaagc tccctgtctg caagtctggg cgaccgggtg        60
```

```
acaatctcct gcagagcctc tcaggatatt aggaactacc tgaattggta tcagcagaaa    120
cctgatggca cagtcaagct gctgatctac tataccagcc ggctgcactc aggcgtgcca    180
agcaaattct caggaagcgg ctccgggact gactactccc tgaccatctc taacctggag    240
caggaagata ttgctaccta tttctgccag cagggcaata cactgccctg gacttttgcc    300
ggaggcacca aactggagat caaggggga ggcgggagtg gaggcggggg atcaggagga    360
ggaggcagcg gaggaggagg gtccgaggtc cagctgcagc agagcggacc agaactggtg    420
aagcccggag caagtatgaa atctcctgt aaggcctcag gatacagctt caccggctat    480
acaatgaact gggtgaaaca gtcccatggc aagaacctgg aatggatggg gctgattaat    540
ccttacaaag gcgtcagcac ctataatcag aagtttaaag acaaggccac actgactgtg    600
gataagtcta gttcaaccgc ttacatggag ctgctgtccc tgacatctga agacagtgcc    660
gtgtactatt gtgctcggtc tggctactat ggggacagtg attggtactt cgatgtctgg    720
ggacagggca ctaccctgac cgtgttttct                                     750
```

<210> SEQ ID NO 8
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Arg Asn
            20                  25                  30

Tyr Leu Asn Trp Tyr Gln Gln Lys Pro Asp Gly Thr Val Lys Leu Leu
        35                  40                  45

Ile Tyr Tyr Thr Ser Arg Leu His Ser Gly Val Pro Ser Lys Phe Ser
    50                  55                  60

Gly Ser Gly Ser Gly Thr Asp Tyr Ser Leu Thr Ile Ser Asn Leu Glu
65                  70                  75                  80

Gln Glu Asp Ile Ala Thr Tyr Phe Cys Gln Gln Gly Asn Thr Leu Pro
                85                  90                  95

Trp Thr Phe Ala Gly Gly Thr Lys Leu Glu Ile Lys Gly Gly Gly Gly
            100                 105                 110

Ser Gly Gly Gly Gly Ser Gly Gly Gly Ser Gly Gly Gly Gly Ser
        115                 120                 125

Glu Val Gln Leu Gln Gln Ser Gly Pro Glu Leu Val Lys Pro Gly Ala
    130                 135                 140

Ser Met Lys Ile Ser Cys Lys Ala Ser Gly Tyr Ser Phe Thr Gly Tyr
145                 150                 155                 160

Thr Met Asn Trp Val Lys Gln Ser His Gly Lys Asn Leu Glu Trp Met
                165                 170                 175

Gly Leu Ile Asn Pro Tyr Lys Gly Val Ser Thr Tyr Asn Gln Lys Phe
            180                 185                 190

Lys Asp Lys Ala Thr Leu Thr Val Asp Lys Ser Ser Ser Thr Ala Tyr
        195                 200                 205

Met Glu Leu Leu Ser Leu Thr Ser Glu Asp Ser Ala Val Tyr Tyr Cys
    210                 215                 220

Ala Arg Ser Gly Tyr Tyr Gly Asp Ser Asp Trp Tyr Phe Asp Val Trp

```
                    225                 230                 235                 240

Gly Gln Gly Thr Thr Leu Thr Val Phe Ser
                245                 250

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
actagtggcg gaggaggatc actcgag                                             27

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Ser Gly Gly Gly Gly Ser Leu Glu
1               5

<210> SEQ ID NO 11
<211> LENGTH: 252
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
agcggacagg tgctgctgga atccaatatc aaagtcctgc ccacttggtc taccccgtg         60 cagcctatgg ctctgattgt gctgggagga gtcgcaggac tgctgctgtt tatcgggctg      120
ggaattttct tttgcgtgcg ctgccggcac cggagaaggc aggccgagcg catgagccag      180
atcaagcgac tgctgagcga aagaaaaacc tgtcagtgtc cccatagatt ccagaagacc      240
tgttcaccca tt                                                          252

<210> SEQ ID NO 12
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Gly Gln Val Leu Leu Glu Ser Asn Ile Lys Val Leu Pro Thr Trp
1               5                   10                  15

Ser Thr Pro Val Gln Pro Met Ala Leu Ile Val Leu Gly Gly Val Ala
                20                  25                  30

Gly Leu Leu Leu Phe Ile Gly Leu Gly Ile Phe Phe Cys Val Arg Cys
            35                  40                  45

Arg His Arg Arg Arg Gln Ala Glu Arg Met Ser Gln Ile Lys Arg Leu
        50                  55                  60

Leu Ser Glu Lys Lys Thr Cys Gln Cys Pro His Arg Phe Gln Lys Thr
65                  70                  75                  80
```

Cys Ser Pro Ile

<210> SEQ ID NO 13
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
agcggacagg tgctgctgga atccaatatc aaagtcctgc ccacttggtc taccccgtg    60 cagcct                                                              66

<210> SEQ ID NO 14
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Gly Gln Val Leu Leu Glu Ser Asn Ile Lys Val Leu Pro Thr Trp
1               5                   10                  15

Ser Thr Pro Val Gln Pro
            20

<210> SEQ ID NO 15
<211> LENGTH: 769
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atggccgaca tcgtgctgac acagagcccc gccatcatgt ctgccagccc tggcgagaaa   60
gtgaccatga cctgtagcgc cagcagcagc gtgtcctaca tgaactggta tcagcagaag  120
tccggcacca gccccaagcg gtggatctac gacacaagca gctggcctc tggcgtgccc   180 gcccacttta gaggctctgg cagcggcaca agctacagcc tgaccatcag cggcatggaa  240
gccgaggatg ccgccaccta ctactgccag cagtggtcca gcaacccctt cacctttggc  300
tccggcacaa agctggaaat caaccgggcc gacaccgccc ctacaggcgg cggaggatct  360
ggcggaggcg gatctggggg cggaggaagt gggggggggag gatctatggc tcaggtgcag  420
ctgcagcagt ctggcgccga actggctaga cctggcgcct ccgtgaagat gagctgcaag  480
gccagcggct acaccttcac ccggtacacc atgcactggg tcaagcagag gcctggacag  540
ggcctggaat ggatcggcta catcaacccc agccggggct acaccaacta caaccagaag  600
ttcaaggaca aggccaccct gaccaccgac aagagcagca gcaccgccta catgcagctg  660
tcctccctga ccagcgagga cagcgccgtg tactactgcg cccggtacta cgacgaccac  720
tactccctgg actactgggg ccagggcacc acactgaccg tgtctagta              769

<210> SEQ ID NO 16
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Met Ala Asp Ile Val Leu Thr Gln Ser Pro Ala Ile Met Ser Ala Ser
1               5                   10                  15

Pro Gly Glu Lys Val Thr Met Thr Cys Ser Ala Ser Ser Ser Val Ser
            20                  25                  30

Tyr Met Asn Trp Tyr Gln Gln Lys Ser Gly Thr Ser Pro Lys Arg Trp
        35                  40                  45

Ile Tyr Asp Thr Ser Lys Leu Ala Ser Gly Val Pro Ala His Phe Arg
    50                  55                  60

Gly Ser Gly Ser Gly Thr Ser Tyr Ser Leu Thr Ile Ser Gly Met Glu
65                  70                  75                  80

Ala Glu Asp Ala Ala Thr Tyr Tyr Cys Gln Gln Trp Ser Ser Asn Pro
                85                  90                  95

Phe Thr Phe Gly Ser Gly Thr Lys Leu Glu Ile Asn Arg Ala Asp Thr
            100                 105                 110

Ala Pro Thr Gly Gly Gly Ser Gly Gly Gly Ser Gly Gly
            115                 120                 125

Gly Ser Gly Gly Gly Ser Met Ala Gln Val Gln Leu Gln Gln Ser
130                 135                 140

Gly Ala Glu Leu Ala Arg Pro Gly Ala Ser Val Lys Met Ser Cys Lys
145                 150                 155                 160

Ala Ser Gly Tyr Thr Phe Thr Arg Tyr Thr Met His Trp Val Lys Gln
                165                 170                 175

Arg Pro Gly Gln Gly Leu Glu Trp Ile Gly Tyr Ile Asn Pro Ser Arg
            180                 185                 190

Gly Tyr Thr Asn Tyr Asn Gln Lys Phe Lys Asp Lys Ala Thr Leu Thr
        195                 200                 205

Thr Asp Lys Ser Ser Ser Thr Ala Tyr Met Gln Leu Ser Ser Leu Thr
    210                 215                 220

Ser Glu Asp Ser Ala Val Tyr Tyr Cys Ala Arg Tyr Tyr Asp Asp His
225                 230                 235                 240

Tyr Ser Leu Asp Tyr Trp Gly Gln Gly Thr Thr Leu Thr Val Ser Ser
                245                 250                 255
```

<210> SEQ ID NO 17
<211> LENGTH: 747
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
cagaccgtgg tgacccagga gcccagcctg accgtgagcc ccggcggcac cgtgaccctg    60
acctgcggca gcagcaccgg cgccgtgacc agcggctact accccaactg ggtgcagcag   120
aagcccggcc aggccccag gggcctgatc ggcggcacca gttcctggc ccccggcacc    180
cccgccaggt tcagcggcag cctgctgggc ggcaaggccg ccctgaccct gagcggcgtg   240
cagcccgagg acgaggccga gtactactgc gccctgtggt acagcaacag gtgggtgttc   300
ggcggcggca ccaagctgac cgtgctgggc ggcggcggca gcggcggcgg cggcagcggc   360
ggcggcggca gcgaggtgca gctgctggag agcggcggcg gcctggtgca gcccggcggc   420
agcctgaagc tgagctgcgc cgccagcggc ttcaccttca acatctacgc catgaactgg   480
gtgaggcagg ccccggcaa gggcctggag tgggtggcca ggatcaggag caagtacaac   540
```

```
aactacgcca cctactacgc cgacagcgtg aagagcaggt tcaccatcag cagggacgac    600
agcaagaaca ccgcctacct gcagatgaac aacctgaaga ccgaggacac cgccgtgtac    660
tactgcgtga ggcacggcaa cttcggcaac agctacgtga gcttcttcgc ctactggggc    720
cagggcaccc tggtgaccgt gagcagc                                        747
```

<210> SEQ ID NO 18
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu Gly Gly Gly
            100                 105                 110

Gly Ser Gly Gly Gly Gly Ser Gly Gly Gly Gly Ser Glu Val Gln Leu
        115                 120                 125

Leu Glu Ser Gly Gly Gly Leu Val Gln Pro Gly Gly Ser Leu Lys Leu
    130                 135                 140

Ser Cys Ala Ala Ser Gly Phe Thr Phe Asn Ile Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Ser Val Lys Ser
            180                 185                 190

Arg Phe Thr Ile Ser Arg Asp Asp Ser Lys Asn Thr Ala Tyr Leu Gln
        195                 200                 205

Met Asn Asn Leu Lys Thr Glu Asp Thr Ala Val Tyr Tyr Cys Val Arg
    210                 215                 220

His Gly Asn Phe Gly Asn Ser Tyr Val Ser Phe Phe Ala Tyr Trp Gly
225                 230                 235                 240

Gln Gly Thr Leu Val Thr Val Ser Ser
                245
```

<210> SEQ ID NO 19
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
gacatccagc tgacccagag ccccgccatc atgagcgcca gccccggcga aaggtgacc      60 atgacctgca gggccagcag cagcgtgagc tacatgaact ggtaccagca aaagagcggc    120
accagcccca agaggtggat ctacgacacc agcaaggtgg ccagcggcgt gccctacagg    180
ttcagcggca gcggcagcgg caccagctac agcctgacca tcagcagcat ggaggccgag    240
gacgccgcca cctactactg ccagcagtgg agcagcaacc ccctgacctt cggcgccggc    300
accaagctgg agctgaaggg cggcggcggc agcggcggcg gcggcagcgg cggcggcggc    360
agcgacatca agctgcagca gagcggcgcc gagctggcca ggcccggcgc cagcgtgaag    420
atgagctgca agaccagcgg ctacaccttc accaggtaca ccatgcactg ggtgaagcag    480
aggcccggcc agggcctgga gtggatcggc tacatcaacc ccagcagggg ctacaccaac    540
tacaaccaga agttcaagga caaggccacc ctgaccaccg acaagagcag cagcaccgcc    600
tacatgcagc tgagcagcct gaccagcgag gacagcgccg tgtactactg cgccaggtac    660
tacgacgacc actactgcct ggactactgg ggccagggca ccaccctgac cgtgagcagc    720
```

<210> SEQ ID NO 20  
<211> LENGTH: 240  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 20

```
Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Gly Gly Gly Gly Ser Gly
            100                 105                 110

Gly Gly Gly Ser Gly Gly Gly Ser Asp Ile Lys Leu Gln Gln Ser
        115                 120                 125

Gly Ala Glu Leu Ala Arg Pro Gly Ala Ser Val Lys Met Ser Cys Lys
    130                 135                 140

Thr Ser Gly Tyr Thr Phe Thr Arg Tyr Thr Met His Trp Val Lys Gln
145                 150                 155                 160

Arg Pro Gly Gln Gly Leu Glu Trp Ile Gly Tyr Ile Asn Pro Ser Arg
                165                 170                 175

Gly Tyr Thr Asn Tyr Asn Gln Lys Phe Lys Asp Lys Ala Thr Leu Thr
            180                 185                 190

Thr Asp Lys Ser Ser Ser Thr Ala Tyr Met Gln Leu Ser Ser Leu Thr
        195                 200                 205

Ser Glu Asp Ser Ala Val Tyr Tyr Cys Ala Arg Tyr Tyr Asp Asp His
    210                 215                 220

Tyr Cys Leu Asp Tyr Trp Gly Gln Gly Thr Thr Leu Thr Val Ser Ser
225                 230                 235                 240
```

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gccgaagcag cagcaaagga ggccgcagcg aaggaagcag ctgcgaaggc c          51

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Glu Ala Ala Ala Lys Glu Ala Ala Ala Lys Glu Ala Ala Ala Lys
1               5                   10                  15

Ala

<210> SEQ ID NO 23
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gccgaggcag ctgcaaagga agctgcggcg aaggaggccg cagcgaaaga agcagcggca      60
aaagaagcag ccgccaaagc c                                               81

<210> SEQ ID NO 24
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 25
<211> LENGTH: 576
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atcgtagtgt tggcatttca aaaagcgtct agcatcgtct ataagaagga aggtgaacaa      60
gtcgagtttt ctttcccct tgcatttacg gtggaaaagc ttacgggtag cggcgagctg     120
tggtggcaag ctgaacgggc ttcaagctca aaatcttgga ttacttttga cttgaagaac     180

```
aaagaggtga gtgtcaaaag agttactcag acccaaagc ttcaaatggg gaagaaactt      240
ccgctgcacc tgacgttgcc tcaggccctg cctcaatatg ccggctcagg caatctgacc      300
ctcgcgctgg aagctaagac cggaaaattg caccaggaag tcaatttggt tgtgatgcgc      360
gccactcagc tccaaaaaaa tctcacttgc gaggtatggg ggcctacgag cccaaaactt      420
atgctgtctt tgaagcttga aaacaaggaa gcgaaagttt ctaagcgcga aaagcggta      480 tgggttttga atcctgaggc tggaatgtgg caatgcctcc tgagcgatag cgggcaggtg      540
ctgttggaga gcaacatcaa ggttttgcca gcagcc                                 576
```

<210> SEQ ID NO 26
<211> LENGTH: 192
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 26

```
Ile Val Val Leu Ala Phe Gln Lys Ala Ser Ile Val Tyr Lys Lys
1               5                   10                  15

Glu Gly Glu Gln Val Glu Phe Ser Phe Pro Leu Ala Phe Thr Val Glu
            20                  25                  30

Lys Leu Thr Gly Ser Gly Glu Leu Trp Trp Gln Ala Glu Arg Ala Ser
        35                  40                  45

Ser Ser Lys Ser Trp Ile Thr Phe Asp Leu Lys Asn Lys Glu Val Ser
    50                  55                  60

Val Lys Arg Val Thr Gln Asp Pro Lys Leu Gln Met Gly Lys Lys Leu
65                  70                  75                  80

Pro Leu His Leu Thr Leu Pro Gln Ala Leu Pro Gln Tyr Ala Gly Ser
                85                  90                  95

Gly Asn Leu Thr Leu Ala Leu Glu Ala Lys Thr Gly Lys Leu His Gln
            100                 105                 110

Glu Val Asn Leu Val Val Met Arg Ala Thr Gln Leu Gln Lys Asn Leu
        115                 120                 125

Thr Cys Glu Val Trp Gly Pro Thr Ser Pro Lys Leu Met Leu Ser Leu
    130                 135                 140

Lys Leu Glu Asn Lys Glu Ala Lys Val Ser Lys Arg Glu Lys Ala Val
145                 150                 155                 160

Trp Val Leu Asn Pro Glu Ala Gly Met Trp Gln Cys Leu Leu Ser Asp
                165                 170                 175

Ser Gly Gln Val Leu Leu Glu Ser Asn Ile Lys Val Leu Pro Ala Ala
            180                 185                 190
```

<210> SEQ ID NO 27
<211> LENGTH: 237
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 27

```
ctcgagctga ggcccgaggc ttctagacct gctgccggcg gagccgtgca caccagaggc      60
ctggacttcg ccagcgacat ctacatctgg gcccctctgg ccggcacctg tggcgtgctg      120
ctgctgagcc tggtcatcac cctgtactgc aaccaccgga accggcggag agtgtgcaag      180
tgccccagac ccgtggtcaa gagcggcgac aagcccagcc tgagcgccag atacgtg        237
```

<210> SEQ ID NO 28
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Leu Glu Leu Arg Pro Glu Ala Ser Arg Pro Ala Ala Gly Gly Ala Val
1               5                   10                  15

His Thr Arg Gly Leu Asp Phe Ala Ser Asp Ile Tyr Ile Trp Ala Pro
            20                  25                  30

Leu Ala Gly Thr Cys Gly Val Leu Leu Leu Ser Leu Val Ile Thr Leu
        35                  40                  45

Tyr Cys Asn His Arg Asn Arg Arg Val Cys Lys Cys Pro Arg Pro
    50                  55                  60

Val Val Lys Ser Gly Asp Lys Pro Ser Leu Ser Ala Arg Tyr Val
65                  70                  75

<210> SEQ ID NO 29
<211> LENGTH: 234
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
ctcgagctga ggcccgaggc ttctagacct gctgccggcg gagccgtgca caccagaggc      60
ctggacttcg ccagcgacat ctacatctgg gcccctctgg ccggcacctg tggcgtgctg     120
ctgctgagcc tggtcatcac cctgtacctg tgctgcagac ggcggagagt gtgcaagtgc     180
cccagacccg tggtcaagag cggcgacaag cccagcctga gcgccagata cgtg           234

<210> SEQ ID NO 30
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Leu Glu Leu Arg Pro Glu Ala Ser Arg Pro Ala Ala Gly Gly Ala Val
1               5                   10                  15

His Thr Arg Gly Leu Asp Phe Ala Ser Asp Ile Tyr Ile Trp Ala Pro
            20                  25                  30

Leu Ala Gly Thr Cys Gly Val Leu Leu Leu Ser Leu Val Ile Thr Leu
        35                  40                  45

Tyr Leu Cys Cys Arg Arg Arg Val Cys Lys Cys Pro Arg Pro Val
    50                  55                  60

Val Lys Ser Gly Asp Lys Pro Ser Leu Ser Ala Arg Tyr Val
65                  70                  75

<210> SEQ ID NO 31
<211> LENGTH: 213
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
ctcgagaaga agtccaccct gaagaaacgg gtgtcccggc tgcccagacc cgagacacag      60
aagggccccc tgagcagccc tatcaccctg gactgctgg tggccggcgt gctggtgctg      120
ctggtgtctc tgggagtggc catccacctg tgctgccggc ggagaagggc ctgcaagtgc      180
cccagactgc ggttcatgaa gcagttctac aag                                  213
```

<210> SEQ ID NO 32
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Leu Glu Lys Lys Ser Thr Leu Lys Lys Arg Val Ser Arg Leu Pro Arg
1               5                   10                  15

Pro Glu Thr Gln Lys Gly Pro Leu Ser Ser Pro Ile Thr Leu Gly Leu
            20                  25                  30

Leu Val Ala Gly Val Leu Val Leu Leu Val Ser Leu Gly Val Ala Ile
        35                  40                  45

His Leu Cys Cys Arg Arg Arg Arg Ala Cys Lys Cys Pro Arg Leu Arg
    50                  55                  60

Phe Met Lys Gln Phe Tyr Lys
65                  70

<210> SEQ ID NO 33
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
atggatatcc agatgaccca gtccccgagc tccctgtccg cctctgtggg cgatagggtc      60
accatcacct gccgtgccag tcaggacatc cgtaattatc tgaactggta tcaacagaaa     120
ccaggaaaag ctccgaaact actgatttac tacctcccg cctggagtc tggagtccct      180
tctcgcttct ctggttctgg ttctgggacg gattacactc tgaccatcag cagtctgcaa     240
ccggaagact tcgcaactta ttactgtcag caaggtaata tctgccgtg acgttcgga      300
cagggcacca aggtggagat caaaggcggc ggcggaagtg gaggaggagg ctcaggcgga     360
ggagggagcg aggttcagct ggtggagtct ggcggtggcc tggtgcagcc aggggctca     420
ctccgtttgt cctgtgcagc ttctggctac tcctttaccg gctacactat gaactgggtg     480
cgtcaggccc caggtaaggg cctggaatgg gttgcactga ttaatcctta taaggtgtt      540
agtacctaca accagaagtt caaggaccgt ttcactataa gcgtagataa atccaaaaac     600
acagcctacc tgcaaatgaa cagcctgcgt gctgaggaca ctgccgtcta ttattgtgct     660
agaagcggat actacggcga tagtgactgg tattttgacg tgtggggtca aggaaccctg     720
gtcaccgtct cctcg                                                     735
```

<210> SEQ ID NO 34
<211> LENGTH: 245
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 34

```
Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Ile Arg Asn
            20                  25                  30

Tyr Leu Asn Trp Tyr Gln Gln Lys Pro Gly Lys Ala Pro Lys Leu Leu
        35                  40                  45

Ile Tyr Tyr Thr Ser Arg Leu Glu Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Asn Thr Leu Pro
                85                  90                  95

Trp Thr Phe Gly Gln Gly Thr Lys Val Glu Ile Lys Gly Gly Gly Gly
            100                 105                 110

Ser Gly Gly Gly Ser Gly Gly Gly Ser Glu Val Gln Leu Val
            115                 120                 125

Glu Ser Gly Gly Leu Val Gln Pro Gly Gly Ser Leu Arg Leu Ser
130                 135                 140

Cys Ala Ala Ser Gly Tyr Ser Phe Thr Gly Tyr Thr Met Asn Trp Val
145                 150                 155                 160

Arg Gln Ala Pro Gly Lys Gly Leu Glu Trp Val Ala Leu Ile Asn Pro
                165                 170                 175

Tyr Lys Gly Val Ser Thr Tyr Asn Gln Lys Phe Lys Asp Arg Phe Thr
            180                 185                 190

Ile Ser Val Asp Lys Ser Lys Asn Thr Ala Tyr Leu Gln Met Asn Ser
        195                 200                 205

Leu Arg Ala Glu Asp Thr Ala Val Tyr Tyr Cys Ala Arg Ser Gly Tyr
    210                 215                 220

Tyr Gly Asp Ser Asp Trp Tyr Phe Asp Val Trp Gly Gln Gly Thr Leu
225                 230                 235                 240

Val Thr Val Ser Ser
                245
```

<210> SEQ ID NO 35
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
atggatatcc agatgaccca gtccccgagc tccctgtccg cctctgtggg cgatagggtc      60
accatcacct gccgtgccag tcaggacatc cgtaattatc tgaactggta tcaacagaaa     120
ccaggaaaag ctccgaaact actgatttac tatacctccc gcctggagtc tggagtccct     180
tctcgcttct ctggttctgg ttctgggacg gattacactc tgaccatcag cagtctgcaa     240
ccggaagact tcgcaactta ttactgtcag caaggtaata ctctgccgtg gacgttcgga     300
cagggcacca aggtggagat caaaggcggc ggcggaagtg gaggaggagg ctcaggcgga     360
ggagggagcg aggttcagct ggtggagtct ggcggtggcc tggtgcagcc agggggctca     420
```

```
ctccgtttgt cctgtgcagc ttctggctac tcctttaccg gctacactat gaactgggtg    480
cgtcaggccc caggtaaggg cctggaatgg gttgcactga ttaatcctac caaggtgtt     540 agtacctaca accagaagtt caaggaccgt ttcactataa gcgtagataa atccaaaaac    600
acagcctacc tgcaaatgaa cagcctgcgt gctgaggaca ctgccgtcta ttattgtgct    660
agaagcggat actacggcga tagtgactgg tatttttgacg tgtggggtca aggaaccctg    720
gtcaccgtct cctcg                                                      735
```

```
<210> SEQ ID NO 36
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36
```

```
Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Ile Arg Asn
            20                  25                  30

Tyr Leu Asn Trp Tyr Gln Gln Lys Pro Gly Lys Ala Pro Lys Leu Leu
        35                  40                  45

Ile Tyr Tyr Thr Ser Arg Leu Glu Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Asn Thr Leu Pro
                85                  90                  95

Trp Thr Phe Gly Gln Gly Thr Lys Val Glu Ile Lys Gly Gly Gly Gly
            100                 105                 110

Ser Gly Gly Gly Gly Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Tyr Ser Phe Thr Gly Tyr Thr Met Asn Trp Val
145                 150                 155                 160

Arg Gln Ala Pro Gly Lys Gly Leu Glu Trp Val Ala Leu Ile Asn Pro
                165                 170                 175

Thr Lys Gly Val Ser Thr Tyr Asn Gln Lys Phe Lys Asp Arg Phe Thr
            180                 185                 190

Ile Ser Val Asp Lys Ser Lys Asn Thr Ala Tyr Leu Gln Met Asn Ser
        195                 200                 205

Leu Arg Ala Glu Asp Thr Ala Val Tyr Tyr Cys Ala Arg Ser Gly Tyr
    210                 215                 220

Tyr Gly Asp Ser Asp Trp Tyr Phe Asp Val Trp Gly Gln Gly Thr Leu
225                 230                 235                 240

Val Thr Val Ser Ser
                245
```

```
<210> SEQ ID NO 37
<211> LENGTH: 60
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 37
atggagaccc ccgcccagct gctgttcctg ctgctgctgt ggctgcccga caccaccggc    60

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Met Glu Thr Pro Ala Gln Leu Leu Phe Leu Leu Leu Leu Trp Leu Pro
1               5                   10                  15

Asp Thr Thr Gly
            20

<210> SEQ ID NO 39
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
atggctttgc ctgtcacggc tcttctgctc cctctggccc tgcttctgca cgcggcgcga    60
ccc                                                                  63

<210> SEQ ID NO 40
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Met Ala Leu Pro Val Thr Ala Leu Leu Leu Pro Leu Ala Leu Leu Leu
1               5                   10                  15

His Ala Ala Arg Pro
            20

<210> SEQ ID NO 41
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Gly Gly Gly Ser Gly Gly Gly Gly Ser Gly Gly Gly Gly Ser Gly
1               5                   10                  15

Gly Gly Gly Ser
            20

<210> SEQ ID NO 42
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
ggaggaggag ggagcggggg aggaggcagc ggcggggggag gctctggagg aggagggagc    60

<210> SEQ ID NO 43
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
atggacatcc agatgactca gaccacaagc tccctgtctg caagtctggg cgaccgggtg    60
acaatctcct gcagagcctc tcaggatatt aggaactacc tgaattggta tcagcagaaa   120
cctgatggca cagtcaagct gctgatctac tataccagcc ggctgcactc aggcgtgcca   180
agcaaattct caggaagcgg ctccgggact gactactccc tgaccatctc taacctggag   240
caggaagata ttgctaccta tttctgccag cagggcaata cactgccctg gacttttgcc   300
ggaggcacca aactggagat caaggggggga ggcgggagtg gaggcggggg atcaggagga   360
ggaggcagcg gaggaggagg gtccgaggtc cagctgcagc agagcggacc agaactggtg   420
aagcccggag caagtatgaa aatctcctgt aaggcctcag atacagcttc accggctat   480 acaatgaact gggtgaaaca gtcccatggc aagaacctgg aatggatggg gctgattaat   540
cctaccaaag cgtcagcac ctataatcag aagtttaaag acaaggccac actgactgtg   600
gataagtcta gttcaaccgc ttacatggag ctgctgtccc tgacatctga agacagtgcc   660
gtgtactatt gtgctcggtc tggctactat ggggacagtg attggtactt cgatgtctgg   720
ggacagggca ctaccctgac cgtgttttct                                     750

<210> SEQ ID NO 44
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Arg Asn
            20                  25                  30

Tyr Leu Asn Trp Tyr Gln Gln Lys Pro Asp Gly Thr Val Lys Leu Leu
        35                  40                  45

Ile Tyr Tyr Thr Ser Arg Leu His Ser Gly Val Pro Ser Lys Phe Ser
    50                  55                  60

Gly Ser Gly Ser Gly Thr Asp Tyr Ser Leu Thr Ile Ser Asn Leu Glu
65                  70                  75                  80

Gln Glu Asp Ile Ala Thr Tyr Phe Cys Gln Gln Gly Asn Thr Leu Pro
                85                  90                  95

Trp Thr Phe Ala Gly Gly Thr Lys Leu Glu Ile Lys Gly Gly Gly Gly
            100                 105                 110

Ser Gly Gly Gly Gly Ser Gly Gly Gly Ser Gly Gly Gly Gly Ser
        115                 120                 125

Glu Val Gln Leu Gln Gln Ser Gly Pro Glu Leu Val Lys Pro Gly Ala

```
                130                 135                 140
Ser Met Lys Ile Ser Cys Lys Ala Ser Gly Tyr Ser Phe Thr Gly Tyr
145                 150                 155                 160

Thr Met Asn Trp Val Lys Gln Ser His Gly Lys Asn Leu Glu Trp Met
                165                 170                 175

Gly Leu Ile Asn Pro Thr Lys Gly Val Ser Thr Tyr Asn Gln Lys Phe
            180                 185                 190

Lys Asp Lys Ala Thr Leu Thr Val Asp Lys Ser Ser Ser Thr Ala Tyr
        195                 200                 205

Met Glu Leu Leu Ser Leu Thr Ser Glu Asp Ser Ala Val Tyr Tyr Cys
    210                 215                 220

Ala Arg Ser Gly Tyr Tyr Gly Asp Ser Asp Trp Tyr Phe Asp Val Trp
225                 230                 235                 240

Gly Gln Gly Thr Thr Leu Thr Val Phe Ser
                245                 250

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Gly Gly Gly Ser
1               5

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Gly Gly Gly Ser Gly Gly Gly Gly Ser Gly Gly Gly Gly Ser
1               5                   10                  15

<210> SEQ ID NO 47
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ggcggcggcg gaagtggagg aggaggctca ggcggaggag ggagc              45

<210> SEQ ID NO 48
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 48

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30
```

Trp Ile Asn Trp Val Lys Gln Arg Pro Gly Gln Gly Leu Glu Trp Ile
                35                  40                  45

Gly Asn Ile Tyr Pro Ser Asp Ser Tyr Thr Asn Tyr Asn Gln Lys Phe
         50                  55                  60

Lys Asp Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
                100                 105                 110

Thr Leu Thr Val Ser Ser
        115

<210> SEQ ID NO 49
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 49

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
                100                 105                 110

Lys

<210> SEQ ID NO 50
<211> LENGTH: 1125
<212> TYPE: DNA
<213> ORGANISM: Artificial Sequence
<220> FEATURE:
<223> OTHER INFORMATION: Synthetic polynucleotide

<400> SEQUENCE: 50
gagcagaagc tgatctccga ggaagatctg aatccaggcg aggcggagg aagtggcggc      60 ggaggtagcg gaggtggtgg aagcggaggc ggcggatctg gatctatgga tatccagatg    120
acccagtccc cgagctccct gtccgcctct gtgggcgata gggtcaccat cacctgccgt    180
gccagtcagg acatccgtaa ttatctgaac tggtatcaac agaaaccagg aaaagctccg    240
aaactactga tttactatac ctcccgcctg gagtctggag tcccttctcg cttctctggt    300
tctggttctg ggacggatta cactctgacc atcagcagtc tgcaaccgga agacttcgca    360
acttattact gtcagcaagg taatactctg ccgtggacgt tcggacaggg caccaaggtg    420
gagatcaaag gcggcggcgg aagtggagga ggaggctcag gcggaggagg gagcgaggtt    480
cagctggtgg agtctggcgg tggcctggtg cagccagggg gctcactccg tttgtcctgt    540

-continued

```
gcagcttctg gctactcctt taccggctac actatgaact gggtgcgtca ggccccaggt      600
aagggcctgg aatgggttgc actgattaat ccttataaag gtgttagtac ctacaaccag      660
aagttcaagg accgtttcac tataagcgta gataaatcca aaacacagc ctacctgcaa       720 atgaacagcc tgcgtgctga ggacactgcc gtctattatt gtgctagaag cggatactac      780
ggcgatagtg actggtattt tgacgtgtgg ggtcaaggaa ccctggtcac cgtctcctcg      840
acatcaggtg gtggcggatc tctggaatct ggccaggtgc tgctggaaag caacatcaag      900
gtgctgccca cctggtctac cccagttcag cctatggctc tgattgtgct tggcggagtt      960
gccggcctgc tgctgtttat cggcctgggc atcttctttt gcgtgcggtg cagacatcgg     1020
cggagacagg ctgagagaat gagccagatc aagcggctgc tgagcgagaa gaaaacctgt     1080
cagtgccctc accggttcca gaaaacatgc agccccatct gatga                     1125
```

<210> SEQ ID NO 51
<211> LENGTH: 373
<212> TYPE: PRT
<213> ORGANISM: Artificial Sequence
<220> FEATURE:
<223> OTHER INFORMATION: Synthetic polypeptide

<400> SEQUENCE: 51

```
Glu Gln Lys Leu Ile Ser Glu Glu Asp Leu Asn Pro Gly Gly Gly Gly
1               5                   10                  15

Gly Ser Gly Gly Gly Ser Gly Gly Gly Ser Gly Gly Gly Gly
            20                  25                  30

Ser Gly Ser Met Asp Ile Gln Met Thr Gln Ser Pro Ser Ser Leu Ser
        35                  40                  45

Ala Ser Val Gly Asp Arg Val Thr Ile Thr Cys Arg Ala Ser Gln Asp
    50                  55                  60

Ile Arg Asn Tyr Leu Asn Trp Tyr Gln Gln Lys Pro Gly Lys Ala Pro
65                  70                  75                  80

Lys Leu Leu Ile Tyr Tyr Thr Ser Arg Leu Glu Ser Gly Val Pro Ser
                85                  90                  95

Arg Phe Ser Gly Ser Gly Ser Gly Thr Asp Tyr Thr Leu Thr Ile Ser
            100                 105                 110

Ser Leu Gln Pro Glu Asp Phe Ala Thr Tyr Tyr Cys Gln Gln Gly Asn
        115                 120                 125

Thr Leu Pro Trp Thr Phe Gly Gln Gly Thr Lys Val Glu Ile Lys Gly
    130                 135                 140

Gly Gly Gly Ser Gly Gly Gly Gly Ser Gly Gly Gly Gly Ser Glu Val
145                 150                 155                 160

Gln Leu Val Glu Ser Gly Gly Gly Leu Val Gln Pro Gly Gly Ser Leu
                165                 170                 175

Arg Leu Ser Cys Ala Ala Ser Gly Tyr Ser Phe Thr Gly Tyr Thr Met
            180                 185                 190

Asn Trp Val Arg Gln Ala Pro Gly Lys Gly Leu Glu Trp Val Ala Leu
        195                 200                 205

Ile Asn Pro Tyr Lys Gly Val Ser Thr Tyr Asn Gln Lys Phe Lys Asp
    210                 215                 220

Arg Phe Thr Ile Ser Val Asp Lys Ser Lys Asn Thr Ala Tyr Leu Gln
225                 230                 235                 240

Met Asn Ser Leu Arg Ala Glu Asp Thr Ala Val Tyr Tyr Cys Ala Arg
                245                 250                 255
```

Ser Gly Tyr Tyr Gly Asp Ser Asp Trp Tyr Phe Asp Val Trp Gly Gln
              260                 265                 270

Gly Thr Leu Val Thr Val Ser Ser Thr Ser Gly Gly Gly Gly Ser Leu
            275                 280                 285

Glu Ser Gly Gln Val Leu Leu Glu Ser Asn Ile Lys Val Leu Pro Thr
        290                 295                 300

Trp Ser Thr Pro Val Gln Pro Met Ala Leu Ile Val Leu Gly Gly Val
305                 310                 315                 320

Ala Gly Leu Leu Leu Phe Ile Gly Leu Gly Ile Phe Phe Cys Val Arg
                325                 330                 335

Cys Arg His Arg Arg Arg Gln Ala Glu Arg Met Ser Gln Ile Lys Arg
            340                 345                 350

Leu Leu Ser Glu Lys Lys Thr Cys Gln Cys Pro His Arg Phe Gln Lys
        355                 360                 365

Thr Cys Ser Pro Ile
    370

<210> SEQ ID NO 52
<211> LENGTH: 1122
<212> TYPE: DNA
<213> ORGANISM: Artificial Sequence
<220> FEATURE:
<223> OTHER INFORMATION: Synthetic polynucleotide

<400> SEQUENCE: 52
gaacagaagc tcatttctga agaagacctc aaccccggag ggggaggggg aagtggggga    60
gggggtagtg gtggcggagg atcaggcggg gggggatcag gatccatgga tatccagatg   120
acccagtccc cgagctccct gtccgcctct gtgggcgata gggtcaccat cacctgccgt   180
gccagtcagg acatccgtaa ttatctgaac tggtatcaac agaaaccagg aaaagctccg   240
aaactactga tttactatac ctcccgcctg gagtctggag tcccttctcg cttctctggt   300
tctggttctg ggacggatta cactctgacc atcagcagtc tgcaaccgga agacttcgca   360
acttattact gtcagcaagg taatactctg ccgtggacgt tcggacaggg caccaaggtg   420
gagatcaaag gcggcggcgg aagtggagga ggaggctcag gcggaggagg gagcgaggtt   480
cagctggtgg agtctggcgg tggcctggtg cagccagggg gctcactccg tttgtcctgt   540
gcagcttctg gctactcctt taccggctac actatgaact gggtgcgtca ggccccaggt   600
aagggcctgg aatgggttgc actgattaat cctaccaaag gtgttagtac ctacaaccag   660
aagttcaagg accgtttcac tataagcgta gataaatcca aaaacacagc ctacctgcaa   720
atgaacagcc tgcgtgctga ggacactgcc gtctattatt gtgctagaag cggatactac   780
ggcgatagtg actggtattt tgacgtgtgg ggtcaaggaa ccctggtcac cgtctcctcg   840
actagtggcg gaggaggatc actcgagagc ggacaggtgc tgctggaatc caatatcaaa   900
gtcctgccca cttggtctac ccccgtgcag cctatggctc tgattgtgct gggaggagtc   960
gcaggactgc tgctgtttat cgggctggga atttttcttt tcgtgcgctg ccggcaccgg  1020
agaaggcagg ccgagcgcat gagccagatc aagcgactgc tgagcgagaa gaaaacctgt  1080
cagtgtcccc atagattcca gaagacctgt tcacccattt ga                    1122

<210> SEQ ID NO 53
<211> LENGTH: 373
<212> TYPE: PRT
<213> ORGANISM: Artificial Sequence
<220> FEATURE:
<223> OTHER INFORMATION: Synthetic polypeptide

<400> SEQUENCE: 53

```
Glu Gln Lys Leu Ile Ser Glu Glu Asp Leu Asn Pro Gly Gly Gly
1               5                   10                  15
Gly Ser Gly Gly Gly Ser Gly Gly Gly Ser Gly Gly Gly Gly
            20                  25                  30
Ser Gly Ser Met Asp Ile Gln Met Thr Gln Ser Pro Ser Ser Leu Ser
        35                  40                  45
Ala Ser Val Gly Asp Arg Val Thr Ile Thr Cys Arg Ala Ser Gln Asp
    50                  55                  60
Ile Arg Asn Tyr Leu Asn Trp Tyr Gln Gln Lys Pro Gly Lys Ala Pro
65                  70                  75                  80
Lys Leu Leu Ile Tyr Tyr Thr Ser Arg Leu Glu Ser Gly Val Pro Ser
                85                  90                  95
Arg Phe Ser Gly Ser Gly Ser Gly Thr Asp Tyr Thr Leu Thr Ile Ser
            100                 105                 110
Ser Leu Gln Pro Glu Asp Phe Ala Thr Tyr Tyr Cys Gln Gln Gly Asn
        115                 120                 125
Thr Leu Pro Trp Thr Phe Gly Gln Gly Thr Lys Val Glu Ile Lys Gly
130                 135                 140
Gly Gly Gly Ser Gly Gly Gly Gly Ser Gly Gly Gly Gly Ser Glu Val
145                 150                 155                 160
Gln Leu Val Glu Ser Gly Gly Gly Leu Val Gln Pro Gly Gly Ser Leu
                165                 170                 175
Arg Leu Ser Cys Ala Ala Ser Gly Tyr Ser Phe Thr Gly Tyr Thr Met
            180                 185                 190
Asn Trp Val Arg Gln Ala Pro Gly Lys Gly Leu Glu Trp Val Ala Leu
        195                 200                 205
Ile Asn Pro Thr Lys Gly Val Ser Thr Tyr Asn Gln Lys Phe Lys Asp
210                 215                 220
Arg Phe Thr Ile Ser Val Asp Lys Ser Lys Asn Thr Ala Tyr Leu Gln
225                 230                 235                 240
Met Asn Ser Leu Arg Ala Glu Asp Thr Ala Val Tyr Tyr Cys Ala Arg
                245                 250                 255
Ser Gly Tyr Tyr Gly Asp Ser Asp Trp Tyr Phe Asp Val Trp Gly Gln
            260                 265                 270
Gly Thr Leu Val Thr Val Ser Thr Ser Gly Gly Gly Gly Ser Leu
        275                 280                 285
Glu Ser Gly Gln Val Leu Leu Glu Ser Asn Ile Lys Val Leu Pro Thr
290                 295                 300
Trp Ser Thr Pro Val Gln Pro Met Ala Leu Ile Val Leu Gly Gly Val
305                 310                 315                 320
Ala Gly Leu Leu Leu Phe Ile Gly Leu Gly Ile Phe Phe Cys Val Arg
                325                 330                 335
Cys Arg His Arg Arg Gln Ala Glu Arg Met Ser Gln Ile Lys Arg
            340                 345                 350
Leu Leu Ser Glu Lys Lys Thr Cys Gln Cys Pro His Arg Phe Gln Lys
        355                 360                 365
Thr Cys Ser Pro Ile
    370
```

<210> SEQ ID NO 54
<211> LENGTH: 15
<212> TYPE: DNA

<213> ORGANISM: Artificial Sequence
<220> FEATURE:
<223> OTHER INFORMATION: Synthetic polynucleotide

<400> SEQUENCE: 54
ggaggaggag ggagc                                                                                      15

<210> SEQ ID NO 55
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 55

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Asn Ile Pro
            20                  25                  30

Val Met Gly Trp Tyr Arg Gln Ala Pro Gly Lys Gln Arg Glu Leu Val
        35                  40                  45

Ala Gly Ile Ser Thr Gly Gly Thr Thr Asn Tyr Gly Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val Leu Val Val Ser Gly Ile Gly Ser Thr Leu Glu Val Trp Gly Gln
            100                 105                 110

Gly Thr Leu Val Thr Val Ser Ser
        115                 120

<210> SEQ ID NO 56
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 56

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe His Ile Pro
            20                  25                  30

Val Met Gly Trp Tyr Arg Gln Ala Pro Gly Lys Gly Leu Glu Leu Val
        35                  40                  45

Ala Gly Ile Ser Arg Gly Gly Thr Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Val Leu Val Val Ser Gly Ile Gly Ser Thr Leu Glu Val Trp Gly Gln
            100                 105                 110

Gly Thr Leu Val Thr Val Ser Ser
        115                 120

<210> SEQ ID NO 57
<211> LENGTH: 5

```
<212> TYPE: PRT
<213> ORGANISM: Artificial Sequence
<220> FEATURE:
<223> OTHER INFORMATION: Synthetic polypeptide

<400> SEQUENCE: 57

Ile Pro Val Met Gly
1               5

<210> SEQ ID NO 58
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 58

Gly Ile Ser Thr Gly Gly Thr Thr Asn Tyr Gly Asp Ser Val Lys Gly
1               5                   10                  15

<210> SEQ ID NO 59
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 59

Leu Val Val Ser Gly Ile Gly Ser Thr Leu Glu Val
1               5                   10

<210> SEQ ID NO 60
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 60

Gly Ser Ile Phe Asn Ile Pro Val
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 61

Ile Ser Thr Gly Gly Thr Thr
1               5

<210> SEQ ID NO 62
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 62

Asn Val Leu Val Val Ser Gly Ile Gly Ser Thr Leu Glu Val
1               5                   10

<210> SEQ ID NO 63
<211> LENGTH: 16
<212> TYPE: PRT
```

<213> ORGANISM: Artificial Sequence
<220> FEATURE:
<223> OTHER INFORMATION: Synthetic polypeptide

<400> SEQUENCE: 63

Gly Ile Ser Arg Gly Gly Thr Thr Asn Tyr Ala Asp Ser Val Lys Gly
1               5                   10                  15

<210> SEQ ID NO 64
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 64

Gly Ser Ile Phe His Ile Pro Val
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 65

Ile Ser Arg Gly Gly Thr Thr
1               5

<210> SEQ ID NO 66
<211> LENGTH: 1542
<212> TYPE: DNA
<213> ORGANISM: Artificial Sequence
<220> FEATURE:
<223> OTHER INFORMATION: Synthetic oligonucleotide

<400> SEQUENCE: 66

| | | |
|---|---|---|
| atggctctgc ctgtgacagc tctgttgctg cctctggctc tgctgctgca tgctgctaga | 60 |
| cctcaggtgc agctggttga atctggcgga ggacttgttc agcctggcgg ctctctgaga | 120 |
| ctgtcttgtg ccgccagcgg cagcatcttc aatatccccg tgatgggctg gtacagacag | 180 |
| gcccctggaa agcagagaga gctggttgcc ggaatctcta ccggcggcac cacaaattac | 240 |
| ggcgacagcg tgaagggcag attcaccatc agccgggaca cgccaagaa caccgtgtac | 300 |
| ctgcagatga acagcctgaa gcctgaggac accgccgtgt actactgcaa tgtgctggtg | 360 |
| gtgtctggca tcggcagcac actggaagtt tggggccagg gcacactggt cacagtgtct | 420 |
| agcgagcaga gctgatctc cgaggaagat ctgaatccag gcggaggcgg aggaagtggc | 480 |
| ggcggaggta gcgaggtgg tggaagcgga ggcggcggat ctggatctat ggatatccag | 540 |
| atgacccagt ccccgagctc cctgtccgcc tctgtgggcg ataggtcac catcacctgc | 600 |
| cgtgccagtc aggacatccg taattatctg aactggtatc aacagaaacc aggaaaagct | 660 |
| ccgaaactac tgatttacta tacctcccgc ctggagtctg gagtcccttc tcgcttctct | 720 |
| ggttctggtt ctgggacgga ttacactctg accatcagca gtctgcaacc ggaagacttc | 780 |
| gcaacttatt actgtcagca aggtaatact ctgccgtgga cgttcggaca gggcaccaag | 840 |
| gtggagatca aaggcggcgg cggaagtgga ggaggaggct caggcggagg agggagcgag | 900 |
| gttcagctgg tggagtctgg cggtggcctg gtgcagccag ggggctcact ccgtttgtcc | 960 |
| tgtgcagctt ctggctactc ctttaccggc tacactatga actgggtgcg tcaggcccca | 1020 |

```
ggtaagggcc tggaatgggt tgcactgatt aatccttata aaggtgttag tacctacaac    1080
cagaagttca aggaccgttt cactataagc gtagataaat ccaaaaacac agcctacctg    1140
caaatgaaca gcctgcgtgc tgaggacact gccgtctatt attgtgctag aagcggatac    1200
tacggcgata tgtgactggta ttttgacgtg tggggtcaag aaccctggt caccgtctcc    1260 tcgacatcag gtggtggcgg atctctggaa tctggccagg tgctgctgga atccaacatc    1320
aaggtgctgc ccacctggtc tacccagtt cagcctatgg ctctgattgt gcttggcgga    1380
gttgccggcc tgctgctgtt tatcggcctg ggcatcttct tttgcgtgcg gtgcagacat    1440
cggcggagac aggctgagag aatgagccag atcaagcggc tgctgagcga agaaaaacc    1500 tgtcagtgcc ctcaccggtt ccagaaaaca tgcagcccca tc                      1542
```

<210> SEQ ID NO 67
<211> LENGTH: 514
<212> TYPE: PRT
<213> ORGANISM: Artificial Sequence
<220> FEATURE:
<223> OTHER INFORMATION: Synthetic peptide

<400> SEQUENCE: 67

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Ala Ala Ser Gly Ser
        35                  40                  45

Ile Phe Asn Ile Pro Val Met Gly Trp Tyr Arg Gln Ala Pro Gly Lys
    50                  55                  60

Gln Arg Glu Leu Val Ala Gly Ile Ser Thr Gly Gly Thr Thr Asn Tyr
65                  70                  75                  80

Gly Asp Ser Val Lys Gly Arg Phe Thr Ile Ser Arg Asp Asn Ala Lys
                85                  90                  95

Asn Thr Val Tyr Leu Gln Met Asn Ser Leu Lys Pro Glu Asp Thr Ala
            100                 105                 110

Val Tyr Tyr Cys Asn Val Leu Val Val Ser Gly Ile Gly Ser Thr Leu
        115                 120                 125

Glu Val Trp Gly Gln Gly Thr Leu Val Thr Val Ser Ser Glu Gln Lys
    130                 135                 140

Leu Ile Ser Glu Glu Asp Leu Asn Pro Gly Gly Gly Gly Ser Gly
145                 150                 155                 160

Gly Gly Gly Ser Gly Gly Gly Ser Gly Gly Gly Ser Gly Ser
                165                 170                 175

Met Asp Ile Gln Met Thr Gln Ser Pro Ser Ser Leu Ser Ala Ser Val
            180                 185                 190

Gly Asp Arg Val Thr Ile Thr Cys Arg Ala Ser Gln Asp Ile Arg Asn
        195                 200                 205

Tyr Leu Asn Trp Tyr Gln Gln Lys Pro Gly Lys Ala Pro Lys Leu Leu
    210                 215                 220

Ile Tyr Tyr Thr Ser Arg Leu Glu Ser Gly Val Pro Ser Arg Phe Ser
225                 230                 235                 240

Gly Ser Gly Ser Gly Thr Asp Tyr Thr Leu Thr Ile Ser Ser Leu Gln
                245                 250                 255

Pro Glu Asp Phe Ala Thr Tyr Tyr Cys Gln Gln Gly Asn Thr Leu Pro
            260                 265                 270
```

```
Trp Thr Phe Gly Gln Gly Thr Lys Val Glu Ile Lys Gly Gly Gly
            275                 280                 285
Ser Gly Gly Gly Ser Gly Gly Gly Ser Glu Val Gln Leu Val
    290                 295                 300
Glu Ser Gly Gly Gly Leu Val Gln Pro Gly Gly Ser Leu Arg Leu Ser
305                 310                 315                 320
Cys Ala Ala Ser Gly Tyr Ser Phe Thr Gly Tyr Thr Met Asn Trp Val
                325                 330                 335
Arg Gln Ala Pro Gly Lys Gly Leu Glu Trp Val Ala Leu Ile Asn Pro
            340                 345                 350
Tyr Lys Gly Val Ser Thr Tyr Asn Gln Lys Phe Lys Asp Arg Phe Thr
        355                 360                 365
Ile Ser Val Asp Lys Ser Lys Asn Thr Ala Tyr Leu Gln Met Asn Ser
    370                 375                 380
Leu Arg Ala Glu Asp Thr Ala Val Tyr Tyr Cys Ala Arg Ser Gly Tyr
385                 390                 395                 400
Tyr Gly Asp Ser Asp Trp Tyr Phe Asp Val Trp Gly Gln Gly Thr Leu
                405                 410                 415
Val Thr Val Ser Ser Thr Ser Gly Gly Gly Gly Ser Leu Glu Ser Gly
            420                 425                 430
Gln Val Leu Leu Glu Ser Asn Ile Lys Val Leu Pro Thr Trp Ser Thr
        435                 440                 445
Pro Val Gln Pro Met Ala Leu Ile Val Leu Gly Gly Val Ala Gly Leu
    450                 455                 460
Leu Leu Phe Ile Gly Leu Gly Ile Phe Phe Cys Val Arg Cys Arg His
465                 470                 475                 480
Arg Arg Arg Gln Ala Glu Arg Met Ser Gln Ile Lys Arg Leu Leu Ser
                485                 490                 495
Glu Lys Lys Thr Cys Gln Cys Pro His Arg Phe Gln Lys Thr Cys Ser
            500                 505                 510
Pro Ile
```

<210> SEQ ID NO 68
<211> LENGTH: 1542
<212> TYPE: DNA
<213> ORGANISM: Artificial Sequence
<220> FEATURE:
<223> OTHER INFORMATION: Synthetic oligonucleotide

<400> SEQUENCE: 68

```
atggctctgc ctgtgacagc tctgttgctg cctctggctc tgctgctgca tgctgctaga      60
cctcaggtgc agctggttga atctggcgga ggacttgttc agcctggcgg ctctctgaga     120
ctgtcttgtg ccgccagcgg cagcatcttc aatatcccg tgatgggctg gtacagacag     180
gcccctggaa agcagagaga gctggttgcc ggaatctcta ccggcggcac cacaaattac     240
ggcgacagcg tgaagggcag attcaccatc agcggaca cgccaagaa caccgtgtac     300
ctgcagatga acagcctgaa gcctgaggac accgccgtgt actactgcaa tgtgctggtg     360
gtgtctggca tcggcagcac actggaagtt tggggccagg gcacactggt cacagtgtct     420
agcgagcaga agctgatctc cgaggaagat ctgaatccag cggaggcgg aggttctggt     480
ggcggaggaa gtggtggcgg cggatcaggc ggcggtggat ctggatctat ggatatccag     540
atgacccagt ccccgagctc cctgtccgcc tctgtgggcg atagggtcac catcacctgc     600
cgtgccagtc aggacatccg taattatctg aactggtatc aacagaaacc aggaaaagct     660
```

```
ccgaaactac tgatttacta tacctcccgc ctggagtctg gagtcccttc tcgcttctct    720
ggttctggtt ctgggacgga ttacactctg accatcagca gtctgcaacc ggaagacttc    780
gcaacttatt actgtcagca aggtaatact ctgccgtgga cgttcggaca gggcaccaag    840
gtggagatca aaggcggcgg cggaagtgga ggaggaggct caggcggagg agggagcgag    900
gttcagctgg tggagtctgg cggtggcctg gtgcagccag ggggctcact ccgtttgtcc    960
tgtgcagctt ctggctactc ctttaccggc tacactatga actgggtgcg tcaggcccca   1020
ggtaagggcc tggaatgggt tgcactgatt aatcctacca aaggtgttag tacctacaac   1080
cagaagttca aggaccgttt cactataagc gtagataaat ccaaaaacac agcctacctg   1140
caaatgaaca gcctgcgtgc tgaggacact gccgtctatt attgtgctag aagcggatac   1200
tacggcgata gtgactggta ttttgacgtg tggggtcaag aaccctggt caccgtctcc   1260
tcgacatctg gcggcggagg atctctggaa tctggacagg tgctgctgga aagcaacatc   1320
aaggtgctgc ccacctggtc tacccccagtt cagcctatgg ctctgattgt gcttggaggc   1380
gtggccggcc tgctgctgtt tatcggcctg ggcatcttct tttgcgtgcg gtgcagacat   1440
cggcggagac aggctgagag aatgagccag atcaagcggc tgctgagcga aagaaaaacc   1500
tgtcagtgcc ctcaccggtt ccagaaaaca tgcagcccca tc                      1542

<210> SEQ ID NO 69
<211> LENGTH: 514
<212> TYPE: PRT
<213> ORGANISM: Artificial Sequence
<220> FEATURE:
<223> OTHER INFORMATION: Synthetic peptide

<400> SEQUENCE: 69

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Ala Ala Ser Gly Ser
        35                  40                  45

Ile Phe Asn Ile Pro Val Met Gly Trp Tyr Arg Gln Ala Pro Gly Lys
    50                  55                  60

Gln Arg Glu Leu Val Ala Gly Ile Ser Thr Gly Gly Thr Thr Asn Tyr
65                  70                  75                  80

Gly Asp Ser Val Lys Gly Arg Phe Thr Ile Ser Arg Asp Asn Ala Lys
                85                  90                  95

Asn Thr Val Tyr Leu Gln Met Asn Ser Leu Lys Pro Glu Asp Thr Ala
            100                 105                 110

Val Tyr Tyr Cys Asn Val Leu Val Val Ser Gly Ile Gly Ser Thr Leu
        115                 120                 125

Glu Val Trp Gly Gln Gly Thr Leu Val Thr Val Ser Ser Glu Gln Lys
    130                 135                 140

Leu Ile Ser Glu Glu Asp Leu Asn Pro Gly Gly Gly Gly Ser Gly
145                 150                 155                 160

Gly Gly Gly Ser Gly Gly Gly Ser Gly Gly Gly Ser Gly Ser
                165                 170                 175

Met Asp Ile Gln Met Thr Gln Ser Pro Ser Ser Leu Ser Ala Ser Val
            180                 185                 190

Gly Asp Arg Val Thr Ile Thr Cys Arg Ala Ser Gln Asp Ile Arg Asn
        195                 200                 205
```

```
Tyr Leu Asn Trp Tyr Gln Gln Lys Pro Gly Lys Ala Pro Lys Leu Leu
    210                 215                 220
Ile Tyr Tyr Thr Ser Arg Leu Glu Ser Gly Val Pro Ser Arg Phe Ser
225                 230                 235                 240
Gly Ser Gly Ser Gly Thr Asp Tyr Thr Leu Thr Ile Ser Ser Leu Gln
                245                 250                 255
Pro Glu Asp Phe Ala Thr Tyr Tyr Cys Gln Gln Gly Asn Thr Leu Pro
            260                 265                 270
Trp Thr Phe Gly Gln Gly Thr Lys Val Glu Ile Lys Gly Gly Gly Gly
        275                 280                 285
Ser Gly Gly Gly Gly Ser Gly Gly Gly Gly Ser Glu Val Gln Leu Val
    290                 295                 300
Glu Ser Gly Gly Gly Leu Val Gln Pro Gly Gly Ser Leu Arg Leu Ser
305                 310                 315                 320
Cys Ala Ala Ser Gly Tyr Ser Phe Thr Gly Tyr Thr Met Asn Trp Val
                325                 330                 335
Arg Gln Ala Pro Gly Lys Gly Leu Glu Trp Val Ala Leu Ile Asn Pro
            340                 345                 350
Thr Lys Gly Val Ser Thr Tyr Asn Gln Lys Phe Lys Asp Arg Phe Thr
        355                 360                 365
Ile Ser Val Asp Lys Ser Lys Asn Thr Ala Tyr Leu Gln Met Asn Ser
370                 375                 380
Leu Arg Ala Glu Asp Thr Ala Val Tyr Tyr Cys Ala Arg Ser Gly Tyr
385                 390                 395                 400
Tyr Gly Asp Ser Asp Trp Tyr Phe Asp Val Trp Gly Gln Gly Thr Leu
                405                 410                 415
Val Thr Val Ser Ser Thr Ser Gly Gly Gly Gly Ser Leu Glu Ser Gly
            420                 425                 430
Gln Val Leu Leu Glu Ser Asn Ile Lys Val Leu Pro Thr Trp Ser Thr
        435                 440                 445
Pro Val Gln Pro Met Ala Leu Ile Val Leu Gly Gly Val Ala Gly Leu
    450                 455                 460
Leu Leu Phe Ile Gly Leu Gly Ile Phe Phe Cys Val Arg Cys Arg His
465                 470                 475                 480
Arg Arg Arg Gln Ala Glu Arg Met Ser Gln Ile Lys Arg Leu Leu Ser
                485                 490                 495
Glu Lys Lys Thr Cys Gln Cys Pro His Arg Phe Gln Lys Thr Cys Ser
            500                 505                 510
Pro Ile

<210> SEQ ID NO 70
<211> LENGTH: 1542
<212> TYPE: DNA
<213> ORGANISM: Artificial Sequence
<220> FEATURE:
<223> OTHER INFORMATION: Synthetic oligonucleotide

<400> SEQUENCE: 70
atggctctgc ctgtgacagc tctgttgctg cctctggctc tgctgctgca tgctgctaga      60
cctcaggtgc agctggttga atctggcgga ggacttgttc agcctggcgg ctctctgaga     120
ctgtcttgtg ccgccagcgg cagcatcttt cacatccctg tgatgggctg gtacagacag     180
gcccctggaa aggactgga actggtggcc ggaatctcta gaggcggcac cacaaattac      240
gccgacagcg tgaagggcag attcaccatc agccgggaca cgccaagaa caccctgtac     300
```

-continued

```
ctgcagatga acagcctgag agccgaggac accgccgtgt actactgtaa tgtgctggtg    360
gtgtctggca tcggcagcac actggaagtt tggggccagg gcacactggt cacagtgtct    420
agcgagcaga agctgatctc cgaggaagat ctgaatccag gcggaggcgg aggaagtggc    480
ggcggaggta gcggaggtgg tggaagcgga ggcggcggat ctggatctat ggatatccag    540
atgacccagt ccccgagctc cctgtccgcc tctgtgggcg ataggotcac catcacctgc    600
cgtgccagtc aggacatccg taattatctg aactggtatc aacagaaacc aggaaaagct    660
ccgaaactac tgatttacta tacctcccgc ctggagtctg gagtccottc tcgcttctct    720
ggttctggtt ctgggacgga ttacactctg accatcagca gtctgcaacc ggaagacttc    780
gcaacttatt actgtcagca aggtaatact ctgccgtgga cgttcggaca gggcaccaag    840
gtggagatca aggcggcgg cggaagtgga ggaggaggct caggcggagg agggagcgag    900
gttcagctgg tggagtctgg cggtggcctg gtgcagccag ggggctcact ccgtttgtcc    960
tgtgcagctt ctggctactc ctttaccggc tacactatga actgggtgcg tcaggcccca   1020
ggtaagggcc tggaatgggt tgcactgatt aatccttata aggtgttag tacctacaac   1080
cagaagttca aggaccgttt cactataagc gtagataaat ccaaaaacac agcctacctg   1140
caaatgaaca gcctgcgtgc tgaggacact gccgtctatt attgtgctag aagcggatac   1200
tacggcgata tgactggta tttgacgtg tggggtcaag aaccctggt caccgtctcc   1260
tcgacatcag gtggtggcgg atctctggaa tctggccagg tgctgctgga agcaacatc   1320
aaggtgctgc ccacctggtc taccccagtt cagcctatgg ctctgattgt gcttggcgga   1380
gttgccggcc tgctgctgtt tatcggcctg gcatcttct tttgcgtgcg gtgcagacat   1440
cggcggagac aggctgagag aatgagccag atcaagcggc tgctgagcga agaaaaacc   1500
tgtcagtgcc ctcaccggtt ccagaaaaca tgcagccca tc                     1542
```

<210> SEQ ID NO 71
<211> LENGTH: 514
<212> TYPE: PRT
<213> ORGANISM: Artificial Sequence
<220> FEATURE:
<223> OTHER INFORMATION: Synthetic peptide

<400> SEQUENCE: 71

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Ala Ala Ser Gly Ser
        35                  40                  45

Ile Phe His Ile Pro Val Met Gly Trp Tyr Arg Gln Ala Pro Gly Lys
    50                  55                  60

Gly Leu Glu Leu Val Ala Gly Ile Ser Arg Gly Thr Thr Asn Tyr
65                  70                  75                  80

Ala Asp Ser Val Lys Gly Arg Phe Thr Ile Ser Arg Asp Asn Ala Lys
                85                  90                  95

Asn Thr Leu Tyr Leu Gln Met Asn Ser Leu Arg Ala Glu Asp Thr Ala
            100                 105                 110

Val Tyr Tyr Cys Asn Val Leu Val Ser Gly Ile Gly Ser Thr Leu
        115                 120                 125

Glu Val Trp Gly Gln Gly Thr Leu Val Thr Val Ser Ser Glu Gln Lys
    130                 135                 140
```

```
Leu Ile Ser Glu Glu Asp Leu Asn Pro Gly Gly Gly Gly Ser Gly
145                 150                 155                 160

Gly Gly Gly Ser Gly Gly Gly Ser Gly Gly Gly Ser Gly Ser
            165                 170                 175

Met Asp Ile Gln Met Thr Gln Ser Pro Ser Ser Leu Ser Ala Ser Val
                180                 185                 190

Gly Asp Arg Val Thr Ile Thr Cys Arg Ala Ser Gln Asp Ile Arg Asn
        195                 200                 205

Tyr Leu Asn Trp Tyr Gln Gln Lys Pro Gly Lys Ala Pro Lys Leu Leu
    210                 215                 220

Ile Tyr Tyr Thr Ser Arg Leu Glu Ser Gly Val Pro Ser Arg Phe Ser
225                 230                 235                 240

Gly Ser Gly Ser Gly Thr Asp Tyr Thr Leu Thr Ile Ser Ser Leu Gln
            245                 250                 255

Pro Glu Asp Phe Ala Thr Tyr Tyr Cys Gln Gln Gly Asn Thr Leu Pro
        260                 265                 270

Trp Thr Phe Gly Gln Gly Thr Lys Val Glu Ile Lys Gly Gly Gly Gly
    275                 280                 285

Ser Gly Gly Gly Gly Ser Gly Gly Gly Gly Ser Glu Val Gln Leu Val
290                 295                 300

Glu Ser Gly Gly Gly Leu Val Gln Pro Gly Gly Ser Leu Arg Leu Ser
305                 310                 315                 320

Cys Ala Ala Ser Gly Tyr Ser Phe Thr Gly Tyr Thr Met Asn Trp Val
                325                 330                 335

Arg Gln Ala Pro Gly Lys Gly Leu Glu Trp Val Ala Leu Ile Asn Pro
        340                 345                 350

Tyr Lys Gly Val Ser Thr Tyr Asn Gln Lys Phe Lys Asp Arg Phe Thr
    355                 360                 365

Ile Ser Val Asp Lys Ser Lys Asn Thr Ala Tyr Leu Gln Met Asn Ser
370                 375                 380

Leu Arg Ala Glu Asp Thr Ala Val Tyr Tyr Cys Ala Arg Ser Gly Tyr
385                 390                 395                 400

Tyr Gly Asp Ser Asp Trp Tyr Phe Asp Val Trp Gly Gln Gly Thr Leu
                405                 410                 415

Val Thr Val Ser Ser Thr Ser Gly Gly Gly Gly Ser Leu Glu Ser Gly
        420                 425                 430

Gln Val Leu Leu Glu Ser Asn Ile Lys Val Leu Pro Thr Trp Ser Thr
    435                 440                 445

Pro Val Gln Pro Met Ala Leu Ile Val Leu Gly Gly Val Ala Gly Leu
450                 455                 460

Leu Leu Phe Ile Gly Leu Gly Ile Phe Phe Cys Val Arg Cys Arg His
465                 470                 475                 480

Arg Arg Arg Gln Ala Glu Arg Met Ser Gln Ile Lys Arg Leu Leu Ser
                485                 490                 495

Glu Lys Lys Thr Cys Gln Cys Pro His Arg Phe Gln Lys Thr Cys Ser
        500                 505                 510

Pro Ile
```

<210> SEQ ID NO 72
<211> LENGTH: 1542
<212> TYPE: DNA
<213> ORGANISM: Artificial Sequence
<220> FEATURE:
<223> OTHER INFORMATION: Synthetic oligonucleotide

<400> SEQUENCE: 72

```
atggctctgc ctgtgacagc tctgttgctg cctctggctc tgctgctgca tgctgctaga      60
cctcaggtgc agctggttga atctggcgga ggacttgttc agcctggcgg ctctctgaga     120
ctgtcttgtg ccgccagcgg cagcatcttt cacatccctg tgatgggctg gtacagacag     180
gcccctggaa aaggactgga actggtggcc ggaatctcta gaggcggcac cacaaattac     240
gccgacagcg tgaagggcag attcaccatc agccgggaca cgccaagaa cacccctgtac     300
ctgcagatga acagcctgag agccgaggac accgccgtgt actactgtaa tgtgctggtg     360
gtgtctggca tcggcagcac actggaagtt tggggccagg gcacactggt cacagtgtct     420
agcgagcaga agctgatctc cgaggaagat ctgaatccag gcggaggcgg aggttctggt     480
ggcggaggaa gtggtggcgg cggatcaggc ggcggtggat ctggatctat ggatatccag     540
atgacccagt ccccgagctc cctgtccgcc tctgtgggcg ataggtcac catcacctgc     600
cgtgccagtc aggacatccg taattatctg aactggtatc aacagaaacc aggaaaagct     660
ccgaaactac tgatttacta tacctcccgc ctggagtctg gagtcccttc tcgcttctct     720
ggttctggtt ctgggacgga ttacactctg accatcagca gtctgcaacc ggaagacttc     780
gcaacttatt actgtcagca aggtaatact ctgccgtgga cgttcggaca gggcaccaag     840
gtggagatca aaggcggcgg cggaagtgga ggaggaggct caggcggagg agggagcgag     900
gttcagctgg tggagtctgg cggtggcctg gtgcagccag ggggctcact ccgtttgtcc     960
tgtgcagctt ctggctactc ctttaccggc tacactatga actgggtgcg tcaggcccca    1020
ggtaagggcc tggaatgggt tgcactgatt aatcctacca aggtgttag tacctacaac    1080
cagaagttca aggaccgttt cactataagc gtagataaat ccaaaaacac agcctacctg    1140
caaatgaaca gcctgcgtgc tgaggacact gccgtctatt attgtgctag aagcggatac    1200
tacggcgata gtgactggta ttttgacgtg tggggtcaag aaccctggt caccgtctcc    1260
tcgacatctg gcggcggagg atctctggaa tctggacagg tgctgctgga agcaacatc    1320
aaggtgctgc ccacctggtc tacccccagtt cagcctatgg ctctgattgt gcttggaggc    1380
gtggccggcc tgctgctgtt tatcggcctg ggcatcttct tttgcgtgcg gtgcagacat    1440
cggcggagac aggctgagag aatgagccag atcaagcggc tgctgagcga aagaaaaacc    1500
tgtcagtgcc ctcaccggtt ccagaaaaca tgcagcccca tc                       1542
```

<210> SEQ ID NO 73
<211> LENGTH: 514
<212> TYPE: PRT
<213> ORGANISM: Artificial Sequence
<220> FEATURE:
<223> OTHER INFORMATION: Synthetic peptide

<400> SEQUENCE: 73

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Ala Ala Ser Gly Ser
        35                  40                  45

Ile Phe His Ile Pro Val Met Gly Trp Tyr Arg Gln Ala Pro Gly Lys
    50                  55                  60

Gly Leu Glu Leu Val Ala Gly Ile Ser Arg Gly Gly Thr Thr Asn Tyr
65                  70                  75                  80
```

```
Ala Asp Ser Val Lys Gly Arg Phe Thr Ile Ser Arg Asp Asn Ala Lys
                 85                  90                  95

Asn Thr Leu Tyr Leu Gln Met Asn Ser Leu Arg Ala Glu Asp Thr Ala
            100                 105                 110

Val Tyr Tyr Cys Asn Val Leu Val Ser Gly Ile Gly Ser Thr Leu
        115                 120                 125

Glu Val Trp Gly Gln Gly Thr Leu Val Thr Val Ser Ser Glu Gln Lys
130                 135                 140

Leu Ile Ser Glu Glu Asp Leu Asn Pro Gly Gly Gly Gly Ser Gly
145                 150                 155                 160

Gly Gly Gly Ser Gly Gly Gly Ser Gly Gly Gly Gly Ser Gly Ser
                165                 170                 175

Met Asp Ile Gln Met Thr Gln Ser Pro Ser Ser Leu Ser Ala Ser Val
            180                 185                 190

Gly Asp Arg Val Thr Ile Thr Cys Arg Ala Ser Gln Asp Ile Arg Asn
            195                 200                 205

Tyr Leu Asn Trp Tyr Gln Gln Lys Pro Gly Lys Ala Pro Lys Leu Leu
            210                 215                 220

Ile Tyr Tyr Thr Ser Arg Leu Glu Ser Gly Val Pro Ser Arg Phe Ser
225                 230                 235                 240

Gly Ser Gly Ser Gly Thr Asp Tyr Thr Leu Thr Ile Ser Ser Leu Gln
                245                 250                 255

Pro Glu Asp Phe Ala Thr Tyr Tyr Cys Gln Gln Gly Asn Thr Leu Pro
            260                 265                 270

Trp Thr Phe Gly Gln Gly Thr Lys Val Glu Ile Lys Gly Gly Gly Gly
            275                 280                 285

Ser Gly Gly Gly Gly Ser Gly Gly Gly Gly Ser Glu Val Gln Leu Val
            290                 295                 300

Glu Ser Gly Gly Gly Leu Val Gln Pro Gly Gly Ser Leu Arg Leu Ser
305                 310                 315                 320

Cys Ala Ala Ser Gly Tyr Ser Phe Thr Gly Tyr Thr Met Asn Trp Val
                325                 330                 335

Arg Gln Ala Pro Gly Lys Gly Leu Glu Trp Val Ala Leu Ile Asn Pro
            340                 345                 350

Thr Lys Gly Val Ser Thr Tyr Asn Gln Lys Phe Lys Asp Arg Phe Thr
            355                 360                 365

Ile Ser Val Asp Lys Ser Lys Asn Thr Ala Tyr Leu Gln Met Asn Ser
370                 375                 380

Leu Arg Ala Glu Asp Thr Ala Val Tyr Tyr Cys Ala Arg Ser Gly Tyr
385                 390                 395                 400

Tyr Gly Asp Ser Asp Trp Tyr Phe Asp Val Trp Gly Gln Gly Thr Leu
                405                 410                 415

Val Thr Val Ser Ser Thr Ser Gly Gly Gly Ser Leu Glu Ser Gly
            420                 425                 430

Gln Val Leu Leu Glu Ser Asn Ile Lys Val Leu Pro Thr Trp Ser Thr
            435                 440                 445

Pro Val Gln Pro Met Ala Leu Ile Val Leu Gly Gly Val Ala Gly Leu
450                 455                 460

Leu Leu Phe Ile Gly Leu Gly Ile Phe Phe Cys Val Arg Cys Arg His
465                 470                 475                 480

Arg Arg Arg Gln Ala Glu Arg Met Ser Gln Ile Lys Arg Leu Leu Ser
            485                 490                 495

Glu Lys Lys Thr Cys Gln Cys Pro His Arg Phe Gln Lys Thr Cys Ser
```

Pro Ile

<210> SEQ ID NO 74
<211> LENGTH: 1542
<212> TYPE: DNA
<213> ORGANISM: Artificial Sequence
<220> FEATURE:
<223> OTHER INFORMATION: Synthetic polynucleotide

<400> SEQUENCE: 74

| | |
|---|---|
| atggctctgc ctgtgacagc tctgttgctg cctctggctc tgctgctgca tgctgctaga | 60 |
| cctcaggtgc agctggttga atctggcgga ggacttgttc agcctggcgg ctctctgaga | 120 |
| ctgtcttgtg ccgccagcgg cagcatcttc aatatccccg tgatgggctg gtacagacag | 180 |
| gcccctggaa agcagagaga gctggttgcc ggaatctcta ccggcggcac cacaaattac | 240 |
| ggcgacagcg tgaagggcag attcaccatc agccgggaca cgccaagaa caccgtgtac | 300 |
| ctgcagatga acagcctgaa gcctgaggac accgccgtgt actactgcaa tgtgctggtg | 360 |
| gtgtctggca tcggcagcac actggaagtt tggggccagg gcacactggt cacagtgtct | 420 |
| agcgagcaga agctgatctc cgaggaagat ctgaatccag gcgaggcgg aggaagtggc | 480 |
| ggcggaggta gcggaggtgg tggaagcgga ggcggcggat ctggatctat ggatatccag | 540 |
| atgacccagt ccccgagctc cctgtccgcc tctgtgggcg ataggtcac catcacctgc | 600 |
| cgtgccagtc aggacatccg taattatctg aactggtatc aacagaaacc aggaaaagct | 660 |
| ccgaaactac tgatttacta tacctcccgc ctggagtctg gagtcccttc tcgcttctct | 720 |
| ggttctggtt ctgggacgga ttacactctg accatcagca gtctgcaacc ggaagacttc | 780 |
| gcaacttatt actgtcagca aggtaatact ctgccgtgga cgttcggaca gggcaccaag | 840 |
| gtggagatca aaggcggcgg cggaagtgga ggaggaggct caggcggagg agggagcgag | 900 |
| gttcagctgg tggagtctgg cggtggcctg gtgcagccag ggggctcact ccgtttgtcc | 960 |
| tgtgcagctt ctggctactc ctttaccggc tacactatga actgggtgcg tcaggcccca | 1020 |
| ggtaagggcc tggaatgggt tgcactgatt aatcctacca aggtgttag tacctacaac | 1080 |
| cagaagttca ggaccgtttt cactataagc gtagataaat ccaaaaacac agcctacctg | 1140 |
| caaatgaaca gcctgcgtgc tgaggacact gccgtctatt attgtgctag aagcggatac | 1200 |
| tacggcgata gtgactggta ttttgacgtg tggggtcaag aaccctggt caccgtctcc | 1260 |
| tcgacatcag gtggtggcgg atctctggaa tctggccagg tgctgctgga atccaacatc | 1320 |
| aaggtgctgc ccacctggtc taccccagtt cagcctatgg ctctgattgt gcttggcgga | 1380 |
| gttgccggcc tgctgctgtt tatcggcctg gcatcttct tttgcgtgcg gtgcagacat | 1440 |
| cggcggagac aggctgagag aatgagccag atcaagcggc tgctgagcga aagaaaaacc | 1500 |
| tgtcagtgcc ctcaccggtt ccagaaaaca tgcagcccca tc | 1542 |

<210> SEQ ID NO 75
<211> LENGTH: 1542
<212> TYPE: DNA
<213> ORGANISM: Artificial Sequence
<220> FEATURE:
<223> OTHER INFORMATION: Synthetic polynucleotide

<400> SEQUENCE: 75

| | |
|---|---|
| atggctctgc ctgtgacagc tctgttgctg cctctggctc tgctgctgca tgctgctaga | 60 |
| cctcaggtgc agctggttga atctggcgga ggacttgttc agcctggcgg ctctctgaga | 120 |

```
ctgtcttgtg ccgccagcgg cagcatcttt cacatccctg tgatgggctg gtacagacag        180 gccoctggaa aaggactgga actggtggcc ggaatctcta gaggcggcac cacaaattac        240
gccgacagcg tgaagggcag attcaccatc agccgggaca acgccaagaa caccctgtac        300
ctgcagatga acagcctgag agccgaggac accgccgtgt actactgtaa tgtgctggtg        360
gtgtctggca tcggcagcac actggaagtt tggggccagg gcacactggt cacagtgtct        420
agcgagcaga agctgatctc cgaggaagat ctgaatccag gcggaggcgg aggaagtggc        480
ggcggaggta gcggaggtgg tggaagcgga ggcggcggat ctggatctat ggatatccag        540
atgacccagt ccccgagctc cctgtccgcc tctgtgggcg atagggtcac catcacctgc        600
cgtgccagtc aggacatccg taattatctg aactggtatc aacagaaacc aggaaaagct        660
ccgaaactac tgatttacta tacctcccgc ctggagtctg gagtcccttc tcgcttctct        720
ggttctggtt ctgggacgga ttacactctg accatcagca gtctgcaacc ggaagacttc        780
gcaacttatt actgtcagca aggtaatact ctgccgtgga cgttcggaca gggcaccaag        840
gtggagatca aaggcggcgg cggaagtgga ggaggaggct caggcggagg agggagcgag        900
gttcagctgg tggagtctgg cggtggcctg gtgcagccag ggggctcact ccgtttgtcc        960
tgtgcagctt ctggctactc ctttaccggc tacactatga actgggtgcg tcaggcccca       1020
ggtaagggcc tggaatgggt tgcactgatt aatcctacca aaggtgttag tacctacaac       1080
cagaagttca aggaccgttt cactataagc gtagataaat ccaaaaacac agcctacctg       1140
caaatgaaca gcctgcgtgc tgaggacact gccgtctatt attgtgctag aagcggatac       1200
tacggcgata gtgactggta ttttgacgtg tggggtcaag aaccctggt caccgtctcc       1260 tcgacatcag gtggtggcgg atctctggaa tctggccagg tgctgctgga aagcaacatc       1320
aaggtgctgc ccacctggtc taccccagtt cagcctatgg ctctgattgt gcttggcgga       1380
gttgccggcc tgctgctgtt tatcggcctg ggcatcttct tttgcgtgcg gtgcagacat       1440
cggcggagac aggctgagag aatgagccag atcaagcggc tgctgagcga aagaaaacc        1500 tgtcagtgcc ctcaccggtt ccagaaaaca tgcagcccca tc                          1542
```